US010822385B2

(12) United States Patent
Chen et al.

(10) Patent No.: US 10,822,385 B2
(45) Date of Patent: Nov. 3, 2020

(54) EGF(A) ANALOGUES WITH FATTY ACID SUBSTITUENTS

(71) Applicant: Novo Nordisk A/S, Bagsvaerd (DK)

(72) Inventors: Jianhe Chen, Beijing (CN); Jesper F. Lau, Farum (DK); Janos Tibor Kodra, Copenhagen (DK); Birgit Wieczorek, Copenhagen (DK); Lars Linderoth, Hilleroed (DK); Henning Thoegersen, Farum (DK); Salka Elboel Rasmussen, Vaerloese (DK); Patrick William Garibay, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/069,932

(22) PCT Filed: Jan. 13, 2017

(86) PCT No.: PCT/EP2017/050668
§ 371 (c)(1),
(2) Date: Jul. 13, 2018

(87) PCT Pub. No.: WO2017/121850
PCT Pub. Date: Jul. 20, 2017

(65) Prior Publication Data
US 2019/0016768 A1 Jan. 17, 2019

(30) Foreign Application Priority Data
Oct. 27, 2016 (EP) ..................................... 16195965

(51) Int. Cl.
| C07K 14/485 | (2006.01) |
| A61K 38/17 | (2006.01) |
| C07K 14/705 | (2006.01) |
| A61K 38/00 | (2006.01) |

(52) U.S. Cl.
CPC .......... *C07K 14/485* (2013.01); *A61K 38/177* (2013.01); *C07K 14/705* (2013.01); *A61K 38/00* (2013.01)

(58) Field of Classification Search
None
See application file for complete search history.

(56) References Cited

U.S. PATENT DOCUMENTS

| 8,557,771 | B2 | 10/2013 | Fan et al. | |
| 8,673,850 | B2 | 3/2014 | Seidah et al. | |
| 9,745,359 | B2 | 8/2017 | Qin | |
| 2014/0212431 | A1* | 7/2014 | Kirchhofer | C07K 14/485 424/158.1 |
| 2014/0357838 | A1* | 12/2014 | Madsen | C07K 14/62 530/303 |
| 2019/0016768 | A1 | 1/2019 | Chen et al. | |
| 2020/0165313 | A1 | 5/2020 | Lau et al. | |
| 2020/0231645 | A1 | 7/2020 | Tornoee et al. | |

FOREIGN PATENT DOCUMENTS

| CN | 102153652 A | 8/2011 |
| CN | 104558198 A | 4/2015 |
| CN | 105367884 A | 3/2016 |
| EP | 2296694 A2 | 3/2011 |
| JP | 2010535849 A | 11/2010 |
| JP | 2014510516 A | 5/2014 |
| RU | 2528735 C2 | 9/2014 |
| WO | 2007018619 A2 | 2/2007 |
| WO | 2007022123 A2 | 2/2007 |
| WO | 2009022006 | 2/2009 |
| WO | 2010029513 | 3/2010 |
| WO | 2011020319 A1 | 2/2011 |
| WO | 2012110422 | 8/2012 |
| WO | 12177741 A1 | 12/2012 |
| WO | 13049234 A2 | 4/2013 |
| WO | 2013170636 A1 | 11/2013 |
| WO | 2014031420 A1 | 2/2014 |
| WO | 2014037373 A1 | 3/2014 |
| WO | 15051214 A1 | 4/2015 |
| WO | 2015/127273 A1 | 8/2015 |
| WO | WO 2016/147162 * | 9/2016 |
| WO | 2017121850 A1 | 7/2017 |

OTHER PUBLICATIONS

Boswell et al, Global Defects in the Expression and Function of the Low Density; Lipoprotein Receptor (LDLR) Associated With Two Familial; Hypercholesterolemia Mutations Resulting in Misfolding of the; LDLR Epidermal Growth Factor-AB Pair, vol. 279, No. 29, Issue of Jul. 16, pp. 30611-30621, 2004.

Burgeron et al., "Proprotein Convertase Subtilisin/Kexin Type 9 Inhibition A New Therapeutic Mechanism for Reducing cardiovascular Disease Risk," Circulation, 2015, vol. 132, No. 17, pp. 1648-1666.

Gu et al., Characterization of the Rose of EGF-A of Low Density Lipoprotein Receptor in PCSK9 Binding, The Journal of Lipid Research, 2013, vol. 54, No. 12, pp. 3345-3357.

Lim et al., "Site-Specific Fatty Acid-Conjugation to Prolong Protein Half-Lifein Vivo," Journal of Controlled Release, 2013, vol. 170, No. 2, pp. 219-225.

Schroeder et al., Design and Synthesis of Truncated EGF-A Peptides That Restore LDL-R Recycling in the Presence of PCSK9 In Vitro, Chemistry & Biology 21, 284-294, ; Feb. 20, 2014.

(Continued)

*Primary Examiner* — Marianne P Allen
(74) *Attorney, Agent, or Firm* — Jianjie Hu

(57) ABSTRACT

The invention relates to compounds derived from the EGF (A) domain of LDL-R, in particular compounds comprising a peptide analogue of the wild-type EGF(A) (LDL-R(293-332)) sequence and at least one substituent comprising at least one fatty acid group. The invention also relates to a pharmaceutical composition thereof and use a medicament. The novel EGF(A) compounds of the invention are useful as treatment e.g. in the field of cholesterol lowering, dyslipidaemia and cardiovascular disease.

28 Claims, 3 Drawing Sheets
Specification includes a Sequence Listing.

(56) References Cited

OTHER PUBLICATIONS

Shan et. al., "PCSK9 Binds to Multiple Receptors and Can Be Functionally Inhibited by an EGF-A Peptide," Biochemical and Biophysical Research Communications, 2008, vol. 375, No. 1, pp. 69-73.
Zhang et al, Identification of a Small Peptide That Inhibits PCSK9 Protein Binding to the Low Density Lipoprotein Receptor, The Journal of Biological Chemistry vol. 289, No. 2, pp. 942-955, Jan. 10, 2014.
Zhang et al., Calcium-Independent Inhibition of PCSK9 by; Affinity-Improved Variants of the LDL Receptor EGF(A) Domain, J. Mol. Biol. (2012) 422, 685-696.
Lau Jesper et al.,"Discovery of the Once-Weekly Glucagon-Lik Peptide-1(GLP-1) Analogue Semaglutide," Journal of Medicinal Chemistry, 2015, vol. 58, No. 18, pp. 7370-7380.
Scheen Andre J. "Dulaglutide for the treatment of type 2 diabetes," Expert Opinion on Biological Therapy, 2017, vol. 17, No. 4, pp. 485-496.
Shan et. al., PCSK9 binds to multiple receptors and can be functionally inhibited by an EGF-A peptide, Biochemical and Biophysical Research Communications, 2008, vol. 375, pp. 69-73.
Trevaskis et al., "MED14166: A PCSK9 Ab-GLP-1 Fusion Molecule that Elicits Robust Antidiabetic and Antihyperlipidemic Effects in Rodents and Nonhuman Primates,"Diabetologia, Aug. 2016, vol. 59, Suppl 1, pp. S528-3529.
Trevaskis et al., "MED14166: A PCSK9 Ab-GLP-1 Fusion Molecule that Elicits Robust Antidiabetic and Antihyperlipidemic Effects in Rodents and Nonhuman Primates,"American Diabetes Association, Late Breaking Abstracts, Jun. 2016, vol. 65, Suppl 1A, 35-LB, pp. LB9.
Zhang et al., "Calcium-Independent Inhibition of PCSK9 by Affinity-Improved Variants of the LDL Receptor EGF(A) Domain," Journal of Molecular Biology, 2012, vol. 422, No. 5, pp. 685-696.
Avanti et al., "A New Strategy to Stabilize Oxytocin in Aqueous Solutions: I. The effects of Divaltent Metal Ions and citrate Buffer," the AAPS Journal, 2011, vol. 13, No. 2, pp. 284-290.
Avanti et al., "A New Strategy to Stabilize Oxytocin in Aqueous Solutions: II. Suppression of Cystein-Mediated Intermolecular Reactions by Combination of Divalent Metal Ions and Citrate," Molecular Pharmaceutics, 2012, vol. 9, No. 3, pp. 554-562.
B. Chen et al., "Influence of Calcium Ions on the Structure and Stability of Recombinant Human Deoxyribonuclease I in Ihe Aqueous and Lyophilized States," Journal of Pharmaceutical Sciences, 1999, vol. 88, No. 4, pp. 477-482.
M.C. Manning et al., "Stability of Protein Pharmaceuticals: An Update," Pharmaceutical Research, 2010, vol. 27, No. 1, pp. 544-575.
N.D. Kurniawan et al., "NMR Structure and Backbone Dynamics of a Concatemer of Epidermal Growth Factor Homology Modules of the Human Low-Density Lipoprotein Receptor," Journal of Molecular Biology, 2001, vol. 311, pp. 341-356.
Schroeder et al., "Design and Synthesis of Truncated EGF-A Peptides that Restore LDL-R Recycling in the Presence of PCSK9 in Vitro," Chemistry and Biology, 2014, vol. 21, pp. 284-294.
Wakankar et al., "Formulation Considerations for Proteins Susceptible to Asparagine Deamidation and Aspartate somerization," Journal of Pharmaceutical Sciences, 2006, vol. 95, No. 11, pp. 2321-2336.

\* cited by examiner

EGF(A) ANALOGUES WITH FATTY ACID SUBSTITUENTS

CROSS-REFERENCE TO RELATED APPLICATIONS

This application is a 35 U.S.C. § 371 National Stage application of International Application PCT/EP2017/050668 (WO 2017/121850), filed Jan. 13, 2017, which claims priority to Chinese Patent Applications PCT/CN2016/070791, filed Jan. 13, 2016 and PCT/CN2016/076580, filed Mar. 17, 2016, and European Patent Application 16195965.5, filed Oct. 27, 2016; the contents of which are incorporated herein by reference.

TECHNICAL FIELD OF THE INVENTION

The present invention relates to EGF(A) analogues and derivatives thereof, more particularly to EGF(A) peptide analogues with a fatty acid substituent, and their pharmaceutical use.

INCORPORATION-BY-REFERENCE OF THE SEQUENCE LISTING

The Sequence Listing, entitled "SEQUENCE LISTING", is 48 KB, was created on Jan. 11, 2017 and is incorporated herein by reference.

BACKGROUND

High LDL-C(Low Density Lipoprotein cholesterol) levels and dyslipidaemia are well-recognised drivers of cardiovascular disease.

Statins have been approved for the treatment of dyslipidemia for 25 years. This class has demonstrated substantial and consistent reduction of cardiovascular events with an acceptable safety profile. The best-selling statin, atorvastatin (Lipitor™) was the world's best-selling drug of all time, with more than $125 billion in sales from 1996 to 2012.

Despite the availability and widespread use of statins and other lipid lowering agents, many patients do not reach their target LDL-C levels and remain at high risk for developing cardiovascular disease. PCSK9 (Proprotein Convertase Subtilisin/Kexin type 9) promotes hepatic LDL-R (LDL receptor) degradation, thereby reducing hepatic LDL-R surface expression and consequently clearance of LDL particles. Conversely, blocking PCSK9 increase the clearance of LDL-C as well as other atherogenic lipoproteins. Indeed, LDL receptors contribute to the clearance of atherogenic lipoproteins other than LDL, such as intermediate-density lipoproteins and remnant particles. Increased intermediate-density lipoproteins and remnant particle clearance may have therapeutic benefits beyond that provided by LDL reduction.

Statins increase the expression of both LDL-R and PCSK9 via the SREBP2 transcription factor. The increased expression of PCSK9 may diminish the effect of statins on LDL-C clearance from the circulation. By inhibiting the binding of PCSK9 to the LDL-R and thereby preventing LDL-R degradation the efficacy of statins is enhanced. Taken together, PCSK9 inhibition offers a novel approach to lipid management.

Two anti-PCSK9 antibodies, alirocumab/Praluent® and evolocumab/Repatha®, have recently been approved for the treatment of high LDL-C levels. These are administered by 1 ml subcutaneous injections every two weeks. However, compliance with this dose regimen of a subcutaneously administered drug, especially for an asymptomatic condition could be questioned.

The EGF(A) (Epidermal Growth Factor-like domain A) sequence (40 amino acids) of the LDL-R (LDL-R-(293-332)) is well recognized as the site for PCSK9 binding. The isolated wild-type EGF(A) peptide has been shown to inhibit the binding of PCSK9 to the LDL-R with an $IC_{50}$ in the low μM range (Biochemical and Biophysical Research Communications 375 (2008) 69-73). This poor potency will prevent a practical pharmaceutical use of the EGF(A) peptide. Furthermore, the half-life of such peptides would be expected to be too short to be of therapeutic use.

WO2012177741 and J. Mol. Biol. (2012) 422, 685-696 disclose analogues of the EGF(A) and Fc-Fusion thereof.

There is still a need to improve patients treatment, for example in terms of efficacy, also or alternatively in terms of convenience, comfort for the patients, such as comfort and convenience of the administration mode, and thereby compliance.

SUMMARY

The present invention relates to novel EGF(A) compounds which have potential for improved patient treatments, in particular in the field of cholesterol lowering, dyslipidaemia and cardiovascular diseases.

In one aspect, the invention provides compounds with improved pharmacokinetic (PK) properties. In particular, the compounds of the invention have long half-lives and still show good ability to inhibit PCSK9 in binding to the LDL-R.

Also or alternatively, in another aspect, the invention provides EGF(A) compounds with improved ability to inhibit PCSK9 binding to the LDL-R or alternatively, in another aspect, the invention provides compounds with improved binding capacity to PCSK9. Also or alternatively, in another aspect, the invention provides EGF(A) compounds with prolonged half-life. Also or alternatively, in another aspect, the invention provides EGF(A) compounds with prolonged half-life and no loss or no substantial loss of ability to inhibit PCSK9 binding to the LDL-R. Also or alternatively, in another aspect, the invention provides EGF (A) compounds with prolonged half-life and preserved binding capacity. In an aspect the invention provides EGF(A) compounds with a high liquid stability suitable for liquid formulations. In an aspect the invention provides EGF(A) compounds with a high in vivo stability. Also or alternatively, in another aspect, the invention provides compounds with potential for oral administration. Also or alternatively, in another aspect, the invention provides EGF(A) compounds with potential for a more convenient treatment for the patient. Also or alternatively, in another aspect, the invention provides compounds with potential for improved patient compliance. The invention may also solve further problems that will be apparent from the disclosure of the exemplary embodiments.

In one aspect, the invention relates to a compound comprising an EGF(A) peptide analogue of the EGF(A) peptide defined by sequence SEQ ID NO: 1: Gly-Thr-Asn-Glu-Cys-Leu-Asp-Asn-Asn-Gly-Gly-Cys-Ser-His-Val-Cys-Asn-Asp-Leu-Lys-Ile-Gly-Tyr-Glu-Cys-Leu-Cys-Pro-Asp-Gly-Phe-Gln-Leu-Val-Ala-Gln-Arg-Arg-Cys- Glu, wherein the peptide analogue comprises 301Leu.

In one aspect, the invention relates to an EGF(A) derivative comprising an EGF(A) peptide analogue comprising 301Leu and at least one substituent comprising at least one fatty acid group.

In one embodiment the EGF(A) derivative, comprises an EGF(A) peptide analogue wherein, as describe above amino acid 301 is Leu (L), while the peptide further comprises the wild type residue(s) in one or more of positions 295 (Asn/N), 296 (Glu/E), 298 (Leu/L), 302 (Gly/G) and 310 (Asp/D).

In further embodiments the EGF(A) peptide analogue of the EGF(A) derivative has 1-15 amino acid substitutions compared to SEQ ID NO.: 1.

In a further embodiment the substituent of the EGF(A) derivative is not attached to the EGF(A) peptide analogue via an amino acid residue in any the positions 295, 298, 301, 302, 307 and 310.

In a further embodiment the substituent is attached to the EGF(A) peptide analogue via an amino acid residue other than the positions 295, 298, 301, 302, 307 and 310.

In an aspect the invention relates to an EGF(A) peptide analogue of the EGF(A) domain of LDL-R defined by SEQ ID NO.: 1, wherein the peptide analogue comprises 301Leu and 310Asp and wherein the peptide analogue has an amino acid substitution of 312Lys or where in the peptide analogue does not have a substitution of 299Asp to Glu, Val or His.

In further embodiments the EGF(A) peptide analogues have one, two, three, four or all five of the following (wild type) amino acid residue(s) 295Asn, 296Glu, 298Leu, 302Gly and 310Asp/D).

In a further embodiment said peptide analogue comprises three disulphide bridges in positions 297Cys-308Cys, 304Cys-317Cys and 319Cys-331Cys.

In another aspect, the invention relates to a pharmaceutical composition comprising a compound according to the invention.

In another aspect, the invention relates to a compound according to the invention for use as a medicament.

In another aspect, the invention relates to medical use of the compounds according to the invention.

BRIEF DESCRIPTION OF SEQUENCE LISTING

Figure 1:
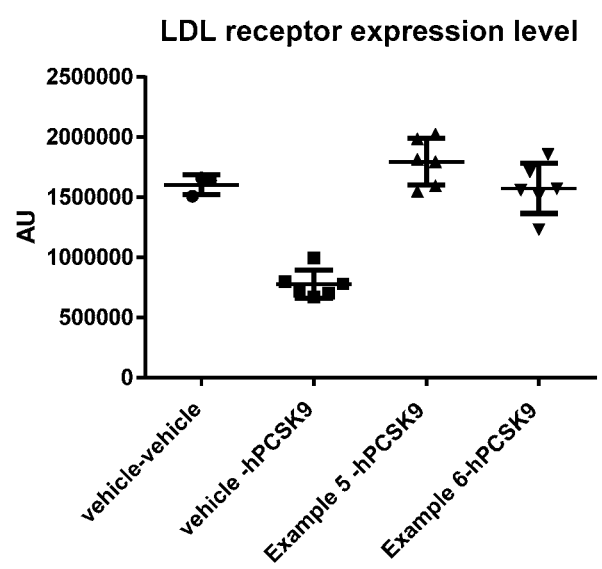
FIG. 1 shows hepatic LDL-R expression levels in mice measured by Western Blot, presented as scatter plot for the individual animals.

The amino acid sequence of wild-type EGF(A) (LDL-R (293-332)) is included in the sequence listing as SEQ ID NO: 1. SEQ ID NO's 2-78 are the amino acid sequences of the EGF(A) peptides of specific EGF(A) compounds of the invention.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μμM=uM.

In what follows, "a" means "one or more". Unless otherwise indicated in the specification, terms presented in singular form also include the plural situation.

An asterisk (*) in a chemical formula designates i) a point of attachment, ii) a radical, and/or iii) an unshared electron.

In its first aspect the invention relates to a compound comprising a peptide analogue of SEQ ID NO.: 1, and at least one substituent comprising at least one fatty acid group, or a pharmaceutically acceptable salt, amide, or ester thereof.

In a second aspect, the invention relates to a peptide analogue of SEQ ID NO.: 1, which may be considered an intermediate product for the preparation of the derivatives of the invention.

In its third aspect, the invention relates to a pharmaceutical composition comprising a compound of the invention and a pharmaceutically acceptable excipient, in particular suitable for oral administration; and the use of the compound of the invention as a medicament. Further aspects of the invention are described below.

Structural Features

EGF(A) Compound

The term "EGF(A) compound" is used herein to generally refer to a compound comprising an EGF(A) peptide, encompassing wt-LDL-R(293-332) as defined by SEQ ID NO: 1 and analogues hereof. The term EGF(A) compound encompasses derivatives of EGF-(A) peptide and analogue thereof i.e. EGF(A) peptide analogues with a substituent as described herein is a typical example of an EGF(A) compound.

EGF(A) Peptides

The term "peptide", as e.g. used in the context of the invention, refers to a compound which comprises a series of amino acids interconnected by amide (or peptide) bonds. In a particular embodiment the peptide consists of amino acids interconnected by peptide bonds.

The peptide of the invention comprises at least 35, such as 36, 37, 38, 39 or at least 40 amino acids. In a particular embodiment the peptide is composed of 36, such as 38 or 40 amino acids. In an additional particular embodiment the peptide consists of 35, 36, 37, 38, 39 or 40 amino acids.

In the presence of amino acid additions, referred to herein as N-terminal and C-terminal elongations, the peptide of the invention may comprise up to 140 amino acids. In an embodiment, the peptide of the invention may comprise or consist of 41 amino acid residues. In a particular embodiment, it comprises 40-140, 40-120, 40-100, 40-80, 40-60 or 40-50 amino acids.

The terms "EGF(A) domain of the LDL-R", "LDL-R (293-332)", "native LDL-R (293-332), "EGF(A) (293-332)", "wild-type EGF(A)", "wt-EGF(A)" or "native EGF(A)" as used herein refer to a peptide consisting of the sequence SEQ ID NO: 1.

```
SEQ ID NO: 1 is:
Gly-Thr-Asn-Glu-Cys-Leu-Asp-Asn-Asn-Gly-Gly-Cys-

Ser-His-Val-Cys-Asn-Asp-Leu-Lys-Ile-Gly-Tyr-Glu-

Cys-Leu-Cys-Pro-Asp-Gly-Phe-Gln-Leu-Val-Ala-Gln-

Arg-Arg-Cys-Glu.
```

In this formula the numbering of the amino acid residues follows the numbering for the EGF(A) domain of the LDL-R (LDL-R-(293-332)), wherein the first (N-terminal) amino acid residue is numbered or accorded position no. 293, and the subsequent amino acid residues towards the C-terminus are numbered 294, 295, 296 and so on, until the last (C-terminal) amino acid residue, which in the EGF(A) domain of the LDL-R is Glu with number 332.

The numbering is done differently in the sequence listing, where the first amino acid residue of SEQ ID NO: 1 (Gly) is assigned no. 1, and the last (Glu) no. 40. The same applies for the other sequences of the sequence listing, i.e. the N-terminal amino acid assigned is no. 1 irrespective of its positioning relative to 293Gly or 293 substituting amino acid residue by reference to LDL-R(293-332). However, herein the numbering of amino acid positions is with reference to LDL-R(293-332), as explained above.

The present invention relates to analogues of the EGF(A) peptide identified by SEQ ID NO:1 and derivatives of such EGF(A) peptide analogues of the wild-type EGF(A) domain of LDLR defined by SEQ ID NO: 1.

The term "analogue" generally refers to a peptide, the sequence of which has one or more amino acid changes when compared to a reference amino acid sequence.

The terms "analogue of the invention", "peptide analogue of the invention", "LDL-R(293-332) analogue", "EGF(A) analogue" or "analogue of SEQ ID NO: 1" as used herein may be referred to as a peptide, the sequence of which comprises amino acid substitutions, i.e. amino acid replacement, relative to sequence SEQ ID NO: 1. An "analogue" may also include amino acid elongations in the N-terminal and/or C-terminal positions and/or truncations in the N-terminal and/or C-terminal positions.

The level of identity to SEQ ID NO.:1 can be calculated by determining the number of amino acids that are not changed relative to SEQ ID NO 1. SEQ ID NO: 1 consists of 40 amino acid residues and if three amino acid substitutions are introduced the level of identity is 37/40%=92.5%. If 5 amino acid residues are changed the level of identity is 87, 5%. If the peptide is N-terminal or C-terminal elongated that part is usually not included in the comparison, whereas a deletion of one or more amino acids shortens the comparator. For instance, in the examples above, if the N-terminal amino acid is deleted the level of identity is slightly reduced to 36/39×100% and 34/39×100%, respectively. When discussing identity of the back-bone sequence of a derivative the amino acid residue of the substituent e.g. the residue to which the substituent is attached, also termed the amino acid residue of the substituent, may be either a wild type (wt) or a substituted amino acid. If the amino acid residue of the substituent is a wild type residue, such as the N-term Gly or 312K this residue is included in the calculation of identity level, whereas a Lys in any other position from 293 to 332 would be an amino acid substitution and not included when calculated amino acid identity to SEQ ID NO.:1.

In one embodiment the EGF(A) peptide analogue has 1-15 amino acid substitutions compared to SEQ ID NO.: 1. In one embodiments the EGF(A) peptide analogue has 1-10 amino acid substitutions compared to SEQ ID NO.: 1. In one embodiments the EGF(A) peptide analogue has 1-8 amino acid substitutions compared to SEQ ID NO.: 1, such as 1-7, 1-6, 1-5 amino acid substitutions compared to SEQ ID NO.: 1. In a particular embodiment, up to 7 amino acid substitutions may be present, for example up to 6, 5, 4, 3, 2 or 1 amino acid substitutions may be present in the EGF-1 peptide analogue.

In one embodiment the analogue of the invention has at least 75% identity, such as 80%, such as 85, such as 90 or even 95% identity to SEQ ID NO.:1 corresponding to up to 10, 8, 6, 4 and 2 amino acid substitutions relative to SEQ ID NO 1, respectively in case of no truncation.

Each of the peptide analogues of the invention may be described by reference to i) the number of the amino acid residue in the native EGF(A) (LDL-R(293-332)) which corresponds to the amino acid residue which is changed (i.e., the corresponding position in native LDL-R(293-332) EGF (A)), and to ii) the actual change.

In other words, the peptide analogues of the invention may be described by reference to the native LDL-R(293-332) EGF(A) peptide, namely as a variant thereof in which a number of amino acid residues have been changed when compared to native LDL-R(293-332) EGF(A) (SEQ ID NO: 1). These changes may represent, independently, one or more amino acid substitutions.

The followings are non-limiting examples of suitable analogue nomenclature:

The EGF(A) peptide incorporated in the derivative of Example 2 herein may be referred to as the following LDL-R(293-332) EGF(A) analogue: (301Leu, 309Arg) LDL-R(293-332) EGF(A), or (Leu301, Arg309)-LDL-R (293-332) EGF(A) or (301L, 309R) LDL-R(293-332) or (L301, R309) LDL-R(293-332). This means that when this analogue is aligned with native LDL-R(293-332), it has i) a Leu at the position in the analogue which corresponds, according to the alignment, to position 301 in native LDL-R(293-332) EGF(A), ii) an Arg at the position in the analogue which corresponds to position 309 in native LDL-R(293-332) EGF(A).

Analogues "comprising" certain specified changes may comprise further changes, when compared to SEQ ID NO: 1.

In a particular embodiment, the analogue "has" or "comprises" the specified changes. In a particular embodiment, the analogue "consists of" the changes. When the term "consists" or "consisting" is used in relation to an analogue e.g. an analogue consists or consisting of a group of specified amino acid substitutions, it should be understood that the specified amino acid substitutions are the only amino acid substitutions in the peptide analogue. In contrast an analogue "comprising" a group of specified amino acid substitutions may have additional substitutions.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant LDL-R(293-332) EGF(A) sequence by reference to the reference sequence native LDL-R(293-332) EGF(A) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm.

In what follows, it may occur that a chemical formula is defined such that two subsequent chemical groups may both be selected to be "a bond". In such instances, the two subsequent chemical groups would actually be absent, and just one bond would connect the surrounding chemical groups.

Amino acids are molecules containing an amino group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid, or 2-aminoisobutyric acid), norleucine, norvaline as well as the D-isomers of the proteinogenic amino acids.

In what follows, each amino acid of the peptides of the invention for which the optical isomer is not stated is to be understood to mean the L-isomer (unless otherwise specified).

Peptide Analogues of the Invention

An aspect of the invention relates to an analogue of a peptide of SEQ ID NO: 1.

The peptide analogues of the invention may be defined as peptides comprising an amino acid sequence which is an analogue of SEQ ID NO: 1. The peptide analogues of the invention have the ability to bind to PCSK9. In a specific embodiment, the analogues of the invention have an improved ability to bind to PCSK9, for example compared to native LDL-R(293-332) (native EGF-(A)) or to other PCSK9-binding compounds.

The peptide analogues of the invention have the ability to inhibit PCSK9 binding to the LDL-R. In one embodiment the peptide is a PCSK9 inhibitor. In one embodiment the peptide inhibits PCSK9 binding to human Low Density Lipoprotein Receptor (LDL-R). Such binding may be assessed using the assay described in Example D.1.1 herein. In one embodiment the peptide analogues and peptide derivatives of the invention are PCSK9 inhibitor peptides or simply PCSK9 inhibitors. In one embodiment the invention relates to a peptide analogue of SEQ ID NO.:1, wherein peptide analogue is a capable of inhibiting PCSK9 binding to human Low Density Lipoprotein Receptor (LDL-R).

In one embodiment the peptide analogues, compounds or PCSK9 inhibitors of the invention have an improved ability to bind PCSK9 compared to EGF(A), LDL-R(293-332) (SEQ ID 1).

In one embodiment the peptide analogues, compounds or PCSK9 inhibitors of the invention have an improved ability to bind PCSK9 compared to Ex. 48 (SEQ ID 2).

In one embodiment the $K_i$ of the peptide analogues, compounds or PCSK9 inhibitors as described herein as measured in the PCSK9-LDL-R binding competitive ELISA assay is below 10 nM, such as below 8 nM or such as below 5 nM.

Functionality of EGF-(A) analogues and derivatives hereof may be further characterized by their ability to improve LDL uptake, such as described in Example D1.2 herein. In one embodiment the peptide analogues, compounds or PCSK9 inhibitors of the invention increases LDL uptake in the presence of PCSK9. In one embodiment the peptide analogues, compounds or PCSK9 inhibitors of the invention are capable of reversing or reducing PCSK9 mediated reduction of LDL uptake.

In one embodiment the peptide analogues, compounds or PCSK9 inhibitors of the invention have a EC50 as measured in the LDL uptake assay of below 1500 nM, such as below 1000 nM or such as below 500 nM.

In an embodiment, a peptide analogue of the invention may be defined as comprising at least 1 amino acid substitution compared to SEQ ID NO: 1, and optionally an elongation. In an embodiment, a peptide analogue of the invention may be defined as comprising up to 15, up to 14, up to 13, up to 12, up to 11, up to 10, up to 9, up to 8, up to 7, up to 6, up to 5, up to 4, up to 3, up to 2 or 1 amino acid(s) substitution(s) compared to SEQ ID NO: 1, and optionally an elongation. This means that a peptide comprising an elongation in the N-terminal and/or in the C-terminal may comprise up to 15 amino acids substitutions in positions from 293 to 332 in addition to said elongation.

An amino acid "elongation" may also be referred to as "extension". In an embodiment, peptide analogues of the invention comprise an elongation. Said elongation may be an addition of up to 50 amino acid residues in position N-terminal of SEQ ID NO: 1 or an analogue thereof, also referred to as an N-terminal elongation, meaning that a peptide of the invention may comprise up to 50 amino acids from position 292 down to, for example position 242. Additionally or alternatively, said elongation may be an addition of up to 50 amino acid residues in position C-terminal of SEQ ID NO: 1 or analogue thereof, also referred to as a C-terminal elongation, meaning that a peptide of the invention may comprise up to 50 amino acids from position 333 up to, for example position 383.

Said elongation may be present either in N-terminal, in C-terminal or both. Said elongation may also be of any length between 0 and 50 amino acids on each side, independently of each other. In one embodiment, the peptide analogues of the invention comprise a N-terminal elongation of 1-50, 1-40, 10-40, 1-30, 10-30, 20-30, 20-40, 20-50, 30-50, 1-10, 11-20, 21-30, 31-40 or 41-50 amino acid residues or of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. In addition or alternatively, the peptide analogues of the invention may comprise a C-terminal elongation of 1-50, 1-40, 10-40, 1-30, 10-30, 20-30, 20-40, 20-50, 30-50, 1-10, 11-20, 21-30, 31-40 or 41-50 amino acid residues or of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues.

An elongation may in some situation be referred to a substitution as a new amino acid residue is introduced, such as the 292A, 292Lys or 333Lys exemplified herein.

Minor truncations at the N-terminal and/or C-terminal of the EGF(A) peptide may be present in the EGF(A) peptide analogue.

In one embodiment the EGF(A) peptide comprise at least 35 amino acid residues, such as 36 amino acid residues, such as 37 amino acid residues, such as 38 amino acid residues or such as such as 39 amino acid residues. In one embodiment the EGF(A) peptide analogue according comprises an N-terminal truncation of 1-2 amino acid residues. In one embodiment one or two N-terminal amino acid residues are deleted. In further embodiments the EGF(A) peptide analogue accordingly comprises an N-terminal truncation deleting at least or specifically amino acid 293Gly.

In further embodiments the EGF(A) peptide analogue comprises an N-terminal truncation deleting at least or specifically 293Gly-294Thr.

In one embodiment the EGF(A) peptide analogue comprises a C-terminal truncation of 1 amino acid residue. In one embodiment a single C-terminal amino acid residue is deleted. In on embodiment the peptide analogue comprises a C-terminal truncation deleting specifically amino acid 332Glu.

In addition or alternatively, a peptide analogue of the invention may comprise at least one amino acid elongation in the N-terminal or the C-terminal for example in position 292 and/or 333.

The EGF(A) peptide analogue of the invention comprises the amino acid substitution of amino acid residue 301 from Asn to Leu, also described by Asn301Leu or simply 301Leu. In a specific embodiment, the EGF(A) peptide analogue comprises the substitution 301Leu.

In addition or alternatively the EGF(A) peptide analogue comprises the amino acid residues 297Cys, 304Cys, 308Cys, 317Cys, 319Cys and 331Cys. Those Cys residues are wild type residues which may be engaged in disulphide bridges, such as the disulphide bridges between 297Cys and 308Cys, between 304Cys and 317Cys and between 319Cys and 331Cys.

In one embodiment, the EGF(A) peptide analogue comprises 301Leu and a number of further amino acid substitutions, as described above.

In one embodiment the EGF(A) peptide analogue comprises 301Leu, 310Asp and an amino acid substitution of 312Lys.

In one embodiment, the EGF(A) peptide analogue comprises 301Leu and 310Asp and wherein the peptide analogue does not have a substitution of 299Asp to Glu, Val or His.

In one embodiment the EGF(A) peptide analogue comprises 301Leu, 309Arg and 312Glu.

In one embodiment the EGF(A) peptide analogue comprises 301Leu and 309Arg with a proviso that the peptide analogue does not have a substitution of 310Asp to 310Lys or In one embodiment the EGF(A) peptide analogue comprises 301Leu and 309Arg with a proviso that the peptide analogue does not have a substitution of 299Asp to Glu, Val or His.

In a further embodiment the peptide analogue does not have any of the substitutions D310K, D310N, D310Q, D310Q, D310R and D310A or even any substitution of 310Asp.

In one embodiment the EGF(A) peptide analogue comprises one, two, three or all four wild type residues: 295Asn, 296Glu, 298Leu and 302Gly.

In one embodiment the EGF(A) peptide analogue comprises one, two, three, four or all five wild type residues: 295Asn, 296Glu, 298Leu, 302Gly and 310Asp.

In one embodiment the peptide has 295Asn.

In one embodiment the peptide analogue has 296Glu. In one embodiment the peptide analogue has 298Leu. In one embodiment the peptide analogue has 302Gly. In one embodiment the peptide analogue has 310Asp.

In one embodiment the peptide analogue has two or more of 310Asp, 295Asn and 296Glu. In one embodiment the peptide analogue has all three of 310Asp, 295Asn and 296Glu.

The EGF(A) peptide analogue may comprise further amino acid substitutions as described herein. In one embodiment the analogue of the invention may further comprise one or more amino acid substitution in a position(s) selected from the group of positions: 293, 294, 296, 299, 300, 303, 305, 306, 309, 311, 312, 313, 314, 315, 316, 318, 320, 321, 322, 323, 324, 325, 326, 328, 329, 330 and 332.

In one embodiment the analogue of the invention may further comprise one or more amino acid substitution(s) in a position(s) selected from the group of positions: 293, 294, 299, 300, 303, 305, 306, 309, 311, 312, 313, 314, 316, 318, 321, 322, 323, 324, 325, 326, 328, 329, 330, 331 and 332.

In one embodiment the analogue of the invention may further comprise one or more amino acid substitution(s) in a position(s) selected from the 294, 299, 300, 303, 309, 312, 313, 314, 316, 318, 321, 322, 323, 324, 325, 326, 328, 329, 330 and 332.

In one embodiment the analogue of the invention may further comprise one or more amino acid substitution(s) in a position(s) selected from the 299, 300, 309, 313, 316, 318, 321, 322, 323, 324, 326, 328, 329, 330 and 332.

In one embodiment the analogue of the invention may further comprise one or further amino acid substitution(s) in a position(s) selected from the group of positions: 309, 312, 313, 321, 324, 328 and 332.

In a further embodiment the peptide analogue comprise either the wt amino acid residue or a different residue i.e. an amino acid substitution, in certain specific positions in addition to the amino acid residues specified herein above.

In one such embodiment the analogue of the invention comprises the amino acid residue Gly(G) or Asn(N) in position 293.

In one such embodiment the analogue of the invention comprises the amino acid residue Trp (W), Thr(T) or Gly(G) in position 294.

In one such embodiment the analogue of the invention comprises the amino acid residue Asp(D), Gly(G), Pro(P), Arg(R), Lys(K), Ser(S), Thr(T), Asn(N), Gln(Q), Ala(A), Ile(I), Leu(L), Met(M), Phe(F), Tyr(Y) or Trp(W) in position 299.

In one such embodiment the analogue of the invention comprises the amino acid residue Asp(D), Gly(G), Pro (P), Arg(R), Lys(K), Ser(S), Thr(T), Asn(N), Gln(Q), Ala(A), Met(M), Phe(F), Tyr(Y) or Trp(W) in position 299.

In one such embodiment the analogue of the invention comprises the amino acid residue Asp(D), Ser (S), Arg(R), Leu (L), Ala (A), Lys(K) or Tyr(Y) in position 299.

In one such embodiment the analogue of the invention comprises the amino acid residue Asp(D) or Ala(A) in position 299.

In one such embodiment the analogue of the invention comprises the amino acid residue His(H) or Asn(N) in position 300.

In one such embodiment the analogue of the invention comprises the amino acid residue Val(V), Ser(S), Thr (T) or Ile (I) in position 307.

In one such embodiment the analogue of the invention comprises the amino acid residue Val(V) or Ile (I) in position 307.

In one such embodiment the analogue of the invention comprises Ser (S), Thr (T) or Ile (I) in position 307.

In one such embodiment the analogue of the invention comprises Ile (I) in position 307.

In one such embodiment the analogue of the invention comprises the amino acid residue Asn(N), Glu (E), His (H) Arg (R), Ser (S) or Lys (K) in position 309.

In one such embodiment the analogue of the invention comprises the amino acid residue Asn(N), Arg (R), Ser (S) or Lys (K) in position 309.

In one such embodiment the analogue of the invention comprises the amino acid residue Asn(N), Arg (R) or Ser (S) in position 309.

In one such embodiment the analogue of the invention comprises the amino acid residue Asn(N) or Arg (R) in position 309.

In one such embodiment the analogue of the invention comprises the amino acid residue Lys(K) or Arg (R) in position 309.

The EGF(A) peptide analogue may comprise several amino acid substitutions as described herein, such as one or more amino acid substitutions selected from the group of: 299Ala, 307Ile and 321Glu.

In further embodiments, the EGF(A) peptide analogue comprises the amino acid residue Asp(D), Lys (K) or Glu(E) in position 321.

In further embodiments, the EGF(A) peptide analogue comprises the amino acid residue Asp(D) or Glu(E) in position 321.

In further embodiments, the EGF(A) peptide analogue comprises the amino acid residue Glu(E) in position 321.

In further embodiments, the EGF(A) peptide analogue comprises the amino acid residue Gln (Q) or Gly (G) in position 324.

In further embodiments, the EGF(A) peptide analogue comprises the amino acid residue Arg (R) or His (H) in position 329.

In further embodiments, the EGF(A) peptide analogue does not have a substitution of 300Asn(N) to Pro(P).

The EGF(A) domain of LDL-R includes a Lysine in position 312 which may be useful for substitution as described herein. In embodiments where attachment of the substituent to 312 is not wanted 312Lys may be substituted by another amino acid as described herein.

In one embodiment, Lys in position 312 is substituted by an amino acid residue selected from: Gly, Pro, Asp, Glu, Arg, His, Ser, Thr, Asn, Gln, Ala, Val, Ile, Leu, Met, Phe and Tyr. In one embodiment, Lys in position 312 is substituted by an amino acid residue selected from: Gly, Asp, Glu, Ser, Thr, Asn, Ala, Val, Ile, Leu, Phe and Tyr. In one embodiment, Lys in position 312 is substituted by an amino acid residue selected from: Asp, Glu, Thr, Asn, Ile, Leu, Phe and Tyr. In one embodiment, 312Lys is substituted by 312Asp, 312Glu, 312Thr, 312Asn, 312Ile or 312Phe. In one embodiment, 312Lys is substituted by 312Glu, 312Asp, 312Gln or 312Arg.

In one embodiment, 312Lys is substituted by 312Glu, 312Thr, 312Asn, 312Ile, 312Phe or 312Tyr. In one embodiment, 312Lys is substituted by 312Glu, 312Asn or 312Ile, In one embodiment, 312Lys is substituted by 312Glu or 312Arg. In one embodiment 312Lys is substituted by 312Arg. In one embodiment, 312Lys is substituted by 312Glu.

To include an option for attaching the substituent in various positions (see further below), a Lys may be introduced by amino acid substitution of a wild type residue of SEQ ID NO.: 1 or by a peptide elongation of SEQ ID NO.: 1, such as a 292Lys or a 333Lys.

In cases where more than one substituent is desired one may be via 312Lys while the second is via a Lys introduced by peptide elongation or substitution in SEQ ID NO.: 1.

In one embodiment the peptide analogue of SEQ ID NO: 1 comprises at least one Lys residue in a position selected from the group of: 292Lys, 293Lys, 294Lys, 296Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In one embodiment the peptide analogue of SEQ ID NO: 1 comprises at least one Lys residue in a position selected from the group of: 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In one embodiment the peptide analogue of SEQ ID NO: 1 comprises at least one Lys residue in a position selected from the group of: 292Lys, 293Lys, 294Lys, 300Lys, 303Lys, 305Lys, 306Lys, 309Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In one embodiment the peptide analogue of SEQ ID NO: 1 comprises at least one Lys residue in a position selected from the group of: 292Lys, 293Lys, 294Lys, 300Lys, 303Lys, 305Lys, 306Lys, 311Lys, 312Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.

In one embodiment the peptide analogue of SEQ ID NO: 1 comprises at least one Lys residue in a position selected from the group of: 292Lys, 293Lys, 294Lys, 300Lys, 303Lys, 305Lys, 306Lys, 311Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.

In addition or alternatively, the peptide analogue of the invention comprises at least one amino acid substitution selected from 292Lys, 293Lys, 294Lys, 295Lys, 296Lys, 298Lys, 299Lys, 301Lys, 302Lys, 303Lys, 305Lys, 306Lys, 307Lys, 309Lys, 310Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from: 292Lys, 293Lys, 294Lys, 295Lys, 296Lys, 298Lys, 299Lys, 302Lys, 303Lys, 305Lys, 306Lys, 307Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 295Lys, 296Lys, 298Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 295Lys, 296Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue peptide of the invention comprises at least one amino acid substitution selected from 292Lys, 293Lys, 294Lys, 296Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 299Lys, 303Lys, 305Lys, 306Lys, 310Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 299Lys, 303Lys, 305Lys, 306Lys, 309Lys, 310Lys, 311Lys, 313Lys, 314Lys, 315Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) peptide analogue of the invention comprises at least one amino acid substitution selected from 292Lys, 293Lys, 294Lys, 303Lys, 305Lys, 306Lys, 310Lys, 311Lys, 313Lys, 314Lys, 315Lys, 316Lys, 318Lys, 321Lys, 322Lys, 323Lys, 324Lys, 325Lys, 326Lys, 327Lys, 328Lys, 329Lys, 330Lys, 332Lys and 333Lys. In one embodiment, the peptide analogues of the invention do not comprise any of the following substitutions: 296K, 298K, 301K, 302K and 307K.

In one embodiment, the peptide analogues of the invention do not comprise any of the following substitution: 296K, 298K, 301K, 302K, 307K and 310K.

In one embodiment, the peptide analogues of the invention do not comprise any of the following substitution: 296K, 298K, 301K, 302K, 307, and 295K.

In one embodiment, the peptide analogues of the invention do not comprise any of the following substitution: 296K, 298K, 301K, 302K, 307K and 295D.

In a particular embodiment, the peptide analogue of the invention comprises 1 or 2, of such Lys substitutions.

In addition or alternatively, the peptide of the invention may comprise 312Lys.

In one embodiment the peptide analogue of the invention comprises two Lys residues. In one embodiment the peptide analogue of the invention comprises two Lys residues selected from the pairs consisting of:

| |
| --- |
| i. 293K and 294K |
| ii. 293K and 312K |
| iii. 293K and 333K |
| iv. 309K and 313K |
| v. 309K and 324K |
| vi. 309K and 328K |
| vii. 309K and 332K |
| viii. 309K and 333K |
| ix. 311K and 313K |
| x. 312K and 333K |
| xi. 312K and 313K |
| xii. 312K and 314K |
| xiii. 313K and 314K |
| xiv. 313K and 321K |
| xv. 313K and 324K |
| xvi. 313K and 328K |
| xvii. 313K and 332K |
| xviii. 313K and 333K |
| xix. 314K and 333K |
| xx. 321K and 332K |
| xxi. 321K and 333K |
| xxii. 324K and 333K |
| xxiii. 324K and 328K |
| xxiv. 328K and 333K |
| xxv. 330K and 333K and |
| xxvi. 332K and 333K. |

As seen herein above various peptide analogues are provided by the present invention. In a further embodiment the EGF(A) peptide analogue according to the invention comprises at least two amino acid substitutions identified by any of the groups i-xxiv shown below compared to SEQ ID NO.:1.

In a still further embodiment, the EGF(A) peptide analogue of the invention consists of the amino acid substitutions identified by any of the groups i-xxiv as shown below.

In a further embodiment the EGF(A) peptide analogue according to the invention comprises at least two amino acid substitutions identified by any of the groups i-xvi shown below compared to SEQ ID NO.:1.

In a still further embodiment, the EGF(A) peptide analogue of the invention consists of the amino acid substitutions identified by any of the groups i-xvi as shown below.

i. 301Leu and 309Arg
    ii. 301Leu, 309Arg, 312Glu
    iii. 301Leu, 307Ile and 309Arg
    iv. 301Leu, 307Ile, 309Arg and 312Glu
    v. 301Leu, 309Arg and 321Glu
    vi. 301Leu, 309Arg, 321Glu and 312Glu
    vii. 301Leu, 307Ile, 309Arg and 299Ala
    viii. 301Leu, 307Ile, 309Arg, 299Ala and 312Glu
    ix. 301Leu and 309Arg and at least one Lys substitution
    x. 301Leu, 309Arg, 312Glu and at least one Lys substitution
    xi. 301Leu, 307Ile and 309Arg and at least one Lys substitution
    xii. 301Leu, 307Ile, 309Arg and 312Glu and at least one Lys substitution
    xiii. 301Leu, 309Arg and 321Glu and at least one Lys substitution
    xiv. 301Leu, 309Arg, 321Glu and 312Glu and at least one Lys substitution
    xv. 301Leu, 307Ile, 309Arg and 299Ala and at least one Lys substitution or
    xvi. 301Leu, 307Ile, 309Arg, 299Ala and 312Glu and at least one Lys substitution.

In a further embodiment the EGF(A) peptide analogue according to the invention comprises at least two amino acid substitutions identified by any of the groups xvii-xx shown below compared to SEQ ID NO.: 1.

In a still further embodiment, the EGF(A) peptide analogue of the invention consists of at the amino acid substitutions identified by any of the groups xvii-xx as shown below.

xvii. 301Leu and 309Lys
    xviii. 301Leu, 309Lys and 312Glu
    xix. 301Leu and 309Lys and at least one further Lys substitution
    xx. 301Leu, 309Lys and 312Glu and at least one further Lys substitution.

In a further embodiment the EGF(A) peptide analogue according to the invention comprises at least two amino acid substitutions identified by any of the groups xxi-xxiv shown below compared to SEQ ID NO.: 1.

In a still further embodiment, the EGF(A) peptide analogue of the invention consists of the amino acid substitution identified by any of the groups xxi-xxiv as shown below
    xxi. 301Leu and 307Ile,
    xxii. 301Leu, 307Ile and 312Glu
    xxiii. 301Leu and 307Ile and at least one further Lys substitution and
    xxiv. 301Leu, 3307Ile and 312Glu and at least one further Lys substitution.

In further specific embodiments the peptide analogue or the peptide analogue of the compounds according to the invention comprises or consists of anyone of the amino acid sequences identified by SEQ ID 1 to 106.

In one embodiment the peptide analogue comprises or consists of anyone of the amino acid sequences identified by SEQ ID NO.: 2-106.

In one embodiment the peptide analogue comprises or consists of anyone of the amino acid sequences identified by SEQ ID NO.: 2-47 and 49-106.

In one embodiment the peptide analogue comprises or consists of anyone of the amino acid sequences identified by anyone of the amino acid sequences SEQ ID NO.: 2-44, 46, 47 and 49-106.

In one embodiment the peptide analogue comprises or consists of anyone of the amino acid sequences identified by of SEQ ID NO.: 2-44, 46, 47, 49-53, 55, 58-106.

In one embodiment the peptide analogue comprises or consists of anyone of the amino acid sequences identified by SEQ ID NO.: 2-4, 6-44, 46, 47, 49-53, 55, 58-106.

In one embodiment the peptide analogue comprises or consists of anyone of the amino acid sequences identified by SEQ ID NO.: 2-4, 6-19, 21-44, 46, 47, 49-53, 55, 58-106.

Intermediate Compounds

The present invention also relates to peptide analogues which may be incorporated in the derivatives of the invention. Such peptide analogues may be referred to as "intermediate product" or "intermediate compound". They are in the form of novel LDL-R(293-332) analogues, which as described above can be incorporated in EGF(A) derivatives of the invention as further describe below. Such peptide analogues are as defined in the above section.

In particular, a peptide analogue, or intermediate peptide, according to the present invention may be referred to as a peptide analogue of sequence SEQ ID NO: 1.

In one aspect the invention relates to a EGF(A) peptide analogue as described herein for use in the manufacture of a EGF(A) compound, such as a EGF(A) derivative.

Other features, definitions, aspects and embodiments disclosed herein in connection with peptide analogues of the invention may also be applicable to the intermediates products of the invention.

EGF(A) Derivatives

The peptides analogues of the invention may further comprise a substituent and thereby become derivative compounds.

The term "derivative" generally refers to a compound which may be prepared from a native peptide or an analogue thereof by chemical modification, in particular by covalent attachment of one or two substituents.

The terms "derivative of the invention", "EGF(A) derivative", "EGF(A) derivative or "LDL-R(293-332) derivative" or "derivative of a LDL-R(293-332) analogue" as used herein refers to as a peptide to which one or two substituents are attached. Each of these may, also or alternatively, be referred to as a side chain. In other words, a "derivative of the invention" comprises a peptide i.e. a peptide sequence, which herein is an EGF(A) peptide analogue, and at least one, including such as one or two, substituent(s).

The terms "substituent" is used to describe a moiety covalently bond to the EGF(A) peptide e.g. the substituent is a moiety not part of the EGF(A) peptide itself.

In one embodiment the one or more substituent(s) is/are attached to a nitrogen atom of the EGF(A) peptide analogue. In one embodiment the one or more substituent(s) is/are attached to an amino group of the EGF(A) peptide analogue. In one embodiment the one or more substituent(s) is/are attached to the N-terminal amino acid of the EGF(A) peptide analogue or to a Lys residue of the EGF(A) peptide analogue. In one embodiment the one or more substituent(s) is/are attached to the N-terminal amino acid of the EGF(A) peptide analogue. In one embodiment the one or more substituent(s) is/are attached to the alpha-nitrogen of the N-terminal amino acid residue of the EGF(A) peptide analogue In one embodiment the one or more substituent(s) is/are attached to a Lys residue in the EGF(A) peptide analogue. In one embodiment the one or more substituent(s) is/are attached to the epsilon-nitrogen of a Lys residue in the EGF(A) peptide analogue.

Examples of substituents are various and further described below.

In one aspect, the invention relates to an EGF(A) derivative comprising an EGF(A) peptide analogue and at least one substituent. In one embodiment the substituent of the derivative comprises at least one fatty acid group. For all embodiments the term EGF(A) derivative also encompasses any pharmaceutically acceptable salt, amide, or ester thereof.

Substituents

A substituent is a moiety attached to an EGF(A) peptide analogue. According to the invention it is preferred that the moiety e.g. the substituent has no or minimal effect on the functionality of the EGF(A) peptide while adding other beneficial properties, such as longer half-life and/or improved exposure after oral dosing.

It follows that the derivatives, as well as the analogues of the invention described above, have the ability to bind to PCSK9. Such binding to PCSK9 inhibits PCSK9 binding to the LDL-R, thereby preventing LDL-R degradation hence increasing the clearance of LDL-C and atherogenic lipoproteins.

In a specific embodiment, the derivatives and analogues of the invention have an improved ability to bind to PCSK9, for example compared to native LDL-R(293-332) or to other PCSK9-binding compounds. The analogues and derivatives of the invention can for example be tested for their ability to inhibit PCSK9 binding to LDL-R using the assay described in Example D.1.1 herein.

In an embodiment the substituent is aimed at improving the functionality of the peptides.

In one embodiment the substituent increase half-life of the peptide analogue in a way that the plasma half-live of a derivative comprising a backbone peptide and a substituent have an increase half-life compared to the half-life of the backbone peptide as illustrated by Example 1 and 48 (Section D2, table 7). Methods for determining half-life in different species are well known in the art and exemplified herein for mice and dogs (Section D2 and D5).

In one embodiment the EGF(A) derivative according to the invention has a half-life above 4 hours.

In one embodiment the EGF(A) derivative according to the invention has a half-life above 6 hours, such as above 8 hours or such as above 10 hours in mice measured after either subcutaneously or intravenously dosing.

In one embodiment the EGF(A) derivative according to the invention has a half-life above 25 hours in dogs.

In one embodiment the EGF(A) derivative according to the invention has a half-life above 50 hours, such as above 100 hours or such as above 150 hours in dogs.

In one embodiment, a half-life extending substituent is a protein moiety. In a further such embodiment the protein moiety may include human albumin, an Fc-domain or an unstructured protein extension. In a further embodiment the protein moiety may by fused to the peptide analogue. In a further embodiment, the protein moiety is Fc domain and the Fc domain is fused to the peptide analogue. When an Fc fusion is prepared the resulting compound will usually be divalent as two Fc-polypeptides will form one Fc-domain.

In one embodiment the substituent is not a protein moiety. In one embodiment the substituent is not a protein moiety fused to the EGF(A) peptide analogue. In one embodiment the protein moiety is not an Fc domain.

In another embodiment the substituent is a non-protein moiety.

In a particular embodiment, the substituent is capable of forming non-covalent complexes with albumin, thereby promoting the circulation of the derivative within the blood stream, and also having the effect of protracting the time of action of the derivative. In a particular embodiment, the substituent is capable of protracting the time of action of the EGF(A) compound without substantially decreasing its binding capacity to PCSK9.

In one embodiment the EGF(A) derivative comprises a half-life extending substituent. Various half-life extending substituents are well-known in the art and include in particular albumin binders comprising a fatty acid group as described further below, and such albumin binders are non-protein substituents.

The substituent comprises at least one fatty acid group.

In a particular embodiment, the fatty acid group comprises a carbon chain which contains at least 8 consecutive —$CH_2$— groups. In one embodiment the fatty acid group comprise at least 10 consecutive —$CH_2$— groups, such as least 12 consecutive —$CH_2$— groups, at least 14 consecutive —$CH_2$— groups, at least 16 consecutive —$CH_2$— groups, at least 18 consecutive —$CH_2$— groups.

In one embodiment the fatty acid group comprises 8-20 consecutive —$CH_2$— groups. In one embodiment the fatty acid group comprises 10-18 consecutive —$CH_2$— groups. In one embodiment the fatty acid group comprises 12-18 consecutive —$CH_2$— groups. In one embodiment the fatty acid group comprises 14-18 consecutive —$CH_2$— groups.

In situations where the derivative comprise two substituents, an increased half-life may be obtained with shorter fatty acid groups, thus in an embodiment where the derivate comprise two substituents the fatty acid groups may comprise at least 8 consecutive —$CH_2$— groups, such as least 10 consecutive —$CH_2$— groups, such as least 12 consecutive —$CH_2$— groups, at least 14 consecutive —$CH_2$— groups, at least 16 consecutive —$CH_2$— groups.

In a further embodiment where the derivative comprises two substituents, the substituents each comprise a fatty acid group comprising 8-18 consecutive —$CH_2$— groups. In further such embodiments the fatty acid groups comprise 10-18 consecutive —$CH_2$— groups, such as 12-18 consecutive —$CH_2$— groups, such as 14-18 consecutive —$CH_2$— groups. The term "fatty acid group" as used herein may be referred to as chemical group comprising at least one functional group being a Brønsted-Lowry acid with a pKa<7. Non-limiting examples of such functional groups that are Brønsted-Lowry acids include a carboxylic acid (including also carboxyphenoxy), a sulphonic acid, a tetrazole moiety.

In one embodiment said fatty acid group comprises a functional group selected from a carboxylic acid, a sulphonic acid, a tetrazole moiety, a methylsulfonylcarbamoylamino (MSU) moiety and a 3-Hydroxy-isoxazolelsoxazole moiety. Accordingly the half-life extending substituent of the invention in an embodiment comprises a carboxylic acid, a sulphonic acid, a tetrazole moiety, a methylsulfonylcarbamoylamino moiety or a hydroxy-isoxazolelsoxazole moiety further including 8-20 consecutive —$CH_2$— groups as defined by:

Chem. 1: HOOC—$(CH_2)_n$—CO—* wherein n is an integer in the range of 8-20, which may also be referred to as a C(n+2) diacid or as
Chem. 1 b:

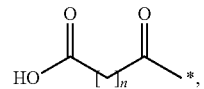

wherein n is an integer in the range of 8-20,
Chem. 2: 5-tetrazolyl-$(CH_2)_n$—CO—* wherein n is an integer in the range of 8-20, which may also be referred to as
Chem. 2b:

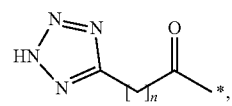

wherein n is an integer in the range of 8-20.
Chem. 3: HOOC—$(C_6H_4)$—O—$(CH_2)_m$—CO—* wherein n is an integer in the range of 8-20, which may also be referred to as
Chem. 3b:

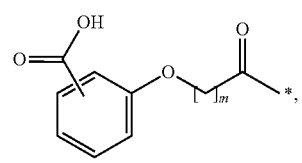

wherein the carboxy group is in position 2, 3 or 4 of the $(C_6H_4)$ group of Chem. 3 and wherein m is an integer in the range of 8-11
Chem. 4: HO—$S(O)_2$—$(CH_2)_n$—CO—* wherein n is an integer in the range of 8-20, which may also be referred to as
Chem. 4b:

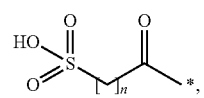

wherein n is an integer in the range of 8-20,
Chem. 5: $MeS(O)_2NH(CO)NH$—$(CH_2)_n$—CO—* wherein n is an integer in the range of 8-20, which may also be referred to as.
Chem. 5b:

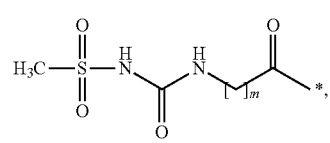

wherein n is an integer in the range of 8-20,
Chem. 6: 3-HO-Isoxazole-$(CH_2)_n$—CO—* wherein n is an integer in the range of 8-20, which may also be referred to as Chem. 6b:

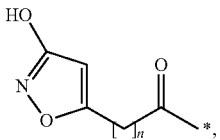

wherein n is an integer in the range of 8-20.

The term functional group in its acidic form is referred to as FG-H and its form as conjugated base referred to as FG⁻. The term "functional group with a pKa<7" as used herein may be referred to as a Brønsted-Lowry acid which in the form of its methyl derivative ($CH_3$—FG-H) in aqueous solution has a equilibrium pKa of below 7, wherein the pKa is the −log to the equilibrium constant (Ka) of the equilibrium shown below:

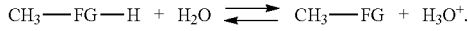

Methods for the determination of pKa are well known in the art. Such a method has for example been described by Reijenga et al. in Anal Chem Insights 2013 (2013; 8: 53-71).

Substituents according to the invention in an embodiment comprise one or more linker elements. The linker elements may be linked to the fatty acid group by amide bonds and referred to as $Z_2$-$Z_{10}$. As further defined herein below the number of linker elements may be at most 10.

In a specific embodiment, the substituent is of Formula I:

$$Z_1—Z_2—Z_3—Z_4—Z_5—Z_6—Z_7—Z_8—Z_9—Z_{10}—$$ [I]

wherein $Z_1$ is selected from:
Chem. 1: HOOC—$(CH_2)_n$—CO—* or
Chem. 1 b:

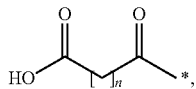

Chem. 2: 5-tetrazolyl-$(CH_2)_n$—CO—* or
Chem. 2b:

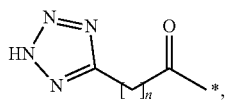

Chem. 3: HOOC—$(C_6H_4)$—O—$(CH_2)_m$—CO* or
Chem. 3b:

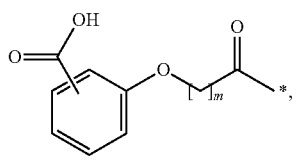

wherein the carboxy group is in position 2, 3 or 4 of —$(C_6H_4)$—,

Chem. 4: $HOS(O)_2$—$(CH_2)_n$—CO—* or
Chem. 4b:

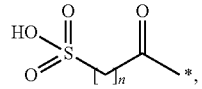

Chem. 5: $MeS(O)_2NH_2N(CO)NHN$—$(CH_2)_n$—CO—* or
Chem. 5b:

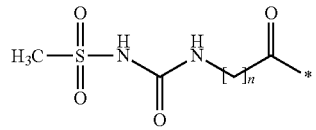

and
Chem. 6: 3-HO-Isoxazole-$(CH_2)_n$—CO—* or
Chem. 6b:

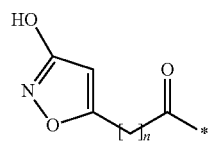

wherein n is an integer in the range of 8-20 and m is an integer in the range of 8-11.

In a particular embodiment, n is 8, 9, 10, 11, 12, 13, 14, 15, 16, 17, 18, 19 or 20 in Chem. 1 or 1b. In a particular embodiment, n is 8, 9, 10, 11, 12, 13, 14, 15, 16, 17, 18, 19 or 20 in Chem. 2 or 2b. In a particular embodiment, n is 8, 9, 10, 11, 12, 13, 14, 15, 16, 17, 18, 19 or 20 in Chem. 4 or 4b. In a particular embodiment, m is 8, 9, 10 or 11 in Chem. 3 or 3b.

In a particular embodiment, n is 8, 9, 10, 11, 12, 13, 14, 15, 16, 17, 18, 19 or 20 in Chem. 5 or 5b.

In a particular embodiment, n is 8, 9, 10, 11, 12, 13, 14, 15, 16, 17, 18, 19 or 20 in Chem. 6 or 6b.

In a particular embodiment, the symbol * indicates the attachment point to the nitrogen in $Z_2$. In another embodiment, where $Z_2$ is a bond, the symbol * indicates the attachment point to the nitrogen of the neighbouring Z element.

The term "bond" as used in the context of Formula I means a covalent bond. When a component of Formula I ($Z_1$-$Z_{10}$) is defined as a bond, it is equivalent to a formula I wherein said component is absent.

The indication herein below that any of $Z_2$-$Z_{10}$ is a bond may also be read as any of $Z_2$-$Z_{10}$ being absent. Logically "a bond" cannot follow "a bond". The indication "a bond" here thus means that the previous Z element is covalently linked to the next Z element that is not "a bond" (or absent).

The linker elements $Z_2$-$Z_{10}$ are selected from chemical moieties that are capable of forming amide bounds, including amino acid like moieties, such as Glu, γGlu (also termed gammal Glu or gGlu and defined by *—NH—CH—(COOH)—$CH_2$—$CH_2$—CO—*), Gly, Ser, Ala, Thr, Ado, Aeep, Aeeep and TtdSuc and further moieties defined below.

$Z_2$ is selected from

Chem. 7: *—NH—SO$_2$—(CH$_2$)$_3$—CO—* or

Chem 7b:

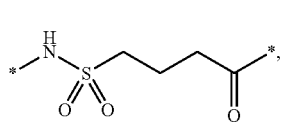

Chem. 8: *—NH—CH$_2$—(C$_6$H$_{10}$)—CO—* or

Chem. 8b:

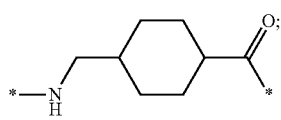 [SMILES: *NCC1CCC(C(*)=O)CC1]

and a bond.

$Z_3$ is selected from γGlu, Glu, or a bond.

$Z_3$ is selected from γGlu, Glu, or a bond when $Z_2$ is Chem. 7 or Chem. 7b.

$Z_3$ is selected from γGlu, Glu, or a bond, provided that $Z_3$ is selected from γGlu, Glu when $Z_2$ is Chem. 8.

$Z_3$ is selected from γGlu and Glu when $Z_2$ is Chem. 8.

$Z_4$, $Z_5$, $Z_6$, $Z_7$, $Z_8$, $Z_9$ are selected, independently of each other, from Glu, γGlu, Gly, Ser, Ala, Thr, Ado, Aeep, Aeeep, TtdSuc and a bond.

Glu, Gly, Ser, Ala, Thr are amino acid residues as well known in the art.

γGlu is of formula Chem. 9: *—NH—CH(COOH)—(CH$_2$)$_2$—CO—* which is the same as Chem. 9b:

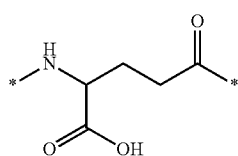 [SMILES: *NC(CCC(*)=O)C(=O)O]

and may also be referred to as gGlu.

TtdSuc is of formula Chem. 10:

*—NH—(CH$_2$)$_3$—O—(CH$_2$)$_2$—O—(CH$_2$)$_2$O—(CH$_2$)$_3$—NHCO* or

*—NH—CH$_2$CH$_2$CH$_2$OCH$_2$CH$_2$OCH$_2$CH$_2$OCH$_2$CH$_2$CH$_2$NHCO* which is the same as Chem. 10b:

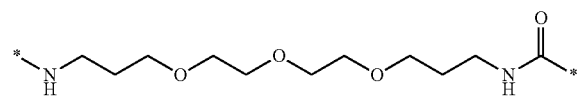 [SMILES: *NCCCOCCOCCOCCCNC(*)=O]

Ado is of formula Chem. 11: *—NH—(CH$_2$)$_2$—O—(CH$_2$)$_2$—O—CH$_2$—CO—* may also be referred to as 8-amino-3,6-dioxaoctanoic acid and which is the same as Chem. b 11 b:

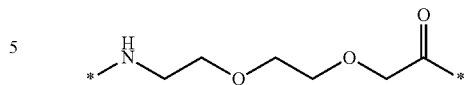

Aeep is of formula Chem. 12: *NH—CH$_2$CH$_2$OCH$_2$CH$_2$OCH$_2$CH$_2$CO*, which may also be referred to as Chem. 12b:

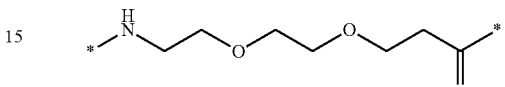

Aeeep is of formula Chem. 13: *NH—CH$_2$CH$_2$OCH$_2$CH$_2$OCH$_2$CH$_2$OCH$_2$CH$_2$CO*, which may also be referred to as Chem. 13b:

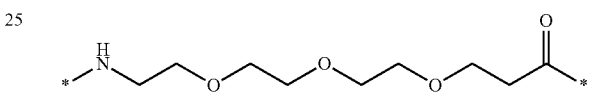

$Z_{10}$ is selected from a bond, and Chem. 14: *—NH—CH$_2$—(C$_6$H$_4$)—CH$_2$—*, which may also be referred to as Chem. 14b:

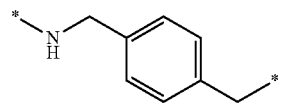 [SMILES: *Cc1ccc(CN*)cc1]

In a particular embodiment, when $Z_{10}$ is Chem. 14, the substituent is attached to the N-terminal amino group of said peptide.

In another embodiment, when $Z_{10}$ is a bond, said substituent is attached to the epsilon position of a Lys residue present in said peptide or to the N-terminal amino acid residue of said peptide.

In one embodiment the derivative comprises two substituents. In one such embodiment the two substituents are identical. In one such embodiment the two substituents are different. In one embodiment the two substituents are attached to nitrogen atoms of the EGF(A) peptide analogue. In one embodiment the two substituents are attached to amino groups of the EGF(A) peptide analogue. In one embodiment the two substituents are attached to the N-terminal amino acid EGF(A) and to a Lys residue of the EGF(A) peptide analogue. In one embodiment one substituent is attached the alpha-nitrogen of the N-terminal amino acid residue of the EGF(A) peptide analogue and one substituent is attach to a Lys residue of the EGF(A) peptide analogue. In one embodiment two substituents are attached to the N-terminal amino acid of the EGF(A) peptide analogue. In one embodiment the two substituents are attached to different Lys residues of the EGF(A) peptide analogue. In one embodiment the two substituents are attached to the epsilon-nitrogen's of different Lys residues in the EGF(A) peptide analogue.

In one embodiment where two substituents are present, $Z_{10}$ is Chem. 14 in one substituent which is attached to the N-terminal amino group of a peptide analogue and $Z_{10}$ is a bond in the other substituent which is attached to the epsilon position of a Lys residue present in said peptide analogue.

In another embodiment where two substituents are present, $Z_{10}$ is a bond in one substituent which is attached to the N-terminal amino group of a peptide analogue and $Z_{10}$ is a bond in the other substituent which is attached to the epsilon position of a Lys residue present in said peptide analogue.

In another embodiment where two substituents are present, $Z_{10}$ is a bond in both substituents and each of the two substituents is attached to the epsilon position of different Lys residues present in a peptide analogue.

In a particular embodiment, the derivatives of the invention may be prepared from a EGF(A) peptide analogue by covalent attachment of one or two substituent(s).

In a particular embodiment, the two substituents are of Formula I: $Z_1$—$Z_2$—$Z_3$—$Z_4$—$Z_5$—$Z_6$—$Z_7$—$Z_8$—$Z_9$—$Z_{10}$— [I]. $Z_1$ to $Z_{10}$ are as defined above. In a particular embodiment, the two substituents are of formula I and are identical, meaning that selected $Z_1$ to $Z_{10}$ are the same in both substituents. In another embodiment, the two substituents are of formula I and are different, meaning that one or more of selected $Z_1$ to $Z_{10}$ are different between one substituent and the other.

Specific Substituents

As seen above various substituents can be prepared by the persons skilled in the art. The substituents include in the present application are thus not to be considered limiting to the invention.

In one embodiment the one or two substituent(s) is/are selected from the group of substituents consisting of:
HOOC—$(CH_2)_{18}$—CO-gGlu-2×ADO
HOOC—$(CH_2)_{18}$—CO—NH—$CH_2$—$(C_6H_{10})$—CO-gGlu-2×ADO
HOOC—$(CH_2)_{16}$—CO-gGlu-2×ADO
HOOC—$(CH_2)_{16}$—CO-gGlu-2×ADO—NH—$CH_2$—$(C_6H_4)$—$CH_2$
HOOC—$(CH_2)_{16}$—CO-gGlu
HOOC—$(CH_2)_{16}$—CO—NH—$CH_2$—$(C_6H_{10})$—CO-gGlu-2×ADO
HOOC—$(CH_2)_{14}$—CO-gGlu-2×ADO
HOOC—$(CH_2)_{14}$—CO-gGlu-
HOOC—$(CH_2)_{14}$—CO-gGlu-2×ACO—
HOOC—$(CH_2)_{12}$—CO-gGlu-2×ADO
4-HOOC—$(C_6H_4)$—O—$(CH_2)_{10}$—CO-gGlu-2×ADO
4-HOOC—(C6H4)-O—(CH2)10-CO-gGlu-3×ADO
4-HOOC—$(C_6H_4)$—O—$(CH_2)_{10}$—CO-gGlu
4-HOOC—$(C_6H_4)$—O—$(CH_2)_{10}$—CO-2×gGlu
4-HOOC—$(C_6H_4)$—O—$(CH_2)_{10}$—CO-gGlu-3×Gly
4-HOOC—$(C_6H_4)$—O—$(CH_2)_{10}$—CO-2×gGlu-2×ADO
4-HOOC—$(C_6H_4)$—O—$(CH_2)_{10}$—CO-gGlu-TtdSuc
4-HOOC—$(C_6H_4)$—O—$(CH_2)_9$—CO
4-HOOC—$(C_6H_4)$—O—$(CH_2)_{10}$—CO-gGlu-4×ADO
4-HOOC—$(C_6H_4)$—O—$(CH_2)_{10}$—CO—NH—$CH_2$—$(C_6H_{10})$—CO-gGlu-2×ADO
4-HOOC—$(C_6H_4)$—O—$(CH_2)_9$—CO-gGlu-2×ADO
3-HOOC—$(C_6H_4)$—O—$(CH_2)_9$—CO-gGlu-2×ADO
3-HO-Isoxazole-$(CH_2)_{12}$—CO-gGlu-2×ADO
HOS(O)2-(CH2)15-CO-gGlu-2×ADO—NH—$CH_2$—$(C_6H_4)$—$CH_2$
HOS(O)$_2$—$(CH_2)_{13}$—CO-gGlu-2×ADO
Tetrazolyl-$(CH_2)_{15}$—CO—NH—$SO_2$—$(CH_2)_3$—CO-ACO-ADO—NH—$CH_2$—$(C_6H_4)$—$CH_2$
Tetrazolyl-$(CH_2)_{12}$—CO-gGlu-2×ADO
Tetrazolyl-$(CH_2)_{15}$—CO-gGlu-2×ADO and
MeS(O)$_2$NH(CO)NH—$(CH_2)_{12}$—CO-gGlu-2×ADO.

In one embodiment, the substituent is of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is Chem. 14: *—NH—$CH_2$—$(C_6H_4)$—$CH_2$—*.

In one embodiment, the substituent is of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, and $Z_9$ are Ado and the remaining four are bonds; $Z_{10}$ is a bond.

In one embodiment, the substituent is of Formula I wherein $Z_1$ is Chem. 1: HOOC—$(CH_2)_n$—CO—*, wherein n is 14 or 16; $Z_2$ is a bond; $Z_3$ is γGlu; and all of $Z_4$, $Z_5$, $Z_6$, $Z_7$, Z8 and $Z_9$ are bonds; $Z_{10}$ is a bond.

In one embodiment, the substituent is of Formula I wherein $Z_1$ is Chem. 1: HOOC—$(CH_2)_n$—CO—*, wherein n is 16 or 18; $Z_2$ is Chem 8 (Trx); $Z_3$ is γGlu; two of $Z_4$, $Z_5$, $Z_6$, $Z_7$, $Z_8$ and $Z_9$ are Ado and the remaining four are bonds; $Z_{10}$ is a bond.

In one embodiment, the substituent is of Formula I wherein $Z_1$ is Chem 2: Tetrazolyl-$(CH_2)_n$—CO—*, wherein n is 15; $Z_2$ is Chem 7 (sulfonimide); $Z_3$ is a bond; two of $Z_4$, $Z_5$, $Z_6$, $Z_7$, $Z_8$ and $Z_9$ are Ado and the remaining four are bonds; $Z_{10}$ is Chem. 14: *—NH—$CH_2$—$(C_6H_4)$—$CH_2$—*.

In one embodiment, the substituent is of Formula I wherein $Z_1$ is Chem 2: Tetrazolyl-$(CH_2)_n$—CO—*, wherein n is 15; $Z_2$ is a bond; $Z_3$ is γGlu; two of $Z_4$, $Z_5$, $Z_6$, $Z_7$, $Z_8$ and $Z_9$ are Ado and the remaining four are bonds; $Z_{10}$ is a bond.

In one embodiment, the substituent is of Formula I wherein $Z_1$ is Chem 2: Tetrazolyl-$(CH_2)_n$—CO—*, wherein n is 12; $Z_2$ is a bond; $Z_3$ is γGlu; two of $Z_4$, $Z_5$, $Z_6$, $Z_7$, $Z_8$ and $Z_9$ are Ado and the remaining four are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a bond; and all off $Z_4$, $Z_5$, $Z_6$, $Z_7$, $Z_8$ and $Z_9$ are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and all off $Z_4$, $Z_5$, $Z_6$, $Z_7$, $Z_8$ and $Z_9$ are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and one off $Z_4$, $Z_5$, $Z_6$, $Z_7$, $Z_8$ and $Z_9$ is a γGlu and the remaining five are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and one off $Z_4$, $Z_5$, $Z_6$, $Z_7$, $Z_8$ and $Z_9$ is a γGlu and two are Ado and the remaining three are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and three off $Z_4$, $Z_5$, $Z_6$, $Z_7$, $Z_8$ and $Z_9$ are Gly and the remaining three are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and two off $Z_4$, $Z_5$, $Z_6$, $Z_7$, $Z_8$ and $Z_9$ are Ado and the remaining four are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and three off $Z_4$, $Z_5$, $Z_6$, $Z_7$, $Z_8$ and $Z_9$ are Ado and the remaining three are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and four of $Z_4$, $Z_5$, $Z_6$, $Z_7$, $Z_8$ and $Z_9$ are Ado and the remaining two are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is a γGlu; and one of $Z_4$, $Z_5$, $Z_6$, $Z_7$, $Z_8$ and $Z_9$ is a TtdSuc and the remaining five are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is Chem 8 (Trx); $Z_3$ is a γGlu; and two of $Z_4$, $Z_5$, $Z_6$, $Z_7$, $Z_8$ and $Z_9$ are Ado and the remaining four are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 9; $Z_2$ is a bond; $Z_3$ is a γGlu; and one of $Z_4$, $Z_5$, $Z_6$, $Z_7$, $Z_8$ and $Z_9$ is a TtdSuc and the remaining five are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the substituent is of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the substituent is of Formula I wherein $Z_1$ is Chem. 4: HO—S(O)$_2$—$(CH_2)_n$—CO—*, wherein n is 15; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the substituent is of Formula I wherein $Z_1$ is Chem. 4: HO—S(O)$_2$—$(CH_2)_n$—CO—*, wherein n is 15; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is Chem. 14: *—NH—CH$_2$—$(C_6H_4)$—CH$_2$—*.

In one embodiment, the substituent is of Formula I wherein $Z_1$ is Chem. 5: MeS(O)$_2$NH(CO)NH—$(CH_2)_n$—CO—*, wherein n is 12; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the substituent is of Formula I wherein $Z_1$ is Chem. 6: 3-OH-Isoxazole-$(CH_2)_{12}$—CO—*, wherein n is 12; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

Specific Substituent Combinations:

In one embodiment, the compound of the invention comprises or has two substituents of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is a bond.

In one embodiment, the compound of the invention comprises or has two substituents of Formula I wherein $Z_1$ is Chem. 1: HOOC—$(CH_2)_n$—CO—*, wherein n is 14; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is a bond.

In one embodiment, the compound of the invention comprises or has two substituents of Formula I wherein $Z_1$ is Chem. 1: HOOC—$(CH_2)_n$—CO—*, wherein n is 14; $Z_2$ is a bond; $Z_3$ is γGlu; all four of $Z_4$, $Z_5$, $Z_6$, $Z_7$, $Z_8$, $Z_9$ are bonds; $Z_{10}$ is a bond.

In one embodiment, the compound of the invention comprises or has two substituents of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the compound of the invention comprises or has two substituents, one being of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is Chem. 14: *—NH—CH$_2$—$(C_6H_4)$—CH$_2$—*; the other substituent being of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is a bond.

In one embodiment, the compound of the invention comprises or has two substituents, one being of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is Chem. 14: *—NH—CH$_2$—$(C_6H_4)$—CH$_2$—*; the other substituent being of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the compound of the invention comprises or has two substituents, one being of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is a bond; the other substituent being of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond.

In one embodiment, the compound of the invention comprises or has two substituents, one being of Formula I wherein $Z_1$ is Chem. 1: HOOC—$(CH_2)_n$—CO—*, wherein n is 16; $Z_2$ is a bond; $Z_3$ is γGlu; two of $Z_4$, $Z_5$, $Z_6$, $Z_7$, $Z_8$, $Z_9$ are Ado and the remaining four are bonds; $Z_{10}$ is a bond; and the other substituent is of formula I wherein $Z_1$ is Chem. 4: HOS(O)$_2$—$(CH_2)_n$—CO—*, wherein m is 15; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is Chem. 14: *—NH—CH$_2$—$(C_6H_4)$—CH$_2$—*.

In one embodiment, the compound of the invention comprises or has two substituents, one being of Formula I wherein $Z_1$ is Chem. 3: HOOC—$(C_6H_4)$—O—$(CH_2)_m$—CO—*, wherein m is 10; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is a bond; the other substituent being of Formula I wherein $Z_1$ is Chem. 4: HOS(O)$_2$—$(CH_2)_n$—CO—*, wherein m is 15; $Z_2$ is a bond; $Z_3$ is γGlu; two of $Z_4$, $Z_5$, $Z_6$, $Z_7$, $Z_8$ and $Z_9$ are Ado, the remaining four are bonds; $Z_{10}$ is Chem. 14: *—NH—CH$_2$—$(C_6H_4)$—CH$_2$—*.

Peptide and Attachment Site

An EGF(A) derivative or compound according to the invention comprises a EGF(A) peptide analogue of the EGF(A) domain of LDL-R as defined by SEQ ID NO.: 1. Such peptide sequence have been described in details herein above and the peptide of the derivative or compound of the invention may be described and defined by identical terms. The EGF(A) derivative or compound further has at least one substituent as described herein above which is linked to the peptide sequence.

In the compounds of the invention, the substituent is covalently attached to the peptide, meaning to one amino acid residue of the peptide sequence.

In one embodiment the EGF(A) derivative of the invention, comprise a substituent which is not attached to any one of the following positions: 295, 296, 298, 301, 302 and 307. In a further embodiment the substituent is not attached to any one of the following positions: 295, 296, 298, 301, 302, 307 and 310. In further such embodiments, it is also not attached to any one of the following positions: 299 and 320.

In a particular embodiment a substituent is attached via any position from 292 to 333 except in any or the positions 297, 304, 308, 317, 319 and 331.

In a particular embodiment a substituent attached via any position from 292 to 333 except in any of the positions 297, 298, 301, 302, 304, 307, 308, 317, 319 and 331.

In a particular embodiment a substituent attached via any position from 292 to 333 except in any of the positions 295, 296, 297, 298, 301, 302, 304, 307, 308, 317, 319 and 331. In a particular embodiment a substituent attached via in any position from 292 to 333 except in any of the positions 295, 296, 297, 298, 301, 302, 304, 307, 308, 310, 317, 319, 320 and 331. In a particular embodiment a substituent attached via any position from 292 to 333 except in any of the positions 295, 296, 297, 298, 301, 302, 304, 307, 308, 309, 310, 317, 319, 320 and 331.

In one embodiment, the substituent(s) is/are attached to any one or two of the positions 292, 293, 294, 299, 300, 303, 305, 306, 309, 311, 312, 313, 314, 315, 316, 318, 320, 321, 322, 323, 324, 325, 326, 327, 328, 329, 330, 332 and 333 of the EGF(A) peptide analogue.

In one embodiment, the substitution(s) is/are attached to any one or two of the positions 292, 293, 294, 300, 303, 305, 306, 309, 311, 312, 313, 314, 315, 316, 318, 321, 322, 323, 324, 325, 326, 327, 328, 329, 330, 332 and 333 of the EGF(A) peptide analogue.

In one embodiment, the substitution(s) is/are attached to any one or two of the positions 292, 293, 294, 300, 303, 305, 306, 311, 312, 313, 314, 315, 316, 318, 321, 322, 323, 324, 325, 326, 327, 328, 329, 330, 332 and 333 of the EGF(A) peptide analogue.

In one embodiment, the substituent is attached to the N-terminal amino acid of the peptide sequence. In a particular embodiment, the N-terminal amino acid is Gly. In a particular embodiment, the N-terminal amino acid is 293Gly. In a particular embodiment, the N-terminal amino acid is 293Lys. In a particular embodiment, the N-terminal amino acid is 292Lys. It may also be a Lys or a Gly or another amino acid residue in the N-terminal position which may be 293 or any position further down from the N-terminus, such as 294Thr, 294Gly or 294Lys or 295Asn. In a particular embodiment, the substituent is attached to the alpha-nitrogen of the N-terminal amino acid residue of the peptide analogue. In another embodiment, if the N-terminal amino acid residue is Lys, the substituent may be covalently linked to the alpha-nitrogen or to the epsilon amino group of the lysine residue.

In a particular embodiment, a substituent is attached to the ε-amino group of a Lys residue present in the peptide.

In another embodiment, a substituent is attached to a Lys in C-terminal position which may be position 332, 333 or any position further towards the C-terminus.

In embodiments wherein the peptides of the invention comprise an elongation, either in N-terminal or C-terminal, the substituent(s) may be attached to an amino acid residue of said elongation(s). In the presence of a N-terminal elongation, a substituent may be attached to the N-terminal amino acid of said elongation or to a Lys present within the elongation sequence. In the presence of a C-terminal elongation, a substituent may be attached to a Lys residue in C-terminal position or to a Lys present within the elongation sequence.

In yet another embodiment, the substituent is attached to an amino acid present in the peptide sequence. In a particular embodiment, the substituent is linked to a lysine residue present in the peptide. In a particular embodiment, the substituent is linked to the epsilon amino group of a lysine residue present in the peptide. The lysine residue to which the substituent is linked may be located in any position of the LDL-R(293-332) EGF(A) analogue including the N-terminal position or C-terminal position of the peptide, any position within or at the N-terminal end residue of a N-terminal elongation if present, any position within or at the C-terminal end residue of a C-terminal elongation if present.

As described herein above the EGF(A) peptide analogue may have one or more Lys residues; and those residues are useful for attachment of substituents.

In a particular embodiment, the lysine(s) to which the substituent(s) is/are linked is selected from the group of: 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a particular embodiment, the lysine(s) to which the substituent(s) is/are linked is selected from 293Lys, 294Lys, 295Lys, 296Lys, 298Lys, 299Lys, 301Lys, 302Lys, 303Lys, 305Lys, 306Lys, 307Lys, 309Lys, 310Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a particular embodiment, the lysine(s) to which the substituent(s) is/are linked is selected from 293Lys, 294Lys, 300Lys, 303Lys, 306Lys, 309Lys, 311Lys, 312Lys, 313Lys, 314Lys, 315Lys, 316Lys, 318Lys, 321Lys, 322Lys, 323Lys, 324Lys, 325Lys, 326Lys, 328Lys, 329Lys, 330Lys, 332Lys and 333Lys.

In another embodiment, the lysine(s) to which the substituent(s) is/are linked is selected from 293Lys, 294Lys, 298Lys, 299Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In another embodiment, the lysine(s) to which the substituent(s) is/are linked is selected from: 292Lys, 293Lys, 294Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In another embodiment, the lysine(s) to which the substituent(s) is/are linked is selected from: 292Lys, 293Lys, 294Lys, 300Lys, 303Lys, 305Lys, 306Lys, 309Lys, 311Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In another embodiment, the lysine(s) to which the substituent(s) is/are linked is selected from: 293Lys, 294Lys, 300Lys, 303Lys, 305Lys, 306Lys, 309Lys, 311Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In another embodiment, the lysine(s) to which the substituent(s) is/are linked is selected from: 293Lys, 294Lys, 300Lys, 303Lys, 305Lys, 306Lys, 311Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In embodiments where the substituent is attached to a C-terminal elongation, the lysine to which the substituent is linked may be selected from anyone of 333Lys to 242Lys position and/or to anyone of 333Lys to 383Lys position.

In embodiments where compounds of the invention have two substituents, the substituents may be linked independently of each other as defined above, meaning that either one may be attached to the N-terminal amino acid of the peptide, to the C-terminal amino acid of the peptide, or to an amino acid within the amino acid sequence of the peptide. In embodiments where a Lys is present in N-terminal position, two substituents may be both linked to the N-terminal Lys of the peptide. One may be linked to the N-terminal alpha-amine of said Lys while the other may be linked to the epsilon nitrogen of said Lys. When two substituents are present, one may be linked to the N-terminal amino acid of the peptide while the other substituent is linked to an amino acid, such as a Lys, within the peptide. Alternatively, one substituent may be linked to a Lys in position C-terminal of the peptide while the other substituent is linked to an amino acid, such as a Lys, in the peptide. Alternatively, one substituent may be linked to an amino acid residue, such as a Lys, within the peptide, including elongations, the other substituent being linked to another amino acid residue, such as a Lys, within the peptide, including elongations.

In an embodiment, the compounds of the invention have one substituent, said substituent is linked to the peptide at the N-terminal; or said substituent is linked to the peptide in position 292Lys; or said substituent is linked to the peptide in position 293Lys, or said substituent is linked to the peptide in position 299Lys; or said substituent is linked to the peptide in position 300Lys; or said substituent is linked to the peptide in position 309Lys; or said substituent is linked to the peptide in position 311Lys; or said substituent is linked to the peptide in position 312Lys; or said substituent is linked to the peptide in position 313Lys; or said substituent is linked to the peptide in position 314Lys; or said substituent is linked to the peptide in position 315Lys; or said substituent is linked to the peptide in position 316Lys; or said substituent is linked to the peptide in position 318Lys; or said substituent is linked to the peptide in position 320Lys; or said substituent is linked to the peptide in position 321Lys; or said substituent is linked to the peptide in position 322Lys; or said substituent is linked to the peptide in position 323Lys; or said substituent is linked to the peptide in position 324Lys; or said substituent is linked to the peptide in position 325Lys; or said substituent is linked to the peptide in position 326Lys; or said substituent is linked to the peptide in position 328Lys; or said substituent is linked to the peptide in position 329Lys; or said substituent is linked to the peptide in position 330Lys; or said substituent is linked to the peptide in position 332Lys; or said substituent is linked to the peptide in position 333Lys.

In an embodiment where the derivative of the invention have two substituents, said substituents may be linked to the peptide via the N-terminal and any of the above mention Lys positions, such as 293Lys, 309Lys, 313Lys, 324Lys, 328Lys, 330Lys, 332Lys and 333Lys.

In further embodiments where the derivative comprises two substituents, they may be linked to two different Lys residues, such as any of the following pairs of Lys residues i. 293K and 294K
ii. 293K and 312K
iii. 293K and 333K
iv. 309K and 313K
v. 309K and 324K
vi. 309K and 328K
vii. 309K and 332K
viii. 309K and 333K
ix. 311K and 313K
x. 312K and 333K
xi. 312K and 313K
xii. 312K and 314K
xiii. 313K and 314K
xiv. 313K and 321K
xv. 313K and 324K
xvi. 313K and 328K
xvii. 313K and 332K
xviii. 313K and 333K
xix. 314K and 333K
xx. 321K and 332K
xxi. 321K and 333K
xxii. 324K and 333K
xxiii. 324K and 328K
xxiv. 328K and 333K
xxv. 330K and 333K and
xxvi. 332K and 333K.

In one embodiment the two substituents are attached via 333Lys and a Lys selected from 293Lys, 309Lys, 312Lys, 313Lys, 314Lys, 321Lys, 324Lys, 328Lys, 330Lys and 332Lys.

In one embodiment the two substituents are attached via 333Lys and a Lys selected from 312Lys, 313Lys, 314Lys, 321Lys, 324Lys, 328Lys and 330Lys.

In one embodiment the two substituents are attached via 333Lys and a Lys selected from 313Lys, 324Lys and 328Lys.

As described above the peptide may have one or more amino acid substitutions which may be combined with specific amino acid residues in specific positions as described herein. Such specific amino acid residues may be wt amino acid residues that should be maintained, such as the cysteines which may in a series of preferred embodiments e.g. in combination with other features described herein, be present in the peptide analogue. In such embodiments the peptide analogue comprises three disulphide bridges in positions 297Cys-308Cys, 304Cys-317Cys and 319Cys-331Cys. In a further example of such embodiments the peptide analogue of a peptide derivative comprises three disulphide bridges in positions 297Cys-308Cys, 304Cys-317Cys and 319Cys-331Cys and at least one substituent, wherein the substituent(s) is not attached to a positions selected from 295, 296, 298, 301, 302 and 307 of said peptide analogue, The skilled person will understand that combinations of peptide sequence information may be combined with information on position and identity of the substituent to define various specific embodiments of the present invention.

In an embodiment, the peptide analogue comprises no Lys in other positions than the positions to which a substituent is linked.

In an embodiment, the compounds of the invention have one substituent, said substituent is linked either in position N-terminal or to a Lys in any position, and the peptide analogue comprises no Lys in all other positions. In an embodiment, the compounds of the invention have one substituent, said substituent is linked to a Lys in any position other than position 312, and the peptide analogue comprises an Arg in position 312Arg.

In an embodiment, the compounds of the invention have two substituents, and the peptide analogue comprises no Lys in positions other than positions to which the substituents are linked.

In one embodiment the EGF(A) derivative according to the invention is selected from the group of EGF(A) derivative consisting of: Examples 1-47, 51-102 and 106-159.

In further embodiments the EGF(A) derivative according to the invention is individually selected from the group of EGF(A) derivative consisting of: Examples 1-47, 51-102 and 106-159.

In one embodiment the EGF(A) derivative according to the invention is selected from the group of EGF(A) derivative consisting of: Examples 1-44, 46-47, 51-55, 57, 60-64, 66-69, 71-102 and 106-159.

In one embodiment the EGF(A) derivative according to the invention is selected from the group of EGF(A) derivative consisting of: Examples 31, 95, 128, 133, 143, 144, 150, 151, 152 and 153.

Pharmaceutical Composition

The invention also relates to pharmaceutical compositions comprising a compound of the invention, including e.g. a peptide analogue of the invention, or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. Non-limiting examples of excipients are: solvents, diluents, buffers, preservatives, tonicity regulating agents, chelating agents, and stabilisers. The formulation of pharmaceutically active ingredients with various excipients is known in the art, see e.g. Remington: The Science and Practice of Pharmacy (e.g. $19^{th}$ edition (1995), and any later editions).

A composition of the invention may be in the form of a liquid formulation, i.e. aqueous formulation comprising water. A liquid formulation may be a solution, or a suspension. Alternatively, it may be a solid formulation, e.g. a freeze-dried or spray-dried composition.

A pharmaceutical composition of the invention may further comprise a second active ingredient, such as a therapeutic agent, which may simplify administration in case of combination treatments.

A composition of the invention may be an oral composition, and the route of administration is per oral. The compounds of the invention and in particular the protracted compounds, i.e. the derivative compounds, are suitable for oral administration. The peptides and compounds of the invention may according to the invention be comprised by an oral formulation i.e. a composition suited for oral administration and capable of providing a suitable level of bioavailability. Oral formulations technologies know in the art may be used. This includes use of salts of N-(8-(2-hydroxybenzoyl)amino)caprylic acid, in particular sodium N-(8-(2-hydroxybenzoyl)amino)caprylate (SNAG) as described in WO96/30036 and WO2008/028859 and GIPET formulations including sodium caprate such as described in EP1154761 and U.S. Pat. No. 8,053,429.

In order to provide compounds for oral compositions the inventors confirmed that a EGF(A) peptide derivatives according to the invention display gastrointestinal absorption in rats (Table 10).

Alternatively, a composition of the invention may be for parenteral administration, e.g. performed by subcutaneous, intramuscular, intraperitoneal, or intravenous injection. Naturally, compounds aimed for subcutaneous administration may not need to display gastrointestinal absorption while other features such as high stability in liquid formulation may be desired.

Combination Treatment

Treatment with a EGF(A) peptide analogue or derivative thereof according to the present invention may also be combined with one or more additional pharmacologically active substances, e.g. selected from anti-diabetic agents, anti-obesity agents, appetite regulating agents, antihypertensive agents, agents for the treatment and/or prevention of complications resulting from or associated with diabetes and agents for the treatment and/or prevention of complications and disorders resulting from or associated with obesity.

Examples of these pharmacologically active substances are: GLP-1 receptor agonists, insulin, DPP-IV (dipeptidyl peptidase-IV) inhibitors, amylin agonists and leptin receptor agonists. Particular examples of such active substances are the GLP-1 receptor agonists liraglutide and semaglutide and insuling degludec.

Pharmaceutical Indications

In one aspect the invention relates to the use of an EGF(A) peptide analogue or an EGF(A) derivative as described herein for use in the manufacture of a medicament.

The invention also relates to a compound of the invention, e.g. a peptide analogue or a derivative according to the invention, or a pharmaceutical composition thereof for use as a medicament or in the manufacture of a medicament.

In an embodiment, a compound of the invention or a composition thereof may be used for (i) improving lipid parameters, such as prevention and/or treatment of dyslipidemia, lowering total serum lipids; lowering LDL-C, increasing HDL; lowering small, dense LDL; lowering VLDL; lowering triglycerides; lowering cholesterol; lowering plasma levels of lipoprotein a (Lp(a)); inhibiting generation of apolipoprotein A (apo(A)); (ii) the prevention and/or the treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or the reduction of blood pressure, such as reduction of systolic blood pressure; the treatment of cardiovascular disease.

The invention also relates to a method for (i) improving lipid parameters, such as prevention and/or treatment of dyslipidemia, lowering total serum lipids; increasing HDL-C; lowering LDL-C, lowering small, dense LDL-C; lowering VLDL-C; lowering triglycerides; lowering cholesterol; lowering plasma levels of lipoprotein a (Lp(a)); inhibiting generation of apolipoprotein A (apo(A)); (ii) prevention and/or treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; the treatment of cardiovascular disease; wherein a pharmaceutically active amount of a compound according to the invention, e.g. a peptide analogue or a derivative according to the invention, is administered.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

EMBODIMENTS

1. A EGF(A) peptide analogue of the EGF(A) domain of the LDL-R defined by SEQ ID NO 1, wherein the peptide analogue comprises 301Leu.
2. The EGF(A) peptide analogue according to embodiment 1, wherein the peptide analogue comprises the wild-type cys residues 297Cys, 304Cys, 308Cys, 317Cys, 319Cys and 331Cys.
3. The EGF(A) peptide analogue according any of the previous embodiments, wherein the peptide analogue comprises one or more of the (wild-type) amino acid residues 295Asn, 296Glu, 298Leu, 302Gly and 310Asp.
4. The EGF(A) peptide analogue according any of the previous embodiments, wherein the peptide analogue comprises the residue Asn(N) in position 295.
5. The EGF(A) peptide analogue according any of the previous embodiments, wherein the peptide analogue comprises the residue Glu(E) in position 296.
6. The EGF(A) peptide analogue according any of the previous embodiments, wherein the peptide analogue comprises the residue Leu(L) in position 298.
7. The EGF(A) peptide analogue according any of the previous embodiments, wherein the peptide analogue comprises the residue Gly(G) in position 302.
8. The EGF(A) peptide analogue according any of the previous embodiments, wherein the peptide analogue comprises the residue Asp(D) in position 310.
9. The EGF(A) peptide analogue according any of the previous embodiments, wherein the peptide analogue comprises the wild-type residues in positions 295 (Asn/N) and 310 (Asp/D).
10. The EGF(A) peptide analogue according any of the previous embodiments, wherein the peptide has 1-15 amino acid substitution(s) compared to SEQ ID NO.: 1.
11. The EGF(A) peptide analogue according any of the previous embodiments, wherein the peptide analogue comprises one or more amino acid substitution(s) in a position(s) selected from the group of positions: 293, 294, 296, 299, 300, 303, 305, 306, 309, 311, 312, 313, 314, 315, 316, 318, 320, 321, 322, 323, 324, 325, 326, 328, 329, 330, 332.
12. The EGF(A) peptide analogue according any of the previous embodiments, wherein the peptide analogue comprises one or more amino acid substitution(s) in a position(s) selected from the group of positions: 294, 299, 300, 303, 309, 312, 313, 314, 316, 318, 321, 322, 323, 324, 325, 326, 328, 329, 330, 332.
13. The EGF(A) peptide analogue according any of the previous embodiments, wherein the peptide analogue comprises one or more further amino acid substitution(s) in a position(s) selected from the group of positions: 309, 312, 313, 321, 324, 328, 332.
14. The EGF(A) peptide analogue according any of the previous embodiments, wherein the peptide analogue comprises the amino acid residue Gly(G) or Asn(N) in position 293.
15. The EGF(A) peptide analogue according any of the previous embodiments, wherein the peptide analogue comprises the amino acid residue Thr(T) or Gly(G) in position 294.
16. The EGF(A) peptide analogue according any of the previous embodiments, wherein the peptide analogue comprises the amino acid residue Asp(D), Gly(G), Pro(P), Arg(R), Lys(K), Ser(S), Thr(T), Asn(N), Gln(Q), Ala(A), Ile(I), Leu(L), Met(M), Phe(F), Tyr(Y) or Trp(W) in position 299.
17. The EGF(A) peptide analogue according any of the previous embodiments, wherein the peptide analogue comprises the amino acid residue Asp(D), Gly(G), Pro (P), Arg(R), Lys(K), Ser(S), Thr(T), Asn(N), Gln(Q), Ala(A), Ile(I), Leu(L), Met(M), Phe(F), Tyr(Y) or Trp(W) in position 299.
18. The EGF(A) peptide analogue according any of the previous embodiments, wherein the peptide analogue comprises the amino acid residue Asp(D), Ser (S), Arg(R), Leu (L), Ala (A), Lys(K) or Tyr(Y) in position 299.
19. The EGF(A) peptide analogue according any of the previous embodiments, wherein the peptide analogue comprises the amino acid residue Asp(D) or Ala(A) in position 299.
20. The EGF(A) peptide analogue according any of the previous embodiments, wherein the peptide analogue comprises the amino acid residue His(H) or Asn(N) in position 300.
21. The EGF(A) peptide analogue according any of the previous embodiments, wherein the peptide analogue comprises the amino acid residue Val(V), Ser(S), Thr (T) or Ile (I) in position 307.
22. The EGF(A) peptide analogue according any of the previous embodiments, wherein the peptide analogue comprises the amino acid residue Val(V) or Ile (I) in position 307.
23. The EGF(A) peptide analogue according any of the previous embodiments, wherein the peptide analogue comprises Ser(S), Thr (T) or Ile (I) in position 307.
24. The EGF(A) peptide analogue according any of the previous embodiments, wherein the peptide analogue comprises Ile (I) in position 307.
25. The EGF(A) peptide analogue according any of the previous embodiments, wherein the peptide analogue comprises the amino acid residue Asn(N), Glu (E), His (H) Arg (R), Ser (S) or Lys (K) in position 309.
26. The EGF(A) peptide analogue according any of the previous embodiments, wherein the peptide analogue comprises the amino acid residue Asn(N), Arg (R), Ser (S) or Lys (K) in position 309.
27. The EGF(A) peptide analogue according any of the previous embodiments, wherein the peptide analogue comprises the amino acid residue Asn(N), Arg (R) or Ser (S) in position 309.
28. The EGF(A) peptide analogue according any of the previous embodiments, wherein the peptide analogue comprises the amino acid residue Asn(N) or Arg (R) in position 309.

29. The EGF(A) peptide analogue according any of the previous embodiments, wherein the peptide analogue comprises the amino acid residue Lys(K) or Arg (R) in position 309.
30. The EGF(A) peptide analogue according any of the previous embodiments, wherein the peptide analogue comprises the amino acid residue Arg (R) in position 309.
31. The EGF(A) peptide analogue according any of the previous embodiments, wherein the peptide analogue comprises the amino acid residue Lys(K), Glu(E), Asp (D), Gln(Q) or Arg (R) in position 312.
32. The EGF(A) peptide analogue according any of the previous embodiments, wherein the peptide analogue comprises an amino acid substitution of Lys(K) in position 312.
33. The EGF(A) peptide analogue according embodiment 32, wherein 312Lys is substituted by an amino acid selected from the group consisting of: 312Gly, 312Pro, 312Asp, 312Glu, 312Arg, 312His, 312Ser, 312Thr, 312Asn, 312Gln, 312Ala, 312Val, 312Ile, 312Leu, 312Met, 312Phe and 312Tyr.
34. The EGF(A) peptide analogue according embodiment 32, wherein 312Lys is substituted by an amino acid selected from the group consisting of: 312Asp, 312Glu, 312Thr, 312Asn, 312Ile, 312Phe and 312Tyr.
35. The EGF(A) peptide analogue according embodiment 32, wherein 312Lys is substituted by an amino acid selected from the group consisting of: 312Asp, 312Glu, 312Thr, 312Asn, 312Ile and 312Phe.
36. The EGF(A) peptide analogue according embodiment 32, wherein 312Lys is substituted by an amino acid selected from the group consisting of: 312Glu, 312Asp, 312Gln and 312Arg.
37. The EGF(A) peptide analogue according any of the previous embodiments, wherein the peptide analogue comprises the amino acid residue Asp(D), Lys (K) or Glu(E) in position 321.
38. The EGF(A) peptide analogue according any of the previous embodiments, wherein the peptide analogue comprises the amino acid residue Asp(D) or Glu(E) in position 321.
39. The EGF(A) peptide analogue according any of the previous embodiments, wherein the peptide analogue comprises the amino acid residue Glu(E) in position 321.
40. The EGF(A) peptide analogue according any of the previous embodiments, wherein the peptide analogue comprises the amino acid residue Gln (Q) or Gly (G) in position 324.
41. The EGF(A) peptide analogue according any of the previous embodiments, wherein the peptide analogue comprises the amino acid residue Arg (R) or His (H) in position 329.
42. The EGF(A) peptide analogue according any of the previous embodiments, wherein the peptide does not have a substitution of 299Asp(D) to Glu(E), Val(V) or His (H).
43. The EGF(A) peptide analogue according any of the previous embodiments, wherein the peptide does not have a substitution of 300Asn(N) to Pro(P).
44. The EGF(A) peptide analogue according to any of the previous embodiments, wherein the peptide analogue comprises at least one Lys amino acid residue.
45. The EGF(A) peptide analogue according to any of the previous embodiments, wherein the peptide analogue comprises a Lys substitution.
46. The EGF(A) peptide analogue according to any of the previous embodiments, wherein the peptide analogue comprises a Lys substitution and wt Lys in position 312.
47. The EGF(A) peptide analogue according to any of the previous embodiments, wherein the peptide analogue comprises a Lys substitution and a non Lys amino acid residue in position 312.
48. The EGF(A) peptide analogue according to any of the previous embodiments, wherein the peptide analogue comprises a Lys substitution and a Glu (E), Asp (D), Gln (Q) or Arg (R) in position 312.
49. The EGF(A) peptide analogue according to any of the previous embodiments, wherein the peptide analogue comprises a Lys substitution and a Glu(E) in position 312.
50. The EGF(A) peptide analogue according to any of the previous embodiments, wherein the peptide analogue comprises one or more Lys substitution(s).
51. The EGF(A) peptide analogue according to any of the previous embodiments, wherein said peptide has at least two amino acid substitutions comprising and/or consisting of:
  i. 301Leu and 309Arg
  ii. 301Leu, 309Arg, 312Glu
  iii. 301Leu, 307Ile and 309Arg
  iv. 301Leu, 307Ile, 309Arg and 312Glu
  v. 301Leu, 309Arg and 321Glu
  vi. 301Leu, 309Arg, 321Glu and 312Glu
  vii. 301Leu, 307Ile, 309Arg and 299Ala
  viii. 301Leu, 307Ile, 309Arg, 299Ala and 312Glu
  ix. 301Leu and 309Arg and at least one Lys substitution
  x. 301Leu, 309Arg, 312Glu and at least one Lys substitution
  xi. 301Leu, 307Ile and 309Arg and at least one Lys substitution
  xii. 301Leu, 307Ile, 309Arg and 312Glu and at least one Lys substitution
  xiii. 301Leu, 309Arg and 321Glu and at least one Lys substitution
  xiv. 301Leu, 309Arg, 321Glu and 312Glu and at least one Lys substitution
  xv. 301Leu, 307Ile, 309Arg and 299Ala and at least one Lys substitution or
  xvi. 301Leu, 307Ile, 309Arg, 299Ala and 312Glu and at least one Lys substitution.
52. The EGF(A) petide analogue according to any of the previous embodiments 1-50, wherein said peptide has at least two amino acid substitutions comprising and/or consisting of:
  xvii. 301Leu and 309Lys
  xviii. 301Leu, 309Lys and 312Glu
  xix. 301Leu and 309Lys and at least one further Lys substitution or
  xx. 301Leu, 309Lys and 312Glu and at least one further Lys substitution.
53. The EGF(A) petide analogue according to any of the previous embodiments 1-50, wherein said peptide has at least two amino acid substitutions comprising and/or consisting of:
  xxi. 301Leu and 307Ile,
  xxii. 301Leu, 307Ile and 312Glu
  xxiii. 301Leu and 307Ile and at least one further Lys substitution or
  xxiv. 301Leu, 3307Ile and 312Glu and at least one further Lys substitution.
54. The EGF(A) peptide analogue according to any of the previous embodiments, wherein the peptide analogue comprises an N-terminal and/or C-term elongation.

55. The EGF(A) peptide analogue according to any of the previous embodiments, wherein the peptide analogue comprises an N-terminal elongation of 1-10 amino acid residues.
56. The EGF(A) peptide analogue according to any of the previous embodiments, wherein the peptide analogue comprises an N-terminal elongation comprising an amino acid residue in position 292, such as 292 Ala (A) or 292 (K).
57. The EGF(A) peptide analogue according to any of the previous embodiments, wherein the peptide analogue comprises a C-terminal elongation of 1-10 amino acid residues.
58. The EGF(A) peptide analogue according to any of the previous embodiments, wherein the peptide analogue comprises an C-terminal elongation comprising an amino acid residue in position 333, such as 333 Ala (A) or 333 (K).
59. The EGF(A) peptide analogue according to any of the previous embodiments, wherein the peptide analogue comprises at least one Lys residue selected from the group consisting of: 292Lys, 293Lys, 294Lys, 296Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
60. The EGF(A) peptide analogue according to any of the previous embodiments, wherein the peptide analogue comprises at least one Lys residue selected from the group consisting of: 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
61. The EGF(A) peptide analogue according to any of the previous embodiments, wherein the peptide analogue comprises at least one Lys residue selected from the group consisting of: 292Lys, 293Lys, 294Lys, 300Lys, 303Lys, 305Lys, 306Lys, 309Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.
62. The EGF(A) peptide analogue according to any of the previous embodiments, wherein the peptide analogue comprises at least one Lys residue selected from the group consisting of: 292Lys, 293Lys, 294Lys, 300Lys, 303Lys, 305Lys, 306Lys, 311Lys, 312Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.
63. The EGF(A) peptide analogue according to any of the previous embodiments, wherein the peptide analogue comprises at least one Lys residue selected from the group consisting of: 292Lys, 293Lys, 294Lys, 300Lys, 303Lys, 305Lys, 306Lys, 311Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.
64. The EGF(A) peptide analogue according to any of the previous embodiments, wherein the peptide analogue comprises at least one Lys residue selected from the group consisting of: 313Lys, 324Lys, 328Lys and 333Lys.
65. The EGF(A) peptide analogue according to any of the previous embodiments, wherein the peptide analogue comprises two Lys residues selected from any of the groups defined in embodiments 59-65.
66. The EGF(A) peptide analogue according to any of the previous embodiments, wherein the peptide analogue comprises two Lys residues selected from the pairs consisting of:

| |
|---|
| i. 293K and 294K |
| ii. 293K and 312K |
| iii. 293K and 333K |
| iv. 309K and 313K |
| v. 309K and 324K |
| vi. 309K and 328K |
| vii. 309K and 332K |
| viii. 309K and 333K |
| ix. 311K and 313K |
| x. 312K and 333K |
| xi. 312K and 313K |
| xii. 312K and 314K |
| xiii. 313K and 314K |
| xiv. 313K and 321K |
| xv. 313K and 324K |
| xvi. 313K and 328K |
| xvii. 313K and 332K |
| xviii. 313K and 333K |
| xix. 314K and 333K |
| xx. 321K and 332K |
| xxi. 321K and 333K |
| xxii. 324K and 333K |
| xxiii. 324K and 328K |
| xxiv. 328K and 333K |
| xxv. 330K and 333K and |
| xxvi. 332K and 333K. |

67. The EGF(A) peptide analogue according to any of the previous embodiments, wherein the peptide analogue comprises an N-terminal or C-term truncation.
68. The EGF(A) peptide analogue according to any of the previous embodiments, wherein the peptide analogue comprises an N-terminal truncation of 1-10 amino acid residues.
69. The EGF(A) peptide analogue according to any of the previous embodiments, wherein the peptide analogue comprises an N-terminal truncation deleting at least or specifically amino acid 293Gly.
70. The EGF(A) peptide analogue according to any of the previous embodiments, wherein the peptide analogue comprises a C-terminal truncation of 1-2 amino acid residues.
71. The EGF(A) peptide analogue according to any of the previous embodiments, wherein the peptide analogue comprises a C-terminal truncation deleting at least or specifically amino acid 332Glu.
72. The EGF(A) peptide analogue according to any of the previous embodiments, wherein said peptide sequence is identified by any one of SEQ ID 2 to 106.
73. The EGF(A) peptide analogue according to any of the previous embodiments, wherein said peptide sequence is identified by any one of SEQ ID NO.: 2-47 and 49-106.
74. The EGF(A) peptide analogue according to any of the previous embodiments, wherein said peptide sequence is identified by any one of SEQ ID NO.: 2-44, 46, 47 and 49-106.
75. The EGF(A) peptide analogue according to any of the previous embodiments, wherein said peptide sequence is identified by any one of SEQ ID NO.: 2-44, 46, 47, 49-53, 55, 58-106.
76. The EGF(A) peptide analogue according to any of the previous embodiments, wherein said peptide sequence is identified by any one of SEQ ID NO.: 2-4, 6-44, 46, 47, 49-53, 55, 58-106.

77. The EGF(A) peptide analogue according to any of the previous embodiments, wherein said peptide sequence is identified by any one of SEQ ID NO.: 2-4, 6-19, 21-44, 46, 47, 49-53, 55, 58-106.
78. An EGF(A) derivative comprising an EGF(A) peptide analogue and a substituent.
79. The EGF(A) derivative according to embodiment 78, wherein the EGF(A) derivative comprise at least one substituent.
80. The EGF(A) derivative according to embodiment 78 or 79, wherein the substituent is a half-life extending substituent.
81. The EGF(A) derivative according to embodiment 78 or 80, wherein the EGF(A) peptide analogue is defined as in any of the above embodiments 1-77.
82. The EGF(A) derivative according to any of the embodiments 78-81, wherein one or two substituent(s) is/are attached to a nitrogen atom of the EGF(A) peptide analogue.
83. The EGF(A) derivative according to any of the embodiments 78-81, wherein one or two substituent(s) is/are attached to an amino group of the EGF(A) peptide.
84. The EGF(A) derivative according to any of the embodiments 78-81, wherein one or more substituent(s) is/are attached to the N-terminal amino acid of the EGF(A) peptide or to a Lys residue of the EGF(A) peptide
85. The EGF(A) derivative according to any of the embodiments 78-81, wherein one or two substituent(s) is/are attached to the N-terminal amino acid of the EGF(A) peptide.
86. The EGF(A) derivative according to any of the embodiments 78-81, wherein one or two substituent(s) is/are attached to the alpha-nitrogen of the N-terminal amino acid residue of the EGF(A) peptide.
87. The EGF(A) derivative according to any of the embodiments 78-81, wherein one or two substituent(s) is/are attached to a Lys residue in the EGF(A) peptide.
88. The EGF(A) derivative according to any of the embodiments 78-81, wherein one or two substituent(s) is/are attached to the epsilon-nitrogen of a Lys residue in the EGF(A) peptide.
89. The EGF(A) derivative according to any of the embodiments 78-81, wherein the EGF(A) derivative comprises two substituents.
90. The EGF(A) derivative according to embodiment 89, wherein the two substituents are identical.
91. The EGF(A) derivative according to embodiment 89, wherein the two substituents are attached to nitrogen atoms of the EGF(A) peptide analogue.
92. The EGF(A) derivative according to embodiment 89, wherein the two substituents are attached to amino groups of the EGF(A) peptide analogue.
93. The EGF(A) derivative according to embodiment 89, wherein the two substituents are attached to the N-terminal amino acid of the EGF(A) peptide and to a Lys residue of the EGF(A) peptide analogue.
94. The EGF(A) derivative according to embodiment 89, wherein one substituent is attached to the alpha-nitrogen of the N-terminal amino acid residue of the EGF(A) peptide analogue and one substituent is attach to a Lys residue of the EGF(A) peptide analogue.
95. The EGF(A) derivative according to embodiment 89, wherein the two substituents are attached to the N-terminal amino acid of the EGF(A) peptide analogue.
96. The EGF(A) derivative according to embodiment 89, wherein the two substituents are attached to Lys residues of the EGF(A) peptide analogue.
97. The EGF(A) derivative according to embodiment 89, wherein the two substituents are attached to the epsilon-nitrogen's of Lys residues in the EGF(A) peptide analogue.
98. The EGF(A) derivative according to any of the embodiment 78-97, wherein one or more substituent(s) is/are attached to a Lys residue in the EGF(A) peptide analogue selected from the group consisting of: 292Lys, 293Lys, 294Lys, 296Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
99. The EGF(A) derivative according to any of the embodiment 78-97, wherein one or more substituent(s) is/are attached to a Lys residue in the EGF(A) peptide analogue selected from the group consisting of: 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
100. The EGF(A) derivative according to any of the embodiment 78-97, wherein one or more substituent(s) is/are attached to a Lys residue in the EGF(A) peptide analogue selected from the group consisting of: 292Lys, 293Lys, 294Lys, 300Lys, 303Lys, 305Lys, 306Lys, 309Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.
101. The EGF(A) derivative according to any of the embodiment 78-100, wherein a substituent is attached to 312K in the EGF(A) peptide analogue.
102. The EGF(A) derivative according to any of the embodiment 78-100, wherein a substituent is attached to a substituted Lys residue in the EGF(A) peptide analogue.
103. The EGF(A) derivative according to embodiment 102, wherein the derivative comprises two substituents and one is attached to a substituted Lys residue and one is attached to 312K in the EGF(A) peptide analogue.
104. The EGF(A) derivative according to any of the embodiment 102 and 103, wherein the derivative comprises two substituents and both are attached to substituted Lys residues in the EGF(A) peptide analogue.
105. The EGF(A) derivative according to any of the embodiments 102-104, wherein one or two substituents is/are attached to a substituted Lys residue in the EGF(A) peptide analogue selected from the group consisting of: 292Lys, 293Lys, 294Lys, 296Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
106. The EGF(A) derivative according to any of the embodiment 102-104, wherein one or two substituents is/are attached to a substituted Lys residue in the EGF(A) peptide analogue selected from the group consisting of: 292Lys, 293Lys, 294Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.
107. The EGF(A) derivative according to any of the embodiment 102-104, wherein one or two substituents is/are attached to a substituted Lys residue in the EGF(A) peptide analogue selected from the group consisting of: 292Lys, 293Lys, 294Lys, 300Lys, 303Lys, 305Lys, 306Lys, 309Lys, 311Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

108. The EGF(A) derivative according to any of the embodiment 102-104, wherein one or two substituents is/are attached to a substituted Lys residue in the EGF(A) peptide analogue selected from the group consisting of: 313Lys, 324Lys, 328Lys and 333Lys.

109. The EGF(A) derivative according to any of the embodiment 78-107, wherein a substituent is not attached to the EGF(A) peptide analogue via an amino acid residue in any of the positions 295, 298, 301, 302, 307 and 310.

110. The EGF(A) derivative according to any of the embodiment 78-107, wherein a substituent is not attached to the EGF(A) peptide analogue via an amino acid residue in any the positions 295, 296, 298, 301, 302, 307, 310.

111. The EGF(A) derivative according to any of the embodiments 78-110, wherein the substituent is not an Fc domain.

112. The EGF(A) derivative according to any of the embodiments 78-110, wherein the substituent is not fused with the EGF (A) peptide.

113. The EGF(A) derivative according to any of the embodiment 78-112, wherein the substituent comprises at least one fatty acid group.

114. The EGF(A) derivative according to embodiment 113, wherein said fatty acid group is a chemical group comprising at least one functional group (FG) with a pKa<7 and a carbon chain which contains at least 8 consecutive —$CH_2$— groups.

115. The EGF(A) derivative according to embodiment 113, wherein said fatty acid group comprise a functional group selected from a carboxylic acid, a sulphonic acid, a tetrazole moiety, a methylsulfonylcarbamoylamino moiety or a 3-hydroxy-isoxazole moiety.

116. The EGF(A) derivative according to embodiment 113, wherein said substituent comprises a carboxylic acid, a sulphonic acid, a tetrazole moiety, a methylsulfonylcarbamoylamino moiety or a hydroxyisoxazole3-hydroxy-isoxazole moiety including 8-20 consecutive —$CH_2$— groups.

117. The EGF(A) derivative according to embodiment 113, wherein said substituent has Formula I:

$$Z_1-Z_2-Z_3-Z_4-Z_5-Z_6-Z_7-Z_8-Z_9-Z_{10}- \quad [I]$$

wherein
$Z_1$ is selected from:
Chem. 1: $HOOC-(CH_2)_n-CO-$*,
Chem. 2: tetrazolyl-$(CH_2)_n-CO-$*,
Chem. 3: $HOOC-(C_6H_4)-O-(CH_2)_m-CO-$*,
Chem. 4: $HOS(O)_2-(CH_2)_n-CO-$*,
Chem. 5: $MeS(O)_2NH(CO)NH-(CH_2)_n-CO-$* and
Chem. 6: 3-HO-Isoxazole-$(CH_2)_n-CO-$*
wherein
n is an integer in the range of 8-20,
m is an integer in the range of 8-11,
the —COOH group in Chem. 3 can be attached to position 2, 3 or 4 on the phenyl ring,
the symbol * indicates the attachment point to the nitrogen in $Z_2$ or, if $Z_2$ is a bond, to the nitrogen on the neighbouring Z element;

$Z_2$ is selected from
Chem. 7: *—$NH-SO_2-(CH_2)_3-CO-$*,
Chem. 8: *—$NH-CH_2-(C_6H_{10})-CO-$* and
a bond;

$Z_3$ is selected from:
γGlu, Glu and a bond;

$Z_4, Z_5, Z_6, Z_7, Z_8, Z_9$ are selected, independently of each other, from:
Glu, γGlu, Gly, Ser, Ala, Thr, Ado, Aeep, Aeeep, TtdSuc and a bond;

$Z_{10}$ is selected from:
Chem. 7: *—$NH-CH_2-(C_6H_4)-CH_2-$* and a bond.

118. The EGF(A) derivative according to embodiment 117, wherein
γGlu is of formula Chem. 9: *$NH-CH(COOH)-(CH_2)_2-CO-$*,
TtdSuc is of formula Chem. 10: *$NH-CH_2CH_2CH_2OCH_2CH_2OCH_2CH_2OCH_2CH_2CH_2NHCO$*,
Ado is of formula Chem. 11: *$NH-(CH_2)_2-O-(CH_2)_2-O-CH_2-CO-$*,
Aeep is of formula Chem. 12 *$NH-CH_2CH_2OCH_2CH_2OCH_2CH_2CO$*, and
Aeeep is of formula Chem. 13 *$NH-CH_2CH_2OCH_2CH_2OCH_2CH_2OCH_2CH_2CO$*.

119. The EGF(A) derivative according to embodiment 117, wherein said substituent has Formula I:

$$Z_1-Z_2-Z_3-Z_4-Z_5-Z_6-Z_7-Z_8-Z_9-Z_{10}- \quad [I]$$

wherein
$Z_1$ is selected from
Chem. 1 b:

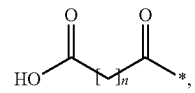

Chem. 2b:

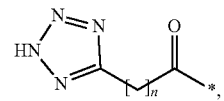

Chem. 3b:

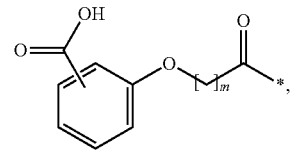

Chem. 4b:

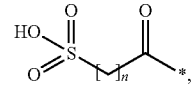

Chem. 5b

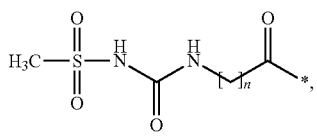

and
Chem 6b

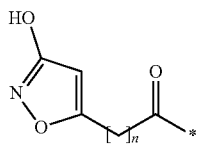

wherein
n in Chem. 1b, 2b, 4b, 5b or 6b is an integer in the range of 8-20,
m in Chem. 3b is an integer in the range of 8-11, the —COOH group in Chem. 3b can be attached to position 2, 3 or 4 on the phenyl ring,
the symbol * indicates the attachment point to the nitrogen in $Z_2$ or, if $Z_2$ is a bond, to the nitrogen on the neighbouring Z element;
$Z_2$ is selected from
Chem. 7b:

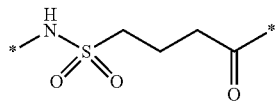

Chem. 8b:

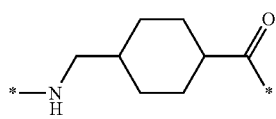

and
a bond;
$Z_3$ is selected from
γGlu, Glu, and a bond;
$Z_4$, $Z_5$, $Z_6$, $Z_7$, $Z_8$, $Z_9$ are selected, independently of each other, from:
Glu, γGlu, Gly, Ser, Ala, Thr, Ado, TtdSuc and a bond;
$Z_{10}$ is selected from Chem. 14b

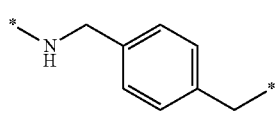

and a bond;
provided that
when $Z_{10}$ is Chem. 14b, said substituent is attached to the alpha-nitrogen of the N-terminal amino group of said peptide; and when $Z_{10}$ is a bond, said substituent is attached to the epsilon position of a Lys residue present in said peptide or to the alpha-nitrogen of the N-terminal amino acid residue of said peptide.

120. The EGF(A) derivative according to embodiment 117, wherein $Z_1$ is formula Chem. 1b:

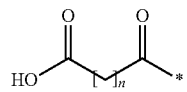

and wherein n is an integer in the range of 8-20.

121. A compound according to any of embodiments 117, wherein $Z_1$ is formula Chem. 2b:

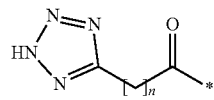

and wherein n is an integer in the range of 8-20.

122. The EGF(A) derivative according to embodiment 117, wherein $Z_1$ is formula Chem. 4b:

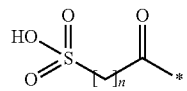

and wherein n is an integer in the range of 8-20.

123. The EGF(A) derivative according to embodiment 117, wherein $Z_1$ is formula Chem. 5b:

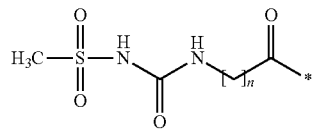

and wherein n is an integer in the range of 8-20.

124. The EGF(A) derivative according to embodiment 117, wherein $Z_1$ is formula Chem. 6b:

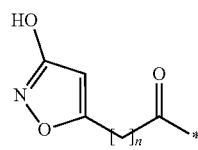

and wherein n is an integer in the range of 8-20.

125. The EGF(A) derivative according to embodiment 117, wherein $Z_1$ is formula Chem. 3b:

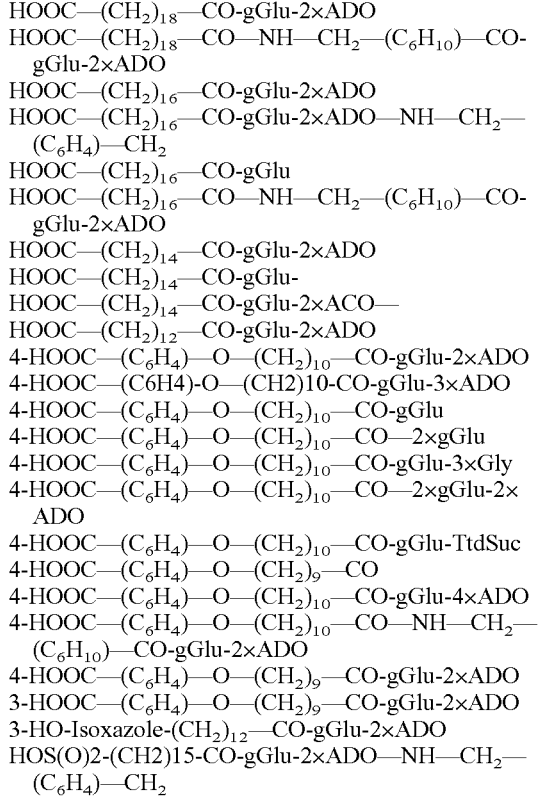

and wherein m is an integer in the range of 8-11.
126. The EGF(A) derivative according to embodiment 125, wherein m is 8, 9, 10 or 11.
127. The EGF(A) derivative according to embodiment 125, wherein m is 10 or 11.
128. The EGF(A) derivative according to any of the embodiments 120-124, wherein n is in the range of 10-18, 10-14, 15-18, 8-15 or 16-20.
129. The EGF(A) derivative according to any of the embodiments 120-124, wherein n is 8, 9, 10, 11 or 12.
130. The EGF(A) derivative according to any of the embodiments 120-124, wherein n is 13, 14, 15 or 16.
131. The EGF(A) derivative according to any of the embodiments 120-124, wherein n is 14, 15, 16, 17 or 18.
132. The EGF(A) derivative according to any of the embodiments 120-124, wherein n is 17, 18, 19 or 20.
133. The EGF(A) derivative according to any of the embodiments 117 and 132, wherein $Z_2$ is Chem. 7 or Chem. 7b and $Z_3$ is selected from γGlu, Glu and a bond.
134. The EGF(A) derivative according to any of the embodiments 117 and 132, wherein $Z_2$ is Chem. 8 or Chem. 8b and $Z_3$ is selected from γGlu and Glu.
135. The EGF(A) derivative according to any of the embodiments 117 and 134, wherein the derivative has one or two substituents selected from the group consisting of:
HOOC—$(CH_2)_{18}$—CO-gGlu-2×ADO
HOOC—$(CH_2)_{18}$—CO—NH—$CH_2$—$(C_6H_{10})$—CO-gGlu-2×ADO
HOOC—$(CH_2)_{16}$—CO-gGlu-2×ADO
HOOC—$(CH_2)_{16}$—CO-gGlu-2×ADO—NH—$CH_2$—$(C_6H_4)$—$CH_2$
HOOC—$(CH_2)_{16}$—CO-gGlu
HOOC—$(CH_2)_{16}$—CO—NH—$CH_2$—$(C_6H_{10})$—CO-gGlu-2×ADO
HOOC—$(CH_2)_{14}$—CO-gGlu-2×ADO
HOOC—$(CH_2)_{14}$—CO-gGlu-
HOOC—$(CH_2)_{14}$—CO-gGlu-2×ACO—
HOOC—$(CH_2)_{12}$—CO-gGlu-2×ADO
4-HOOC—$(C_6H_4)$—O—$(CH_2)_{10}$—CO-gGlu-2×ADO
4-HOOC—(C6H4)-O—(CH2)10-CO-gGlu-3×ADO
4-HOOC—$(C_6H_4)$—O—$(CH_2)_{10}$—CO-gGlu
4-HOOC—$(C_6H_4)$—O—$(CH_2)_{10}$—CO—2×gGlu
4-HOOC—$(C_6H_4)$—O—$(CH_2)_{10}$—CO-gGlu-3×Gly
4-HOOC—$(C_6H_4)$—O—$(CH_2)_{10}$—CO—2×gGlu-2×ADO
4-HOOC—$(C_6H_4)$—O—$(CH_2)_{10}$—CO-gGlu-TtdSuc
4-HOOC—$(C_6H_4)$—O—$(CH_2)_9$—CO
4-HOOC—$(C_6H_4)$—O—$(CH_2)_{10}$—CO-gGlu-4×ADO
4-HOOC—$(C_6H_4)$—O—$(CH_2)_{10}$—CO—NH—$CH_2$—$(C_6H_{10})$—CO-gGlu-2×ADO
4-HOOC—$(C_6H_4)$—O—$(CH_2)_9$—CO-gGlu-2×ADO
3-HOOC—$(C_6H_4)$—O—$(CH_2)_9$—CO-gGlu-2×ADO
3-HO-Isoxazole-$(CH_2)_{12}$—CO-gGlu-2×ADO
HOS(O)2-(CH2)15-CO-gGlu-2×ADO—NH—$CH_2$—$(C_6H_4)$—$CH_2$
HOS(O)$_2$—$(CH_2)_{13}$—CO-gGlu-2×ADO
Tetrazolyl-$(CH_2)_{15}$—CO—NH—$SO_2$—$(CH_2)_3$—CO-ADO-ADO—NH—$CH_2$—$(C_6H_4)$—$CH_2$
Tetrazolyl-$(CH_2)_{12}$—CO-gGlu-2×ADO
Tetrazolyl-$(CH_2)_{15}$—CO-gGlu-2×ADO and
MeS(O)$_2$NH(CO)NH—$(CH_2)_{12}$—CO-gGlu-2×ADO.
136. The EGF(A) derivative according to embodiment 78, wherein the EGF(A) derivative is selected from the group of EGF(A) derivatives consisting of: Example compounds 1-47, 51-102 and 106-159.
137. The EGF(A) derivative according to embodiment 78 wherein the EGF(A) derivative is selected from the group of EGF(A) derivatives consisting of: Example compounds 1-44, 46-47, 51-55, 57, 60-64, 66-69, 71-102 and 106-159.
138. The EGF(A) derivative according to embodiment 78, wherein the EGF(A) derivative is selected from the group of EGF(A) derivatives consisting of: the Example compounds 31, 95, 128, 133, 143, 144, 150, 151, 152 and 153.
139. The EGF(A) derivative according to embodiment 78, wherein the EGF(A) derivative is individually selected from the group of EGF(A) derivatives consisting of: the Examples 1-47, 51-102 and 106-159.
140. The EGF(A) peptide analogue or EGF(A) derivative according to any of the previous embodiments wherein the peptide or derivative is a PCSK9 inhibitor.
141. The EGF(A) peptide analogue or EGF(A) derivative according to Embodiment 135, wherein the PCSK9 inhibitor is a capable of inhibiting PCSK9 binding to human Low Density Lipoprotein Receptor (LDL-R).
142. The EGF(A) peptide analogue or EGF(A) derivative according to Embodiment 135, wherein the PCSK9 inhibitor decreases PCSK9 binding to human Low Density Lipoprotein Receptor (LDL-R).
143. The EGF(A) peptide analogue or EGF(A) derivative according to Embodiment 135, wherein the PCSK9 inhibitor has an apparent binding affinity ($K_i$) below 10 nM, such as below 8 nM, 6 nM, 5 nM, 4 nM, 3 nM or such as below 2 nM as measured in a competitive ELISA.
144. The EGF(A) peptide analogue or EGF(A) derivative according to Embodiment 135, wherein the PCSK9 inhibitor has an apparant binding affinity ($K_i$) below 10 nM, such as below 8 nM, 6 nM, 5 μM, 4 nM, 3 nM or such as below 2 nM as measured in the competitive ELISA described in D1.1.
145. The EGF(A) derivative according to any of the above embodiments, wherein the derivative has a half-life above 6 hours, such as 8 hours or such as 10 hours in mice. The EGF(A) derivative according to any of the above embodiments, wherein the derivative has a half-life above 50 hours, such as 100 hours or such as 150 hours in dogs.
146. A EGF(A) peptide analogue or EGF(A) derivative according to any of the previous embodiments 1-145 for use as a medicament.
147. A EGF(A) peptide analogue or EGF(A) derivative according to any of the previous embodiments 1-145 for use in a method of treatment.
148. A EGF(A) peptide analogue or EGF(A) derivative according to any of the previous embodiments 1-145 for use in a method of prevention or treatment of a cardio-vascular disease.
149. A EGF(A) peptide analogue or EGF(A) derivative according to any of the previous embodiments 1-145 for use in a method for improving lipid parameters.
150. A EGF(A) peptide analogue or EGF(A) derivative according to any of the previous embodiments 1-145 for use in a method of treatment for i. improving lipid parameters, such as prevention and/or treatment of dyslipidemia, lowering total serum lipids, increasing HDL-C, lowering LDL-C, lowering small, dense LDL-C, lowering VLDL-C, lowering triglycerides, lowering cholesterol, lowering plasma levels of lipoprotein a (Lp(a)) or inhibiting generation of apolipoprotein A (apo(A));

ii. prevention and/or treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; the treatment of cardiovascular disease.

151. Use of EGF(A) peptide analogue or EGF(A) derivative according to any of the previous embodiments 1-145 for
   i. improving lipid parameters, such as prevention and/or treatment of dyslipidemia, lowering total serum lipids, increasing HDL, lowering LDL-C, lowering small dense LDL-C, lowering VLDL-C, non-HDL-C, lowering triglycerides, lowering cholesterol, lowering plasma levels of lipoprotein a (Lp(a)), inhibiting generation of apolipoprotein A (apo(A));
   ii. prevention and/or treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; the treatment of cardiovascular disease.

152. A pharmaceutical composition comprising a EGF(A) peptide analogue or EGF(A) derivative according to any of the previous embodiments, and a pharmaceutically acceptable excipient.

153. A pharmaceutical composition according to embodiment 152 for subcutaneous administration.

154. A pharmaceutical composition according to embodiment 152 for oral administration.

155. A method for improving lipid parameters comprising a step of administering a pharmaceutically active amount of a EGF(A) peptide analogue or EGF(A) derivative according to any of the previous embodiments 1-145.

156. A method for improving lipid parameters comprising a step of administering a pharmaceutically active amount of a EGF(A) peptide analogue or EGF(A) derivative according to any of the previous embodiments 1-145 wherein improving lipid parameters, is such as prevention and/or treatment of dyslipidemia, lowering total serum lipids; increasing HDL; lowering LDL-C; lowering small, dense LDL-C; lowering VLDL-C; non_HDL-C; lowering triglycerides; lowering cholesterol; lowering plasma levels of lipoprotein a (Lp(a)); inhibiting generation of apolipoprotein A (apo(A)).

157. A method for prevention and/or treatment of a cardiovascular disease comprising a step of administering a pharmaceutically active amount of a EGF(A) peptide analogue or EGF(A) derivative according to any of the previous embodiments 1-145.

158. A method for prevention and/or treatment of a cardiovascular disease comprising a step of administering a pharmaceutically active amount of a EGF(A) peptide analogue or EGF(A) derivative according to any of the previous embodiments 1-145 wherein a cardiovascular disease is such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure.

159. A methods for producing a EGF(A) peptide analogue or EGF(A) derivative according to any of the previous embodiments 1-145, wherein the EGF(A) peptide is produce recombinantly and optionally linked with a substituent.

EXAMPLES

This experimental part starts with a list of abbreviations, and is followed by a section including general methods for synthesising and characterising analogues and derivatives of the invention. Then follows a number of examples which relate to the preparation of specific EGF(A) compounds of the invention, including analogues and derivatives, and at the end a number of examples have been included relating to the activity and properties of these compounds (section headed pharmacological methods).

The examples serve to illustrate the invention.

List of Abbreviations

AcOH: acetic acid
Ado: 8-amino-3,6-dioxaoctanoic acid
Aeep: 9-Amino-4,7-Dioxanonanoic acid
Aeeep: 12-Amino-4,7,10-trioxa-dodecanoic acid
Alloc: Allyloxycarbonyl
API: Active Pharmaceutical Ingredient
AUC: Area Under the Curve
BG: Blood Glucose
Boc: t-butyloxycarbonyl
BSA: Bovine serum albumin
Clt: 2-chlorotrityl
collidine: 2,4,6-trimethylpyridine
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
EGF: Epidermal growth factor-like
EGF(A): Epidermal growth factor-like domain A
F (table 5): Bio-availability Fmoc: 9-fluorenylmethyloxycarbonyl
HDL: High density lipoprotein
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
hPCKS9: human PCSK9
HPLC: High Performance Liquid Chromatography
HSA: Human Serum Albumin
$IC_{50}$: half maximum inhibitory concentration
Inp: isonipecotic acid
i.v. intravenously
ivDde: 1-(4,4-dimethyl-2,6-dioxocyclohexylidene)-3-methylbutyl
LCMS: Liquid Chromatography Mass Spectroscopy
LDL-R or LDLr: LDL receptor
LDL: low density lipoprotein
LDL-C: LDL cholesterol
MeOH: methanol
Mmt: 4-methoxytrityl
Mtt: 4-methyltrityl
MRT: Mean residence time
MSU: Methylsulfonylcarbamoylamino
NMP: N-methyl pyrrolidone
OBz: benzoyl ester
Ado: 8-amino-3,6-dioxaoctanoic acid
OSu: O-succinimidyl esters (hydroxysuccinimide esters)
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
PK: Pharmacokinetic
QC: Quality control
RP: Reverse Phase
RP-HPLC: Reverse Phase High Performance Liquid Chromatography
RT: Room Temperature
Rt: Retention time
s.c.: Subcutaneously
SD: Standard Deviation
SEM: Standard Error of Mean
SPPS: Solid Phase Peptide Synthesis
tBu: tert. butyl
TFA: trifluoroacetic acid
TIS or TIPS: triisopropylsilane
Tmax: time to reach Cmax
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography
TBS-T: Tris buffered saline
Chemical Methods This section is divided in three: Section A relating to general methods of preparation of compounds of the invention, section B relating to the preparation of a number of specific compounds of the invention, and section C relating to methods of detection and characterisation of compounds of the invention and the results for a number of specific example compounds.

A. Methods of Preparation

The compounds of the invention may be prepared by the method described below.

Preparation of the Peptide, i.e. the EGF(A) Peptide of SEQ ID NO: 1 or Analogues Thereof: SPPS General Methods:

The Fmoc-protected amino acids to be used may be the standard recommended: Fmoc-Ala-OH, Fmoc-Arg(Pbf)-OH, Fmoc-Asn(Trt)-OH, Fmoc-Asp(OtBu)-OH, Fmoc-Cys (Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH or Fmoc-Lys(Alloc)-OH supplied from e.g. Anaspec, Bachem, Iris Biotech or NovabioChem. SPPS may be performed using Fmoc based chemistry on a Prelude Solid Phase Peptide Synthesizer from Protein Technologies (Tucson, Ariz. 85714 U.S.A.). A suitable resin for the preparation of C-terminal carboxylic acids is a Wang resin preloaded with an amino acid such as Fmoc-Glu(tBu)-Wang resin (Low Load, 0.35 mmol/g). In cases where the substituent is attached to a C-terminal lysine, a suitable resin is a pre-loaded Fmoc-Lys(Mtt)-Wang. A suitable resin for the preparation of C-terminal peptide amides is H-Rink Amide-ChemMatrix resin (loading e.g. 0.52 nmol/g) or Rink Amide AM polystyrene resin (Novabiochem, loading e.g. 0.62 mmol/g) or the like. Fmoc-deprotection is achieved with 20% piperidine in NMP. Peptide couplings are performed by using either DIC/HOAt/collidine or DIC/Oxyma Pure with or without collidine with or without preactivation or using DEPBt (3-(diethoxyphosphoryloxy)-1,2,3-benzotriazin-4(3H)-one)/DIPEA for suppression of epimization of eg. His during coupling. Amino acid/HOAt or amino acid/Oxyma Pure solutions (0.3 M/0.3 M in NMP at a molar excess of 3-10 fold) are added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/mL, 0.05 mmol/1.5 mL, 0.10 mmol/3.0 mL, 0.25 mmol/7.5 mL.

If Fmoc-Lys(Mtt)-OH is used, the Mtt group may be removed by washing the resin with HFIP/DCM (75:25) (2×2 min), washing with DCM and suspending the resin in HFIP/DCM (75:25)(2×20 min) and subsequent washing before the substituent can be introduced at the epsilon-position of the lysine moiety.

If Fmoc-Lys(Alloc)-OH is used, the Alloc group may be removed by treating the resin with Pd(PPh$_3$)$_4$ (0.02 equiv) in the presence of one or more scavengers in combination, e.g. morpholine (6.0 equiv) and/or dimethyl borane complex (18.0 equiv) (30 min). The resin is then washed with MeOH, NMP or DMF and IPA (isopropyl alcohol), respectively, before the substituent can be introduced at the epsilon-position of the lysine moiety.

Attachment of the Substituent (Acylation)

The substituent can be introduced in a stepwise procedure by the Prelude peptide synthesizer as described above using suitably protected building blocks, such as the standard amino acids described above, Fmoc-8-amino-3,6-dioxaoctanoic acid or Fmoc-Glu-OtBu. Introduction of the substituent can be achieved using a building block, such as, but not limited to, octadecanedioic acid mono-tert-butyl-ester. After each coupling step, unreacted peptide intermediate can be capped using acetic acid anhydride and collidine in excess (>10 eq.).

The introduction of a substituent on the epsilon-nitrogen of a lysine is achieved using a lysine protected with Mtt (Fmoc-Lys(Mtt)-OH), Alloc (Fmoc-Lys(Alloc)-OH) or an ivDde group (Fmoc-Lys(ivDde)-OH). The incorporation of γGlu moieties in the substituent may be achieved by coupling with the amino acid Fmoc-Glu-OtBu.

Introduction of each moiety in the substituent can be achieved using prolonged coupling time (1×6 hours) followed by capping with acetic anhydride or alternatively acetic acid/DIC/HOAt/collidine.

Cleavage from the Resin

After synthesis the resin is washed with DCM, and the peptide is cleaved from the resin by a 2-3 hour treatment with TFA/TIPS/water (95/2.5/2.5) or TFA/EDT (1,2-ethanedithiol)/water (90/5/5) followed by precipitation with $Et_2O$ (diethyl ether). The precipitate is washed with $Et_2O$.

Oxidative Folding

The precipitate from the step above is dissolved in DMSO and added to a solution consisting of:
50 mM TRIS
5 mM $CaCl_2$
3 mM Cysteine
0.3 mM Cystine
in MQ water, pH 8 to 8.8

The reaction mixture is kept overnight at room temperature or until LCMS shows complete reaction.

Purification and Quantification

The crude peptide (derivative) is acidified with TFA to pH 2-3 and purified by reversed-phase preparative HPLC (Waters Deltaprep 4000 or Gilson) on a column comprising C8- or C18-silica gel. Elution is performed with an increasing gradient of MeCN in water comprising 0.1% TFA. Relevant fractions are checked by analytical HPLC or UPLC. Fractions comprising the pure target peptide derivative are mixed. An additional purification step may be introduced using another gradient, e.g. containing 0.05M $NH_4HCO_3$. The resulting solution is analyzed (HPLC, LCMS) and the product (i.e. the derivative) is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Attachment of the Substituent (Reductive Alkylation)

The purified peptide analogue can be subjected to reductive alkylation using a suitable albumin binding substituent derivatized with an aldehyde functionality.

The peptide analogue is dissolved in citric acid pH=5.5 and a suitable aldehyde is dissolved in water that may contain cyclodextrin to increase the solubility. A reducing agent such as borane pyridine complex dissolved in MeOH is added and the mixture is gently shaken overnight. Subsequent addition of excess of the aldehyde and reducing agent may be required for optimal yield. The mixture is purified using the procedure described above.

B. Synthesis of Compounds of the Invention

The compounds of the invention were prepared by a method not essentially different from the general methods described below.

Method A

Synthesis of LDL-R(293-332) Peptide Analogues (without Substituent)

The Fmoc-protected amino acids used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, BOC-Lys(Fmoc)-OH Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH supplied from e.g. Anaspec, Bachem, Iris Biotech or NovabioChem. SPPS was performed using Fmoc based chemistry on a Prelude Solid Phase Peptide Synthesizer from Protein Technologies (Tucson, Ariz. 85714 U.S.A.). A Wang resin preloaded with an amino acid such as Fmoc-Glu(tBu)-Wang resin (Low Load, 0.35 mmol/g) or the like was used. Fmoc-deprotection was achieved with 20% piperidine in NMP. Peptide couplings were performed by using DIC/Oxyma Pure with collidine. Amino acid/Oxyma Pure solutions (0.3 M/0.3 M in DMF at a molar excess of 3-10 fold) was added to the resin followed by the same molar equivalent of DIC (3 M in NMP) followed by collidine (3 M in NMP).

Cleavage from the Resin

After synthesis the resin was washed with DCM, and the peptide was cleaved from the resin by a 2-3 hour treatment with TFA/TIPS/DTT/water (92.5/2.5/2.5/2.5) followed by precipitation with diethyl ether. The precipitate was subsequently washed with diethyl ether.

Oxidative Folding

The precipitate from the step above was dissolved in DMSO and added to a solution consisting of:
50 mM TRIS
5 mM $CaCl_2$
3 mM Cysteine
0.3 mM Cystine
in MQ water, pH 8.0 to 8.8

The reaction mixture was kept overnight at room temperature or until LCMS showed complete reaction.

Purification and Quantification

The crude peptide was acidified with TFA to pH 2-3 and purified by reversed-phase preparative HPLC (Waters Deltaprep 4000 or Gilson) on a column comprising C8- or C18-silica gel. Elution was performed with an increasing gradient of MeCN in water comprising 0.1% TFA. Relevant fractions were analyzed using UPLC. Fractions comprising the pure target peptide were pooled. The resulting solution was analyzed (UPLC, LCMS) and the peptide derivative was quantified using a chemiluminescent nitrogen specific HPLC detector (Antek 8060 HPLC-CLND) or by measuring UV-absorption at 280 nm. The product was dispensed into glass vials. The vials were capped with Millipore glassfibre prefilters. Freeze-drying afforded the trifluoroacetate salt of the peptide as a white solid.

Method B

Synthesis of Derivatives of LDL-R(293-332) EGF(A) Analogues (with Substituent) (on Resin)

Synthesis of the resin bound EGF(A) peptide proceded as described above.

The introduction of a substituent on the epsilon-nitrogen of a lysine in the N-terminus of the sequence was achieved using Boc-Lys(Fmoc)-OH. Introduction of the substituent at the alpha-position of the N-terminal amino acid was accomplished using a standard Fmoc-protected amino acid i.e. Fmoc-Gly-OH.

For the introduction of a substituent on the epsilon-nitrogen of a lysine in other positions, Fmoc-Lys(Mtt)-OH were used. The Mtt group was removed by treatment with HFIP/DCM (75:25) (2×2 min), followed by a wash with DCM. The resin was then resuspended in HFIP/DCM (75:25)(2×20 min or 2×30 min) and subsequently washed with DCM before the substituent was introduced at the epsilon-position of the lysine moiety.

The moieties of the substituent were introduced in a stepwise procedure by a Prelude peptide synthesizer as described under method A, using suitably protected building blocks, such as the standard Fmoc-protected amino acids described under method A, Fmoc-8-amino-3,6-dioxaoctanoic acid or Fmoc-Glu-OtBu. Introduction of the fatty acid group was achieved using the suitable building block, such as but not limited to, octadecanedioic acid mono-tert-butylester. In some cases the coupling time was increased or the coupling step for each building block was repeated.

Cleavage, oxidative folding, purification and quantification were performed as described under method A.

Method C
Attachment of the Substituent in Solution (Via Reductive Alkylation)

The purified peptide obtained from method A was subjected to reductive alkylation using a suitable substituent derivatized with an aldehyde functionality.

The freeze-dried peptide powder was dissolved in a citric acid buffer (40 mM, pH 5.55; peptide concentration: 4 mg/mL). A solution comprising, the selected substituent (10 eq., 10 mg/mL) in 40% (w/v) aqueous cyclodextrin was added to the peptide solution and gently mixed by inversion of the reaction vial. To this solution was added borane pyridine complex (100 eq., 80 mg/mL solution in MeOH) in small aliquots, followed by gentle inversion of the reaction vial. The reaction solution was gently shaken at room temperature overnight. The progress of the reaction was monitored by LC-MS. The next morning, the reaction solution was acidified to pH 2-3 using TFA and purified using the procedure described above under method A.

Method D
Attachment of the Substituent (N-Terminal Acylation of the Folded Peptide in Solution)

The freeze-dried peptide powder was dissolved in $K_2HPO_4$ buffer (20 mM, pH 8.15) to a target concentration of 5 mg/mL. A solution of 18-[[(1S)-1-carboxy-4-[2-[2-[2-[2-[2-[2-(2,5-dioxopyrrolidin-1-yl)oxy-2-oxo-ethoxy]ethoxy]ethylamino]-2-oxo-ethoxy]ethoxy]ethylamino]-4-oxo-butyl]amino]-18-oxo-octadecanoic acid in DMSO (4 eq.; 4 mg/mL) was added in four aliquots. After addition of each aliquot the peptide solution was gently mixed by inversion of the reaction vial. Subsequently, the pH value of the reaction solution was measured and adjusted to pH 8.0-8.3 by adding small portions of N,N-diisopropylethylamine, after which the solution was left standing at room temperature. The progression of the reaction was followed by LC-MS. After three hours the solution was acidified to pH 5.9 with TFA and purified using the procedure described above.

B.1. Synthesis of Protractors and Linker Elements

For synthesis of octadecanedioic acid mono-tert-butyl ester: see patent application WO 2010102886. The corresponding mono-tert-bytyl esters of C14-, C16- and C20 diacid can be prepared accordingly. For synthesis of 14-sulfo-hexadecanoic acid og 16-sulfo-hexadecanoic acid sulfonsyre see WO2015071355. For synthesis of 16-(1H-tetrazol-5-yl)hexadecanoic acid and 13-(1H-tetrazol-5-yl)hexadecanoic acid see WO2006005667.

13-(methylsulfonylcarbamoylamino)tridecanoic acid

Chem. 6—OH, wherein n=12:

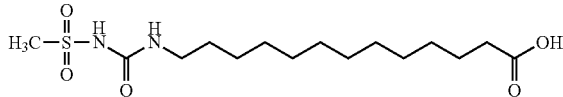

This molecule was made using a modified procedure from Luckhurst et al. Tetrahedron Letters Volume 48, Issue 50, 2007, Pages 8878-8882 http://dx.doi.org/10.1016/j.tetlet.2007.10.046

Triethylamine (4.46 mL, 32.0 mmol) and ethyl chloroformate (3.05 mL, 32.0 mmol) were subsequently added to a solution of the 14-(tert-butoxy)-14-oxotetradecanoic acid (1, C14(OtBu)-OH, 6.29 g, 20.0 mmol) in acetone (176 mL) at 0° C. After 30 minutes at 0° C., a solution of sodium azide (2.60 g, 40.0 mmol) in water (12 mL) was added and the mixture was stirred for 2 hours at 0° C. The mixture was concentrated in vacuo (at 30° C.) and poured into water with ice (300 mL). The resulting mixture was extracted with ethyl acetate (3×250 mL); the organic extracts were combined and washed with water (200 mL), 10% aqueous solution of sodium hydrogencarbonate (200 mL) and water (200 mL); dried over anhydrous magnesium sulfate and evaporated to dryness to give mixture of tert-butyl 14-azido-14-oxotetradecanoate and tert-butyl 14-isocyanato-14-oxotetradecanoate as pale yellow oil.

Methanesulfonamide (1.52 g, 16.0 mmol), potassium carbonate (6.63 g, 48.0 mmol) were added to a solution of mixture tert-butyl 14-azido-14-oxotetradecanoate and tert-butyl 14-isocyanato-14-oxotetradecanoate (5.43 g, 16.0 mmol) in dry toluene (50 mL). The reaction mixture was heated at 85° C. overnight. Water (100 mL) was added followed by 1 M aqueous hydrochloric acid (pH was adjusted to pH=4). The mixture was extracted with diethyl ether (4×150 mL), dried over anhydrous magnesium sulfate and evaporated in vacuo to give tert-butyl 13-(3-(methylsulfonyl)ureido)tridecanoate.

1H NMR spectrum (300 MHz, DMSO, dH): 10.01 (s, 1H); 6.42 (t, J=4.7 Hz, 1H); 3.20 (s, 3H); 3.02 (q, J=6.7 Hz, 2H); 2.16 (t, J=7.3 Hz, 2H); 1.52-1.33 (m, 13H); 1.30-1.11 (m, 16H).

Trifluoroacetic acid (21.0 mL) and water (2.50 mL) were added dropwise to a solution of tert-butyl 13-(3-(methylsulfonyl)ureido)tridecanoate (3, 6.30 g, 15.5 mmol) in dichloromethane (30 mL). Reaction mixture was stirred for 3 hours at room temperature. The solvent was evaporated under reduced pressure, affording 13-(3-(methylsulfonyl)ureido)tridecanoic acid.

1H NMR spectrum (300 MHz, DMSO, dH): 10.02 (s, 1H); 6.43 (t, J=4.5 Hz, 1H); 3.20 (s, 3H); 3.02 (q, J=6.6 Hz, 2H); 2.18 (t, J=7.3 Hz, 2H); 1.56-1.33 (m, 4H); 1.24 (s, 16H).

13-(3-Hydroxyisoxazol-5-yl)tridecanoic acid

Chem. 5—OH, wherein n=12:

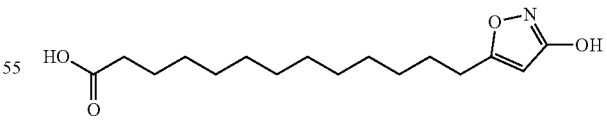

This molecule was made using a modified procedure from Sorensen et al. J. Org. Chem., 2000, 65 (4), pp 1003-1007. DOI: 10.1021/jo991409d 14-(tert-Butoxy)-14-oxotetradecanoic acid (1, 30.0 g, 95.4 mmol), N,N'-dicyclohexylcarbodiimide (43.3 g, 209 mmol) and 4-dimethylaminopyridine (25.6 g, 20.9 mmol) were dissolved in anhydrous dichloromethane (700 mL) and 2,2-dimethyl-1,3-dioxane-4,6-dione (2, 20.6 g, 143 mmol) was added to the solution. The reaction mixture was stirred at room temperature for 16 hours. Volatiles were then evaporated and the mixture was diluted with diethyl ether (500 mL) and white precipitate was filtered off. Filtrate was concentrated under reduced pressure, diluted with diethyl ether (300 mL) and extracted with 1 M aqueous hydrochloric acid (3×100 mL) and brine (1×100 mL). Organic portion was dried with sodium sulfate and evaporated under reduced pressure to give tert-butyl 14-(2,2-dimethyl-4,6-dioxo-1,3-dioxan-5-yl)-14-oxotetradecanoate as yellow oil. The crude product was used for the next step without further purification.

1H NMR spectrum (300 MHz, CDCl3, dH): 3.07 (t, J=7.5 Hz, 2H); 2.20 (t, J=7.5 Hz, 2H); 1.74 (s, 6H); 1.71-1.51 (m, 4H); 1.45 (s, 9H); 1.36-1.23 (m, 16H).

The crude product from above was dissolved in ethanol (300 mL) and the resulting solution was stirred at 80 C for 3 hours and then overnight at room temperature. Solvent was removed under reduced pressure and the residue was purified by flash column chromatography (Silicagel 60, 0.040-0.063 mm; eluent: cyclohexane/ethyl acetate 9:1) to give 1-ethyl 16-methyl 3-oxohexadecanedioate as colorless oil 1H NMR spectrum (300 MHz, CDCl3, dH): 4.21 (q, J=7.2 Hz, 2H); 3.44 (s, 2H); 2.54 (t, J=7.5 Hz, 2H); 2.21 (t, J=7.5 Hz, 2H); 1.67-1.51 (m, 4H); 1.45 (s, 9H); 1.38-1.21 (m, 19H).

Sodium hydroxide (1.09 g, 27.3 mmol) was dissolved in methanol (40.0 mL) and water (10.0 mL) at −30 C under argon atmosphere. The above ester (4, 10.0 g, 26.0 mmol) was dissolved in methanol (40 mL) and dimethoxyethane (50 mL) and added dropwise to the reaction mixture at −30 C. After 20 minutes, solution of hydroxylamine hydrochloride (3.61 g, 52.0 mmol) and sodium hydroxide (2.18 g, 54.6 mmol) in dimethoxyethane (10 mL) and water (10.0 mL) was added dropwise and the reaction mixture was stirred for 3 hours at −30 C. The mixture was then quenched with acetone (5 mL) and after 5 minutes poured at once into concentrated hydrochloric acid (70 mL) and heated to 80 C for 70 minutes. All volatiles were then removed under reduced pressure, solids were dissolved with dichloromethane (400 mL) and extracted with distilled water (100 mL) and brine (70 mL). Organic portion was dried with sodium sulfate. The crude product was purified by flash column chromatography (Silicagel 60, 0.040-0.063 mm; eluent: cyclohexane/ethyl acetate 3:1) to give methyl 13-(3-hydroxyisoxazol-5-yl)tridecanoate as white solid.

1H NMR spectrum (300 MHz, CDCl3, dH): 5.66 (s, 1H); 3.67 (s, 3H); 2.63 (t, J=7.6 Hz, 2H); 2.31 (t, J=7.6 Hz, 1H); 1.72-1.55 (m, 4H); 1.40-1.19 (m, 16H).

Methyl 13-(3-hydroxyisoxazol-5-yl)tridecanoate (5, 6.20 g, 19.9 mmol) was dissolved in methanol (60.0 mL) and water (20.0 mL), lithium hydroxide monohydrate (4.04 g, 96.3 mmol) was added and reaction mixture was stirred for 16 hours at room temperature. Volatiles were then removed under reduced pressure and water (50.0 mL) was added followed by 1 M aqueous hydrochloric acid (50.0 mL). Precipitate was filtered off and washed with water (2×100 mL) and then dried under reduced pressure to give 13-(3-hydroxyisoxazol-5-yl)tridecanoic acid as a beige solid.

1H NMR spectrum (300 MHz, DMSO-d6, dH): 5.74 (s, 1H); 2.57 (t, J=7.5 Hz, 2H); 2.18 (t, J=7.5 Hz, 2H); 1.63-1.41 (m, 4H); 1.34-1.14 (m, 16H).

B.2 Synthesis of Intermediate Substituent Precursors for Reductive Alkylation

18-[[(1S)-1-carboxy-4-[2-[2-[2-[2-[2-[2-[(4-formyl-phenyl)methylamino]-2-oxo-ethoxy]ethoxy]ethyl-amino]-2-oxo-ethoxy]ethoxy]ethylamino]-4-oxo-butyl]amino]-18-oxo-octadecanoic acid

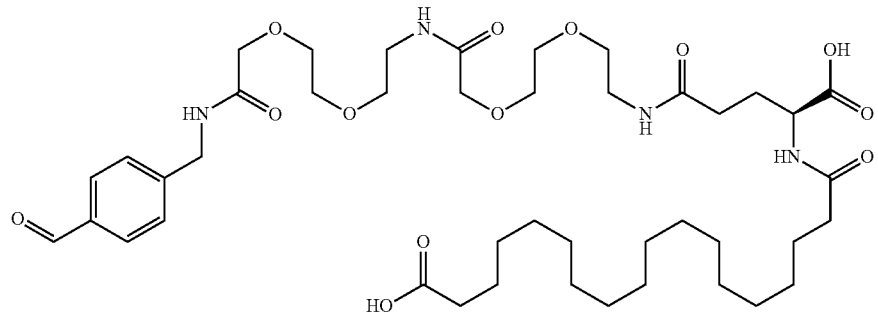

2-Chlorotrityl resin 100-200 mesh (42.6 g, 42.6 mmol) was left to swell in dry dichloromethane (205 mL) for 20 min. A solution of {2-[2-(9H-fluoren-9-ylmethoxycarbonylamino)-ethoxy]ethoxy}-acetic acid (13.7 g, 35.5 mmol) and N,N-diisopropylethylamine (23.5 mL, 135 mmol) in dry dichloromethane (30 mL) was added to resin and the mixture was shaken for 3 hrs. Resin was filtered and treated with a solution of N,N-diisopropylethylamine (12.4 mL, 70.9 mmol) in methanol/dichloromethane mixture (4:1, 250 mL, 2×5 min). Then resin was washed with N,N-dimethylformamide (2×150 mL), dichloromethane (3×150 mL) and N,N-dimethylformamide (3×150 mL). Fmoc group was removed by treatment with 20% piperidine in dimethylformamide (1×5 min, 1×30 min, 2×150 mL). Resin was washed with N,N-dimethylformamide (3×150 mL), 2-propanol (2×150 mL) and dichloromethane (200 mL, 2×150 mL). Solution of {2-[2-(9H-fluoren-9-ylmethoxycarbonylamino)-ethoxy]ethoxy}-acetic acid (20.5 g, 53.2 mmol), O-(6-chloro-benzotriazol-1-yl)-N,N,N',N'-tetramethyluronium tetrafluoroborate (TCTU, 18.9 g, 53.2 mmol) and N,N-diisopropylethylamine (16.7 mL, 95.7 mmol) in N,N-dimethylformamide (100 mL) and dichloromethane (50 mL) was added to resin and mixture was shaken for 1 hr. Resin was filtered and washed with N,N-dimethylformamide (2×150 mL), dichloromethane (3×150 mL) and N,N-dimethylformamide (155 mL). Fmoc group was removed by treatment with 20% piperidine in dimethylformamide (1×5 min, 1×30 min, 2×150 mL). Resin was washed with N,N-dimethylformamide (3×150 mL), 2-propanol (2×150 mL) and dichloromethane (200 mL, 2×150 mL). Solution of Fmoc-Glu-OtBu (22.6 g, 53.2 mmol), O-(6-chloro-benzotriazol-1-yl)-N,N,N',N'-tetramethyluronium tetrafluoroborate (TCTU, 18.9 g, 53.2 mmol) and N,N-diisopropylethylamine (16.7 mL, 95.7 mmol) in N,N-dimethylformamide (155 mL) was added to resin and mixture was shaken for 1 hr. Resin was filtered and washed with N,N-dimethylformamide (2×150 mL), dichloromethane (2×150 mL) and N,N-dimethylformamide (150 mL). Fmoc group was removed by treatment with 20% piperidine in dimethylformamide (1×5 min, 1×30 min, 2×150 mL). Resin was washed with N,N-dimethylformamide (3×150 mL), 2-propanol (2×150 mL) and dichloromethane (200 mL, 2×150 mL). Solution of octadecanedioic acid mono-tert-butyl ester (19.7 g, 53.2 mmol), O-(6-chloro-benzotriazol-1-yl)-N,N,N',N'-tetramethyluronium tetrafluoroborate (TCTU, 18.9 g, 53.2 mmol) and N,N-diisopropylethylamine (16.7 mL, 95.7 mmol) in N,N-dimethylformamide/dichloromethane mixture (1:4, 200 mL) was added to resin. Resin was shaken for 2 hrs, filtered and washed with N,N-dimethylformamide (3×150 mL), dichloromethane (2×150 mL), methanol (2×150 mL) and dichloromethane (300 mL, 6×150 mL). The product was cleaved from resin by treatment with 2,2,2-trifluoroethanol (200 mL) for 19 hrs. Resin was filtered off and washed with dichloromethane (2×150 mL), 2-propanol/dichloromethane mixture (1:1, 2×150 mL), 2-propanol (150 mL) and dichloromethane (2×150 mL). Solutions were combined; solvent evaporated and crude product was purified by flash column chromatography (Silicagel 60, 0.040-0.060 mm; eluent: dichloromethane/methanol 1:0-9:1). Pure product was dried in vacuo and obtained as yellow oil.

Yield of 17-{(S)-1-tert-Butoxycarbonyl-3-[2-(2-{[2-(2-carboxymethoxy-ethoxy)-ethylcarbamoyl]-methoxy}-ethoxy)-ethylcarbamoyl]propylcarbamoyl}-heptadecanoic acid tert-butyl ester: 25.85 g (86%).

RF (SiO2, chloroform/methanol 85:15): 0.25.

1H NMR spectrum (300 MHz, CDCl3, dH): 7.38 (bs, 1H); 7.08 (bs, 1H); 6.61 (d, J=7.5 Hz, 1H); 4.43 (m, 1H); 4.15 (s, 2H); 4.01 (s, 2H); 3.78-3.39 (m, 16H); 2.31 (t, J=6.9 Hz, 2H); 2.27-2.09 (m, 5H); 2.01-1.84 (m, 1H); 1.69-1.50 (m, 4H); 1.46 (s, 9H); 1.43 (s, 9H); 1.24 (bs, 24H).

LC-MS m/z: 846.6 (M+H)+.

(4-Formyl-benzyl)-carbamic acid tert-butyl ester (Boc-aminomethylbenzaldehyde, 1.54 g, 6.60 mmol) was dissolved in dichloromethane (50 mL) and solution of hydrochloric acid in dioxane (3.8 M, 20 mL, 76 mmol) was added. The mixture was stirred for 16 hrs and solid material precipitated from the solution. All solvents were removed by evaporation. 17-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-heptadecanoic acid tert-butyl ester (5.08 g, 6.00 mmol), ethyl-(N',N'-dimethylamino)propylcarbodiimide hydrochloride (EDC, 1.73 g, 9.00 mmol), N,N-dimethylaminopyridine (DMAP, 0.037 g, 0.30 mmol) and dichloromethane (50 mL) were added. The mixture was stirred and diisopropylethylamine (2 mL, 11.6 mmol) was added in 3 portions. The reaction mixture was stirred for 2 hrs and the solvents were evaporated. The residue was dissolved in dichloromethane (10 mL) and a solution of hydrochloric acid was added dropwise until pH was lower than 5. The solution was submitted to column chromatography (Silicagel 60, 0.040-0.060 mm; eluent: dichloromethane/methanol 95:5) to provide the substituent as a yellow oil.

Yield: 3.15 g (54%).

1H NMR spectrum (300 MHz, CDCl3, dH): 9.99 (s, 1H); 7.85 (d, J=7.9 Hz, 2H); 7.54-7.43 (m, 3H); 7.06 (t, J=5.5 Hz, 1H); 6.86 (t, J=5.6 Hz, 1H); 6.48 (d, J=7.7 Hz, 1H); 4.58 (d, J=6.2 Hz, 2H); 4.45-4.36 (m, 1H); 4.09 (s, 2H); 3.94 (s, 2H); 3.73-3.37 (m, 16H); 2.32-2.05 (m, 7H); 1.99-1.80 (m, 1H); 1.69-1.51 (m, 4H); 1.45 (s, 9H); 1.44 (s, 9H); 1.33-1.20 (m, 24H).

LC-MS m/z: 963.5 (M+H)+.

(2S)-5-[2-[2-[2-[2-[2-[2-[(4-formylphenyl)methylamino]-2-oxo-ethoxy]ethoxy]ethylamino]-2-oxo-ethoxy]ethoxy]ethylamino]-5-oxo-2-(16-sulfohexadecanoylamino)pentanoic acid

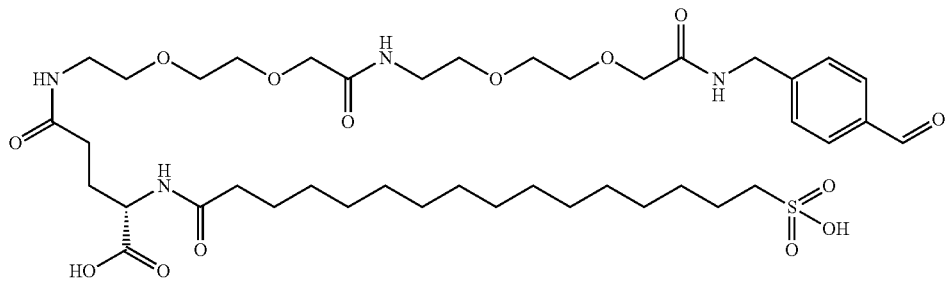

2-Chlorotrityl resin 100-200 mesh 1.8 mmol/g (1, 8.40 g, 14.3 mmol) was left to swell in dry dichloromethane (150 mL) for 30 minutes. A solution of Fmoc-Ado-OH (2.82 g, 9.50 mmol) and N,N-diisopropylethylamine (6.30 mL, 36.1 mmol) in dry dichloromethane (~150 mL) was added to resin and the mixture was shaken for 24 hours. Resin was filtered and treated with a solution of N,N-diisopropylethylamine (3.30 mL, 19.0 mmol) in methanol/dichloromethane mixture (4:1, 2×150 mL, 2×5 min). Then resin was washed with N,N-dimethylformamide (3×150 mL), dichloromethane (3×150 mL) and N,N-dimethylformamide (3×150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (3×150 mL) and dichloromethane (3×150 mL). Solution of {2-[2-(9H-fluoren-9-ylmethoxycarbonylamino)-ethoxy]ethoxy}-acetic acid (Fmoc-Ado-OH, 4.80 g, 16.2 mmol), O-(6-chloro-benzotriazol-1-yl)-N,N,N',N'-tetramethyluronium tetrafluoroborate (TCTU, 5.74 g, 16.2 mmol) and N,N-diisopropylethylamine (4.47 mL, 25.7 mmol) in N,N-dimethylformamide (150 mL) was added to resin and mixture was shaken for 2 hours. Resin was filtered and washed with N,N-dimethylformamide (3×150 mL), dichloromethane (3×150 mL) and N,N-dimethylformamide (3×150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (3×150 mL) and dichloromethane (3×150 mL). Solution of (S)-2-(9H-fluoren-9-ylmethoxycarbonylamino)-pentanedioic acid 1-tert-butyl ester (Fmoc-Glu-OtBu, 6.87 g, 16.2 mmol), O-(6-chloro-benzotriazol-1-yl)-N,N,N',N'-tetramethyluronium tetrafluoroborate (TCTU, 5.74 g, 16.2 mmol) and N,N-diisopropylethylamine (4.47 mL, 25.7 mmol) in N,N-dimethylformamide (150 mL) was added to resin and mixture was shaken for 2 hours. Resin was filtered and washed with N,N-dimethylformamide (3×150 mL), dichloromethane (3×150 mL) and N,N-dimethylformamide (3×150 mL). Fmoc group was removed by treatment with 20% piperidine in N,N-dimethylformamide (1×5 min, 1×30 min, 2×150 mL). Resin was washed with N,N-dimethylformamide (3×150 mL), 2-propanol (3×150 mL) and dichloromethane (3×150 mL). A solution of 16-((4-((tert-butoxycarbonyl)amino)-2,2-dimethylbutoxy)sulfonyl) hexadecanoic acid (6.62 g, 12.4 mmol), O-(6-chlorobenzotriazol-1-yl)-N,N,N',N'-tetramethyluronium tetrafluoroborate (TCTU, 4.39 g, 12.4 mmol) and N,N-diisopropylethylamine (4.47 mL, 25.7 mmol) in N,N-dimethylformamide/dichloromethane mixture (1/1, 150 mL) was added to resin and mixture was shaken for 2 hours. Resin was filtered and washed with N,N-dimethylformamide (3×150 mL), methanol (5×150 mL) and dichloromethane (10×150 mL). The product was cleaved from resin by treatment with 2,2,2-trifluoroethanol (150 mL) for 24 hours. Resin was filtered off and washed with dichloromethane (3×150 mL). Solutions were combined, solvents were evaporated and crude product (7.80 g) was purified by flash column chromatography (Silicagel 60, 0.040-0.060 mm; eluent: dichloromethane/methanol 100:2 to dichloromethane/methanol 100:10) to give the intermediate compounds as a white solid.

Yield: 4.00 g (42%).

RF (SiO2, dichloromethane/methanol 8:1): 0.50.

1H NMR spectrum (300 MHz, CDCl3, dH): 7.79-7.65 (m, 1H); 7.36-7.20 (m, 1H); 6.86 (d, J=7.5 Hz, 1H); 4.49-4.63 (m, 1H); 4.44-4.29 (m, 1H); 4.07-3.93 (m, 4H); 3.90 (s, 2H); 3.77-3.35 (m, 16H); 3.25-3.02 (m, 4H); 2.44-1.75 (m, 8H); 1.72-1.38 (m, 22H); 1.38-1.18 (m, 22H); 1.00 (m, 6H).

LC-MS m/z: 1012.3 (M+H)+.

The intermediate compound from above (3.77 g, 3.73 mmol), N,N-diisopropylethylamine (1.75 mL, 10.1 mmol), [1,2,3]triazolo[4,5-b]pyridin-1-ol (HOAt, 0.51 g, 3.73 mmol), N-(3-dimethylaminopropyl)-N'-ethylcarbodiimide hydrochloride (EDC.HCl, 1.43 g, 7.46 mmol) were dissolved in dichloromethane (120 mL). 4-Formyl-benzylammonium chloride (5, 0.77 g, 4.48 mmol) was added. The mixture was stirred at room temperature for 24 hours. After this time reaction mixture was evaporated, dissolved in ethyl acetate (300 mL) and washed with 0.5 M aqueous solution of hydrochloric acid (200 mL). Organic phase was separated, washed with water (200 mL) and dried over magnesium sulfate. Ethyl acetate was evaporated and the crude mixture was purified by flash column chromatography (Silicagel 60, 0.040-0.060 mm; eluent: dichloromethane to dichloromethane/methanol 100:5) to give the protected aldehyde as a white solid.

Yield: 3.00 g (71%).

RF (SiO2, dichloromethane/methanol 10:1): 0.70.

1H NMR spectrum (300 MHz, CDCl3, dH): 9.99 (s, 1H); 7.85 (d, J=8.1 Hz, 2H); 7.64-7.38 (m, 3H); 7.14-6.97 (m, 1H); 6.91-6.76 (m, 1H); 6.54-6.43 (m, 1H); 4.58 (d, J=6.2 Hz, 2H); 4.47-4.32 (m, 1H); 4.09 (s, 2H); 3.88 (s, 2H); 3.81-3.30 (m, 16H); 3.22-3.02 (m, 4H); 2.38-2.08 (m, 4H); 1.96-1.71 (m, 5H); 1.71-1.16 (m, 41H); 0.99 (m, 6H).

LC-MS m/z: 1129.5 (M+H)+.

The protected aldehyde from above (3.00 g, 2.66 mmol) was stirred with trifluoroacetic acid (15 mL) and water (1 mL) mixture for 3 hours. After this time the mixture was evaporated several times with dichloromethane and toluene under reduced pressure. The residue was poured into water/acetonitrile mixture (1/1, 15 mL). pH was adjusted to 8.0 with saturated aqueous solution of trisodium phosphate and the resulting solution was stirred for 20 minutes at 50° C. pH was adjusted to 6.0 with saturated aqueous solution of potassium hydrogen sulfate. The residue was desalinated by reverse-phase chromatography (DeltaPak, C18, 15 mm 50 mm×500 mm, acetonitrile/water 5-15%/15 min., 5-55%/180 min.+0.05% TFA). Solvents were removed by freeze-drying to give the substituent as a white powder.

Yield: 0.66 g (28%).

H NMR spectrum (300 MHz, D20, dH): 9.81 (s, 1H); 7.79 (d, J=7.7 Hz, 2H); 7.41 (d, J=7.9 Hz, 2H); 4.44 (s, 2H); 4.32-4.19 (m, 1H); 4.05 (s, 2H); 3.90 (s, 2H); 3.74-3.43 (m, 12H); 3.38-3.18 (m, 4H); 2.83-2.60 (m, 2H); 2.37-1.76 (m, 6H); 1.76-1.37 (m, 4H); 1.34-0.91 (m, 22H).

LC-MS m/z: 873.8 (M+H)+.

N-((1-(4-Formylphenyl)-3,12,21-trioxo-5,8,14,17-tetraoxa-2,11,20-triazatetracosan-24-yl)sulfonyl)-16-(1H-tetrazol-5-yl)hexadecanamide

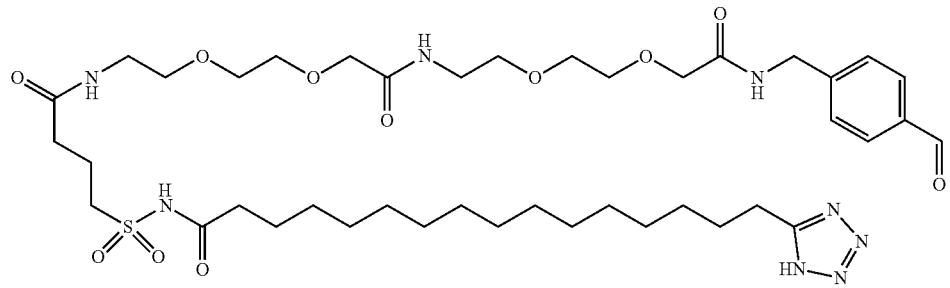

Reaction Scheme:

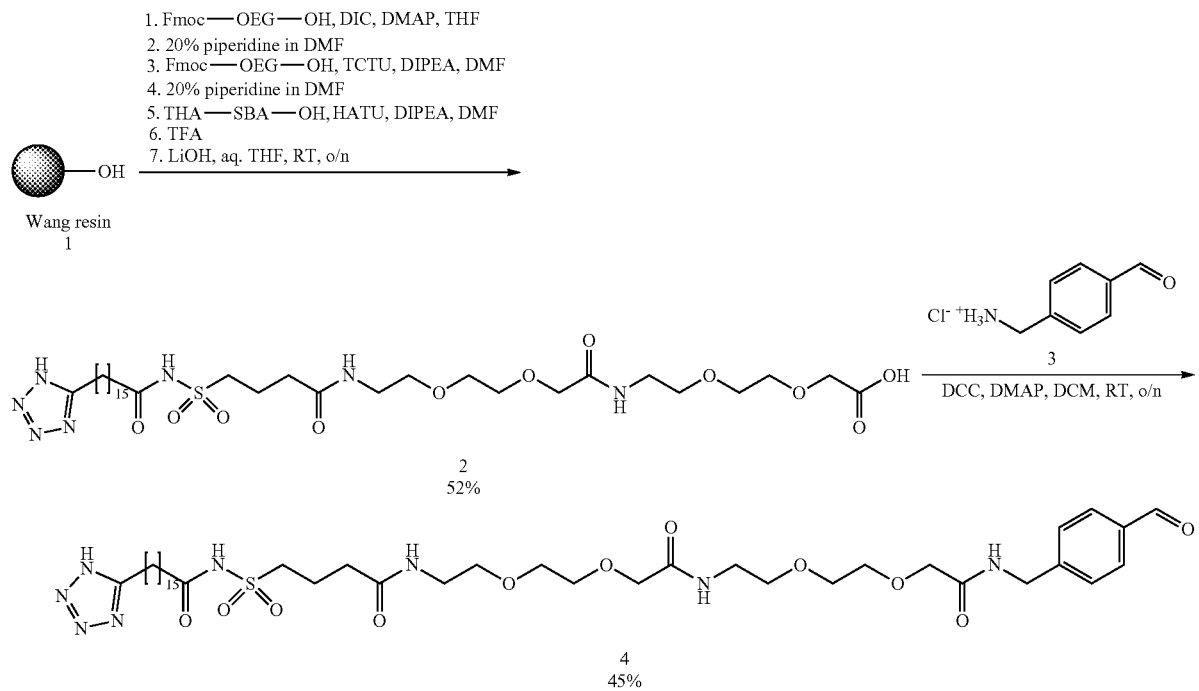

Wang resin 0.68 mmol/g (20.5 g, 13.9 mmol) was left to swell in tetrahydrofuran (200 mL) for 20 minutes. A solution of of {2-[2-(9H-fluoren-9-ylmethoxycarbonylamino)-ethoxy]ethoxy}-acetic acid (Fmoc-Ado-OH, 16.1 g, 41.8 mmol) and 4-dimethylaminopyridine (DMAP, 0.17 g, 1.39 mmol) and N,N'-diisopropylcarbodiimide (DIC, 6.47 mL, 41.8 mmol) in tetrahydrofuran (200 mL) was added to resin and the mixture was shaken for 18 hours. Then resin was filtered and washed with N,N-dimethylformamide (2×180 mL), dichloromethane (2×180 mL) and N,N-dimethylformamide (2×180 mL). Resin was treated with a solution of acetic anhydride (13.2 mL, 139 mmol) and pyridine (11.3 mL, 139 mmol) in N,N-dimethylformamide (180 mL). Then resin was filtered and washed with N,N-dimethylformamide (2×180 mL), dichloromethane (2×180 mL) and N,N-dimethylformamide (2×180 mL). Fmoc group was removed by treatment with 20% piperidine in N,N-dimethylformamide (1×5 min, 1×30 min, 2×180 mL). Resin was filtered and washed with N,N-dimethylformamide (2×180 mL), dichloromethane (2×180 mL) and N,N-dimethylformamide (2×180 mL). A solution of of {2-[2-(9H-fluoren-9-ylmethoxycarbonylamino)-ethoxy]-ethoxy}-acetic acid (Fmoc-Ado-OH, 10.8 g, 27.9 mmol), 5-chloro-1-((dimethylamino)(dimethyliminio)methyl)-1H-benzo[d][1,2,3]triazole 3-oxide tetrafluoroborate (TCTU, 9.91 g, 27.9 mmol) and N,N-diisopropylethylamine (7.28 mL, 41.8 mmol) in N,N-dimethylformamide (180 mL) was added to resin and mixture was shaken for 2 hours. Then resin was filtered and washed with N,N-dimethylformamide (2×180 mL), dichloromethane (2×180 mL) and N,N-dimethylformamide (2×180 mL). Fmoc group was removed by treatment with 20% piperidine in N,N-dimethylformamide (1×5 min, 1×30 min, 2×180 mL). Resin was filtered and washed with N,N-dimethylformamide (2×180 mL), dichloromethane (2×180 mL) and N,N-dimethylformamide (2×180 mL). Solution of of 4-(N-(16-(1H-tetrazol-5-yl)hexadecanoyl)sulfamoyl)butanoic acid (THA-SBA-OH, 8.91 g, 18.8 mmol), 1-((dimethylamino)(dimethyliminio)methyl)-1H-[1,2,3]triazolo[4,5-b]pyridine 3-oxide hexafluorophosphate (HATU, 7.16 g, 18.8 mmol) and N,N-diisopropylethylamine (5.71 mL, 32.8 mmol) in mixture of N,N-dimethylformamide (90 mL) and dichloromethane (90 mL) was added to resin and mixture was shaken for 18 hours.

Resin was filtered and washed with N,N-dimethylformamide (2×180 mL), dichloromethane (2×180 mL), 2-propanol (2×180 mL) and dichloromethane (10×180 mL). The product was cleaved from the resin by the treatment with mixture of trifluoacetic acid (150 mL) and water (7.5 mL) for 1 hour. Resin was filtered and washed with dichloromethane (2×150 mL). The solvent was removed under reduced pressure and the residue was treated with diethyl ether (100 mL). To a solution of the intermediate (7.90 g, 10.3 mmol) in tetrahydrofuran (100 mL) was added lithium hydroxide monohydrate (1.74 g, 41.4 mmol) in water (100 mL). The solution was stirred for 18 hours. The solution was acidified by 10% aqueous solution potassium hydrogen sulfate until pH=3 was achieved, followed by saturation with sodium chloride. Organic phase was removed, aqueous phase was extracted by ethyl acetate (1×300 mL). Combined organic phases were dried over anhydrous sodium sulfate. The solvent was removed under reduced pressure to give the intermediate as white powder.

Yield: 5.50 g (52%).

1H NMR spectrum (300 MHz, AcOD-d4, dH): 4.22 (s, 2H); 4.12 (s, 2H); 3.83-3.61 (m, 12H); 3.59-3.43 (m, 6H); 3.02 (t, J=7.4 Hz, 2H); 2.49 (t, J=7.3 Hz, 2H); 2.41 (t, J=7.5 Hz, 2H); 2.22-2.09 (m, 2H); 1.89-1.75 (m, 2H); 1.74-1.60 (m, 2H); 1.47-1.26 (m, 22H).

A solution of above compound (2.90 g, 3.80 mmol), 4-aminomethylbenzaldehyde hydrochloride (0.78 g, 4.56 mmol), N,N'-dicyclohexylcarbodiimide (DCC, 0.78 g, 3.80 mmol) and 4-dimethylaminopyridine (DMAP, 1.02 g, 8.35 mmol) in dry dichloromethane (100 mL) was stirred for 18 hours. The precipitate was filtered-off and the solution was washed with 10% aqueous solution of potassium hydrogen sulfate (2×100 mL). The solvent was removed under reduced pressure and the residue was crystallized from tetrahydrofuran (30 mL). Purification by flash column chromatography (Silicagel 60, 0.040-0.063 mm; eluent: dichloromethane/methanol, 20:1-5:1) gave final product as pale yellow powder.

Yield: 1.51 g (45%).

1H NMR spectrum (300 MHz, AcOD-d4, dH): 9.96 (s, 1H); 7.91 (d, J=7.9 Hz, 2H); 7.92 (d, J=7.9 Hz, 2H); 4.63 (s, 2H); 4.21 (s, 2H); 4.08 (s, 2H); 3.81-3.57 (m, 12H); 3.54-3.41 (m, 6H); 3.02 (t, J=7.4 Hz, 2H); 2.47 (t, J=7.3 Hz, 2H); 2.38 (t, J=7.4 Hz, 2H); 2.19-2.07 (m, 2H); 1.86-1.72 (m, 2H); 1.70-1.57 (m, 2H); 1.43-1.23 (m, 22H).

LC-MS purity: 100%.

LC-MS Rt (Kinetex 4.6 mm×50 mm, acetonitrile/water 20:50 to 100:0+0.1% FA): 3.58 min.

LC-MS m/z: 882.0 (M+H)+.

A total of 29 substituents were prepared and are listed herein below specifying the Z1-Z10 elements of the individual substituents.

|     | Z1 (protractor) | Z2 | Z3 | Z3-Z9 | Z10 |
| --- | --- | --- | --- | --- | --- |
| 1. | HOOC—(CH$_2$)$_{18}$—CO— | | -gGlu- | -ADO-ADO- | |
| 2. | HOOC—(CH$_2$)$_{18}$—CO— | —NH—CH$_2$—(C$_6$H$_{10}$)—CO— | -gGlu- | -ADO-ADO- | |
| 3. | HOOC—(CH$_2$)$_{16}$—CO— | | -gGlu- | -ADO-ADO- | |
| 4. | HOOC—(CH$_2$)$_{16}$—CO— | | -gGlu- | -ADO-ADO- | —NH—CH$_2$—(C$_6$H$_4$)—CH$_2$— |
| 5. | HOOC—(CH$_2$)$_{16}$—CO— | | -gGlu- | | |
| 6. | HOOC—(CH$_2$)$_{16}$—CO— | —NH—CH$_2$—(C$_6$H$_{10}$)—CO— | -gGlu- | -ADO-ADO- | |
| 7. | HOOC—(CH$_2$)$_{14}$—CO— | | -gGlu- | -ADO-ADO- | |
| 8. | HOOC—(CH$_2$)$_{14}$—CO— | | -gGlu- | | |
| 9. | HOOC—(CH$_2$)$_{14}$—CO— | | -gGlu- | -ADO-ADO- | |
| 10. | HOOC—(CH$_2$)$_{12}$—CO— | | -gGlu- | -ADO-ADO- | |
| 11. | 4-HOOC—(C$_6$H$_4$)—O—(CH$_2$)$_{10}$—CO— | | -gGlu- | -ADO-ADO- | |
| 12. | 4-HOOC—(C$_6$H$_4$)—O—(CH$_2$)$_{10}$—CO— | | -gGlu- | -ADO-ADO-ADO- | |
| 13. | 4-HOOC—(C$_6$H$_4$)—O—(CH$_2$)$_{10}$—CO— | | -gGlu- | | |
| 14. | 4-HOOC—(C$_6$H$_4$)—O—(CH$_2$)$_{10}$—CO— | | 2xgGlu- | | |
| 15. | 4-HOOC—(C$_6$H$_4$)—O—(CH$_2$)$_{10}$—CO— | | -gGlu- | -Gly-Gly-Gly- | |
| 16. | 4-HOOC—(C$_6$H$_4$)—O—(CH$_2$)$_{10}$—CO— | | 2xgGlu- | -ADO-ADO- | |
| 17. | 4-HOOC—(C$_6$H$_4$)—O—(CH$_2$)$_{10}$—CO— | | -gGlu- | -TtdSuc- | |
| 18. | 4-HOOC—(C$_6$H$_4$)—O—(CH$_2$)$_{10}$—CO— | | | | |
| 19. | 4-HOOC—(C$_6$H$_4$)—O—(CH$_2$)$_{10}$—CO— | | -gGlu- | -ADO-ADO-ADO-ADO- | |
| 20. | 4-HOOC—(C$_6$H$_4$)—O—(CH$_2$)$_{10}$—CO— | —NH—CH$_2$—(C$_6$H$_{10}$)—CO— | -gGlu- | -ADO-ADO- | |
| 21. | 4-HOOC—(C$_6$H$_4$)—O—(CH$_2$)$_9$—CO— | | -gGlu- | -ADO-ADO- | |
| 22. | 3-HOOC—(C$_6$H$_4$)—O—(CH$_2$)$_9$—CO— | | -gGlu- | -ADO-ADO- | |
| 23. | 3-HO-Isoxazole-(CH$_2$)$_{12}$—CO— | | -gGlu- | -ADO-ADO- | |
| 24. | HOS(O)$_2$—(CH$_2$)$_{15}$—CO— | | -gGlu- | -ADO-ADO- | —NH—CH$_2$—(C$_6$H$_4$)—CH$_2$— |
| 25. | HOS(O)$_2$—(CH$_2$)$_{13}$—CO— | | -gGlu- | -ADO-ADO- | |
| 26. | Tetrazolyl-(CH$_2$)$_{15}$—CO— | —NH—SO$_2$—(CH$_2$)$_3$—CO— | | -ADO-ADO- | —NH—CH$_2$—(C$_6$H$_4$)—CH$_2$— |
| 27. | Tetrazolyl-(CH$_2$)$_{12}$—CO— | | -gGlu- | -ADO-ADO- | |
| 28. | Tetrazolyl-(CH$_2$)$_{15}$—CO— | | -gGlu- | -ADO-ADO- | |
| 29. | MeS(O)$_2$NH(CO)NH—(CH$_2$)$_{12}$—CO | | -gGlu- | -ADO-ADO- | |

Methods for Detection and Characterization
LCMS Methods
LCMS01 (See Table 1)

TABLE 1

LC-system: Waters Acquity UPLC. Linear gradient: 5% to 95% B.

| | |
|---|---|
| System | LC-system: Waters Acquity UPLC |
| | Column:: Waters Acquity UPLC BEH, C-18, 1.7 µm, 2.1 mm × 50 mm |
| | Detector:: Waters (Micromass) LCT Premier XE |
| Detector setup | Ionisation method: ES |
| | Scanning range: 500-2000 amu |
| | Operating mode: W mode |
| | positive/negative: positive mode |
| | Cone Voltage: 50 V |
| | Scantime 1 |
| | Interscandelay: 0.0 |
| Conditions | Linear gradient: 5% to 95% B |
| | Gradient run-time: 4.0 minutes |
| | Total run-time: 7.0 minutes |
| | Flow rate: 0.4 ml/min |
| | Column temperature: 40° C. |
| Eluents | Solvent A: 99.90% MQ-water, 0.1% formic acid |
| | Solvent B: 99.90% acetonitrile, 0.1% formic acid |
| | Solvent C: NA |
| Results specification and validation | Mass found is the mass found of the compound M/z found is the molecular ion found ((M + z)/z) of the compound Calculated Mass is the molecular weight of the desired compound Calculated M/z is the molecular weight (M + z)/z of the desired compound Purity: Total ion current (TIC) AUC of analyte peak, in percent of total AUC excl solvent peak, as reported by system software. Identity: Mass of each analyte mass peak expressed as m/z from highest to lowest. Scanning range is the range scanned in the method used. Detection method is e.g linear reflector |

LCMS027 (See Table 2)

TABLE 2

Agilent 1290 infinity series UPLC, LC/MSD TOF, 6 min, 5% to 95% B, 100-3200 amu, C18

| | |
|---|---|
| System | System:Agilent 1290 infinity series UPLC Column: Eclipse C18+ 2.1 × 50 mm 1.8u Detector: Agilent Technologies LC/MSD TOF 6230 (G6230A) |
| Detector setup Scanning | Ionisation method: Agilent Jet Stream source range: m/z min. 100, m/z max. 3200 linear reflector mode positive mode |
| Conditions | Linear gradient: 5% to 95% B Gradient run-time: 6 minutes 0-4.5 min 5-95% B, 4.5-5 95% B, 5-5.5 95-5% B 5.5-6 5% B Flow rate: 0.40 ml/min fixed Column temperature: 40° C. |

TABLE 2-continued

Agilent 1290 infinity series UPLC, LC/MSD TOF, 6 min, 5% to 95% B, 100-3200 amu, C18

| | |
|---|---|
| Eluents | Solvent A: 99.90% $H_2O$, 0.02% TFA |
| | Solvent B: 99.90% $CH_3CN$, 0.02% TFA |
| | Solvent C: NA |
| Results specification and validation | Mass found is either m/z ((m + z)/z) of the compound for compounds with m < 4000 or mass (average) as the result of a deconvolution using Masshunter Workstation Software Version B.05.00 Build 5.0.519.13 SP1 (Agilent). Calculated Mass is the average molecular weight of the desired compound Calculated m/z is the molecular weight (m + z)/z of the desired compound |

LCMS029 (See Table 3):

TABLE 3

Waters Acquity UPLC system, 6 min (3.5 min), 5-(15-35)-100-100-5% B

| | |
|---|---|
| System | System: Waters Acquity UPLC system |
| | Column: ACQUITY UPLC BEH C18, 1.7 um, 2.1 mm × 50 mm column |
| | Detectors: Waters Acquity TUV Detector |
| Detector setup | 214 nm or 254 nm |
| Conditions | Step gradient: |
| | Gradient run |
| | 0.0-0.5 min     5-15% B |
| | 0.5-4.0 min     15-35% B |
| | 4.0-4.5 min     35-100% B |
| | 4.5-5.0 min     100-100% B |
| | 5.0-5.5 min     100-5% B |
| | 5.5-6.0 min     5-5% B |
| | Total run-time: 6.0 minutes |
| | Flow rate: 0.45 ml/min fixed |
| | Column temperature: 40° C. |
| Eluents | Solvent A: 99.95% Water, 0.05% Trifluoroacetic acid |
| | Solvent B: 99.95% Acetonitrile, 0.05% Trifluoroacetic acid |
| Results specification and validation | Purity defined as peak AUC in relation to total AUC excl. solvent peak (in percent) as reported by system software for each UV wavelenght. Retention time between 2.8 and 4.2 min, baseline separation of analyte peak required. Peak AU value between 0.5 and 1.5. Results uploaded are based on 214 nm |

C. Example Compounds

C.1. Preparation of Example Compounds

Example 1

N{293}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-[Ala299,Leu301,Ile307,Arg309,Lys310]-LDL-R-(293-332)-peptide

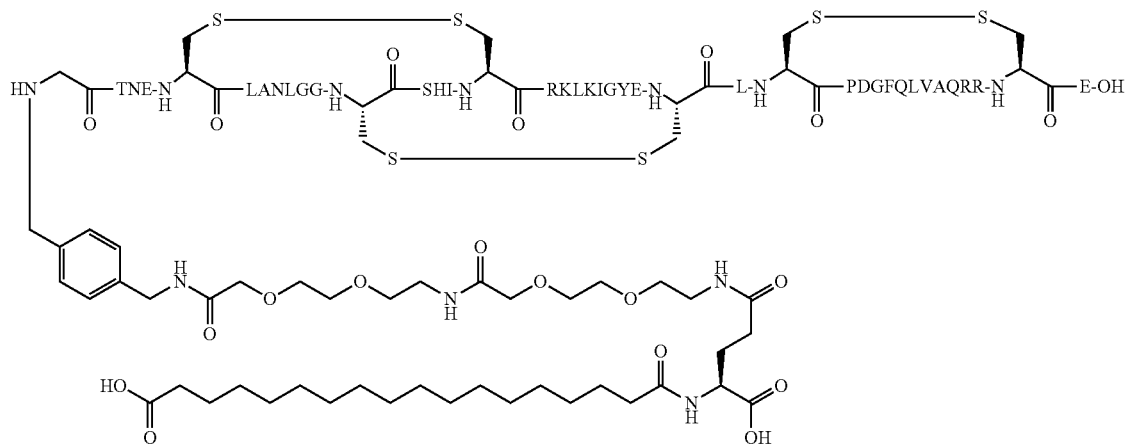

The peptide is SEQ ID NO: 2.
Compound prepared by general method A and C
LCMS029: Found m/3=1743.9; Found m/4=1308.1; Found m/5=1046.7; Calc. mass=5229.1; Found mass=5229.6.

Example 2

N{293}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-[Leu301,Arg309]-LDL-R-(293-332)-peptide

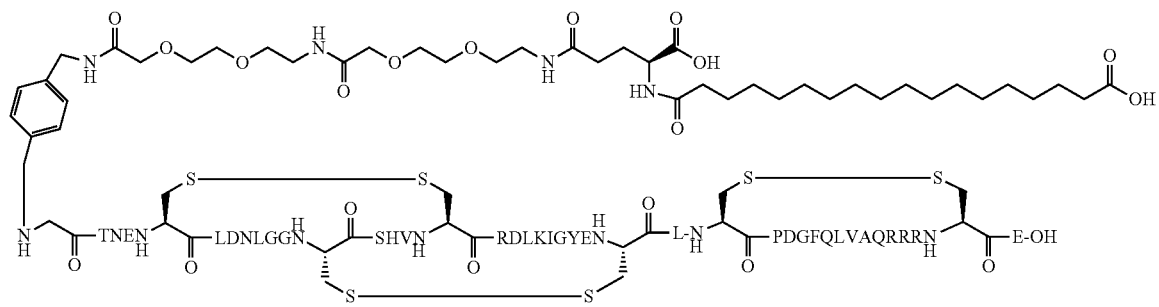

The peptide is SEQ ID NO: 3.
Compound prepared by general method A and C
LCMS029: Found m/3=1749.5; Found m/4=1312.4; Found m/5=1050.1; Calc. mass=5246.0; Found mass=5246.4.

Example 3

N{Alpha}([Leu301,Arg309,Glu312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

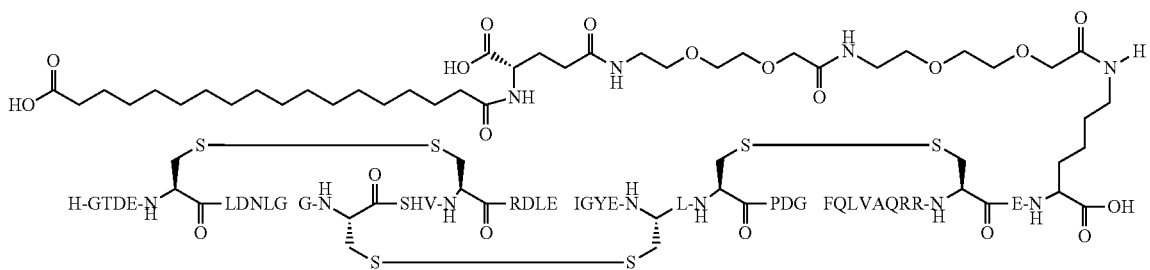

The peptide is SEQ ID NO: 4.
Compound prepared by general method B
LCMS01: Found m/4=1314.6; Found m/5=1052.1; Calc mass=5255.9.

Example 4

N{Epsilon-312}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309]-LDL-R-(293-332)-peptide

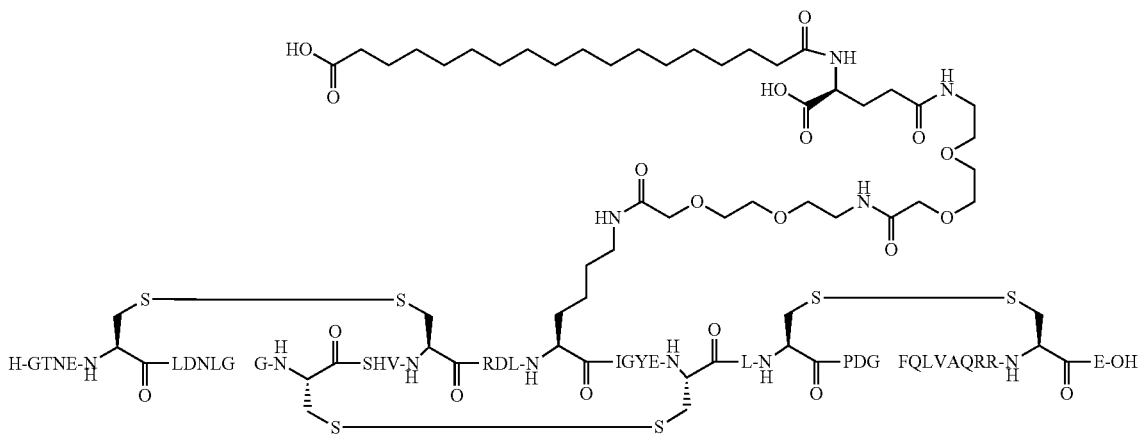

The peptide is SEQ ID NO: 3.
Compound prepared by general method B
LCMS01: Found m/4=1282.3; Found m/5=1026.3; Calc mass=5126.8.

Example 5

N{293}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-[Leu301,Arg309,Glu312]-LDL-R-(293-332)-peptide

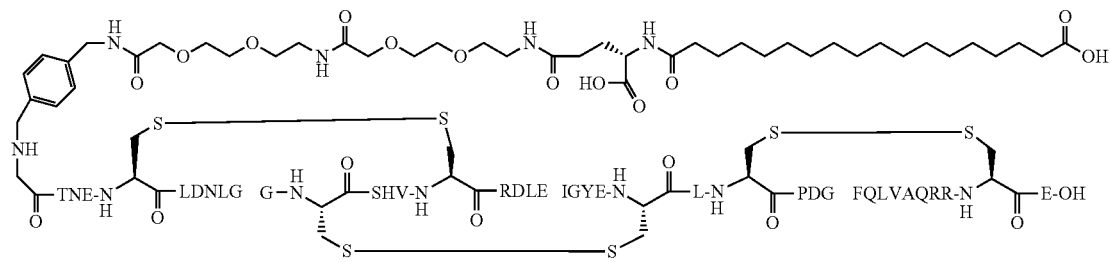

The peptide is SEQ ID NO: 6.
Compound prepared by general method A and C
LCMS029: Calc. mass=5246.92; Found mass=5247.37.

Example 6

N{Epsilon-299}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys299,Leu301,Arg309,Glu312]-LDL-R-(293-332)-peptide

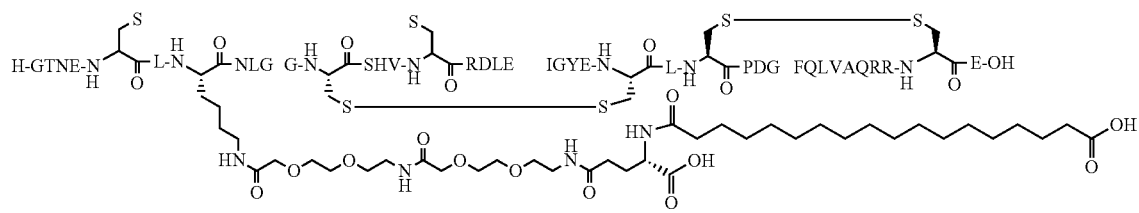

The peptide is SEQ ID NO: 7.
Compound prepared by general method B
LCMS01: Found m/3=1714.2; Found m/4=1286.1; Calc mass=5140.85.

Example 7

N{Epsilon-330}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys330]-LDL-R-(293-332)-peptide

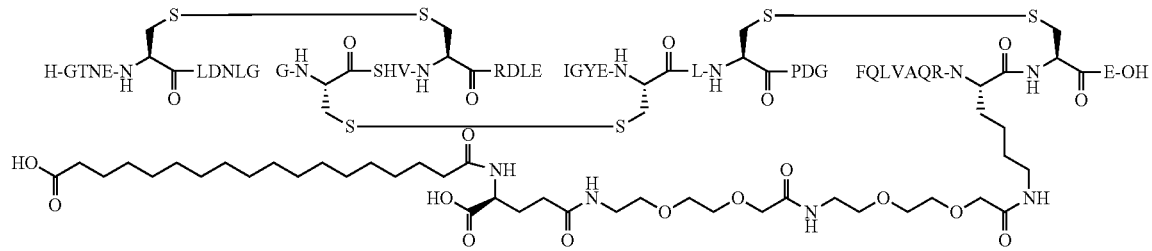

The peptide is SEQ ID NO: 8.
Compound prepared by general method B
LCMS01: Found m/3=1700.8; Found m/4=1275.8; Found m/5=1020.9, Calc. mass 5099.7; Found mass=5099.75.

Example 8

N{293}-[4-[[[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]amino]methyl]phenyl]methyl-[Leu301,Arg309,Glu312]-LDL-R-(293-332)-peptide

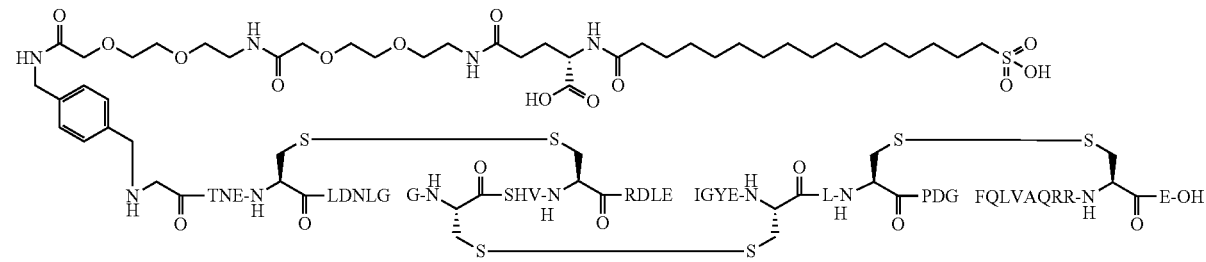

23: The peptide is SEQ ID NO: 6.
Compound prepared by general method A and C
LCMS029: Found m/3=1757.1; Found m/4=1318.04; Calc. mass=5268.95; Found mass=5269.39.

Example 9

N{293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl],
N{Epsilon-330}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys330]-LDL-R-(293-332)-peptide

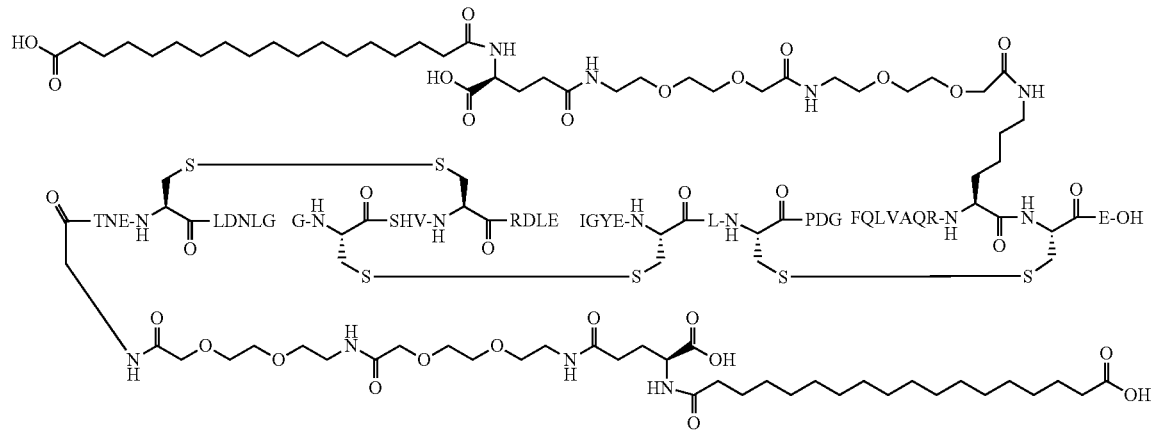

24: The peptide is SEQ ID NO: 8.
Compound prepared by general method B
LCMS029: Found m/3=1939.2; Found m/4=1454.2; Calc. mass=5815.6; Found mass=5816.1.

Example 10

N{Epsilon-332}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys332]-LDL-R-(293-332)-peptide

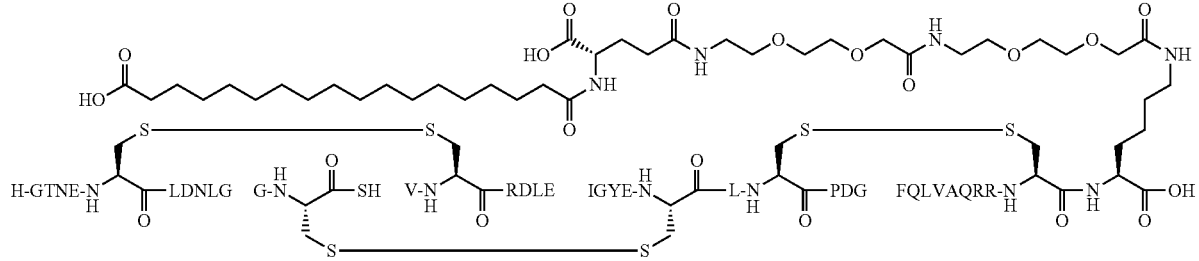

The peptide is SEQ ID NO: 11.
Compound prepared by general method B
LCMS01: Found m/4=1282.6; Found m/5=1026.3; Calc mass=5126.8.

Example 11

N{Epsilon-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys293,Leu301,Arg309,Glu312]-LDL-R-(293-332)-peptide

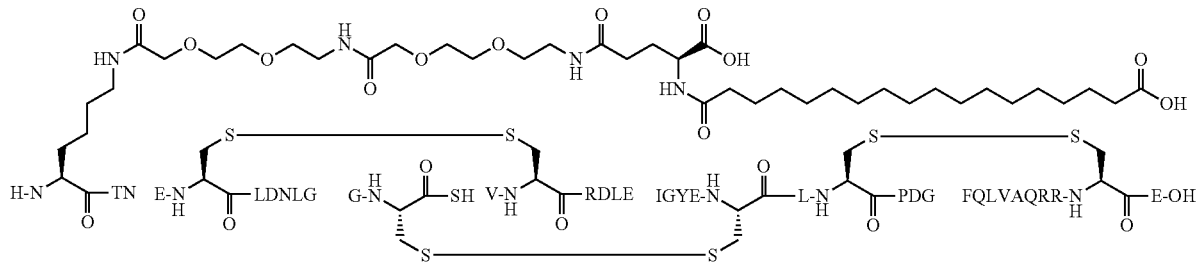

The peptide is SEQ ID NO: 12.
Compound prepared by general method B
LCMS01: Found m/4=1300.6; Found m/5=1040.5; Calc mass=5198.9.

Example 12

N{Alpha}(N{Epsilon-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys293,Leu301,Arg309,Glu312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl] Lys

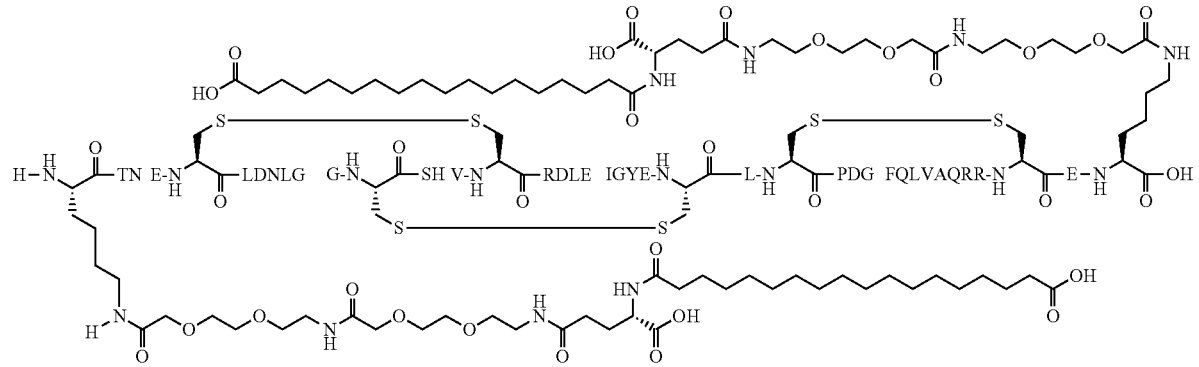

The peptide is SEQ ID NO: 13.
Compound prepared by general method B
LCMS029: Found m/2=3022.4; Found m/3=2015.3; Found m/4=1511.8; Found m/5=1209.6; Found mass=6043.6; Calc. mass=6042.9.

Example 13

N{Alpha}(N{Epsilon-293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Lys293,Leu301,Arg309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

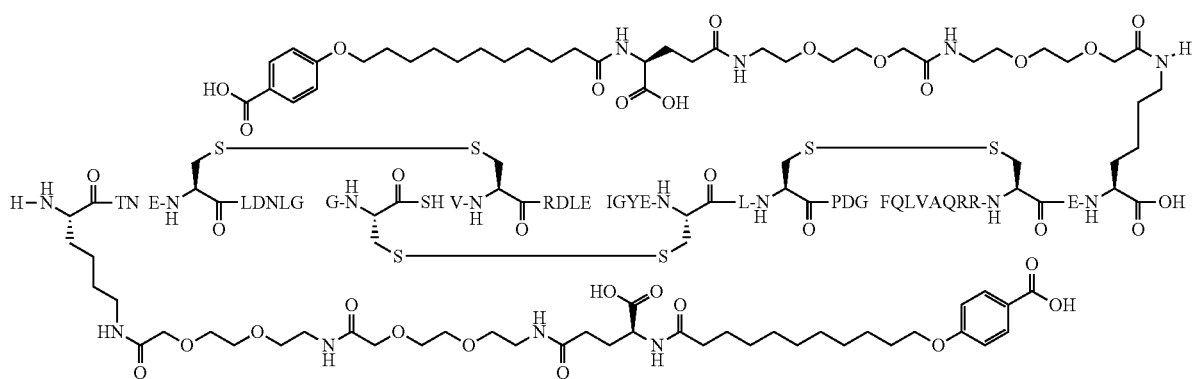

The peptide is SEQ ID NO: 13.
Compound prepared by general method B
LCMS029: Found m/2=3030.4; Found m/3=2020.7; Found m/4=1515.7; Found m/5=1212.8; Found mass=6059.7; Calc. mass=6058.8.

Example 14

N{Alpha}(N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys332]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

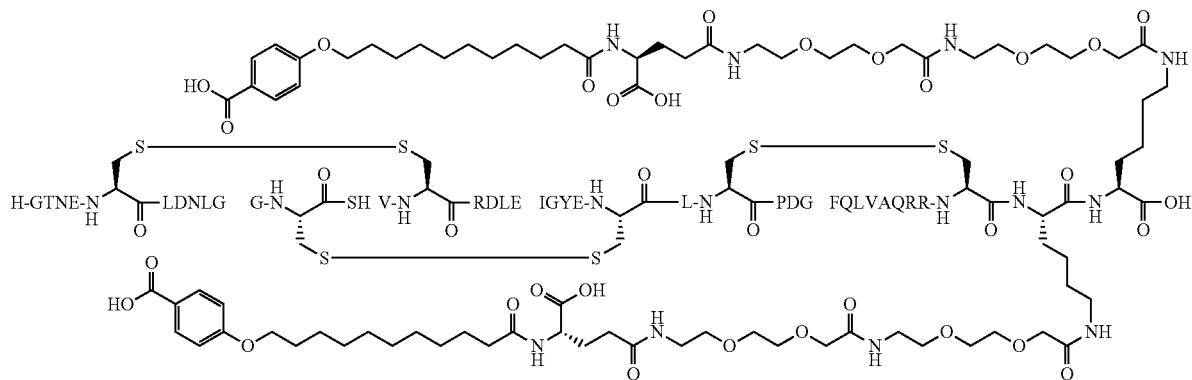

The peptide is SEQ ID NO: 15.
Compound prepared by general method B
LCMS01: Found m/4=1497.4; Found m/5=1198.3; Calc mass=5986.7.

Example 15

N{Alpha}(N{Epsilon-330}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys330]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

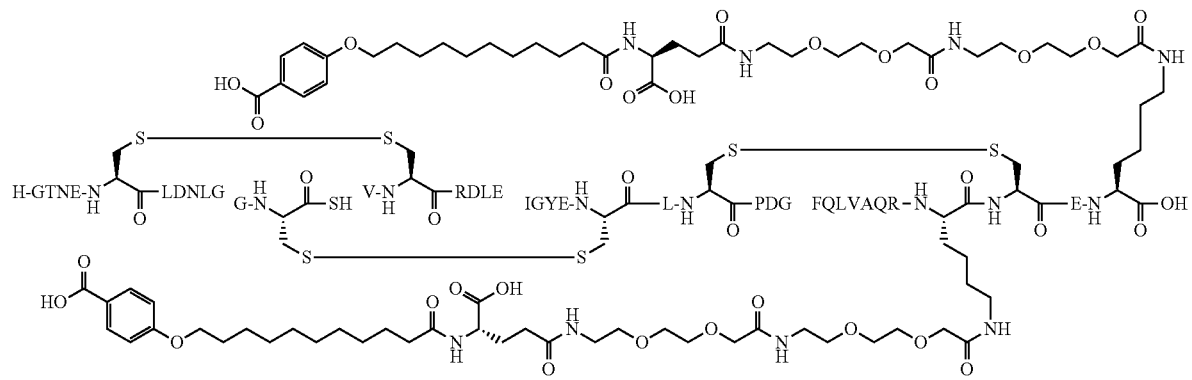

The peptide is SEQ ID NO: 16.
Compound Prepared by General Method B
LCMS01: Found m/3=1987.7; Found m/4=1491.0; Found m/5=1193.0; Calc mass=5959.7.

Example 16

N{Alpha}(N{Epsilon-321}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys321]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

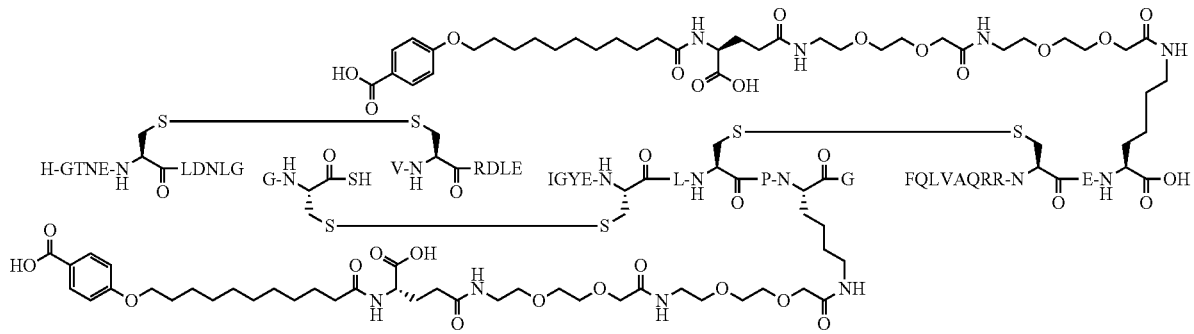

The peptide is SEQ ID NO: 17.
Compound prepared by general method B
LCMS01: Found m/4=1500.9; Found m/5=1201.2; Calc mass=6000.8.

Example 17

N{Alpha}(N{Epsilon-312}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

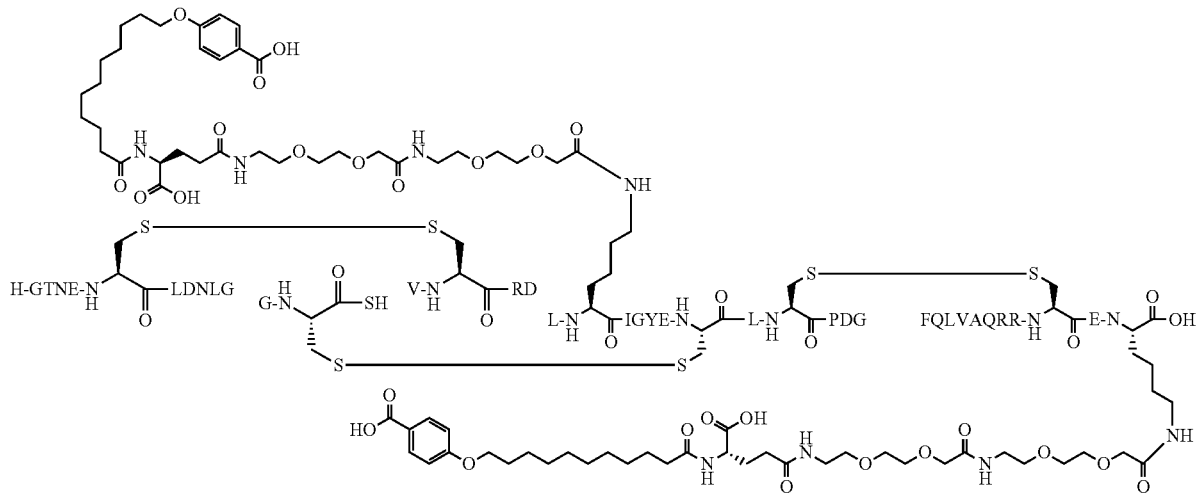

The peptide is SEQ ID NO: 18.
Compound prepared by general method B
LCMS01: Found m/4=1498.2; Found m/5=1198.7; Calc mass=5986.7.

Example 18

N{Alpha}([Leu301,Arg309,Glu312,Glu321]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

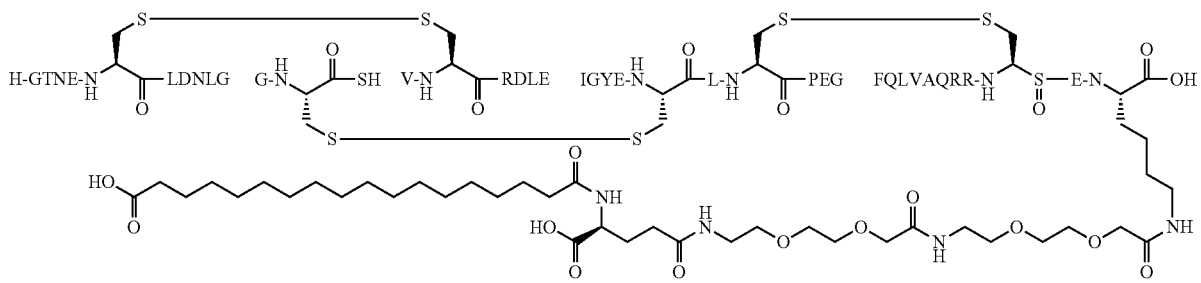

The peptide is SEQ ID NO: 19.
Compound prepared by general method B
LCMS027: Found m/2=2635.7; Found m/3=1757.5; Found m/4=1318.4; Found m/5=1054.9; Calc. mass=5270.0; Found mass=5270.5.

Example 19

N{293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312]-LDL-R-(293-332)-peptide

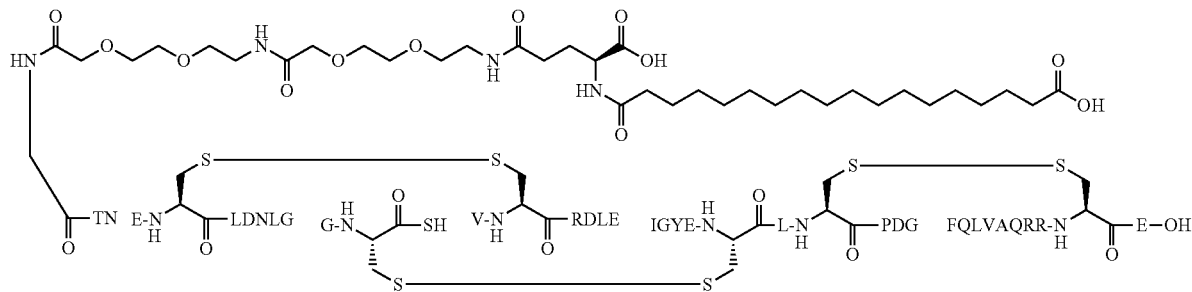

The peptide is SEQ ID NO: 6.
Compound prepared by general method A and D
LCMS01: Found m/1=5127.8; Found m/3=1710.0; Found m/4=1282.3; Found m/5=1026.5; Calc. mass=5127.8.

Example 20

N{Epsilon-321}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys321]-LDL-R-(293-332)-peptide

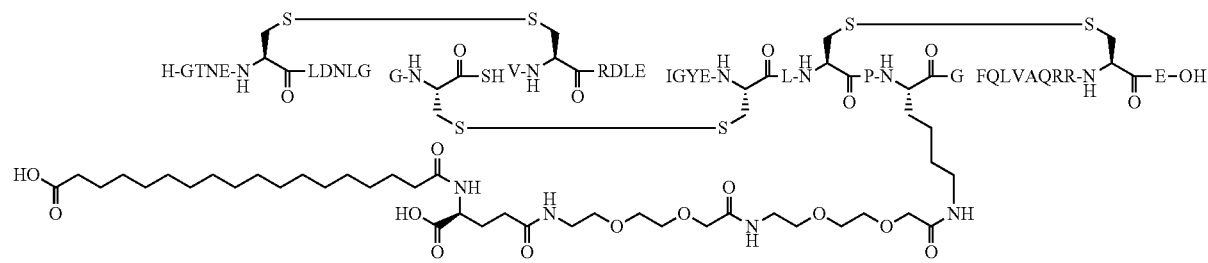

The peptide is SEQ ID NO: 21.
Compound prepared by general method B
LCMS01: Found m/4=1286.1; Found m/5=1029.1; Calc mass=5140.9.

Example 21

N{Epsilon-324}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys324]-LDL-R-(293-332)-peptide

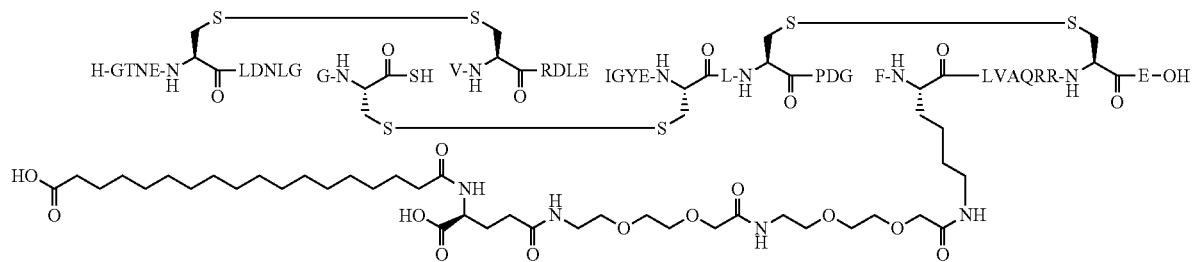

The peptide is SEQ ID NO: 22.
Compound prepared by general method B
LCMS01: Found m/4=1282.9; Found m/5=1026.5; Calc mass=5127.8.

Example 22

N{293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Gln312]-LDL-R-(293-332)-peptide

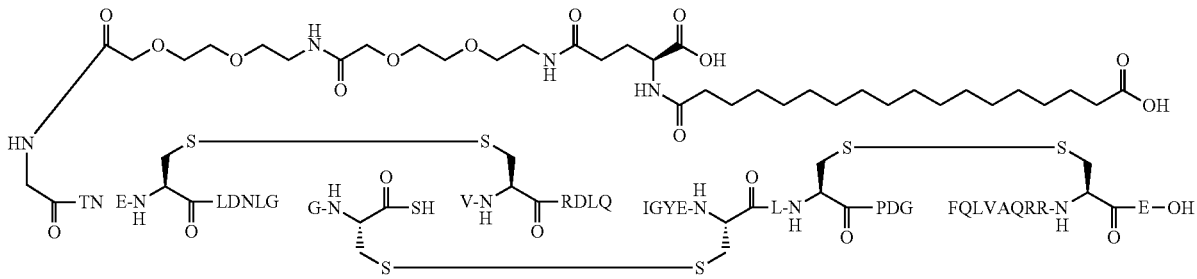

The peptide is SEQ ID NO: 23.
Compound prepared by general method B
LCMS029: Found m/3=1709.8; Found m/4=1282.6; Calc. mass=5126.8; Found mass=5127.3.

Example 23

N{Epsilon-332}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Glu321,Lys332]-LDL-R-(293-332)-peptide

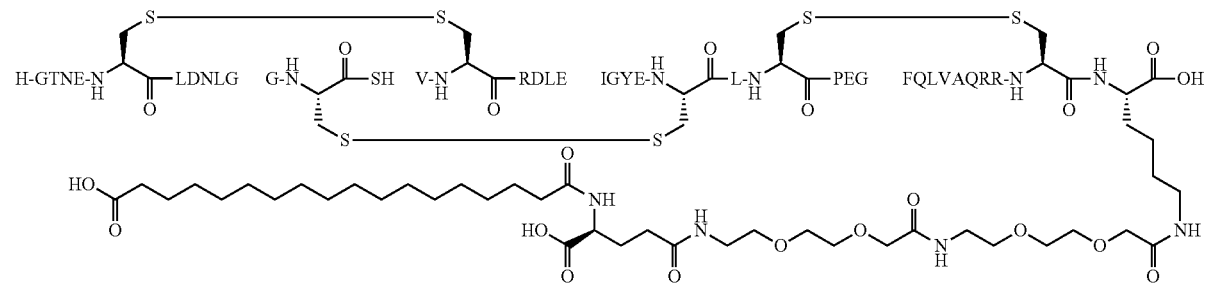

The peptide is SEQ ID NO: 24.
Compound prepared by general method B
LCMS029: Found m/2=2571.2; Found m/3=1714.5; Found m/4=1286.1; Found m/z=5141.4; Calc. mass=5140.9.

Example 24

N{Epsilon-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys293,Leu301,Arg309,Glu312,Glu321]-LDL-R-(293-332)-peptide

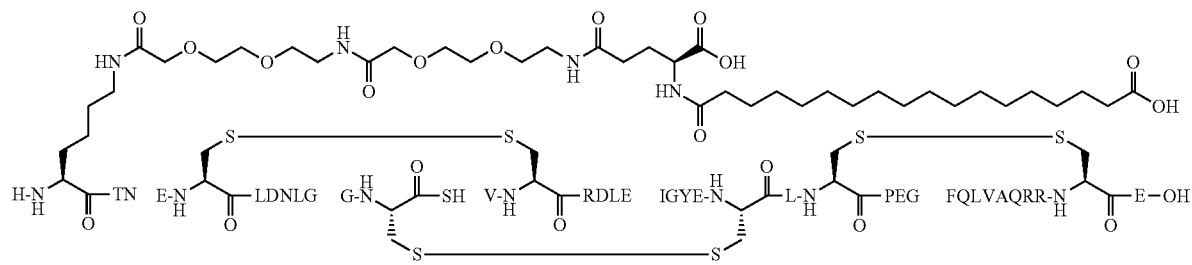

The peptide is SEQ ID NO: 25.
Compound prepared by general method B
LCMS029: Found m/2=2607.2; Found m/3=1738.5; Found m/4=1304.1; Found mass=5213.5; Calc. mass=5212.9.

Example 25

N{Alpha-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl],
N{Epsilon-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys293,Leu301,Arg309,Glu312]-LDL-R-(293-332)-peptide

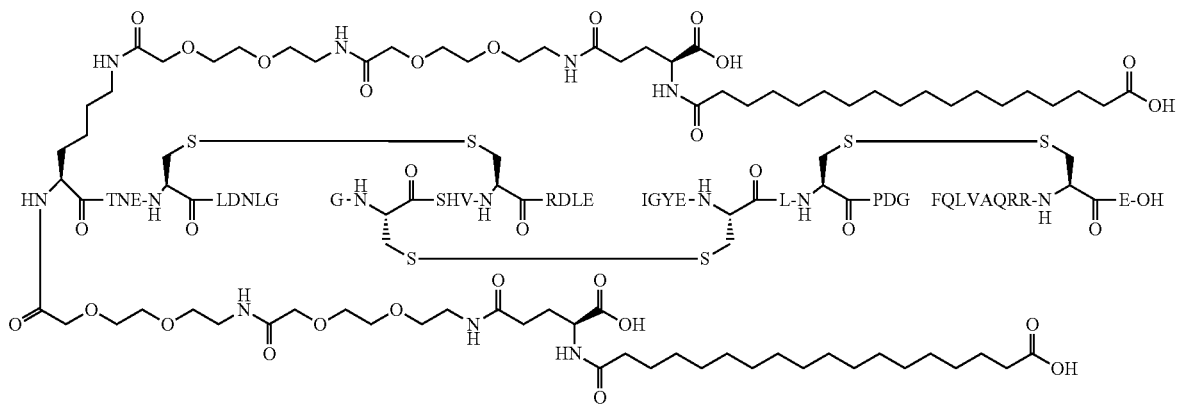

The peptide is SEQ ID NO: 26.
Compound prepared by general method B
LCMS029: Found m/4=1479.7; Calc. mass=5914.8 Da; Found mass=5914.3.

Example 26

N{Epsilon-300}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys300,Leu301,Arg309,Glu312]-LDL-R-(293-332)-peptide

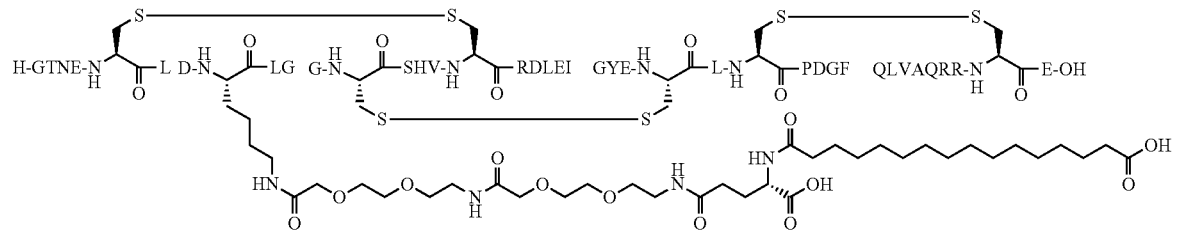

The peptide is SEQ ID NO: 27.
Compound prepared by general method B
LCMS01: Found m/4=1286.9; Found m/5=1029.7; Calc mass=5141.8.

Example 27

N{Epsilon-293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-294}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Lys293,Lys294,Leu301,Arg309,Glu312]-LDL-R-(293-332)-peptide

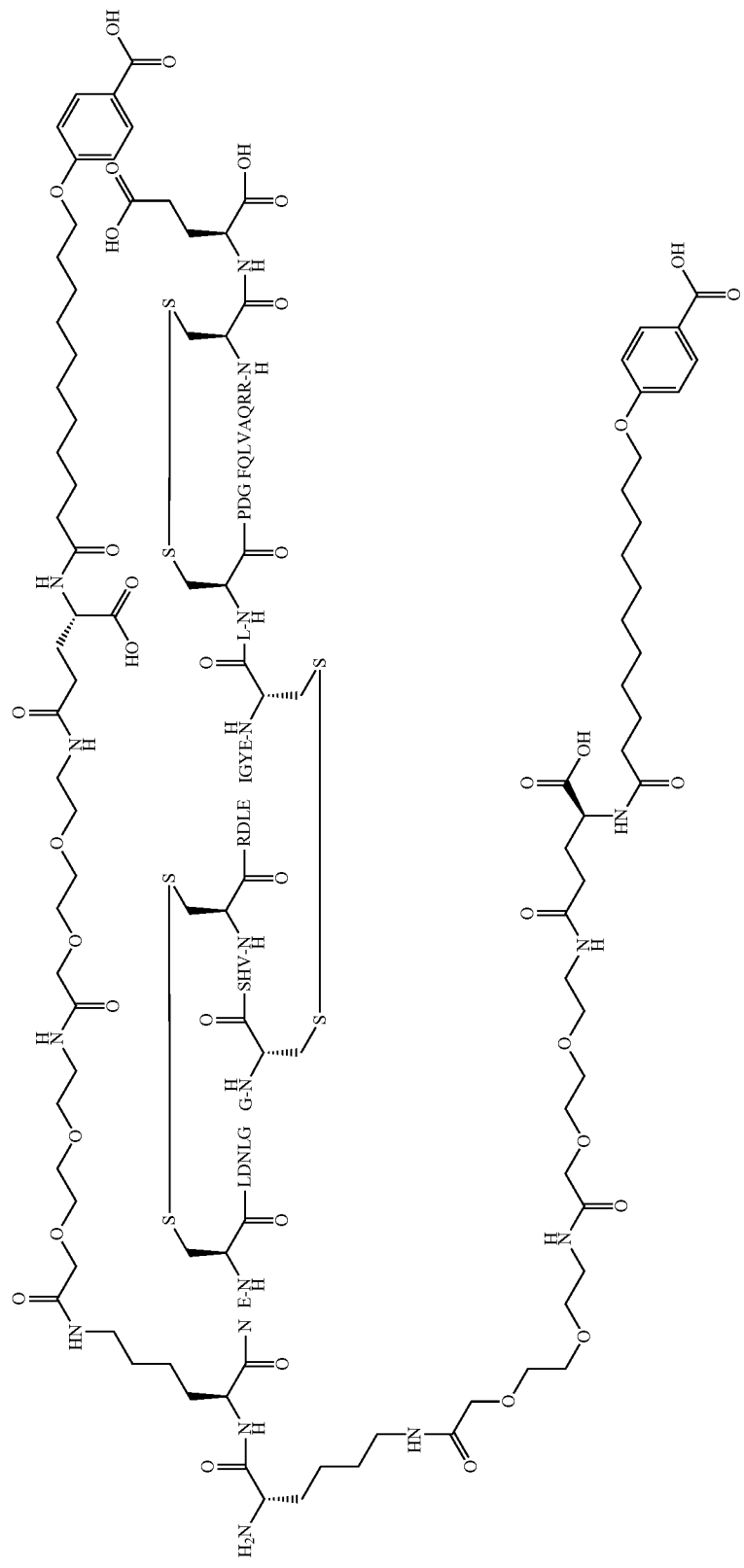

The peptide is SEQ ID NO: 28.
Compound prepared by general method B
LCMS01: Found m/1=5957.6; Found m/4=1490.4; Found m/5=1192.3; Calc m/1=5957.7.

Example 28

N{Epsilon-293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-312}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Lys293,Leu301,Arg309]-LDL-R-(293-332)-peptide

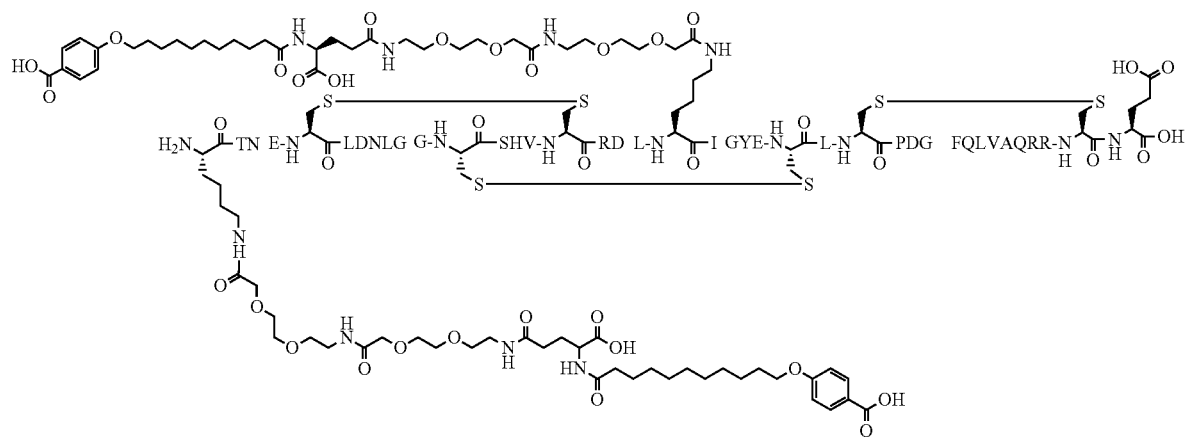

The peptide is SEQ ID NO: 29.
Compound prepared by general method B
LCMS01: Found m/1=5929.4; Found m/4=1483.3; Found m/5=1186.8; Calc m/1=5929.7.

Example 29

N{Epsilon-309}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys309,Glu312]-LDL-R-(293-332)-peptide

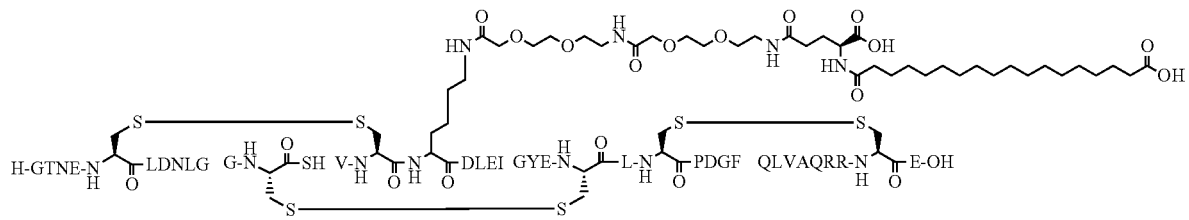

The peptide is SEQ ID NO: 30.
Compound prepared by general method B
LCMS01: Found m/3=1700.8; Found m/4=1275.8; Found m/5=1020.9; Calc mass=5099.8 (1A).

Example 30

N{Epsilon-318}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys318]-LDL-R-(293-332)-peptide

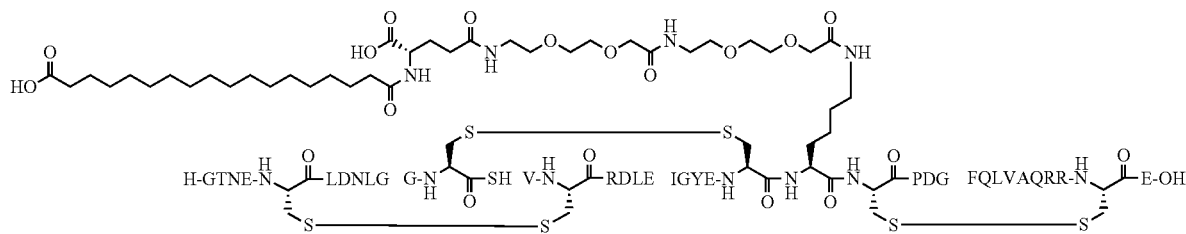

The peptide is SEQ ID NO: 31.
LCMS01: Found m/4=1286.5; Found m/5=1029.5; Calc mass=5142.8.

Example 31

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

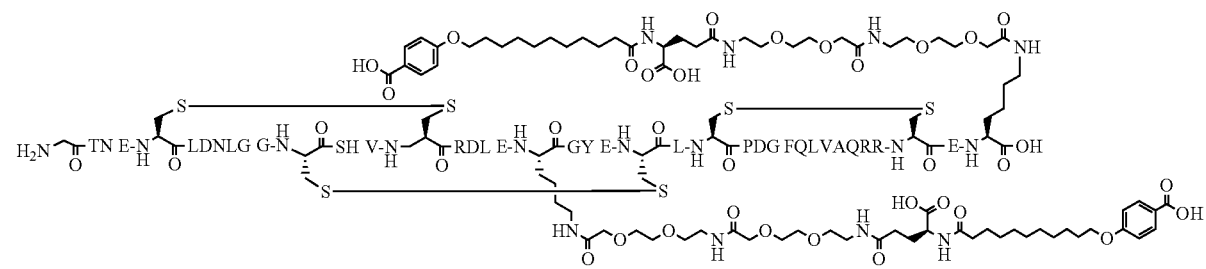

The peptide is SEQ ID NO: 32.
Compound prepared by general method B
LCMS01: Found m/1=6002.8; Found m/4=1501.6; Found m/5=1201.5; Calc m/1=6002.7.

Example 32

N{Epsilon-326}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys326]-LDL-R-(293-332)-peptide

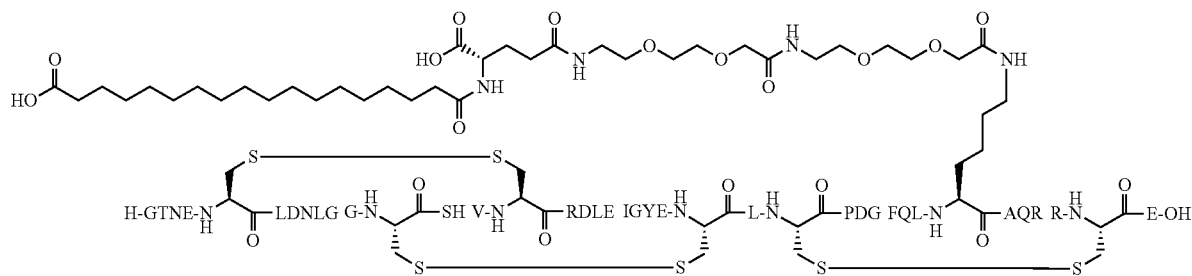

The peptide is SEQ ID NO: 33.
Compound prepared by general method B
LCMS01: Found m/3=1719.8; Found m/4=1290.1; Found m/5=1032.3; Calc mass=5156.8.

Example 33

N{Epsilon-325}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys325]-LDL-R-(293-332)-peptide

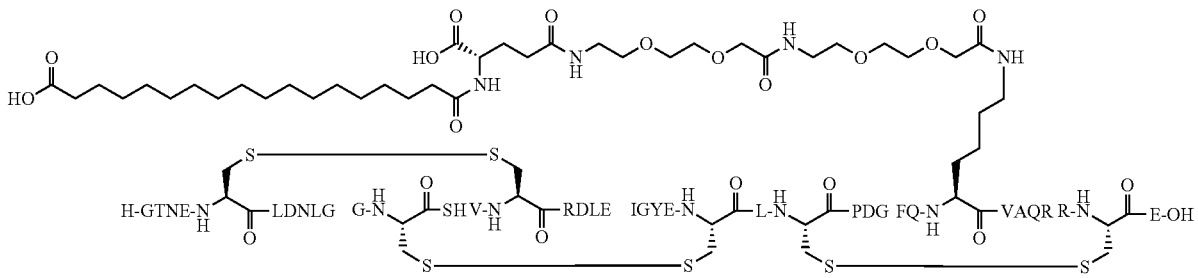

The peptide is SEQ ID NO: 34.
Compound prepared by general method B
LCMS01: Found m/3=1715.1; Found m/4=1286.6; Found m/5=1029.5; Calc mass=5142.8.

Example 34

N{Epsilon-323}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys323]-LDL-R-(293-332)-peptide

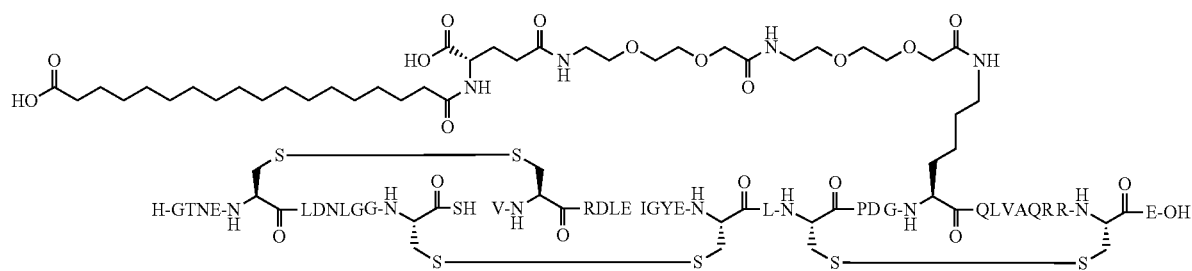

The peptide is SEQ ID NO: 35.
Compound prepared by general method B
LCMS01: Found m/1=5108.8; Found m/3=1703.8; Found m/4=1278.1; Found m/5=1022.5.

Example 35

N{Epsilon-322}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys322]-LDL-R-(293-332)-peptide

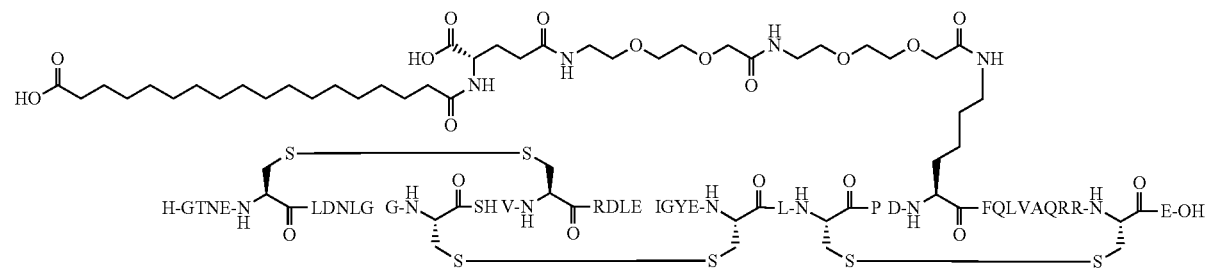

The peptide is SEQ ID NO: 36.
Compound prepared by general method B
LCMS01: Found m/1=5198.9; Found m/3=1733.8; Found m/4=1300.6; Found m/5=1040.7.

Example 36

N{Epsilon-320}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys320]-LDL-R-(293-332)-peptide

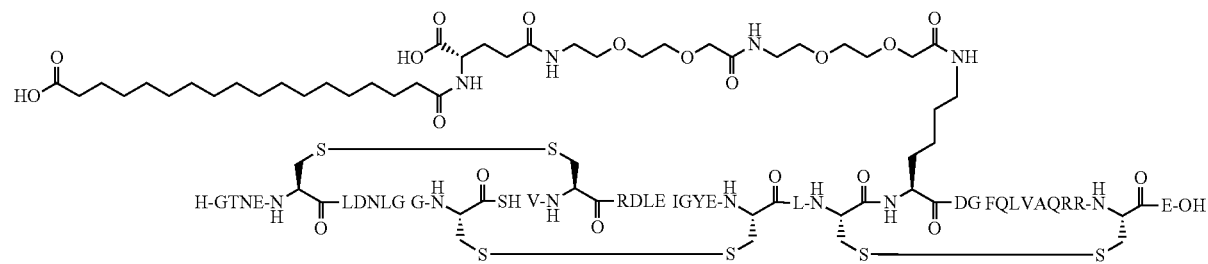

The peptide is SEQ ID NO: 37.
Compound prepared by general method B
LCMS01: Found m/3=1720.4; Found m/4=1290.3; Found m/5=1032.5; Calc mass=5158.8.

Example 37

N{Epsilon-329}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys329]-LDL-R-(293-332)-peptide

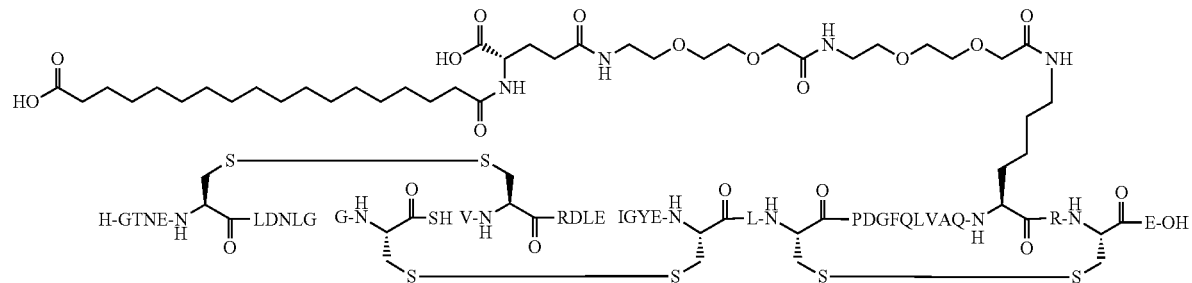

The peptide is SEQ ID NO: 38.
Compound prepared by general method B
LCMS029: Found m/2=2550.7; Found m/3=1700.8; Found m/4=1275.9; Calc. mass=5099.8; Found mass=5100.5.

Example 38

N{Epsilon-313}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys313]-LDL-R-(293-332)-peptide

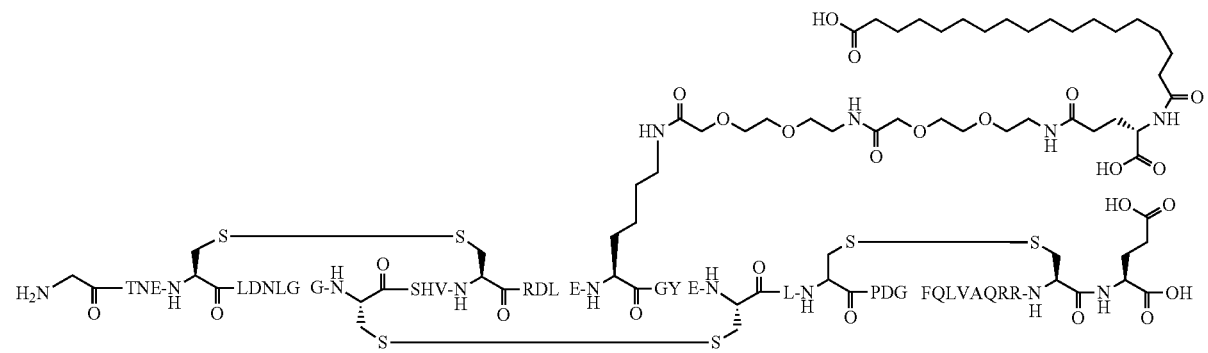

The peptide is SEQ ID NO: 39.
Compound prepared by general method B
LCMS01: Found m/1=5143.0; Found m/4=1286.0; Found m/5=1029.0; Calc m/1=5142.8.

Example 39

N{Epsilon-328}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys328]-LDL-R-(293-332)-peptide

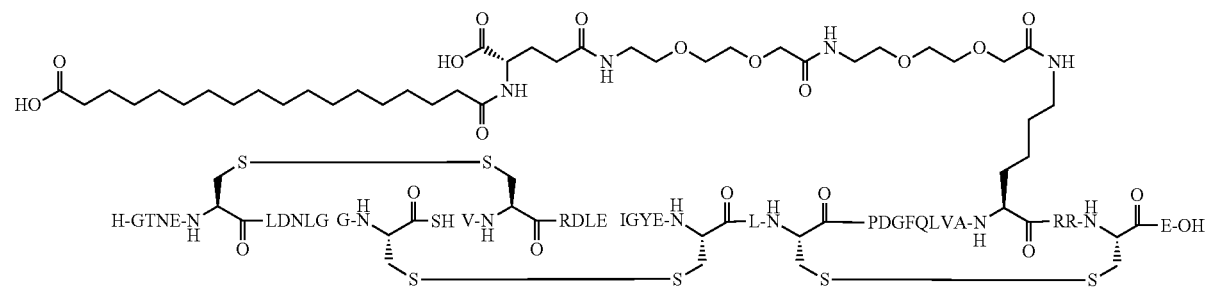

The peptide is SEQ ID NO: 40.
Compound prepared by general method B
LCMS029: Found m/2=2564.7; Found m/3=1710.2; Found m/4=1282.9; Found 5127.8; Calc. mass=5128.5.

Example 40

N{Epsilon-316}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys316]-LDL-R-(293-332)-peptide

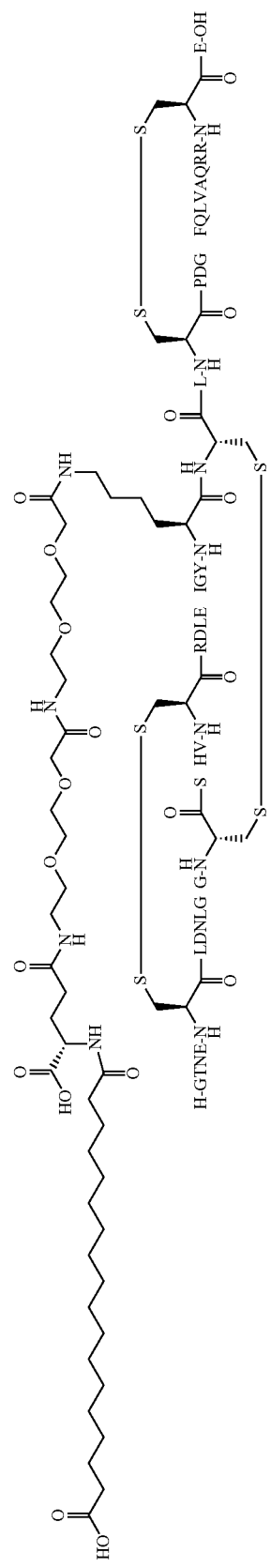

The peptide is SEQ ID NO: 41.
Compound prepared by general method B
LCMS01: Found m/3=1709.7; Found m/4=1282.3; Found m/5=1026.1; Calc mass=5126.8.

Example 41

N{Epsilon-315}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys315]-LDL-R-(293-332)-peptide

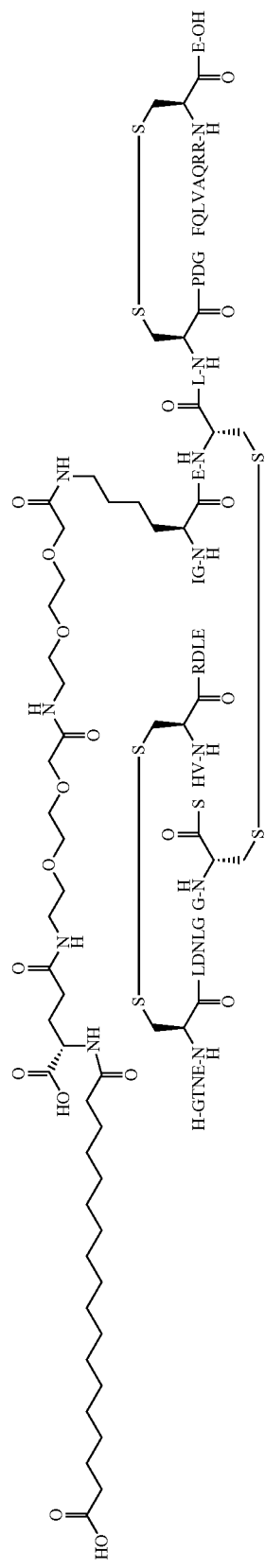

The peptide is SEQ ID NO: 42.
Compound prepared by general method B
LCMS01: Found m/3=1698.3; Found m/4=1273.8; Found m/5=1019.3; Calc m/1=5092.8.

Example 42

N{Alpha}([His300,Leu301,Arg309,Arg312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

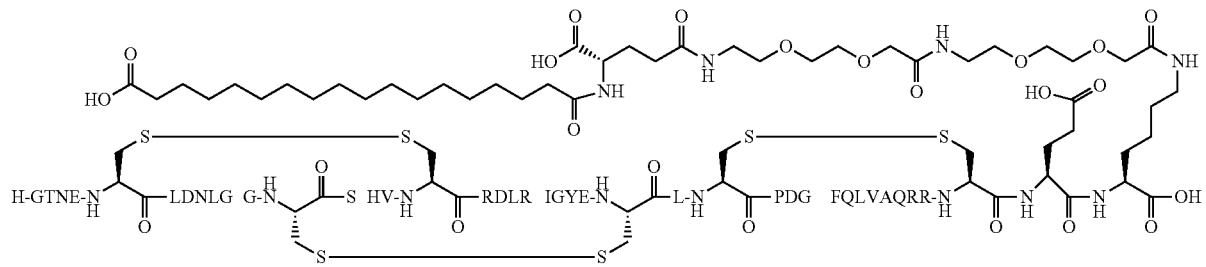

The peptide is SEQ ID NO: 43.
Compound prepared by general method B
LCMS01: Found m/1=5306.3; Found m/3=1768.7; Found m/4=1327.1; Found m/5=1061.7.

Example 43

N{Epsilon-314}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys314]-LDL-R-(293-332)-peptide

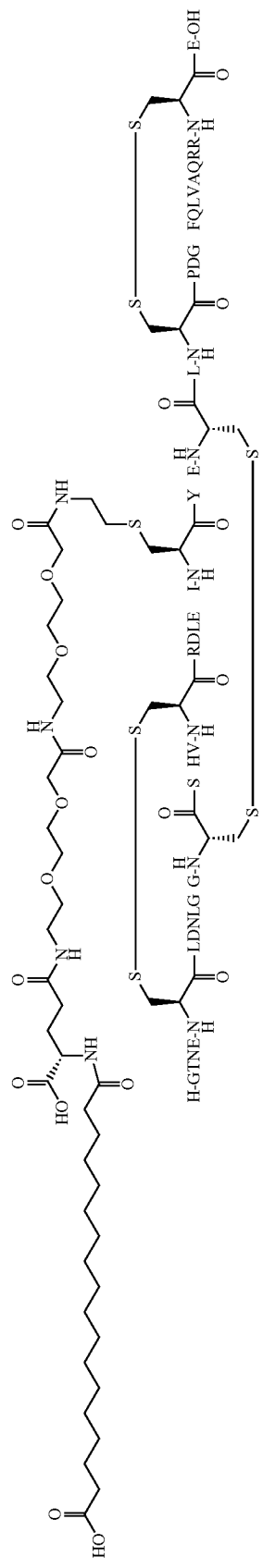

The peptide is SEQ ID NO: 44.
Compound prepared by general method B
LCMS01: Found m/4=1300.2; Found m/5=1040.2; Calc mass=5198.9.

Example 44

N{Epsilon-311}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Lys311,Glu312]-LDL-R-(293-332)-peptide

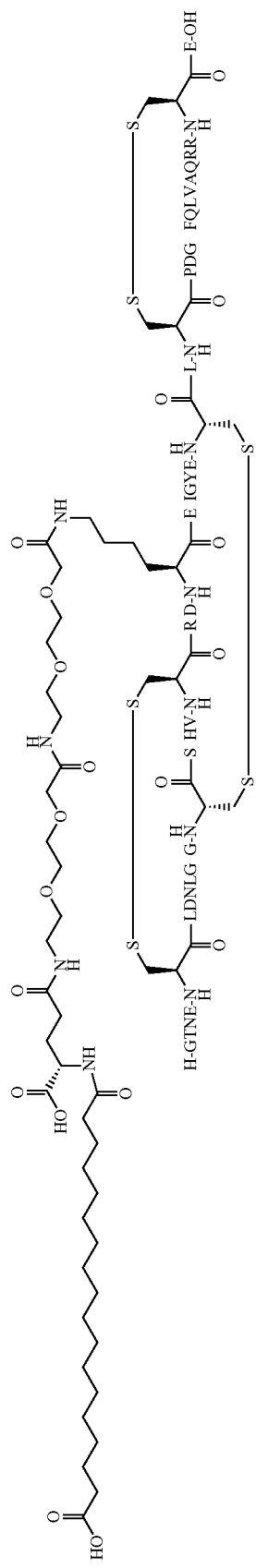

The peptide is SEQ ID NO: 45.
Compound prepared by general method B
LCMS01: Found m/3=1714.9; Found m/4=1286.2; Found m/5=1029.2; Calc mass=5142.8.

Example 45

N{Epsilon-307}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys307,Arg309,Glu312]-LDL-R-(293-332)-peptide

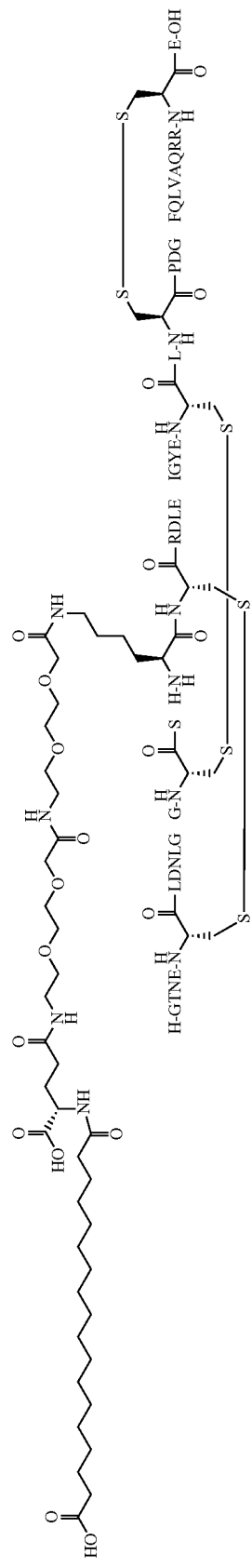

The peptide is SEQ ID NO: 46.
Compound prepared by general method B
LCMS01: Found m/3=1919.8; Found m/4=1290.1; Found m/5=1032.3; Calc mass=5156.8.

Example 46

N{Alpha}([Leu301,Ser309,Arg312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

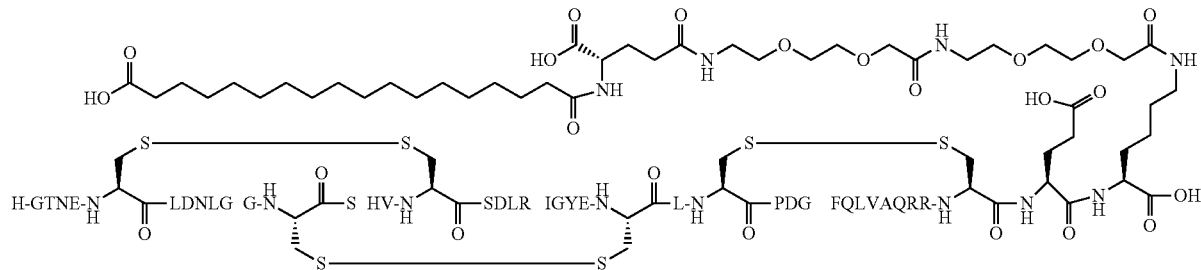

The peptide is SEQ ID NO: 47.
Compound prepared by general method B
LCMS01: Found m/3=1738.8; Found m/4=1304.1; Found m/5=1043.5; Found mass=5214.3.

Example 47

N{Alpha}([Leu301,Ser309,Glu312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

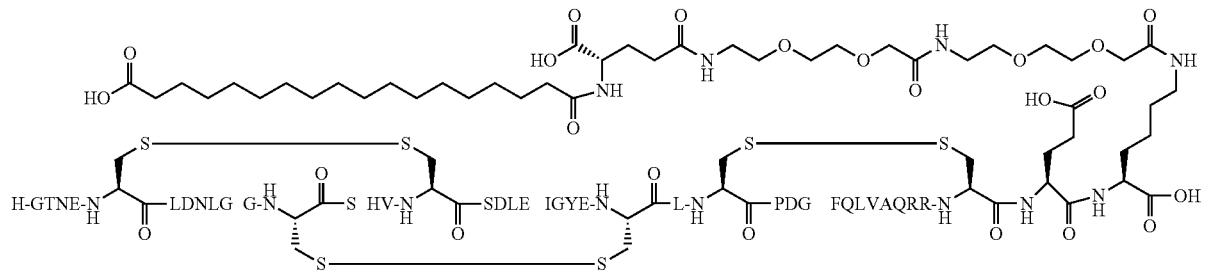

The peptide is SEQ ID NO: 48.
Compound prepared by general method B
LCMS01: Found m/1=5187.2; Found m/3=1729.7; Found m/4=1297.2; Found m/5=1038.4; Calc m/1=5186.8.

Example 48

[Ala299,Leu301,Ile307,Arg309,Lys310]-LDL-R-(293-332)-peptide

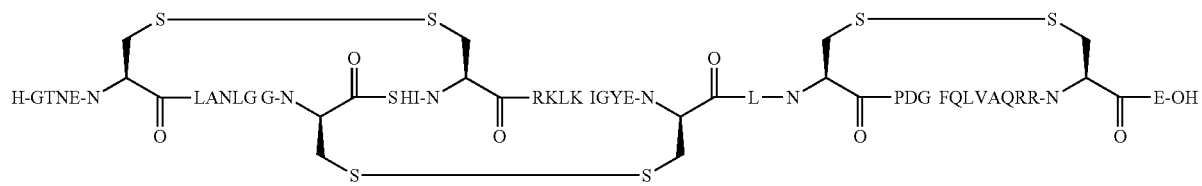

The peptide is SEQ ID NO: 2.
Compound prepared by general method A
LCMS01: Found m/3=1465.3; Found m/4=1099.3; Found m/5=879.6; Calc=4391.0.

Example 49

[Leu301,Arg309]-LDL-R-(293-332)-peptide

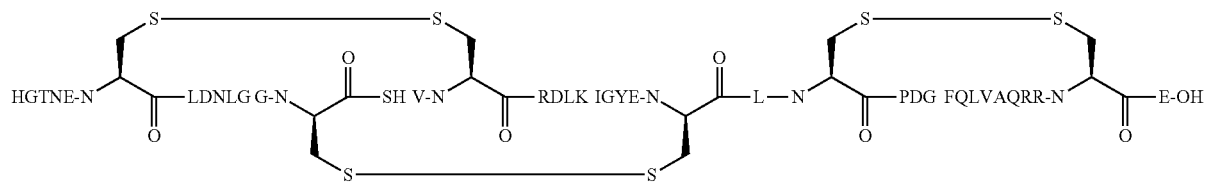

The peptide is SEQ ID NO: 3.
Compound prepared by general method A.
LCMS01: Found m/3=1470.3; Found m/4=1103.0; Found m/5=882.6; Calc=4407.9.

Example 50

[Leu301,Arg309,Glu312]-LDL-R-(293-332)-peptide

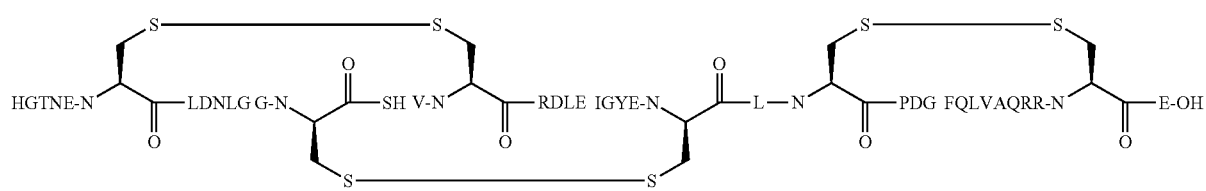

The peptide is SEQ ID NO: 6.
Compound prepared by general method A.
LCMS01: Found m/3=1471.3; Found m/4=1103.7; Found m/5=883.2; Calc=4411.9.

Example 51

N{293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Tyr306,Ser309,Glu312]-LDL-R-(293-332)-peptide

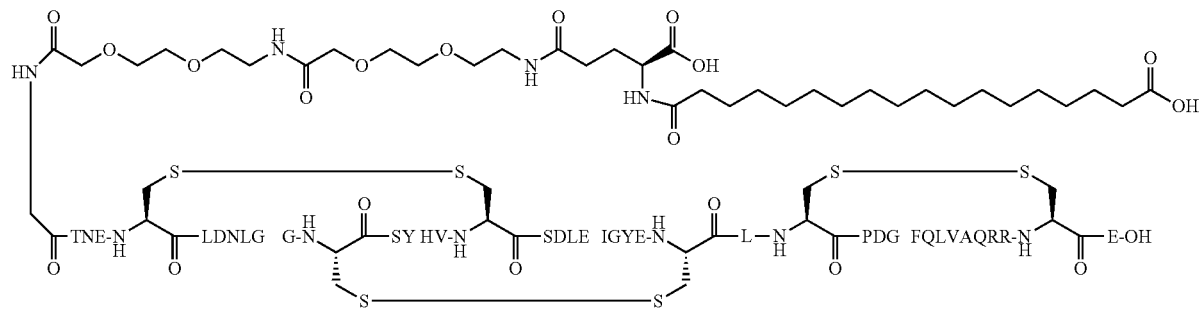

The peptide is SEQ ID NO: 49.
Compound prepared by general method B
LCMS029: Found m/3=1695.8; Calc mass=5085.1.

Example 52

N{Alpha-293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Asn293,Leu301,Ser309,Glu312]-LDL-R-(293-332)-peptide

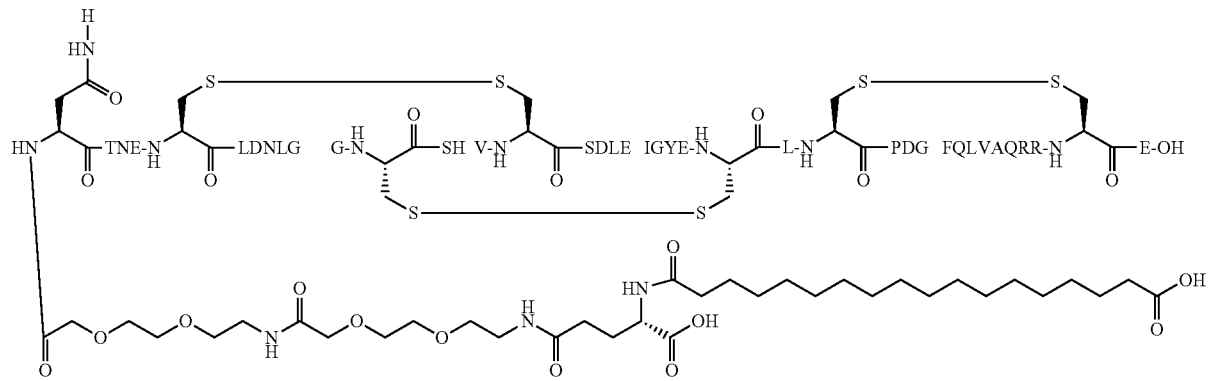

The peptide is SEQ ID NO: 50.
LCMS29: Found m/3=1706.1, Calc mass=5115.7.
Compound prepared by general method B

Example 53

N{Epsilon-306}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys306,Arg309,Glu312]-LDL-R-(293-332)-peptide

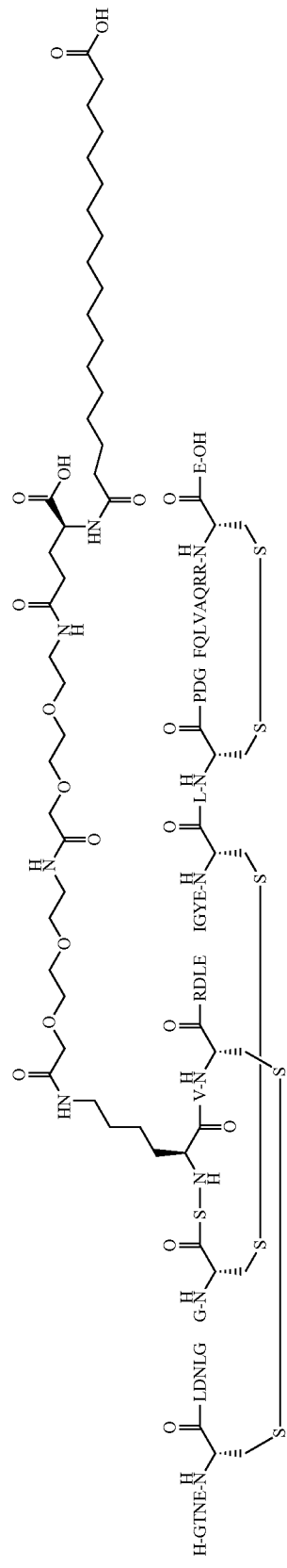

The peptide is SEQ ID NO: 51.
Compound prepared by general method B
LCMS01: Found m/3=1707.0; Found m/4=1280.3; Found m/5=1024.4; Calc mass=5118.8.

Example 54

N{Epsilon-305}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys305,Arg309,Glu312]-LDL-R-(293-332)-peptide

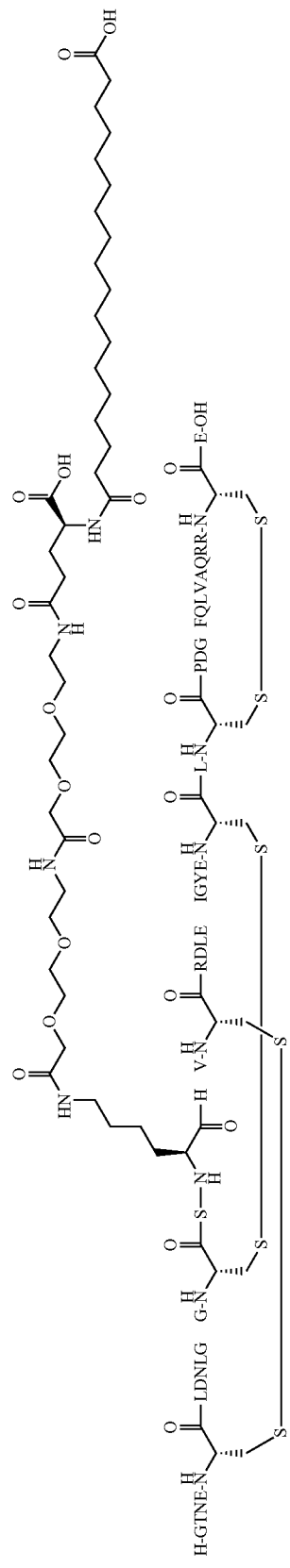

The peptide is SEQ ID NO: 52.
Compound prepared by general method B
LCMS01: Found m/3=1723.8; Found m/4=1292.8; Found m/5=1034.4; Calc mass=5168.8.

Example 55

N{Epsilon-303}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys303,Arg309,Glu312]-LDL-R-(293-332)-peptide

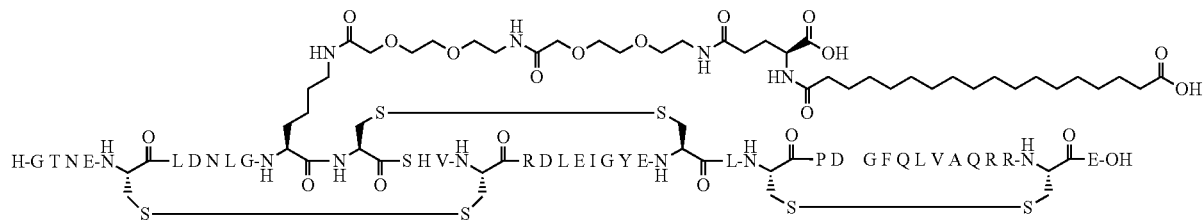

The peptide is SEQ ID NO: 53.
Compound prepared by general method B
LCMS01: Found m/3=1733.7; Found m/4=1300.3; Found m/5=1040.5; Calc mass=5198.9.

Example 56

N{Epsilon-302}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Lys302,Arg309,Glu312]-LDL-R-(293-332)-peptide

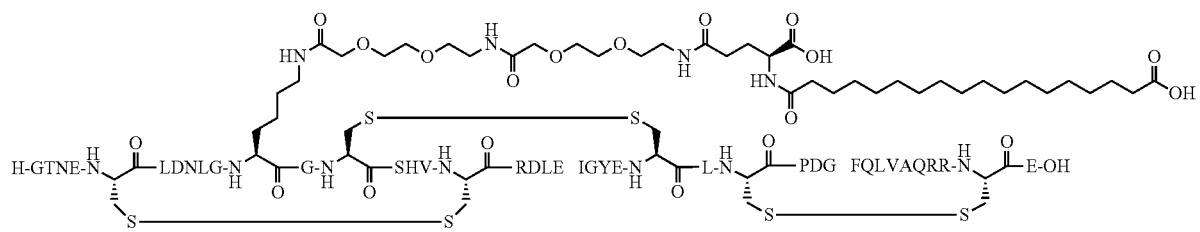

The peptide is SEQ ID NO: 54.
Compound prepared by general method B
LCMS01: Found m/3=1733.7; Found m/4=1300.3; Found m/5=1040.5; Calc mass=5198.9.

Example 57

N{Alpha}([Asn293,His300,Leu301,Arg309, Arg312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

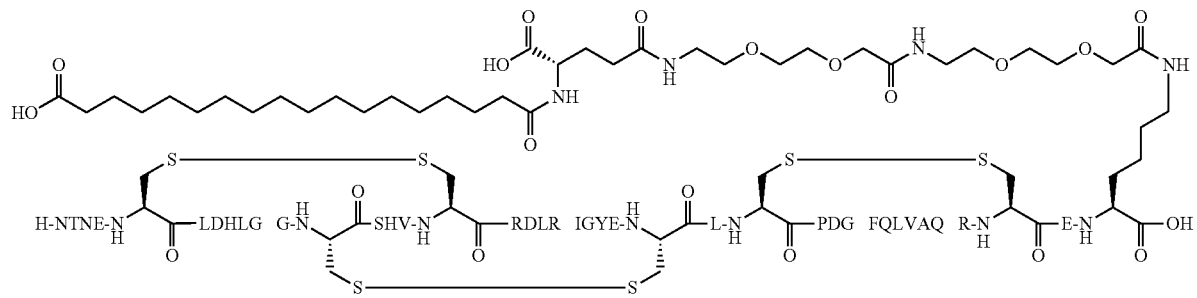

The peptide is SEQ ID NO: 55.
Compound prepared by general method B
LCMS01: Found m/4=1341.5; Found m/5=1073.3; Calc mass=5363.

Example 58

N{Epsilon-301}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys301,Arg309,Glu312]-LDL-R-(293-332)-peptide

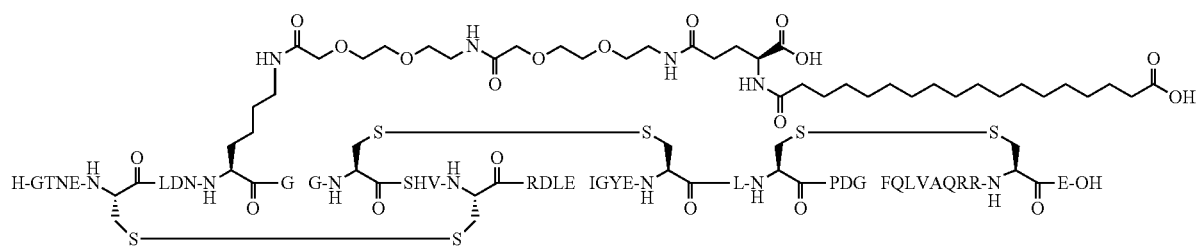

The peptide is SEQ ID NO: 56.
Compound prepared by general method B
LCMS01: Found m/3=1715.2; Found m/4=1286.6; Found m/5=1029.5; Calc mass=5142.8.

Example 59

N{Epsilon-298}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Lys298,Leu301,Arg309,Glu312]-LDL-R-(293-332)-peptide

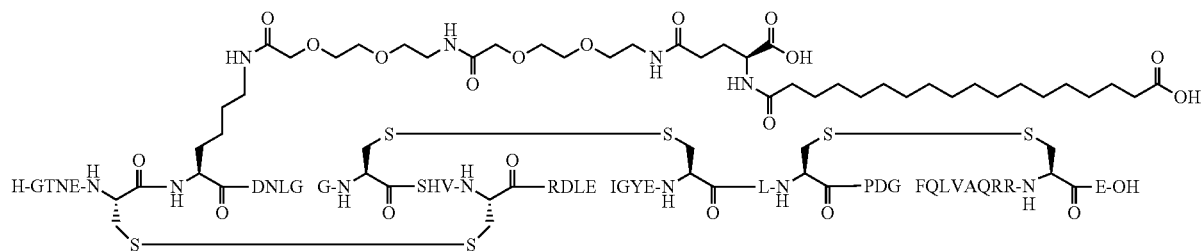

The peptide is SEQ ID NO: 57.
Compound prepared by general method B
LCMS01: Found m/3=1715.1; Found m/4=1286.3; Found m/5=1029.3; Calc m/z=5142.8.

Example 60

N{Alpha}([Asn293,Leu301,Arg309,Arg312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

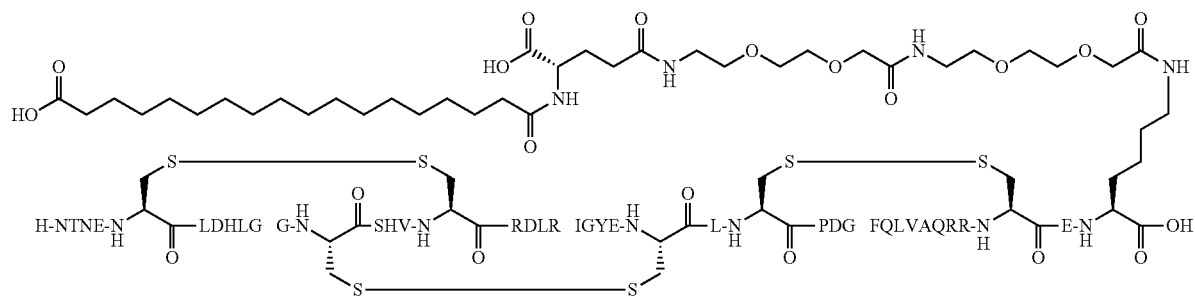

The peptide is SEQ ID NO: 58.
Compound prepared by general method B
LCMS01: Found m/3=1780.7; Found m/4=1335.5; Found m/5=1068.4; Calc mass=5340.1.

Example 61

N{Epsilon-332}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Ile307,Lys332]-LDL-R-(293-332)-peptide

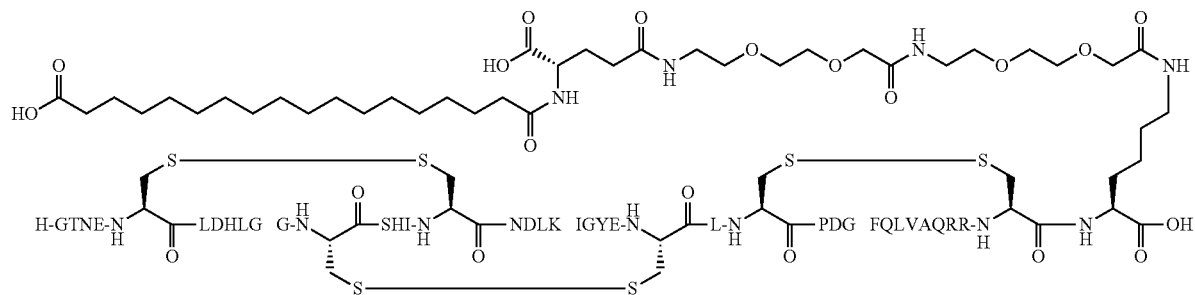

The peptide is SEQ ID NO: 59.
Compound prepared by general method B
LCMS01: Found m/3=1700.0; Found m/4=1275.1; Found m/5=1020.3; Calc mass=5097.8.

Example 62

N{Epsilon-332}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Tyr306,Glu312,Lys332]-LDL-R-(293-332)-peptide

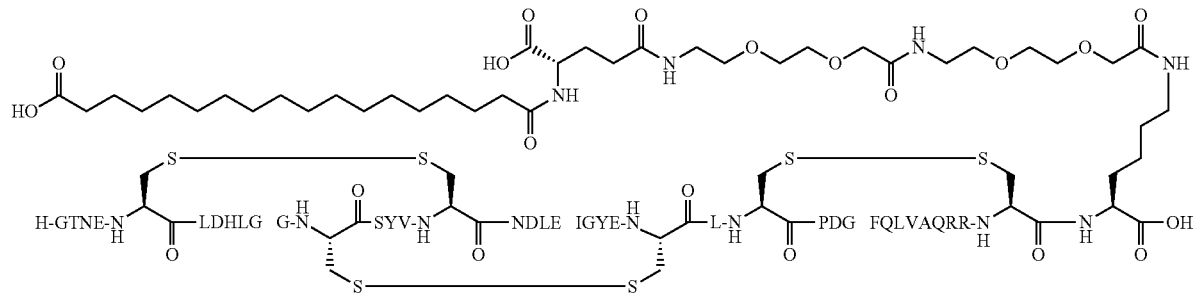

The peptide is SEQ ID NO: 60.
Compound prepared by general method B
LCMS01: Found m/3=1704.3; Found m/4=1278.5; Found m/5=1030.4; Calc m/z=5110.8.

Example 63

N{Epsilon-332}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Ile307,Glu312,Lys332]-LDL-R-(293-332)-peptide

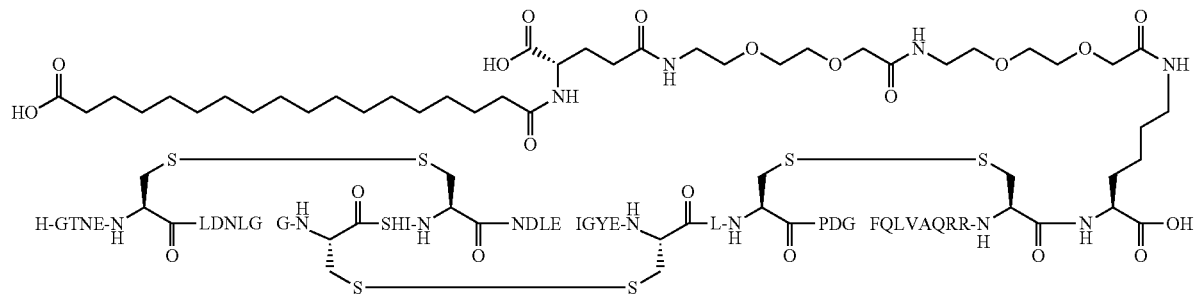

The peptide is SEQ ID NO: 61.
Compound prepared by general method B
LCMS01: Found m/3=1700.3; Found m/4=1275.2; Found m/5=Calc mass=5098.8.

Example 64

N{293}-[4-[[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]methyl]phenyl]methyl-[His300,Leu301,Arg309]-LDL-R-(293-332)-peptide

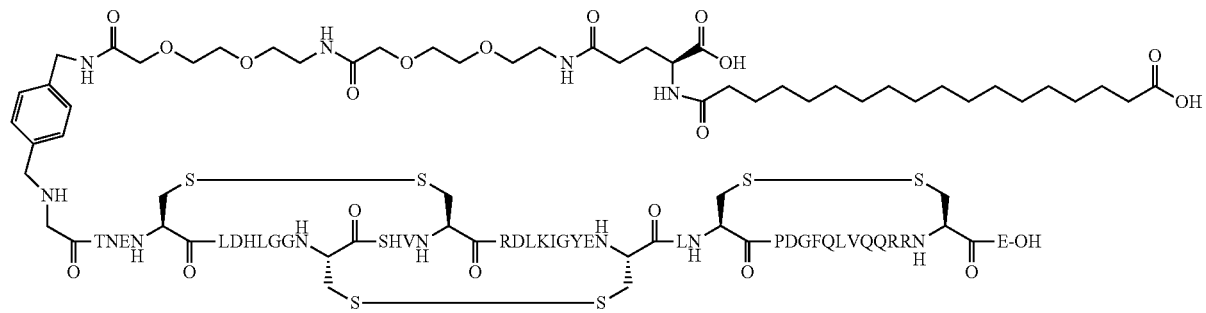

The peptide is SEQ ID NO: 62.
Compound prepared by general method A+C
LCMS01: Found m/3=1757.1; Found m/4=1318.1; Found m/5=1054.2; Calc mass=5269.0.

Example 65

N{293}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Pro300,Leu301,Ile307,Arg309,Glu312]-LDL-R-(293-332)-peptide

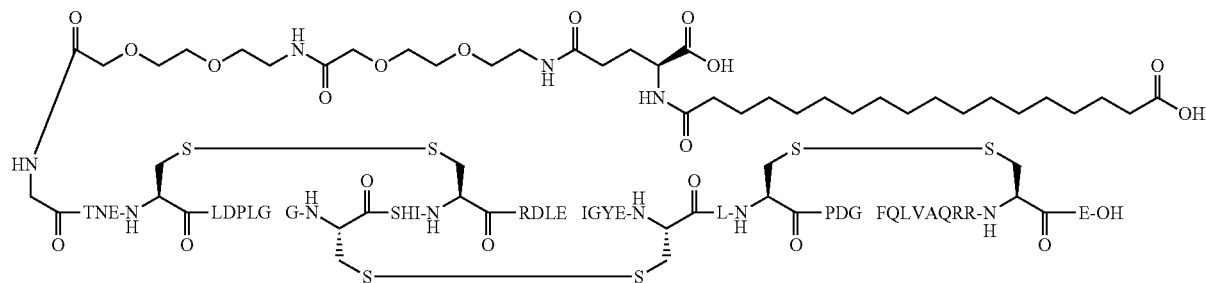

The peptide is SEQ ID NO: 5.
Compound prepared by general method B
LCMS029: Found m/3=1709.1; Calc mass=5124.8.

Example 66

N{Alpha}([Asn293,Leu301,Ile307,Arg309,Asp312]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

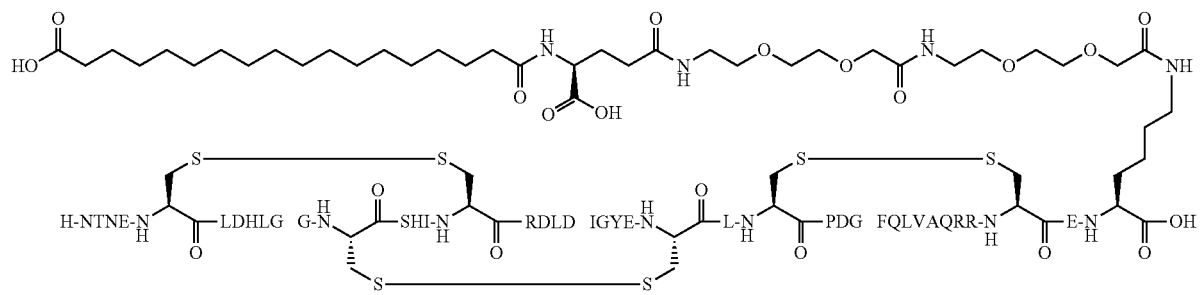

The peptide is SEQ ID NO: 9.
Compound prepared by general method B
LCMS029: Found m/4=1329.1; Calc mass=5313.0.

Example 67

N{Alpha}([Asn293,Leu301,Arg309,Asp312]-LDL-
R-(293-332)-peptidyl)-N{Epsilon}[2-[2-[2-[[2-[2-
[2-[[(4S)-4-carboxy-4-(17-carboxyheptadecanoy-
lamino)butanoyl]amino]ethoxy]ethoxy]acetyl]
amino]ethoxy]ethoxy]acetyl]Lys

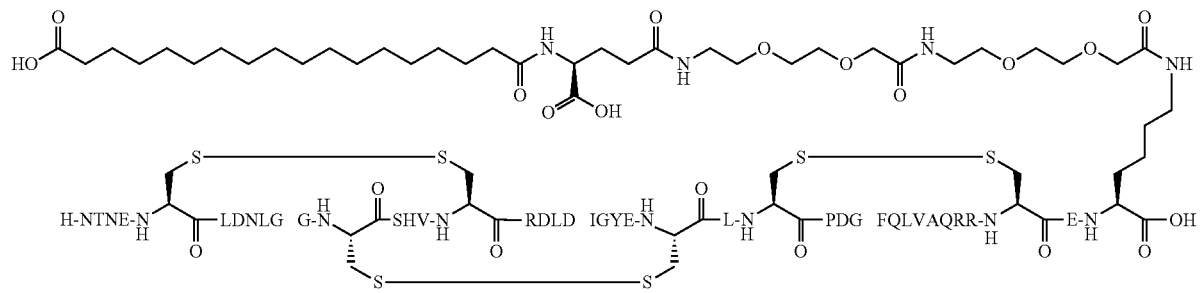

The peptide is SEQ ID NO: 10.
Compound prepared by general method B
LCMS029: Found m/4=1325.6; Calc mass=5299.0.

Example 68

N{293}-[4-[[[2-[2-[2-[[2-[2-[2-[4-[16-(1H-tetrazol-
5-yl)hexadecanoylsulfamoyl]butanoylamino]ethoxy]
ethoxy]acetyl]amino]ethoxy]ethoxy]acetyl]amino]
methyl]phenyl]methyl-[Leu301,Arg309,Glu312]-
LDL-R-(293-332)-peptide

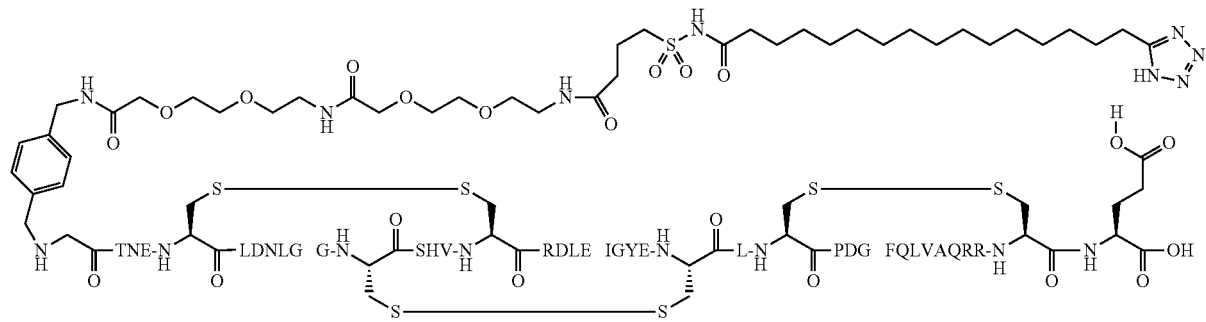

The peptide is SEQ ID NO: 6.
Compound prepared by general method C
LCMS029: Found m/4=1320.1; Calc mass=5276.98.

Example 69

N{Epsilon-328}-[2-[2-[2-[[2-[2-[2-[[(4S)-4-carboxy-
4-(17-carboxyheptadecanoylamino)butanoyl]amino]
ethoxy]ethoxy]acetyl]amino]ethoxy]ethoxy]acetyl]-
[Leu301,Arg309,Glu312,Lys328,His329]-LDL-R-
(293-332)-peptide

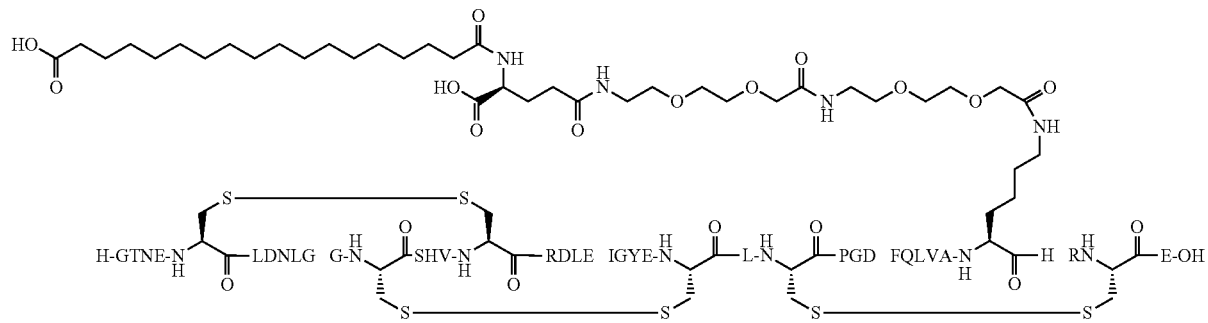

The peptide is SEQ ID NO: 14.
Compound prepared by general method B
LCMS029: Found m/4=1278.09; Calc mass=5108.8 Da.

Example 70

N{Epsilon-332}-[2-[2-[2-[[2-[2-[2-[[(4S)-4-carboxy-
4-(17-carboxyheptadecanoylamino)butanoyl]amino]
ethoxy]ethoxy]acetyl]amino]ethoxy]ethoxy]acetyl]
[Asp295,Leu301,Arg309,Glu312,Lys332]-LDL-R-
(293-332)-peptide

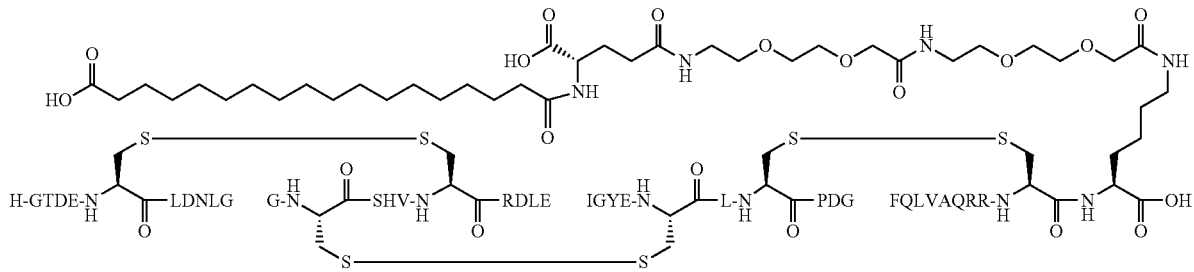

The peptide is SEQ ID NO: 20.
Compound prepared by general method B
LCMS029: Found m/4=1282.84; Calc mass=5127.8 Da.

Example 71

N{Epsilon-312}-[2-[2-[2-[[2-[2-[2-[[(4S)-4-carboxy-
4-(17-carboxyheptadecanoylamino)butanoyl]amino]
ethoxy]ethoxy]acetyl]amino]ethoxy]ethoxy]acetyl]
[His300,Leu301,Arg309]-LDL-R-(293-332)-peptide

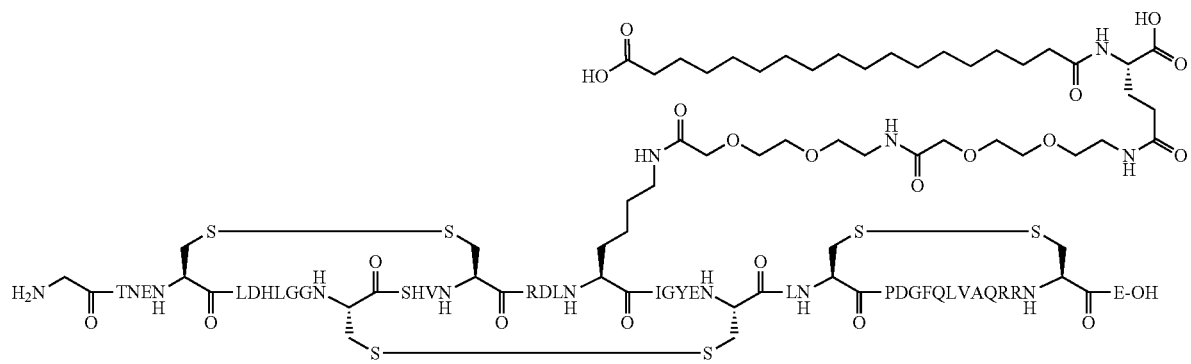

The peptide is SEQ ID NO: 62.
Compound prepared by general method B
LCMS01: Found m/3=1717.5 Found m/4=1288.2 Found m/5=1030.4—Calc mass=5149.9—.

Example 72

N{293}-[2-[2-[2-[[2-[2-[2-[[(4S)-4-carboxy-4-(17-
carboxyheptadecanoylamino)butanoyl]amino]
ethoxy]ethoxy]acetyl]amino]ethoxy]ethoxy]acetyl]-
[His300,Leu301,Ile307,Arg309,Glu312]-LDL-R-
(293-332)-peptide

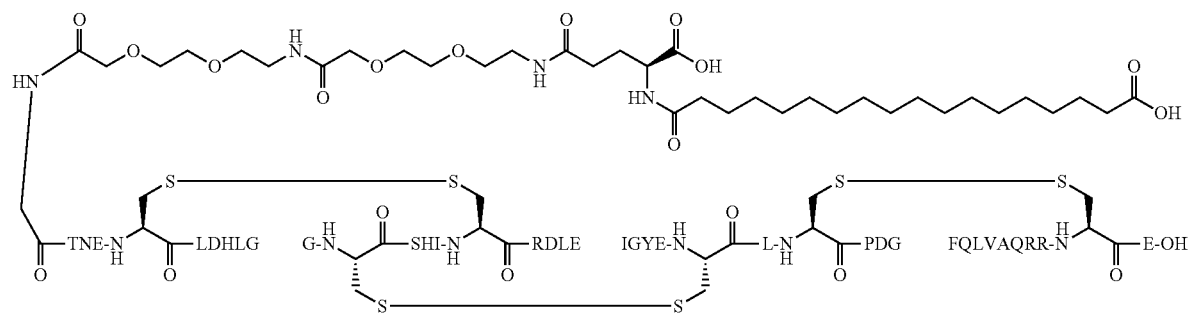

The peptide is SEQ ID NO: 26.
Compound prepared by general method B
LCMS029: Found m/4=1292.1; Calc mass=5164.8 Da.

Example 73

N{Epsilon-296}-[2-[2-[2-[[2-[2-[2-[[(4S)-4-carboxy-
4-(17-carboxyheptadecanoylamino)butanoyl]amino]
ethoxy]ethoxy]acetyl]amino]ethoxy]ethoxy]acetyl]-
[Lys296,Leu301,Arg309,Glu312]-LDL-R-(293-
332)-peptide

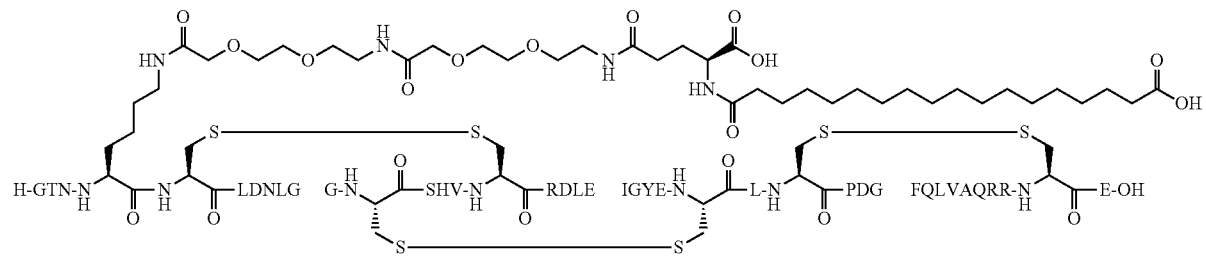

The peptide is SEQ ID NO: 63.
Compound prepared by general method B
LCMS01: Found m/3=1709.9; Found m/4=1282.6; Calc mass 5126.8.

Example 74

N{Epsilon-294}-[2-[2-[2-[[2-[2-[2-[[(4S)-4-carboxy-
4-(17-carboxyheptadecanoylamino)butanoyl]amino]
ethoxy]ethoxy]acetyl]amino]ethoxy]ethoxy]acetyl]-
[Lys294,Leu301,Arg309,Glu312]-LDL-R-(293-
332)-peptide

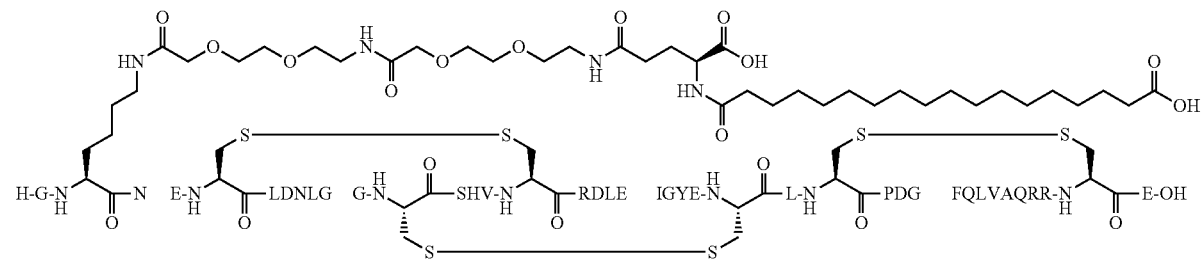

The peptide is SEQ ID NO: 64.
Compound prepared by general method B
LCMS01: Found m/4=1289.7; Found m/5=1031.7; Calc mass=5154.8.

Example 75

N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys[Leu301,Arg309,Glu312]-LDL-R-(293-332)-peptide

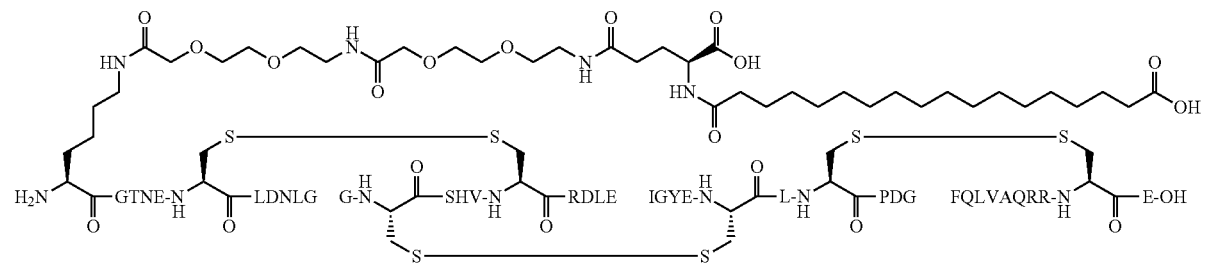

The peptide is SEQ ID NO: 65.
Compound prepared by general method B
LCMS01: Found m/3=1752.9; Found m/4=1315.0; Calc mass=5255.9.

Example 76

N{Epsilon-328}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Gly294,Leu301,Arg309,Glu312,Lys328],des-Gly293-LDL-R-(294-332)-peptide

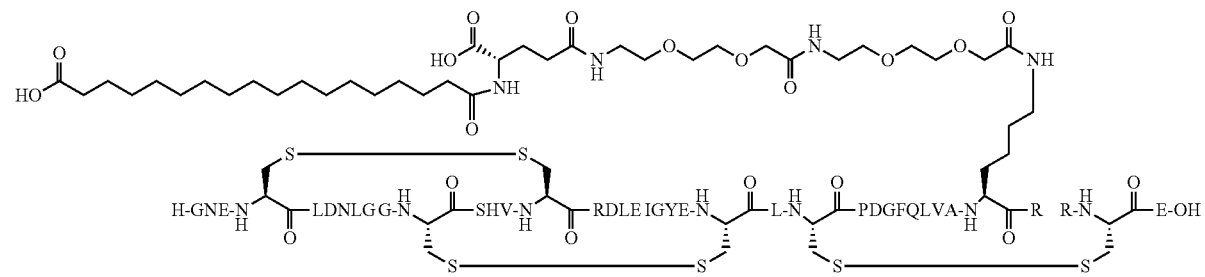

The peptide is SEQ ID NO: 66.
Compound prepared by general method B
LCMS01: Found m/3=1676.6 Found m/4=1257.7 Found m/5=1006)—Calc. mass=5026.7.

Example 77

N{Alpha}([Leu301,Asp306,Arg309,Glu312, Gly324]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

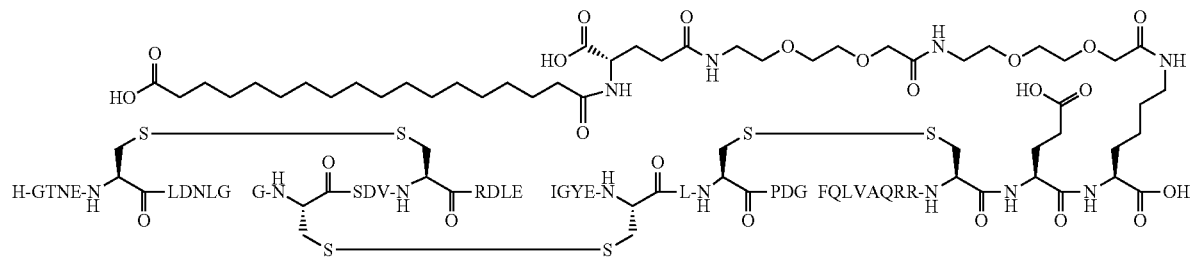

The peptide is SEQ ID NO: 67.
Compound prepared by general method B
LCMS029: Found m/3=1721.8; Calc mass=5162.8 Da.

Example 78

N{Alpha}(N{293}-[2-[2-[2-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]ethoxy]ethoxy]acetyl]-[Leu301,Asp306,Arg309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

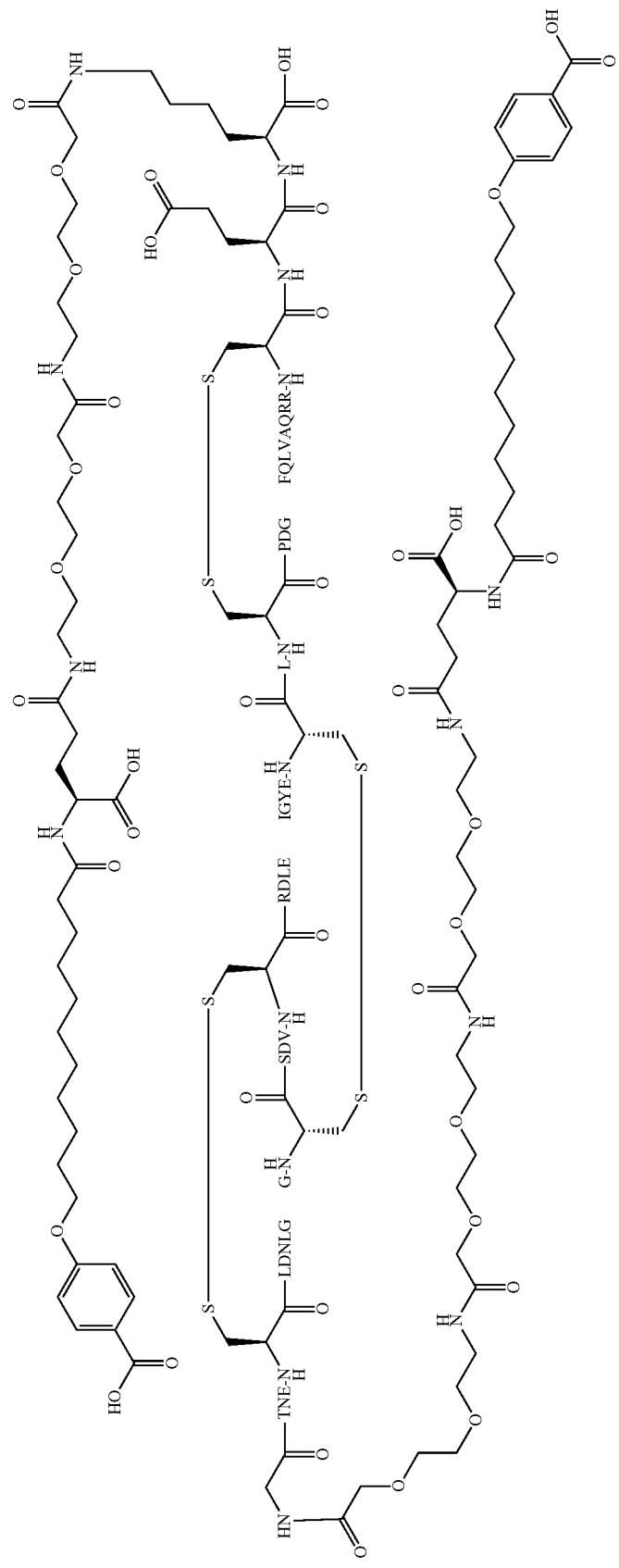

The peptide is SEQ ID NO: 68.
Compound prepared by general method B
LCMS029: Found m/3=1528.7; Calc mass=6110.8 Da.

Example 79

N{Alpha}(N{Epsilon-321}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Leu301,Arg309,Glu312,Lys321]-LDL-R-(293-332)-peptidyl)-N{Epsilon}[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]Lys

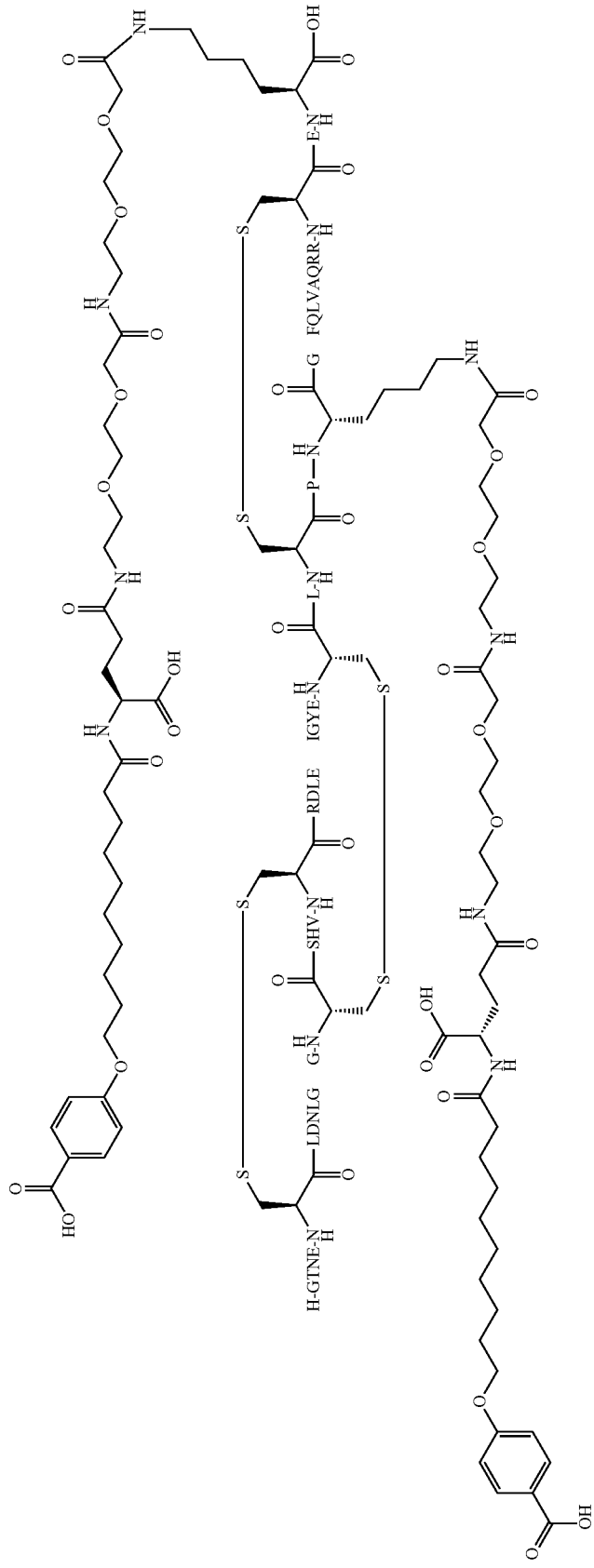

The peptide is SEQ ID NO: 17.
Compound prepared by general method B
LCMS01: Found m/4=1493.9; Found m/5=1195.5; Calc mass=5972.7.

Example 80

N{Alpha}([Leu301,Arg309,Glu312]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys

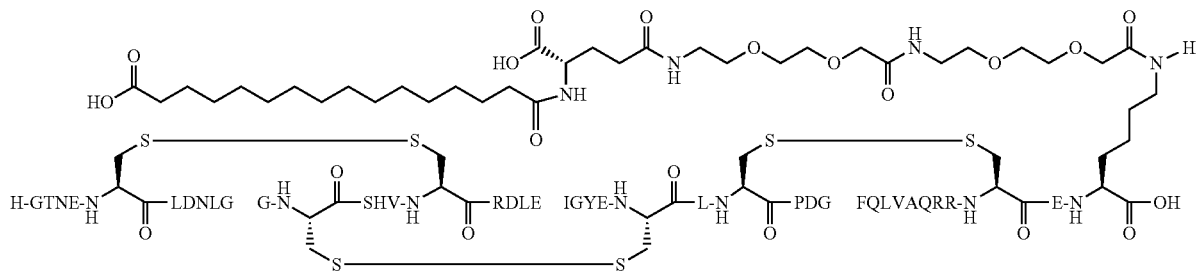

The peptide is SEQ ID NO: 4.
Compound prepared by general method B
LCMS01: Found m/3=1743.6; Found m/4=1307.9; Found m/5=1046.4 Calc mass=5227.9.

Example 81

N{Alpha}([Leu301,Arg309,Glu312]-LDL-R-(293-332)-peptidyl)-N{Epsilon}[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]Lys

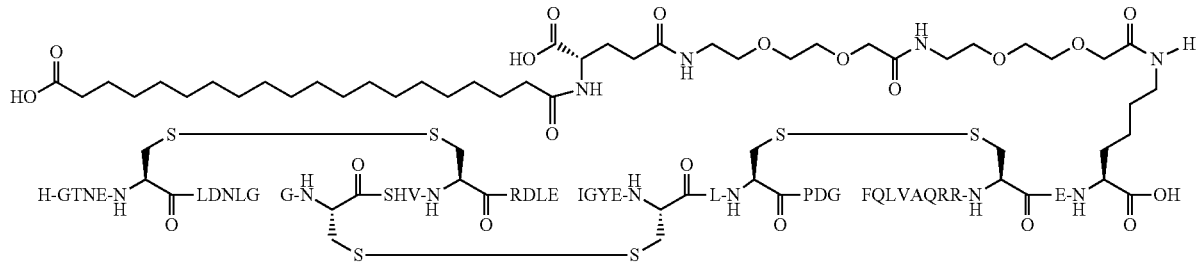

The peptide is SEQ ID NO: 4.
Compound prepared by general method B
LCMS01: Found m/3=1762.3; Found m/4=1321.7; Found m/5=1057.8; Calc mass=5284.0.

Example 82

N{Alpha}([Leu301,Arg309,Glu312]-LDL-R-(293-332)-peptidyl)-N{Epsilon}[(4S)-4-carboxy-4-(17-carboxyheptadecanoylamino)butanoyl]Lys

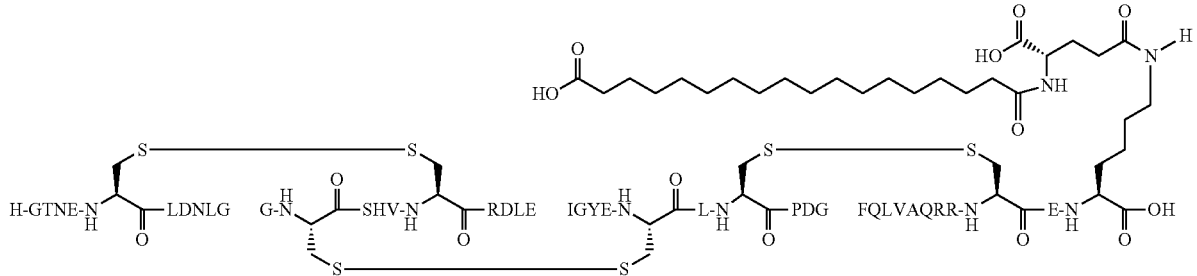

The peptide is SEQ ID NO: 4.
Compound prepared by general method B
LCMS01: Found m/3=1656.2; Found m/4=1242.4; Found m/5=994.0; Calc mass=4965.6.

Example 83

N{Alpha}(N{Epsilon-321}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Leu301,Arg309,Glu312,Lys321]-LDL-R-(293-332)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]Lys

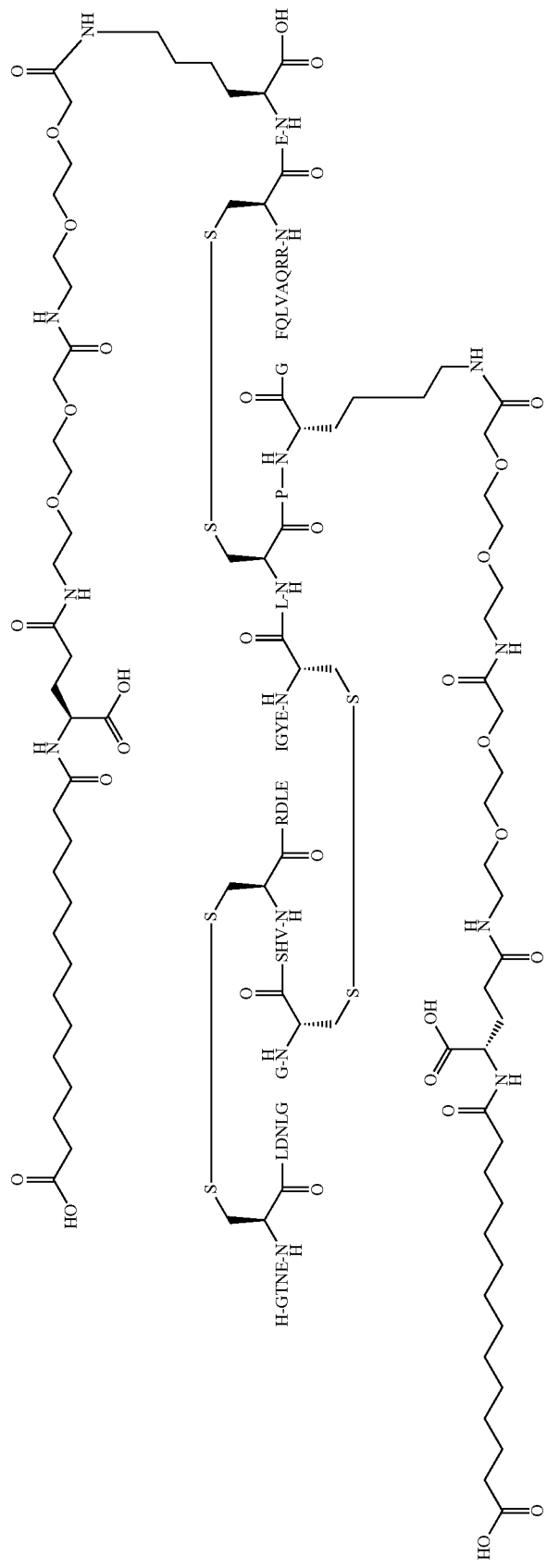

The peptide is SEQ ID NO: 17.
Compound prepared by general method B
LCMS01: Found m/3=1958.5; Found m/4=1468.9; Found m/5=1175.3; Calc mass=5872.7.

Example 84

N{Alpha}(N{Epsilon-321}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys321]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl] Lys

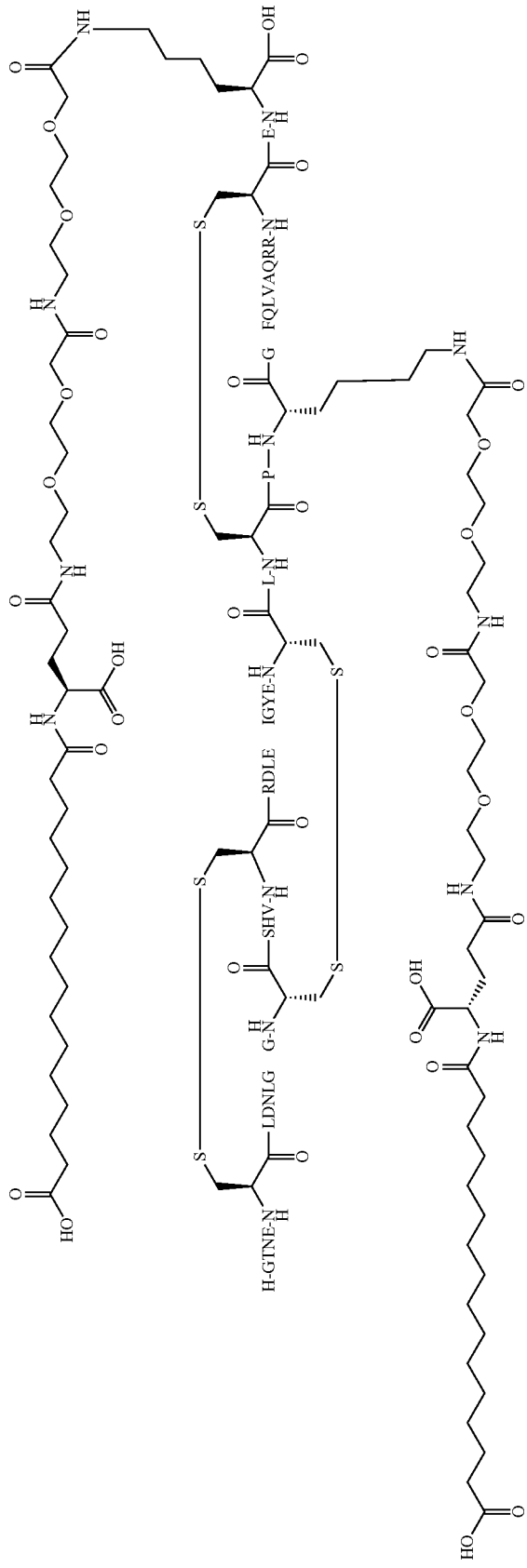

The peptide is SEQ ID NO: 17
Compound prepared by general method B
LCMS01: Found m/4=1483.1; Found m/5=1186.6; Calc mass=5928.8.

Example 85

N{Alpha}(N{Epsilon-313}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[His300,Leu301,Arg309,Glu312,Lys313]-LDL-R-(293-332)-peptidyl)-N{Epsilon}[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]Lys

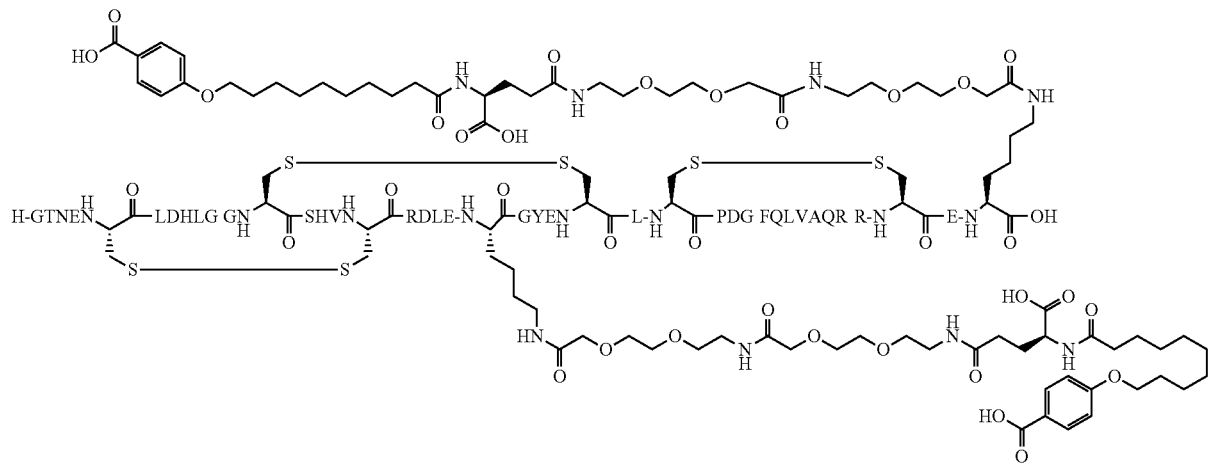

The peptide is SEQ ID NO: 69.
Compound prepared by general method B
LCMS01: Found m/4=1500.1 Found m/5=1200.3 Found m/z=1000. Calc mass=5997.7.

Example 86

N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-328}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313,Lys328]-LDL-R-(293-332)-peptide

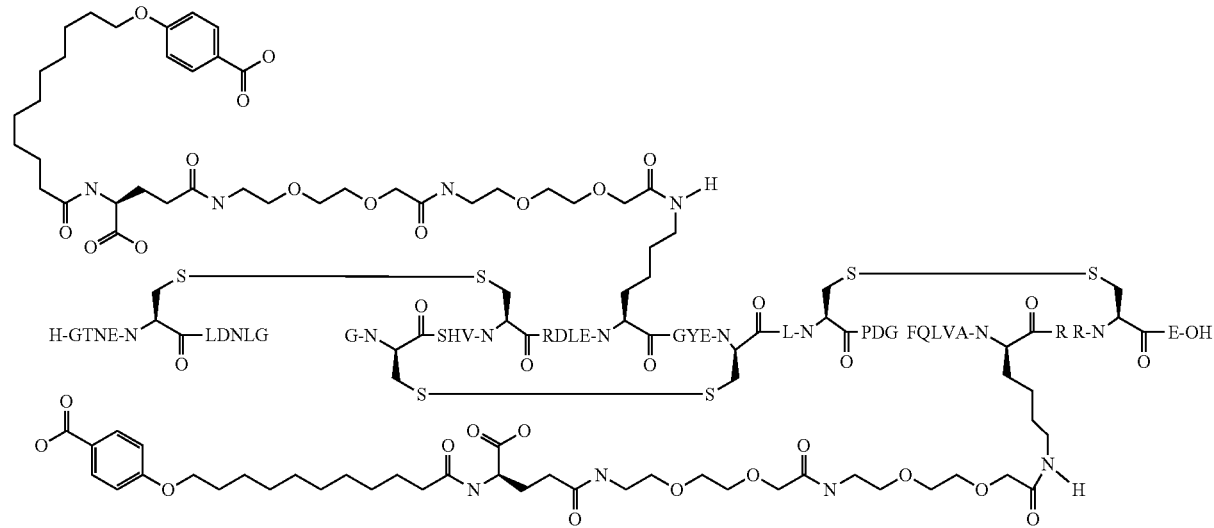

The peptide is SEQ ID NO: 70.
Compound prepared by general method B
LCMS01: Found m/4=1469.3; Found m/5=1175.8; Calc mass=5874.6.

Example 87

N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313,Lys324]-LDL-R-(293-332)-peptide

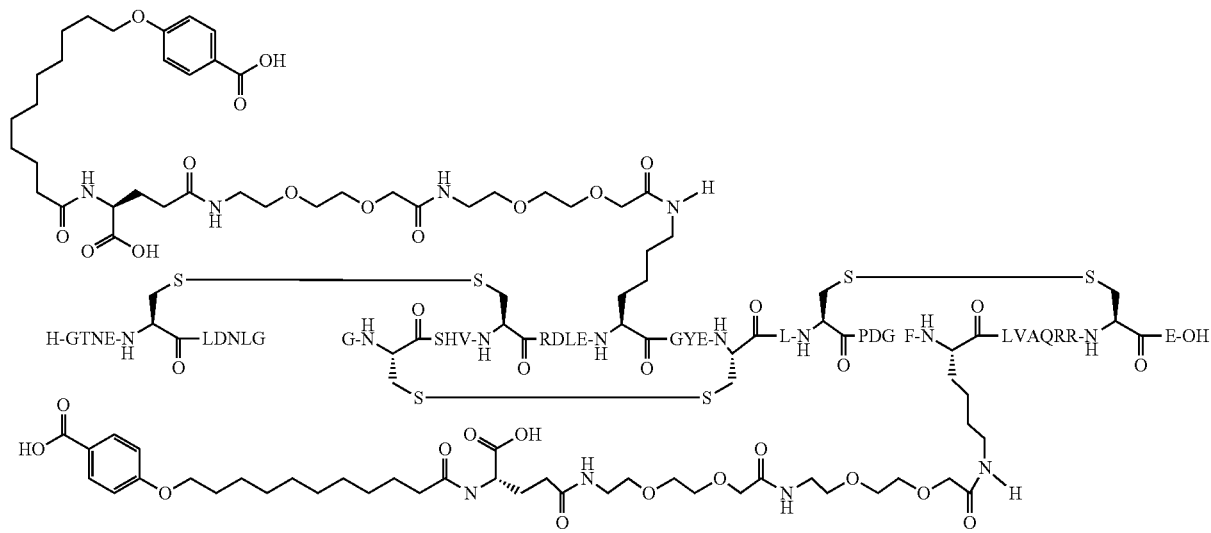

The peptide is SEQ ID NO:71.
Compound prepared by general method B
LCMS01: Found m/4=1469.1; Found m/5=1175.5; Calc mass=5874.6.

Example 88

N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptide

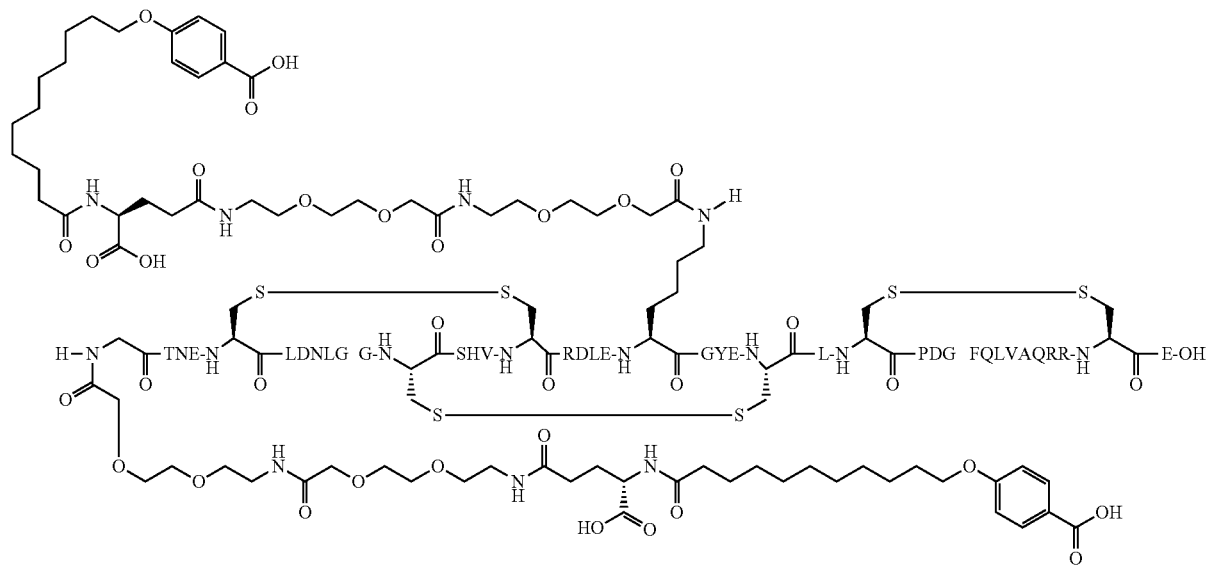

The peptide is SEQ ID NO: 39.
Compound prepared by general method B
LCMS01: Found m/4=1469.3; Found m/5=1175.7; Calc mass=5874.5.

Example 89

N{Alpha}(N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys324]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

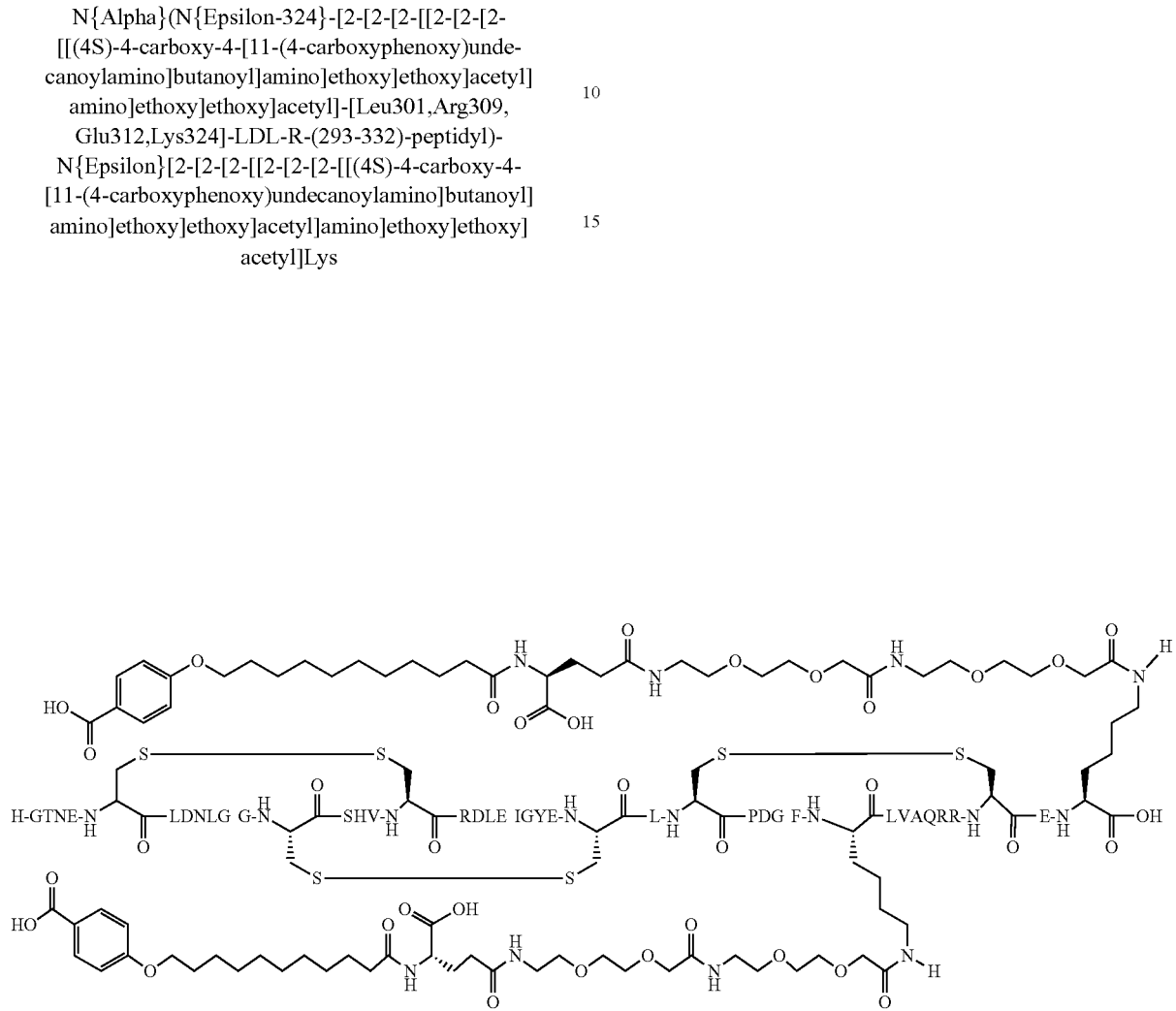

The peptide is SEQ ID NO:72.
Compound prepared by general method B
LCMS01: Found m/4=1497.6; Found m/5=1198.3; Calc mass=5987.7.

Example 90

N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-321}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313,Lys321]-LDL-R-(293-332)-peptide

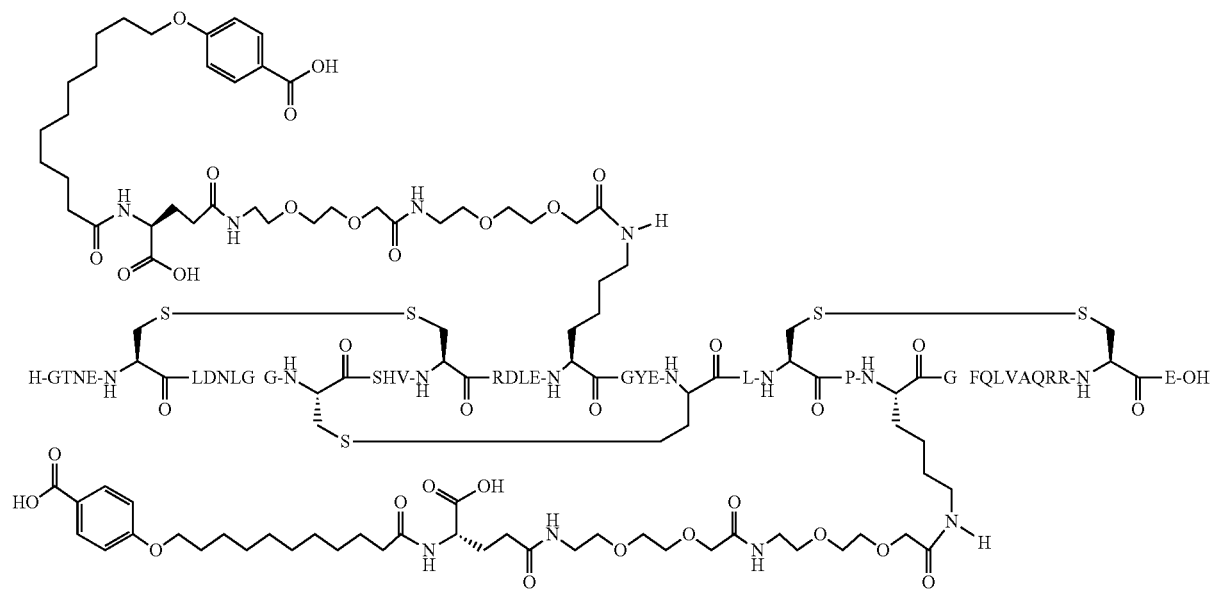

The peptide is SEQ ID NO: 73.
Compound prepared by general method B
LCMS01: Found m/4=1472.6; Found m/5=1178.3; Calc mass=5887.6.

Example 91

N{Alpha}(N{Epsilon-313}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[His300,Leu301,Arg309,Glu312,Lys313],des-Gly293-LDL-R-(294-332)-peptidyl)-N{Epsilon}[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]Lys

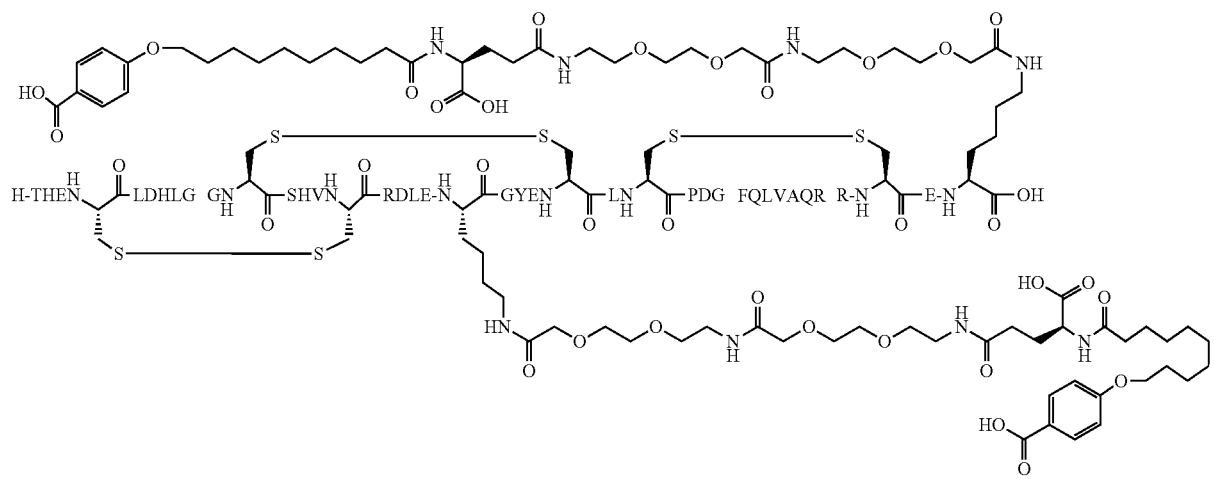

The peptide is SEQ ID NO: 74.
Compound prepared by general method B
LC-MS: Found m/3=1981, m/4=1486: Calculated mass=5940.6.

Example 92

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[His300,Leu301,Arg309,Glu312,Lys313]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

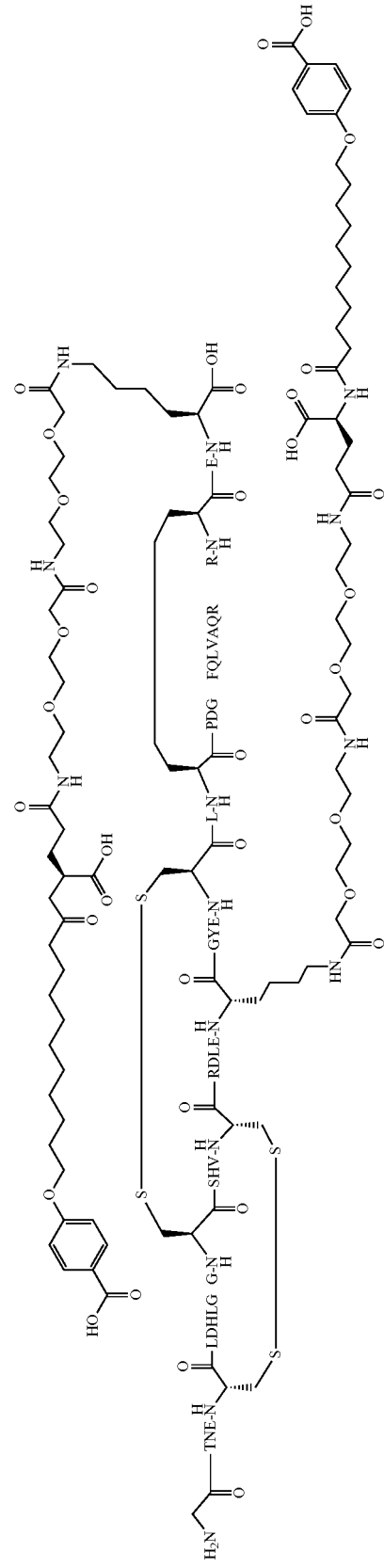

The peptide is SEQ ID NO: 69.
Compound prepared by general method B
LCMS01: Found m/4=1507.3 Found m/5=1205.9 Calc mass=6025.7.

Example 93

N{292}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-Ala[Leu301,Arg309,Glu312,Lys313]-LDL-R-(293-332)-peptide

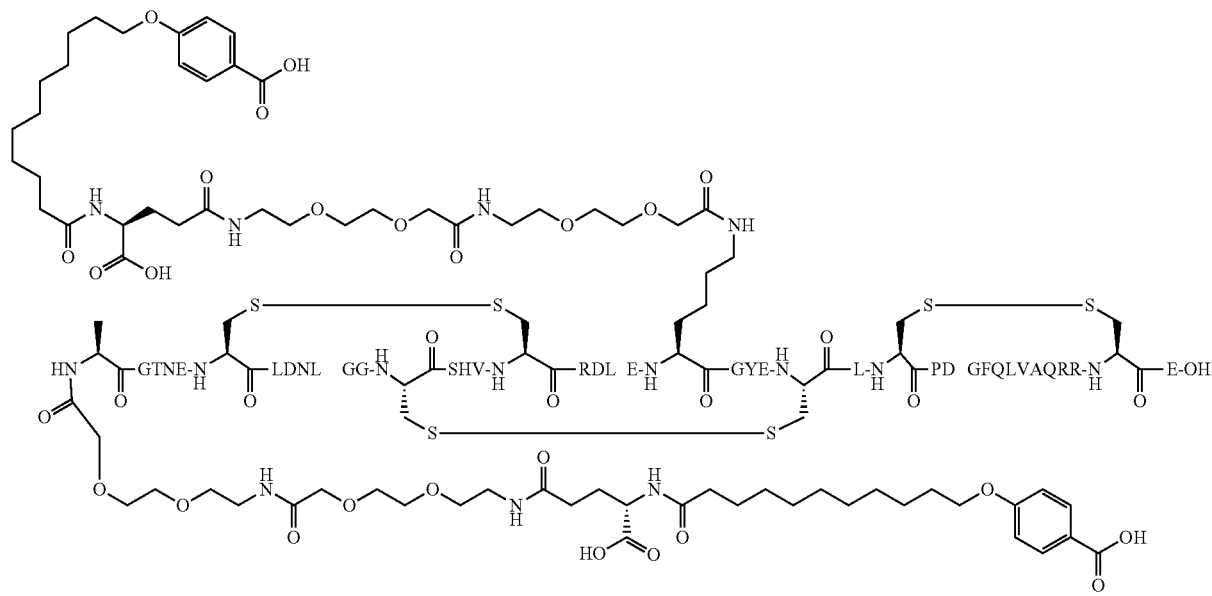

The peptide is SEQ ID NO: 75.
Compound prepared by general method B
LCMS01: Found m/4=1487.1; Found m/5=1190.0; Calc mass=5945.6.

Example 94

N{294}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313],des-Gly293-LDL-R-(294-332)-peptide

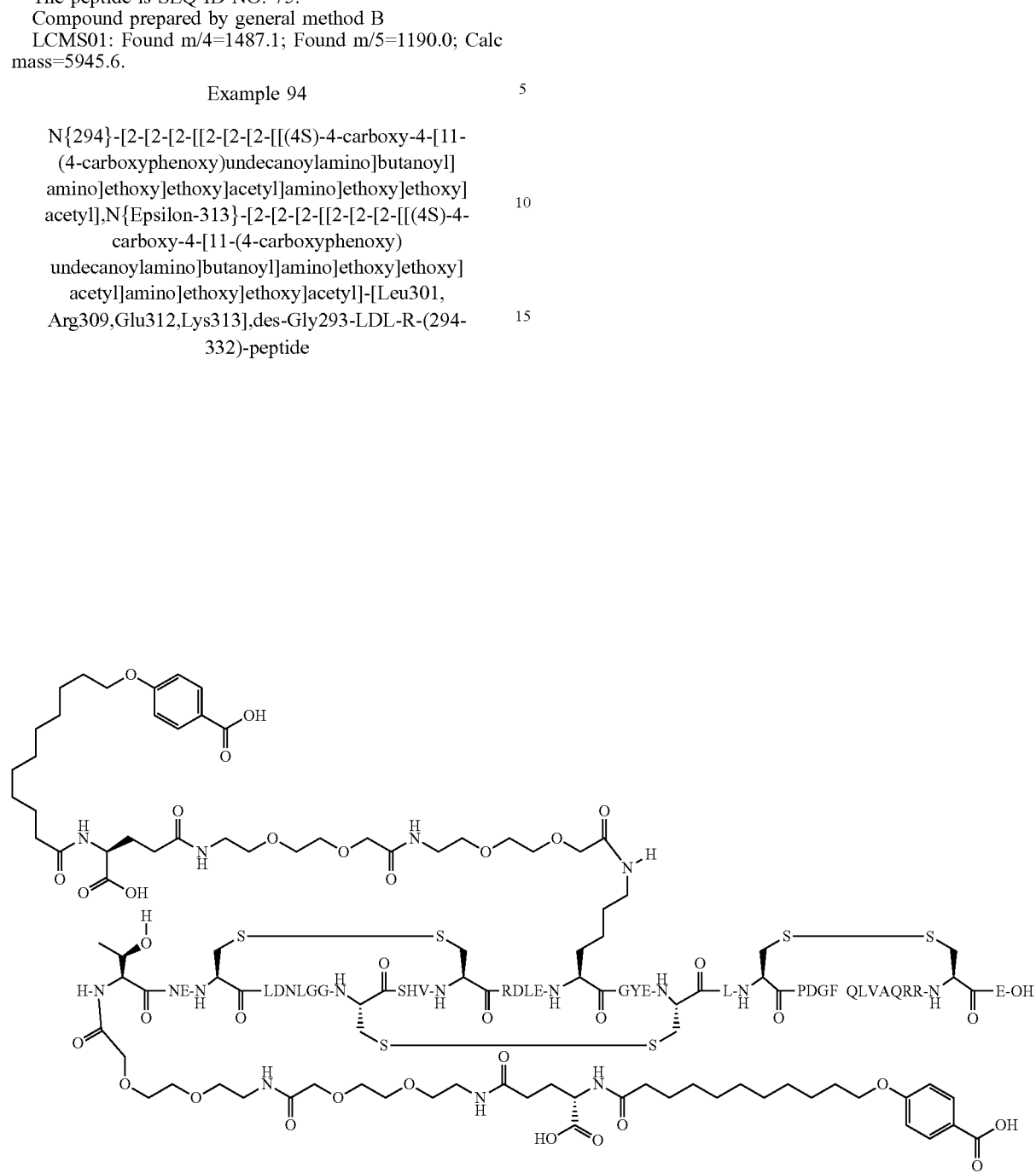

The peptide is SEQ ID NO: 76.
Compound prepared by general method B
LCMS01: Found m/4=1455.1; Calc mass=5817.5.
Example 95
N{Epsilon-313}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Leu301,Arg309,Glu312,Lys313],des-Gly293-LDL-R-(294-332)-peptide
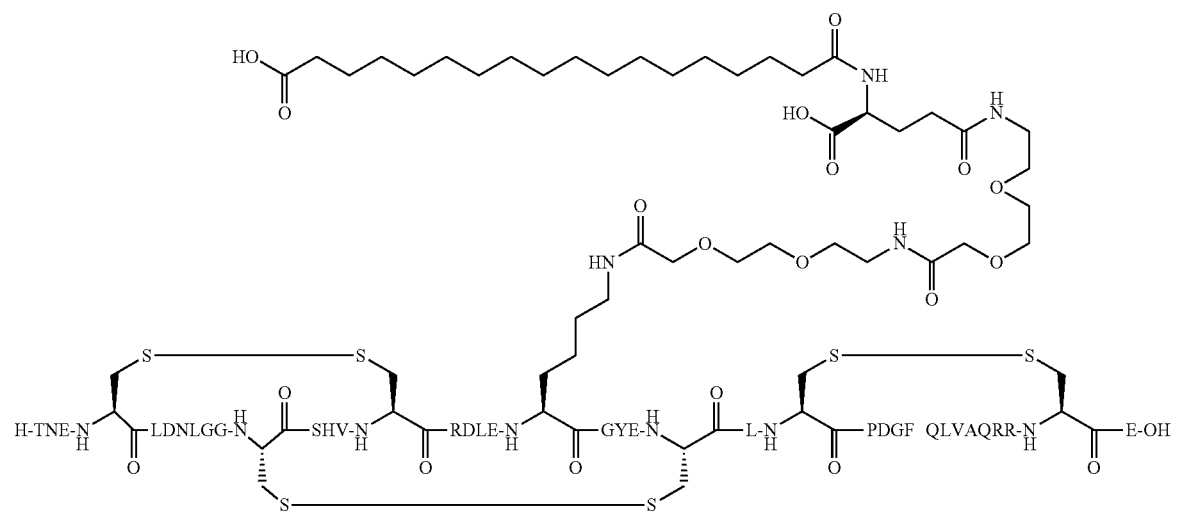

The peptide is SEQ ID NO: 76.
Compound prepared by general method B
LCMS01: Found m/4=1272.4; Found m/5=1017.9; Calc mass=5085.7.

Example 96

N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys313,Lys332]-LDL-R-(293-332)-peptide

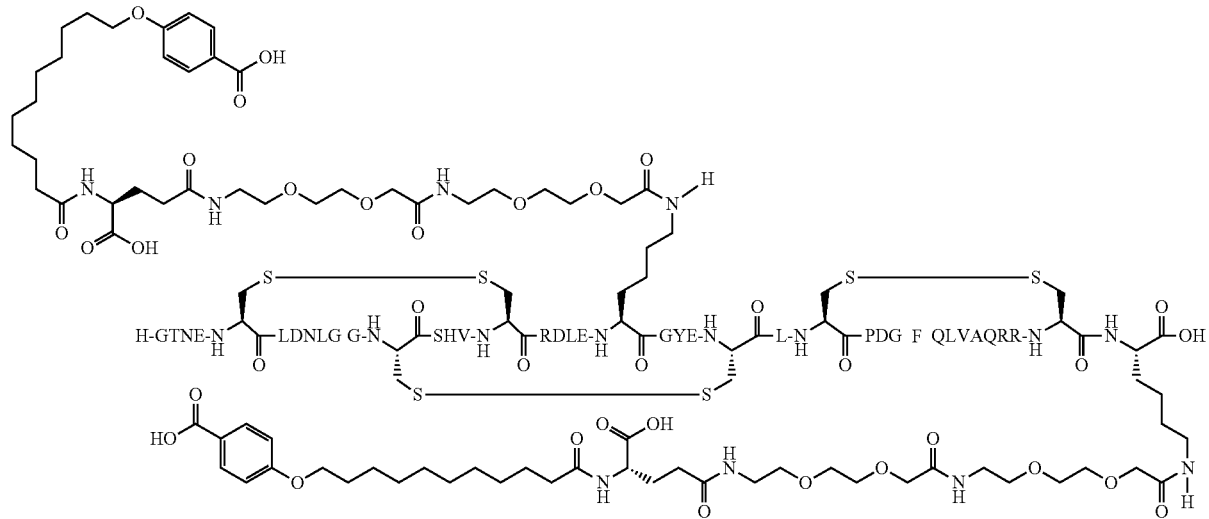

The peptide is SEQ ID NO: 77.
Compound prepared by general method B
LCMS01: Found m/4=1469.1; Found m/5=1175.5; Calc mass=5873.6.

Example 97

N{Alpha}(N{Epsilon-328}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys328]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

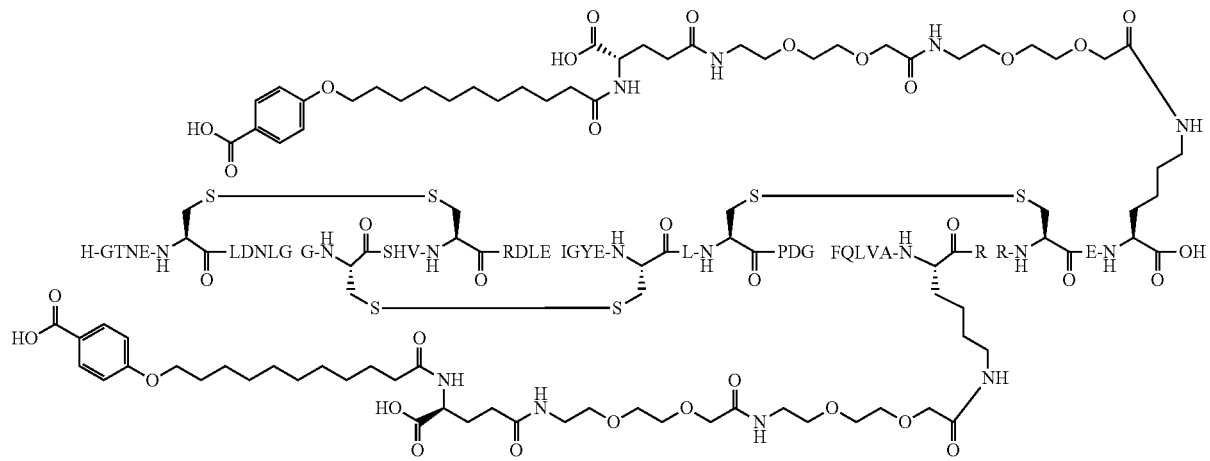

The peptide is SEQ ID NO: 78.
Compound prepared by general method B
LCMS28: Found m/3=1996.9; Found m/4=1497.9; Calc mass=5987.7.

Example 98

N{Alpha}(N{Epsilon-313}-[(4S)-4-carboxy-4-[11-(4-carboxyphenoxy)undecanoylamino]butanoyl]-[Leu301,Arg309,Glu312,Lys313]-LDL-R-(293-332)-peptidyl)-N{Epsilon}[(4S)-4-carboxy-4-[11-(4-carboxyphenoxy)undecanoylamino]butanoyl]Lys

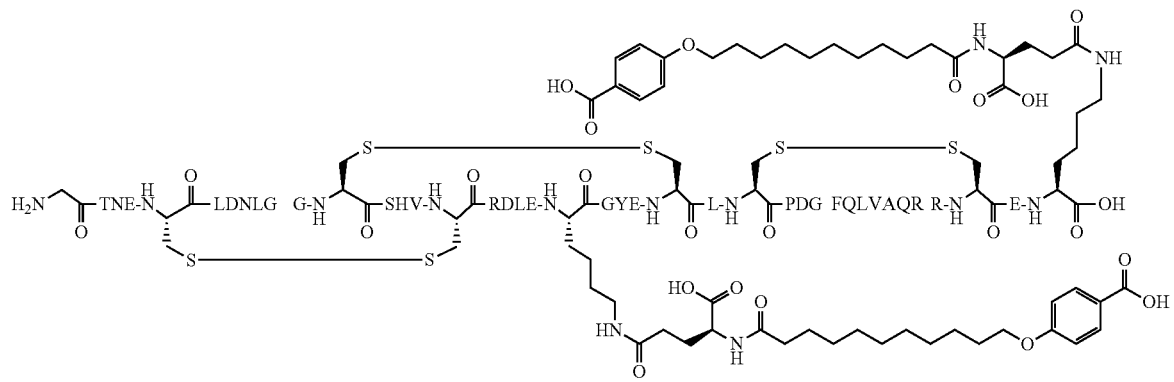

The peptide is SEQ ID NO:32.
Compound prepared by general method B
LCMS01: Found m/3=1808.1; Found m/4=1356.4; Found m/5=1085.3; Calc mass=5422.1.

Example 99

N{Alpha}(N{Epsilon-313}-[(4S)-4-carboxy-4-[[(4S)-4-carboxy-4-[11-(4-carboxyphenoxy)undecanoylamino]butanoyl]amino]butanoyl]-[Leu301, Arg309,Glu312, Lys313]-LDL-R-(293-332)-peptidyl)-N{Epsilon}[(4S)-4-carboxy-4-[[(4S)-4-carboxy-4-[11-(4-carboxyphenoxy)undecanoylamino]butanoyl]amino]butanoyl]Lys

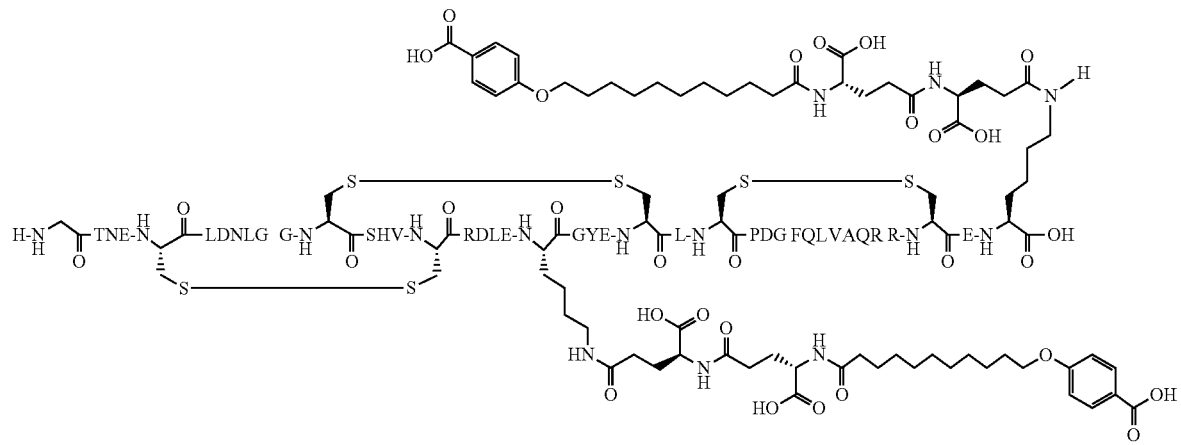

The peptide is SEQ ID NO: 32.
Compound prepared by general method B
LCMS01: Found m/3=1894.2; Found m/4=1420.9; Found m/5=1136.9; Calc mass=5680.3.

Example 100

N{Alpha}(N{Epsilon-313}-[2-[[2-[[2-[[(4S)-4-carboxy-4-[11-(4-carboxyphenoxy)undecanoylamino]butanoyl]amino]acetyl]amino]acetyl]amino]acetyl]-[Leu301,Arg309,Glu312,Lys313]-LDL-R-(293-332)-peptidyl)-N{Epsilon}[2-[[2-[[2-[[(4S)-4-carboxy-4-[11-(4-carboxyphenoxy)undecanoylamino]butanoyl]amino]acetyl]amino]acetyl]amino]acetyl]Lys

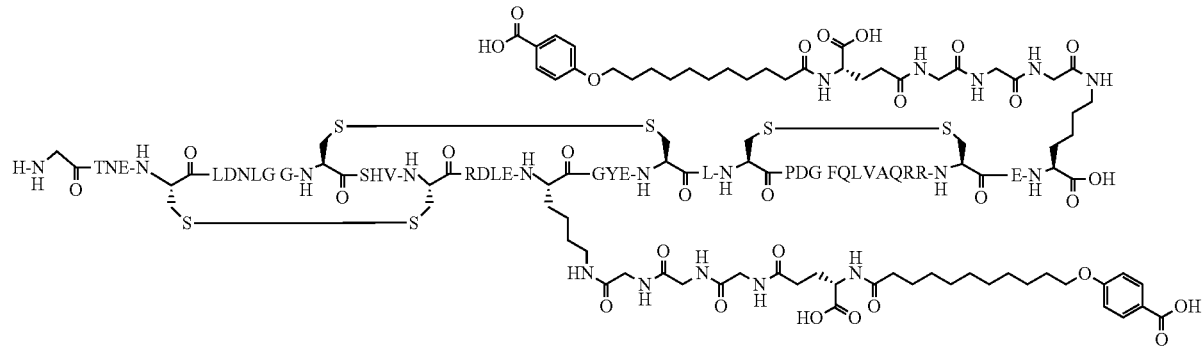

The peptide is SEQ ID NO: 32.
Compound prepared by general method B
LCMS01: Found m/3=1922.2; Found m/4=1441.9; Found m/5=1153.7; Calc mass=5764.4.

Example 101

N{Alpha}(N{Epsilon-313}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl]Lys

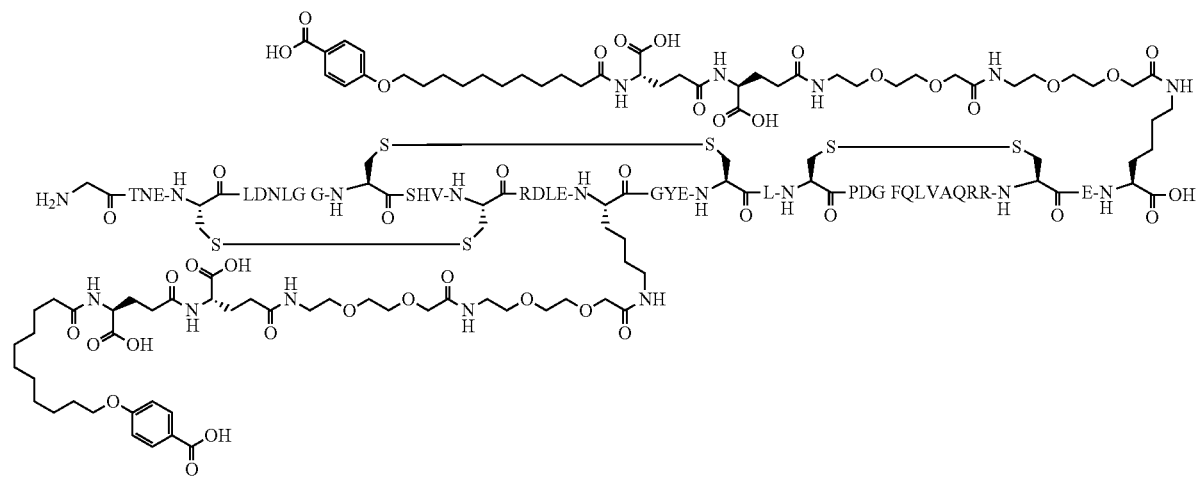

The peptide is SEQ ID NO: 32.
Compound prepared by general method B
LCMS01: Found m/4=1566.2; Found m/5=1252.9; Calc mass=6260.9.

Example 102

N{Alpha}(N{Epsilon-313}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Leu301,Arg309, Glu312, Lys313]-LDL-R-(293-332)-peptidyl)-N{Epsilon}[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]Lys

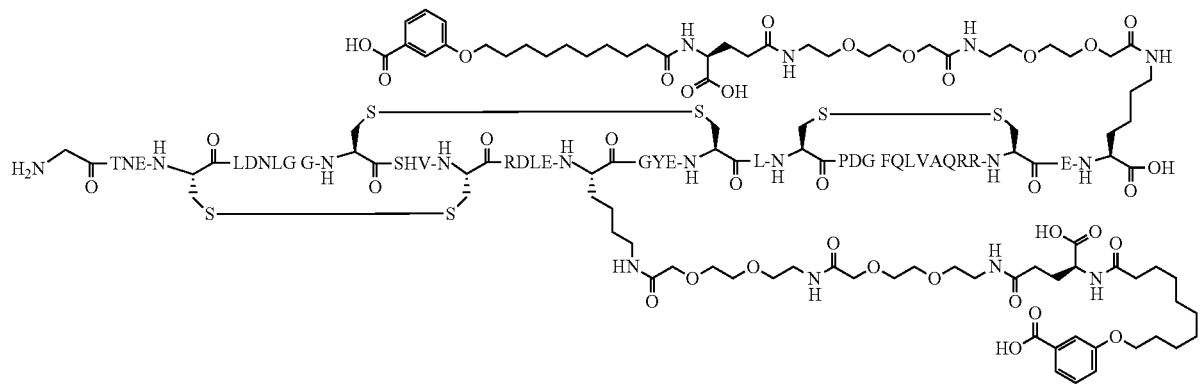

The peptide is SEQ ID NO: 32.
Compound prepared by general method B
LCMS01: Found m/4=1494.6; m/5=1195.9 Calc mass=5974.6.

Example 103

Ala299,Leu301,Ile307,Arg309-LDL-R-(293-332)-peptide

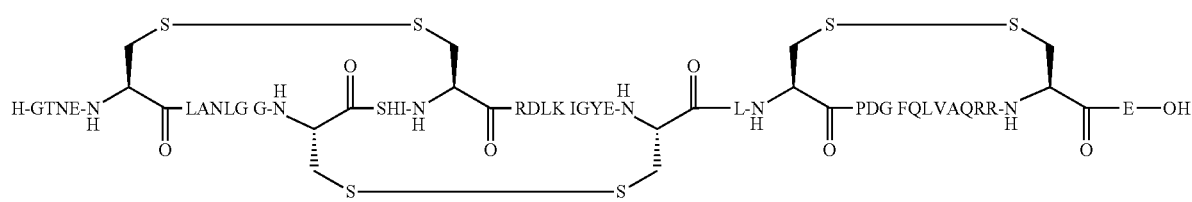

The peptide is SEQ ID NO: 79.
Compound prepared by general method A.
LCMS01: Found m/2=2191.4; Found m/3=1461.0; Calc=4381.0.

Example 104

Leu301,Arg309,Lys310-LDL-R-(293-332)-peptide

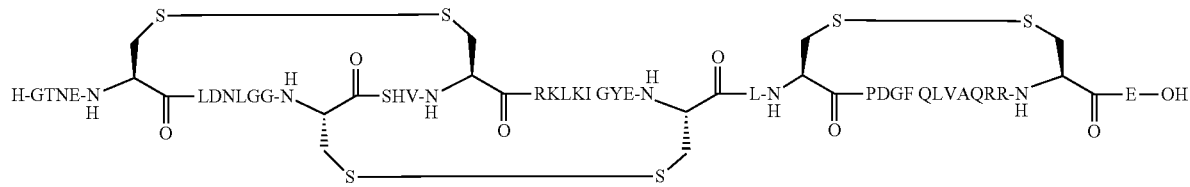

The peptide is SEQ ID NO: 80.
Compound prepared by general method A
LCMS01: Found m/3=1475.3; Found m/4=1107.0; Calc=4424.0.

Example 105

Leu301-LDL-R-(293-332)-peptide

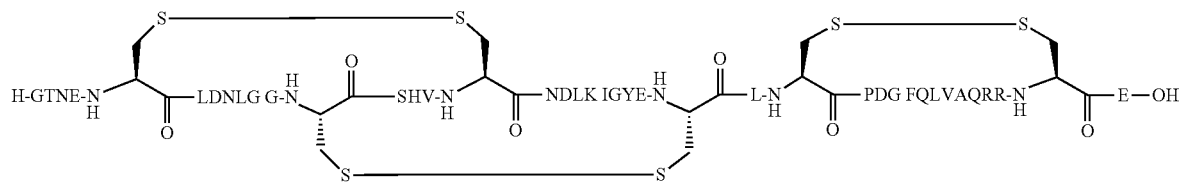

The peptide is SEQ ID NO: 81.
Compound prepared by general method A
LCMS01: Found m/3=1456.3; Found m/4=1217.0; Calc=4368.9.

Example 106

N{Alpha}([His300,Leu301,Arg309,Glu312]-LDL-R-(293-332)-peptidyl)-N{Epsilon}[2-[2-[2-[[2-[2-[2-[[(4S)-4-carboxy-4-(17-carboxyheptadecanoy-lamino)butanoyl]amino]ethoxy]ethoxy]acetyl]amino]ethoxy]ethoxy]acetyl]Lys

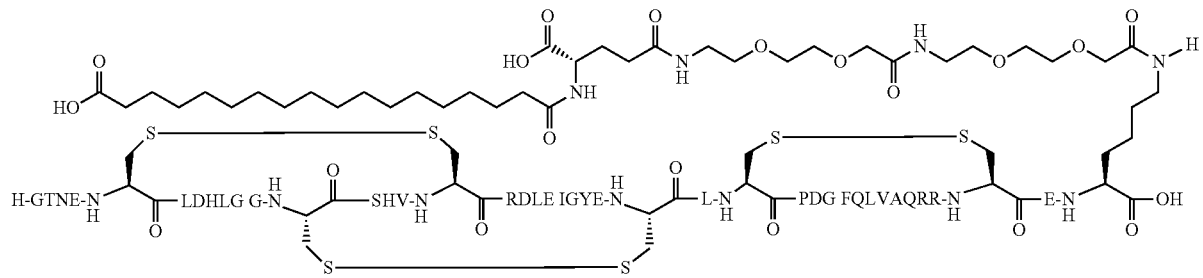

The peptide back-bone is SEQ ID NO:82.
Compound prepared by general method B
LCMS027: Found m/3=1760.5; Found m/4=1320.6; Found m/5=1056.7; Calc mass=5279.0.

Example 107

N{Alpha}(N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

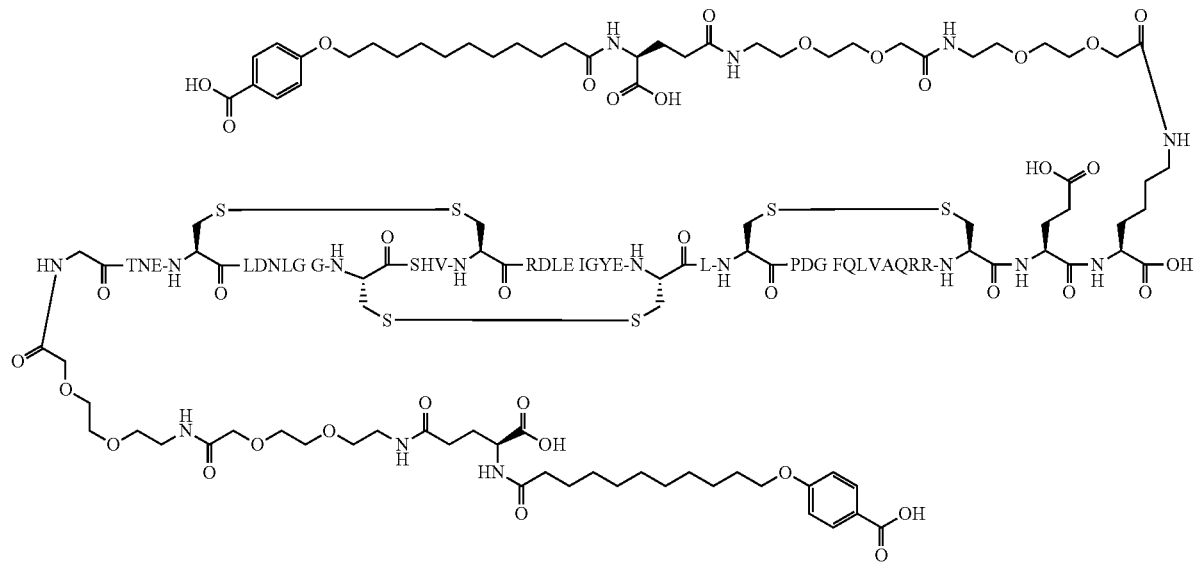

The peptide back-bone is SEQ ID NO: 4
Compound prepared by general method B
LCMS29: Found m/3=1996.9; Found m/4=1497.9; Found m/5=1198.6; Calc mass=5987.7.

Example 108

N{Alpha}(N{Epsilon-313}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[His300,Leu301,Arg309,Glu312,Lys313]-LDL-R-(295-332)-peptidyl)-N{Epsilon}[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]Lys

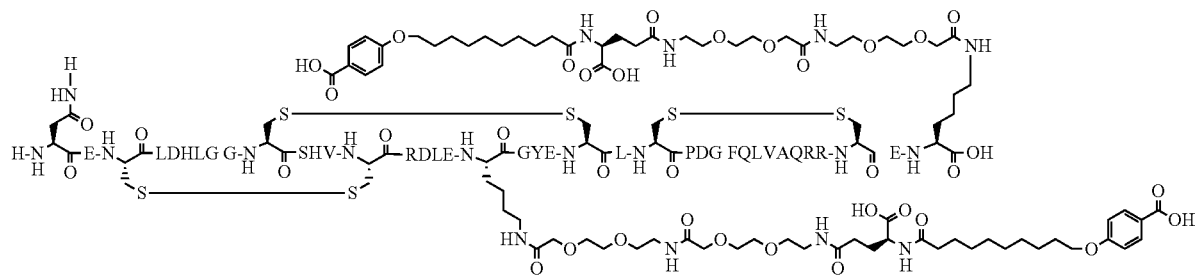

The peptide back-bone is SEQ ID NO: 83
Compound prepared by general method B
LCMS01: Found m/4=1460.8; Found m/5=1168.7; Calc mass=5839.5.

Example 109

N{Alpha}(N{Epsilon-313}-[2-[2-[2-[[2-[2-[2-[[(4S)-4-carboxy-4-[13-(3-hydroxy-1,2-oxazol-5-yl)tridecanoylamino]butanoyl]amino]ethoxy]ethoxy]acetyl]amino]ethoxy]ethoxy]acetyl]-[His300,Leu301,Arg309,Glu312,Lys313]-LDL-R-(293-332)-peptidyl)-N{Epsilon}[2-[2-[2-[[2-[2-[2-[[(4S)-4-carboxy-4-[13-(3-hydroxy-1,2-oxazol-5-yl)tridecanoylamino]butanoyl]amino]ethoxy]ethoxy]acetyl]amino]ethoxy]ethoxy]acetyl]Lys

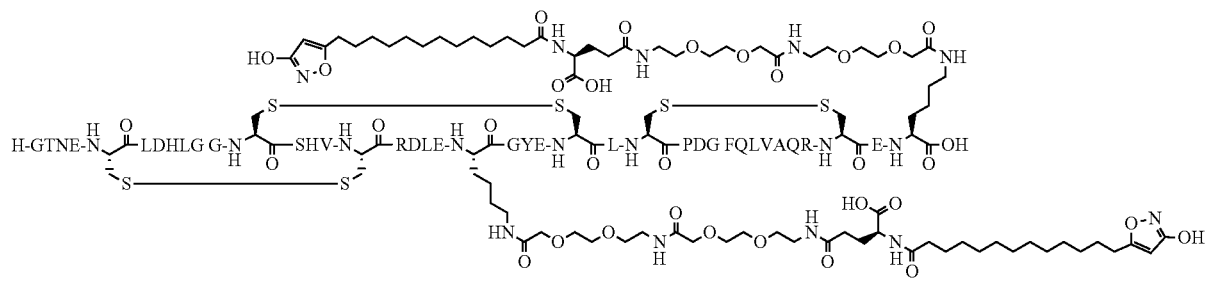

The peptide back-bone is SEQ ID NO: 69
Compound prepared by general method B
LCMS01: Found m/4=1495.0; Found m/5=1196.0; Calc mass=5975.7.

Example 110

N{Alpha}(N{Epsilon-313}-[2-[2-[2-[[2-[2-[2-[[(4S)-4-carboxy-4-[13-(3-hydroxy-1,2-oxazol-5-yl)tridecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[13-(3-hydroxy-1,2-oxazol-5-yl)tridecanoylamino]butanoyl]amino]ethoxy]ethoxy]acetyl]amino]ethoxy]ethoxy]acetyl]Lys

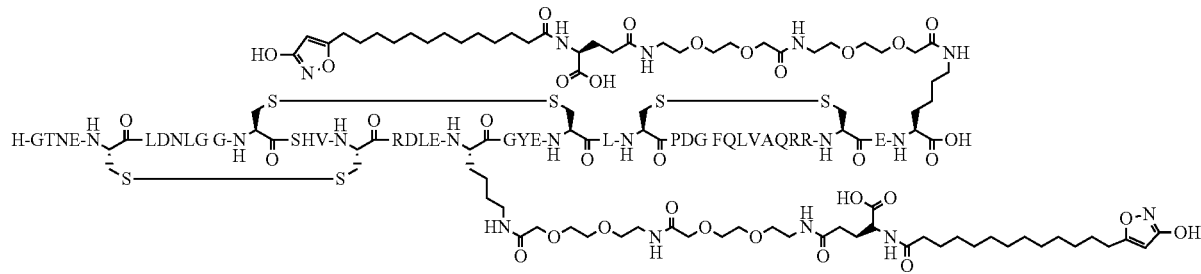

The peptide back-bone is SEQ ID NO: 32
Compound prepared by general method B
LCMS01: Found m/4=1489.0; Found m/5=1191.0; Calc mass=5952.7.

Example 111

N{Alpha}(N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

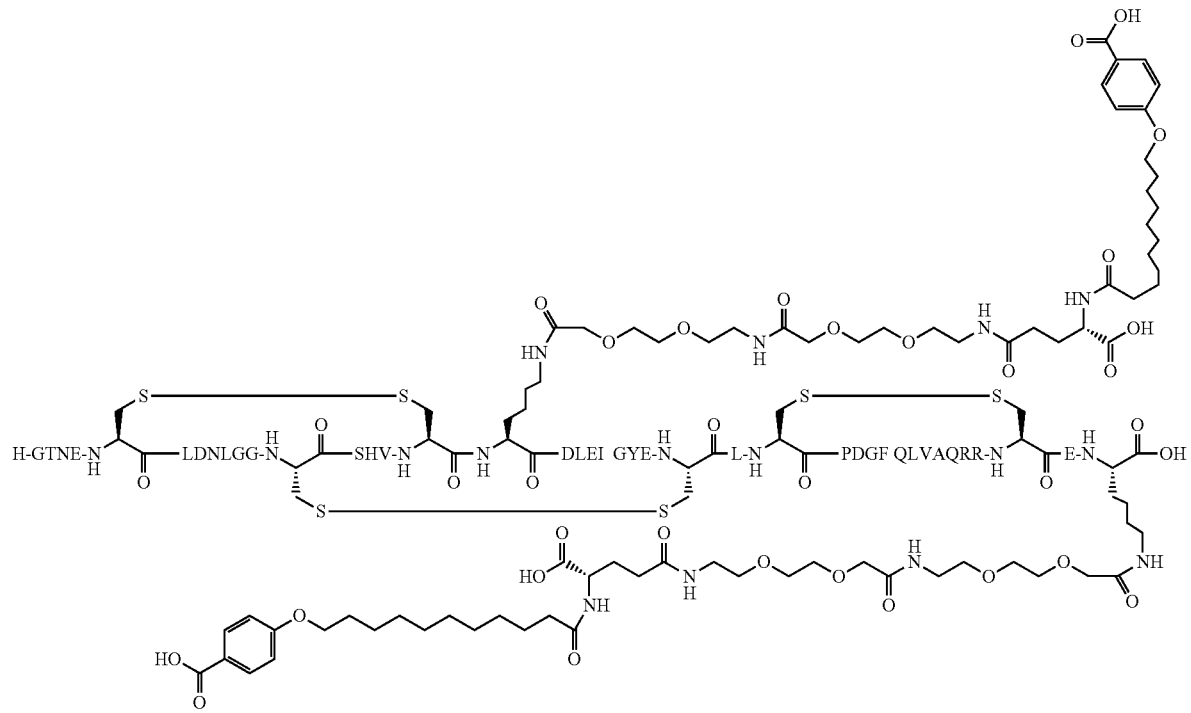

The peptide back-bone is SEQ ID NO:84
Compound prepared by general method B
LCMS29: Found m/3=1987.6; Found m/4=1490.9; Found m/5=1193.0; Calc mass=5959.7.

Example 112

N{Alpha}(N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Tyr306,Glu312,Lys324]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

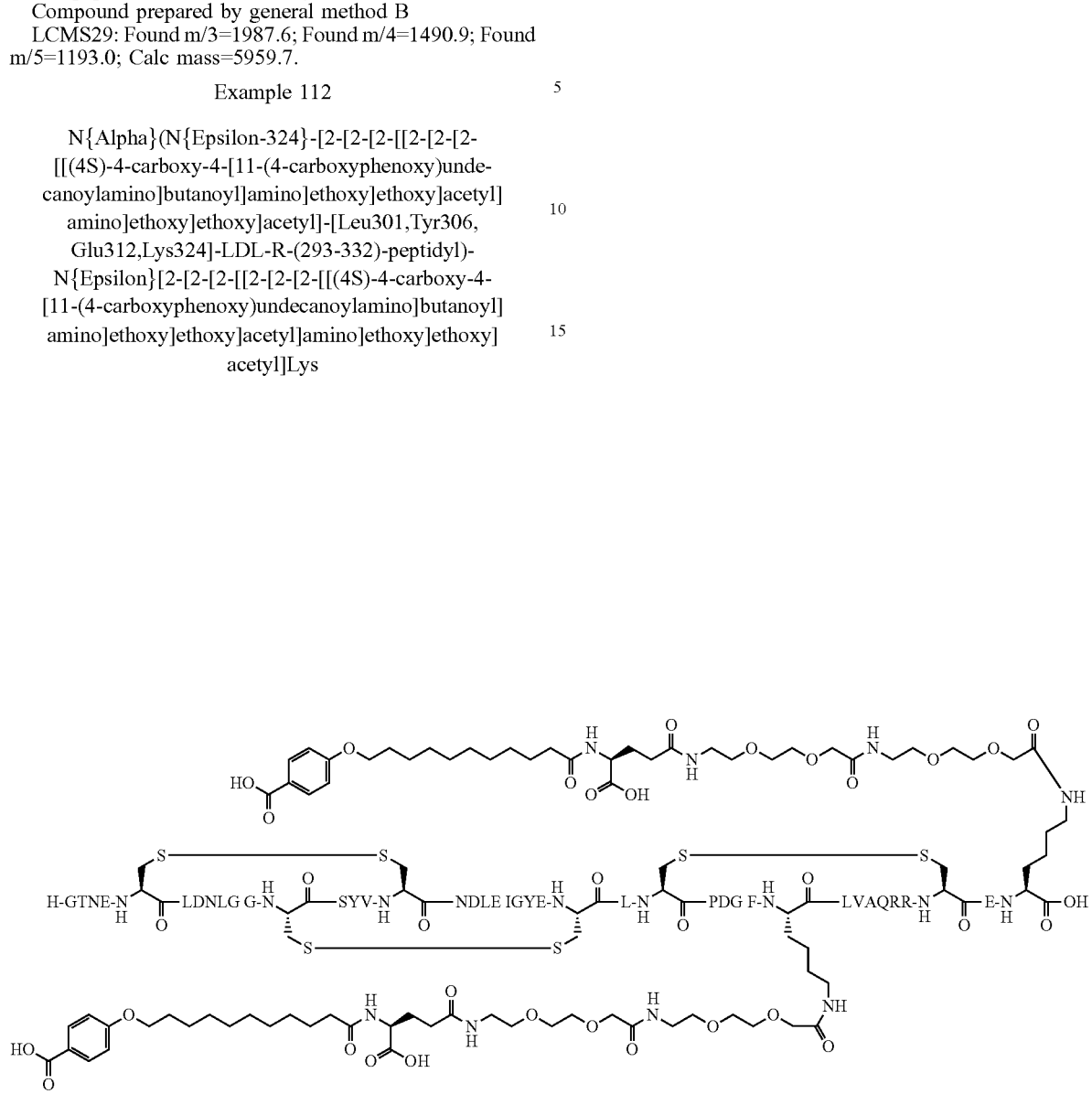

The peptide back-bone is SEQ ID NO: 85
Compound prepared by general method B
LCMS29: Found m/3=1991.6; Found m/4=1493.9; Found m/5=1195.1; Calc mass=5971.7.

Example 113

N{Alpha}(N{Epsilon-314}-[2-[2-[2-[[2-[2-[2-[[(4S)-4-carboxy-4-[11-(4-carboxyphenoxy)unde-canoylamino]butanoyl]amino]ethoxy]ethoxy]acetyl]amino]ethoxy]ethoxy]acetyl]-[His300,Leu301, Arg309,Glu312,Lys314]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

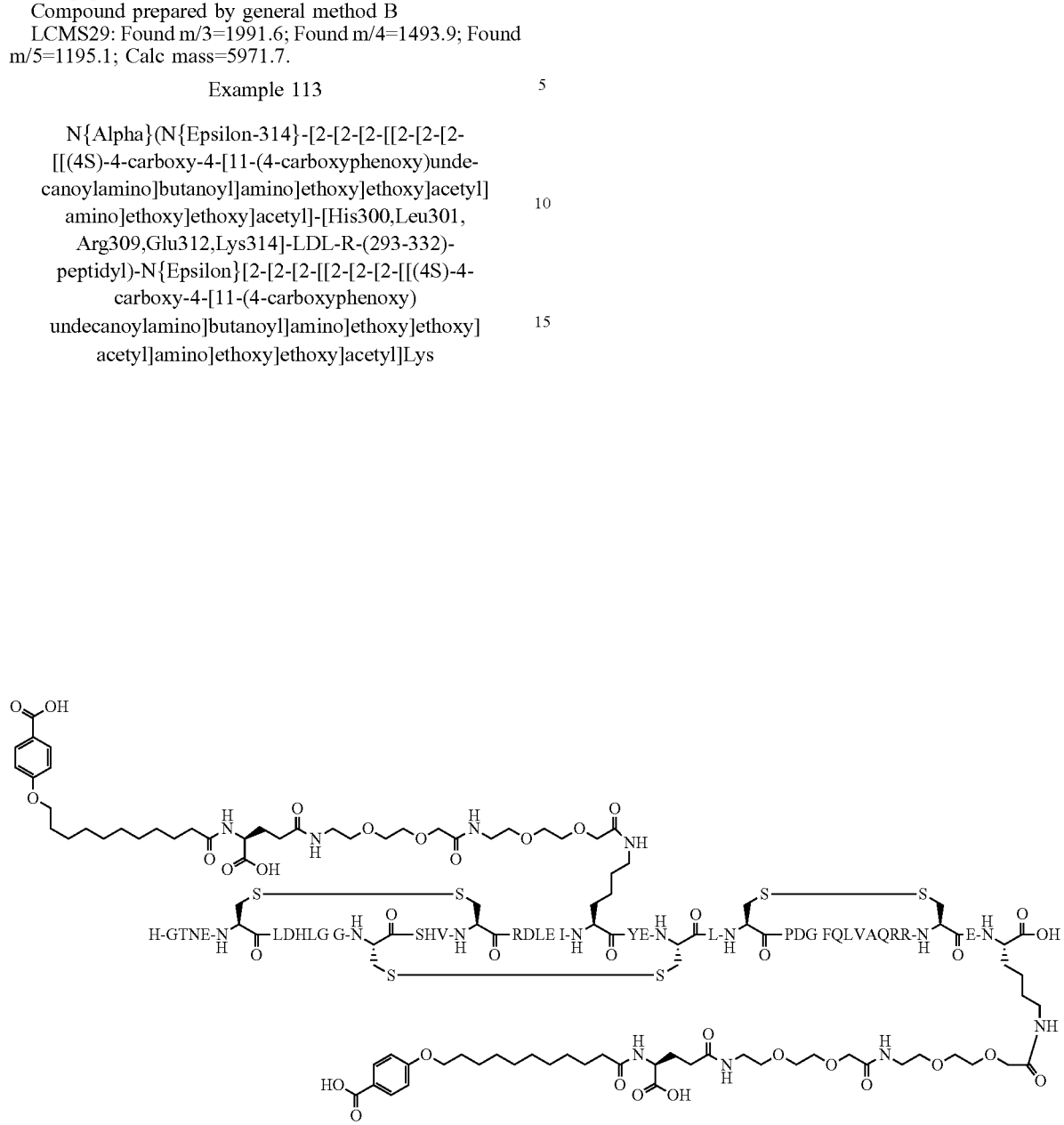

The peptide back-bone is SEQ ID NO: 86
Compound prepared by general method B
LCMS29: Found m/3=2028.3; Found m/4=1521.5; Calc mass=6081.8.

Example 114

N{Alpha}(N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Trp294,Leu301,Arg309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl] Lys

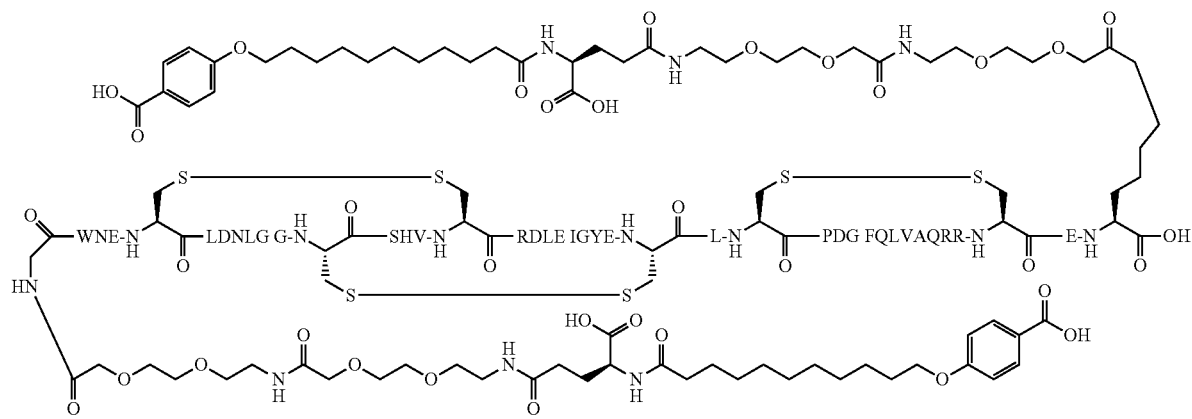

The peptide back-bone is SEQ ID NO: 87
Compound prepared by general method B
LCMS29: Found m/3=2025.3; Found m/4=1519.2; Found m/5=1215.6; Calc mass=6072.8.

Example 115

N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-328}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312,Lys328]-LDL-R-(293-332)-peptide

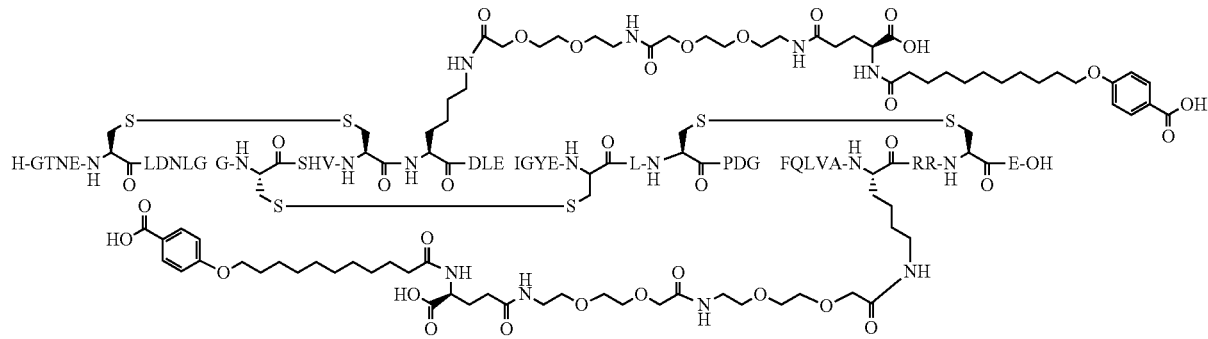

The peptide back-bone is SEQ ID NO: 88
Compound prepared by general method B
LCMS27: Found m/2=2916.7; Found m/3=1944.9; Found m/4=1458.9; Calc mass=5831.5.

Example 116

N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312,Lys313]-LDL-R-(293-332)-peptide

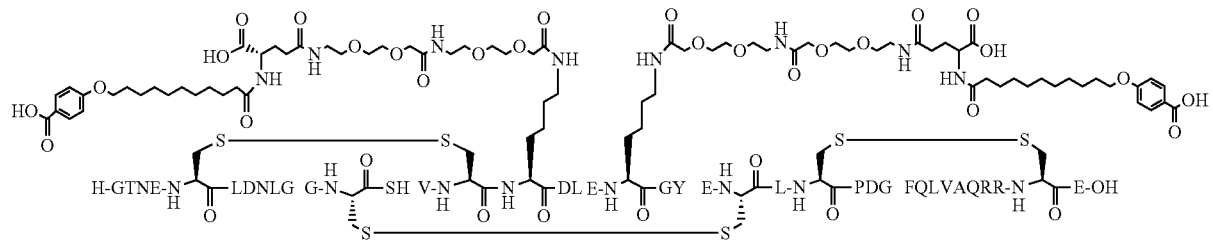

The peptide back-bone is SEQ ID NO: 89
Compound prepared by general method B
LCMS29: Found m/2=2924.1; Found m/3=1949.6 Found m/4=1462.4; Calc mass=5846.5.

Example 117

N{Alpha}(N{294}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312],des-Gly293-LDL-R-(294-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

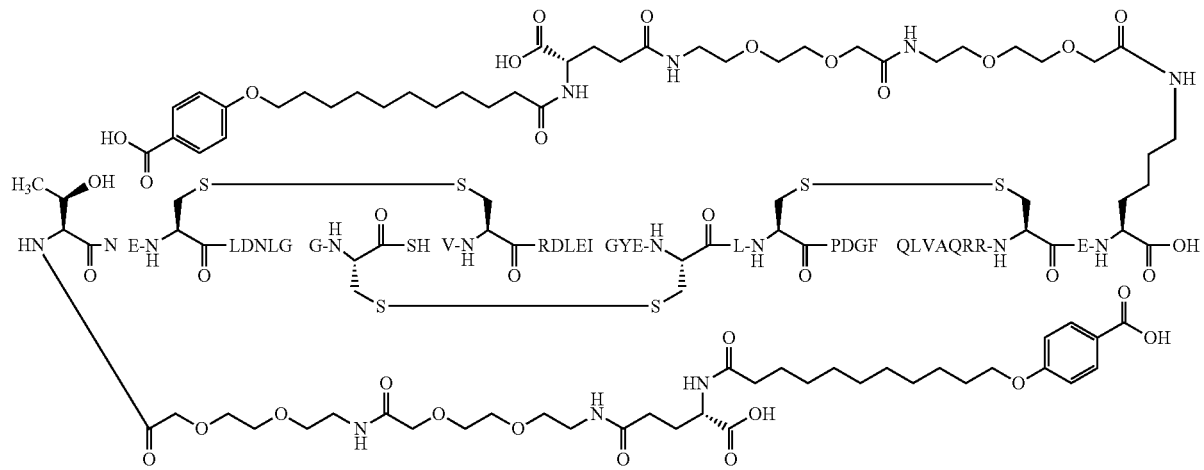

The peptide back-bone is SEQ ID NO: 90
Compound prepared by general method B
LCMS29: Found m/3=1977.6; Found m/4=1483.5; Found m/5=1187.2; Calc mass=5930.6.

Example 118

N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-328}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys324,Lys328]-LDL-R-(293-332)-peptide

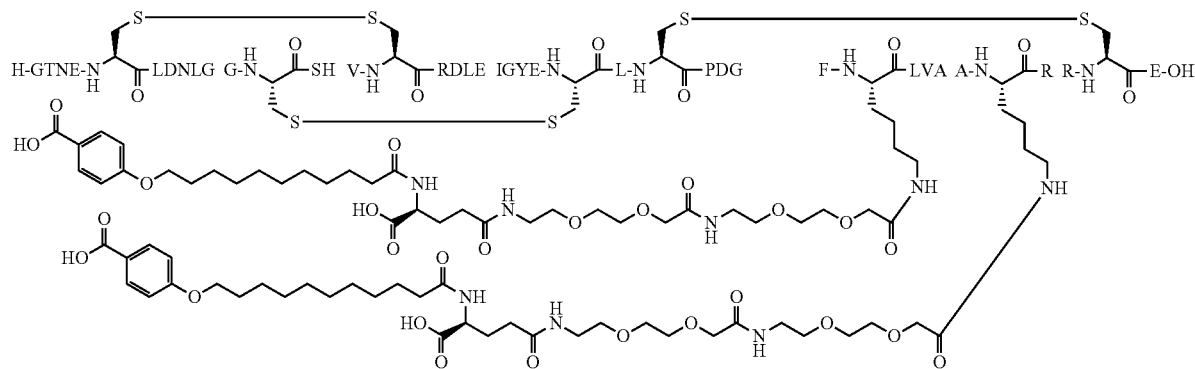

The peptide back-bone is SEQ ID NO: 91
Compound prepared by general method B
LCMS27: Found m/2=2930.4; Found m/3=1953.9; Found m/4=1465.7; Calc mass=5859.6.

Example 119

N{Alpha}(N{292}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-Ala[Leu301,Arg309,Glu312]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

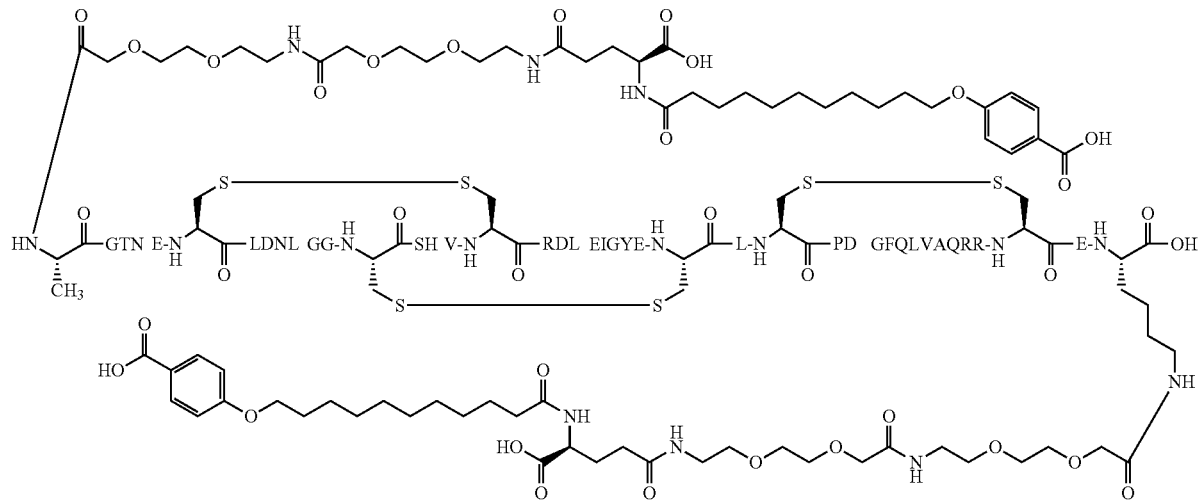

The peptide back-bone is SEQ ID NO: 92
Compound prepared by general method B
LCMS29: Found m/3=2020.6; Found m/4=1515.7; Found m/5=1212.8; Calc mass=6058.8.

Example 120

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Tyr306,Arg309,Glu312,Lys313]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

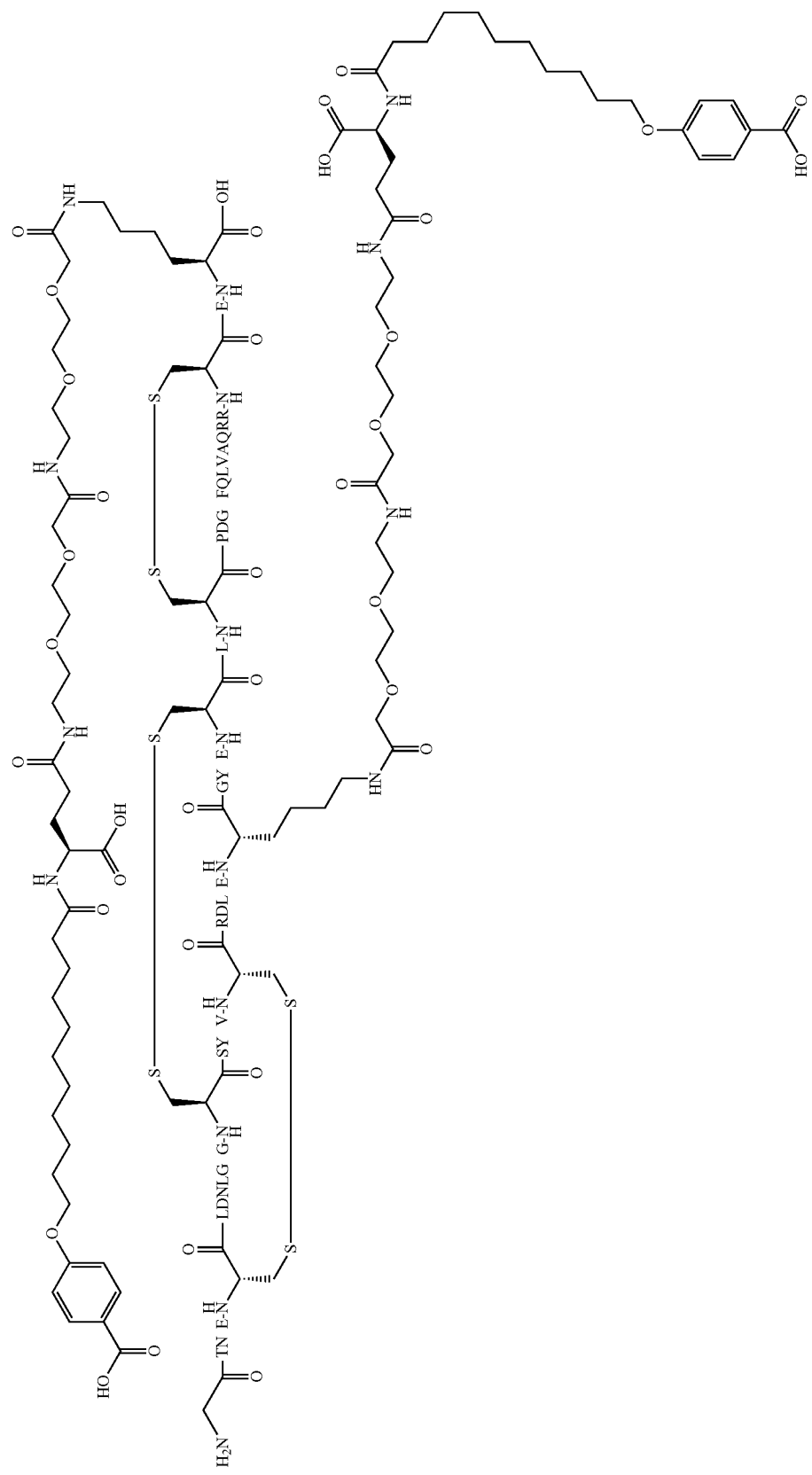

The peptide back-bone is SEQ ID NO: 93
Compound prepared by general method B
LCMS29: Found m/3=2010.2; Found m/4=1508.2; Found m/5=1206.8; Calc mass=6028.7.

Example 121

N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],
N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys332]-LDL-R-(293-332)-peptide

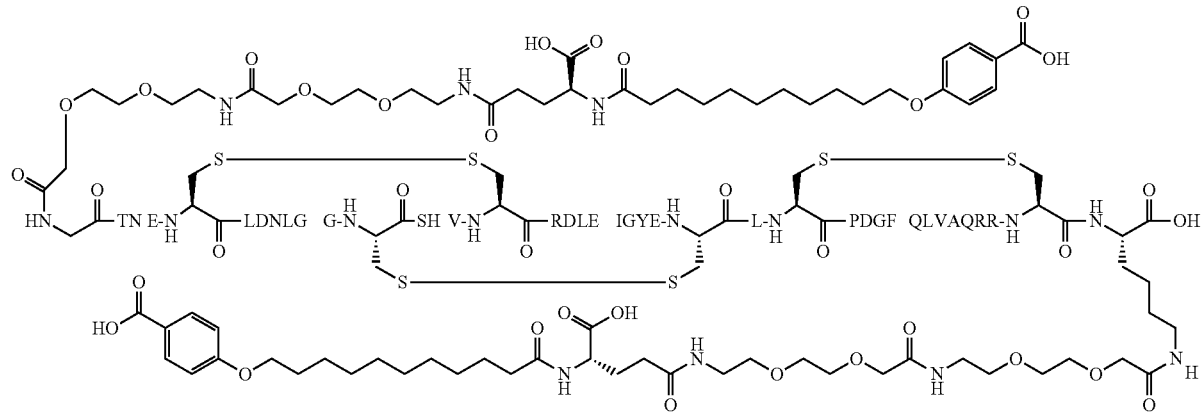

The peptide back-bone is SEQ ID NO: 11
Compound prepared by general method B
LCMS27: Found m/2=2930.3; Found m/3=1953.7; Found m/4=1465.8; Calc mass=5858.6.

Example 122

N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],
N{Epsilon-328}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys328]-LDL-R-(293-332)-peptide

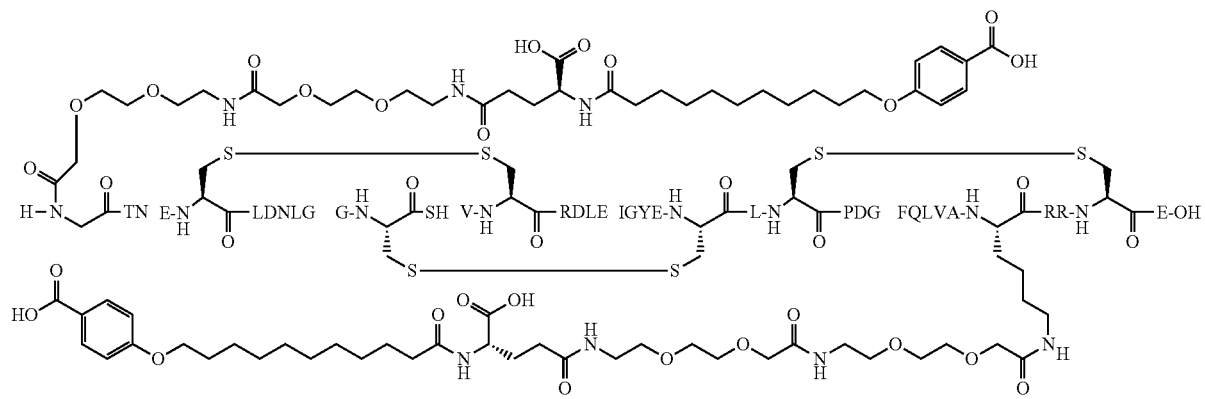

The peptide back-bone is SEQ ID NO: 40
Compound prepared by general method B
LCMS27: Found m/2=2930.1; Found m/3=1953.9; Found m/4=1465.7; Calc mass=5859.6.

Example 123

N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys324]-LDL-R-(293-332)-peptide

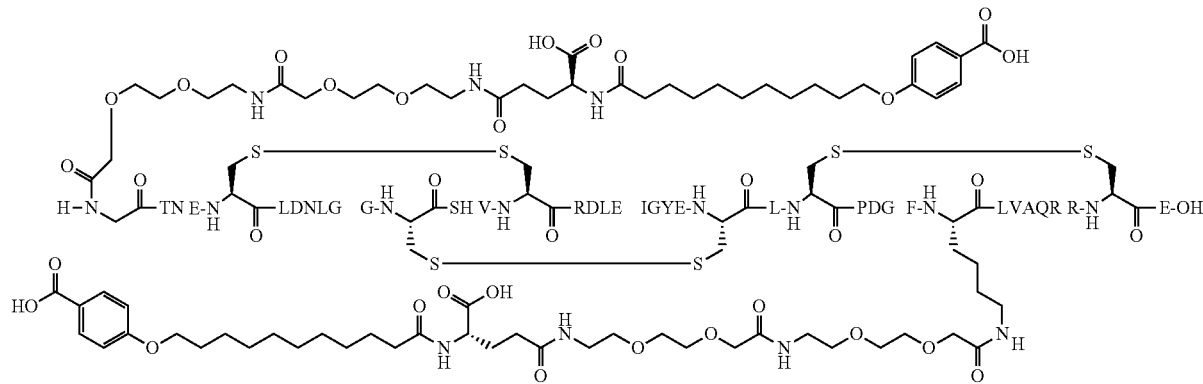

The peptide back-bone is SEQ ID NO: 22
Compound prepared by general method B
LCMS29: Found m/2=2930.9; Found m/3=1954.3; Found m/4=1465.9; Calc mass=5859.6.

Example 124

N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312,Lys332]-LDL-R-(293-332)-peptide

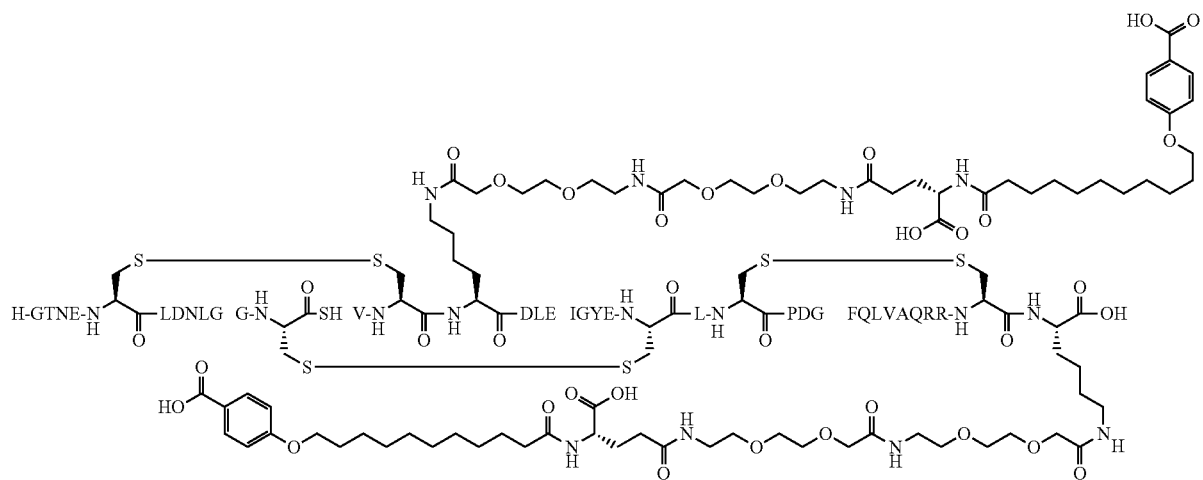

The peptide back-bone is SEQ ID NO: 94
Compound prepared by general method B
LCMS29: Found m/2=2916.1; Found m/3=1944.2; Found m/4=1458.4; Calc mass=5830.6.

Example 125

N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-324}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312,Lys324]-LDL-R-(293-332)-peptide

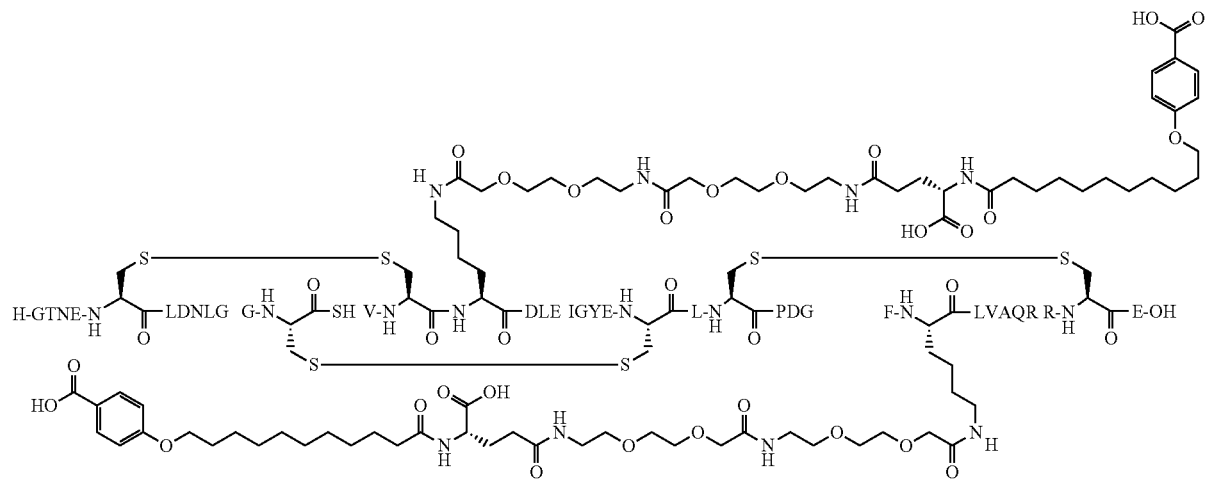

The peptide back-bone is SEQ ID NO: 106
Compound prepared by general method B
LCMS29: Found m/2=2916.6; Found m/3=1944.5; Found m/4=1458.9; Calc mass=5831.5.

Example 126

N{293}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-309}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Lys309,Glu312]-LDL-R-(293-332)-peptide

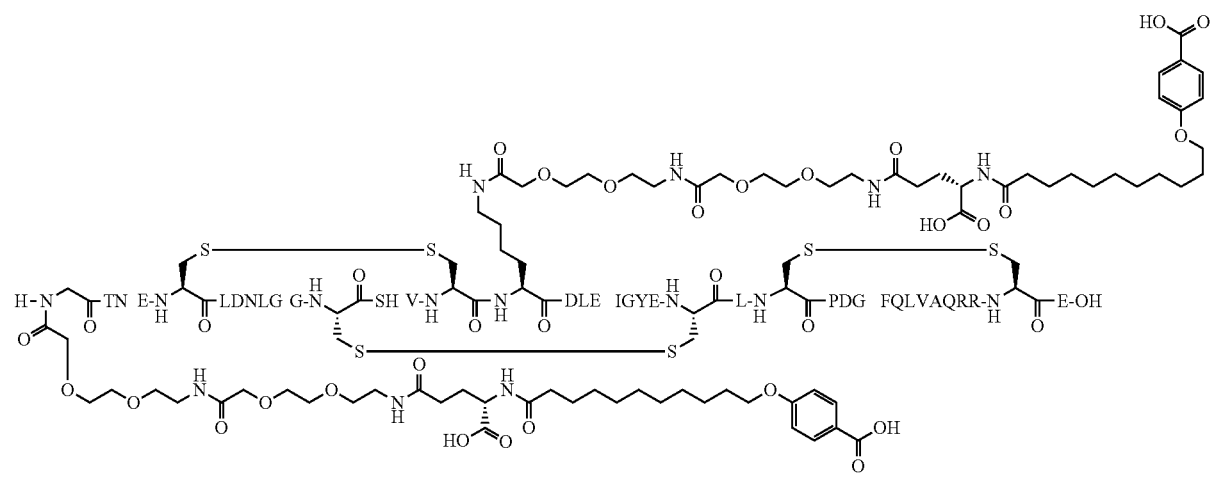

The peptide back-bone is SEQ ID NO: 30
Compound prepared by general method B
LCMS29: Found m/2=2916.7; Found m/3=1944.6; Found m/4=1458.7; Calc mass=5831.5.

Example 127

N{Epsilon-321}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Glu312,Lys321,Lys332]-LDL-R-(293-332)-peptide

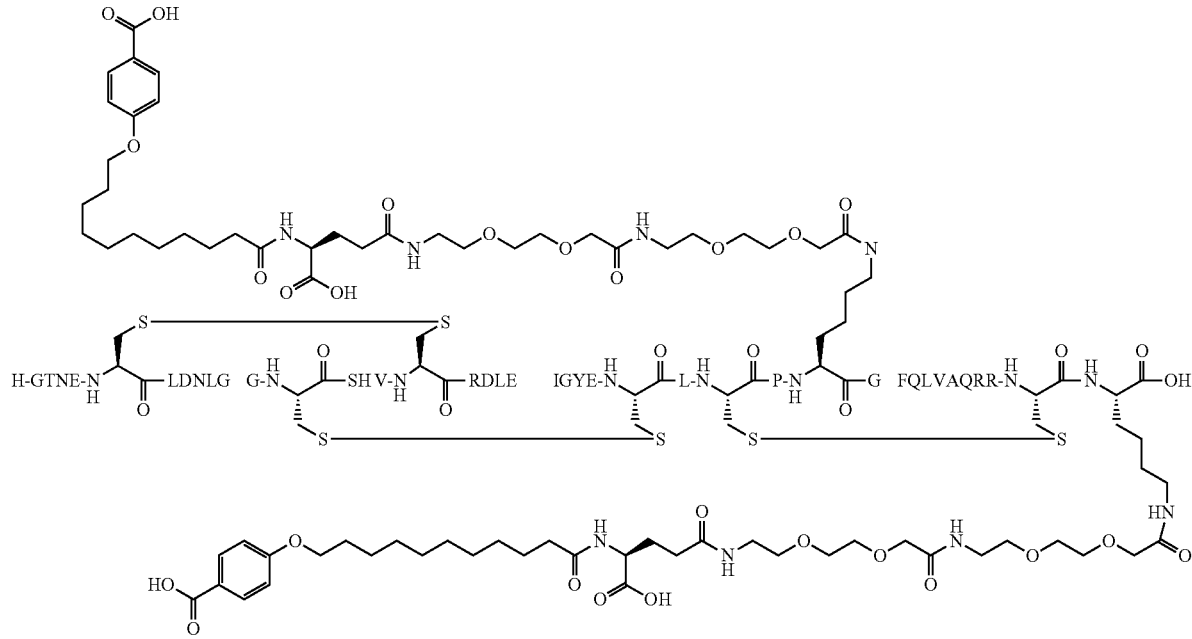

The peptide back-bone is SEQ ID NO: 95
Compound prepared by general method B
LCMS29: Found m/3=1958.3; Found m/4=1469.0; Calc mass=5871.6.

Example 128

N{Alpha}(N{Epsilon-313}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys

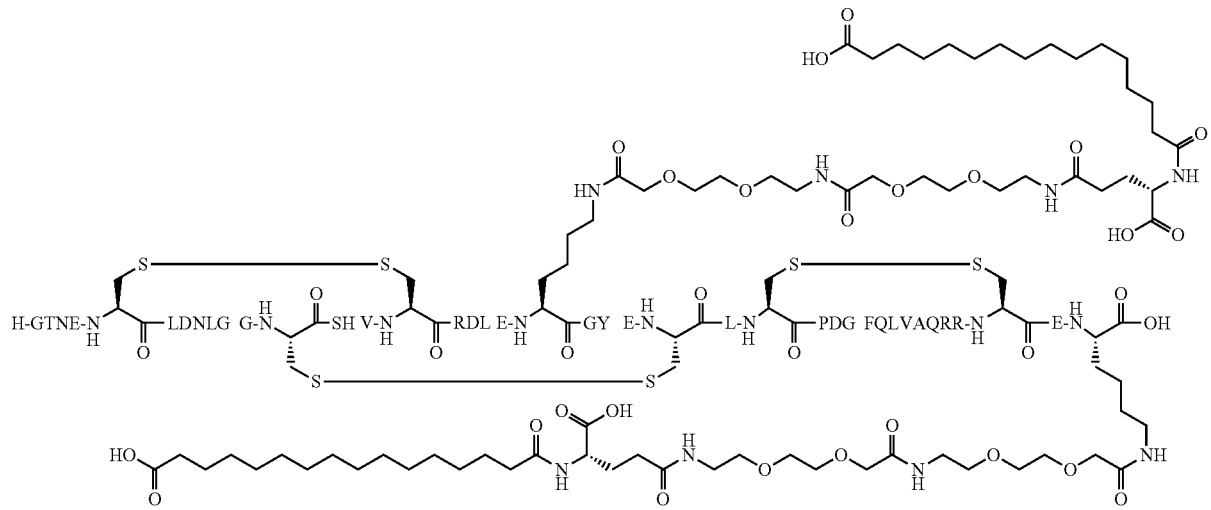

The peptide back-bone is SEQ ID NO: 32
Compound prepared by general method B
LCMS29: Found m/2=2966.28; Found m/3=1978.0; Found m/4=1483.5; Calc mass=5930.7.

Example 129

N{Alpha}(N{Epsilon-313}-[(4S)-4-carboxy-4-(15-carboxypentadecanoylamino)butanoyl]-[Leu301,Arg309,Glu312,Lys313]-LDL-R-(293-332)-peptidyl)-N{Epsilon}[(4S)-4-carboxy-4-(15-carboxypentadecanoylamino)butanoyl]Lys

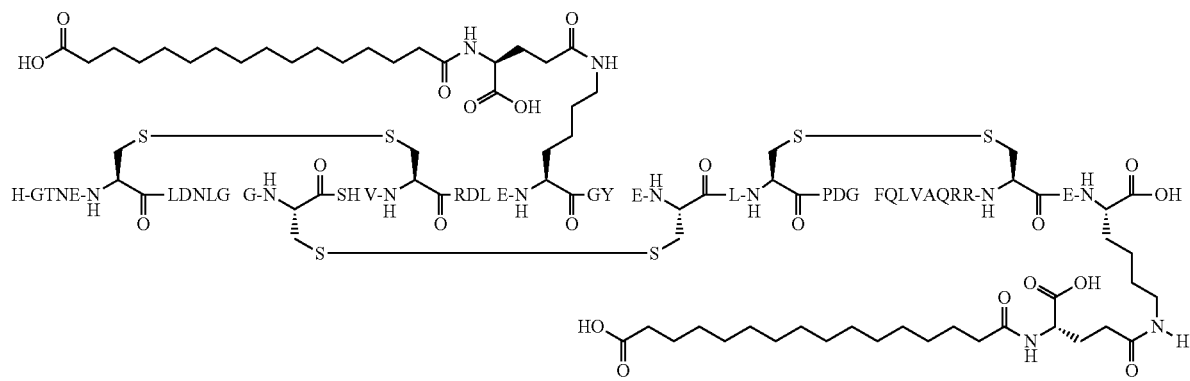

The peptide back-bone is SEQ ID NO: 32
Compound prepared by general method B
LCMS29: Found m/2=2676.0; Found m/3=1784.2; Found m/4=1338.4; Calc mass=5330.1.

Example 130

N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-332}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[His300,Leu301,Arg309,Glu312,Lys313,Lys332]-LDL-R-(293-332)-peptide

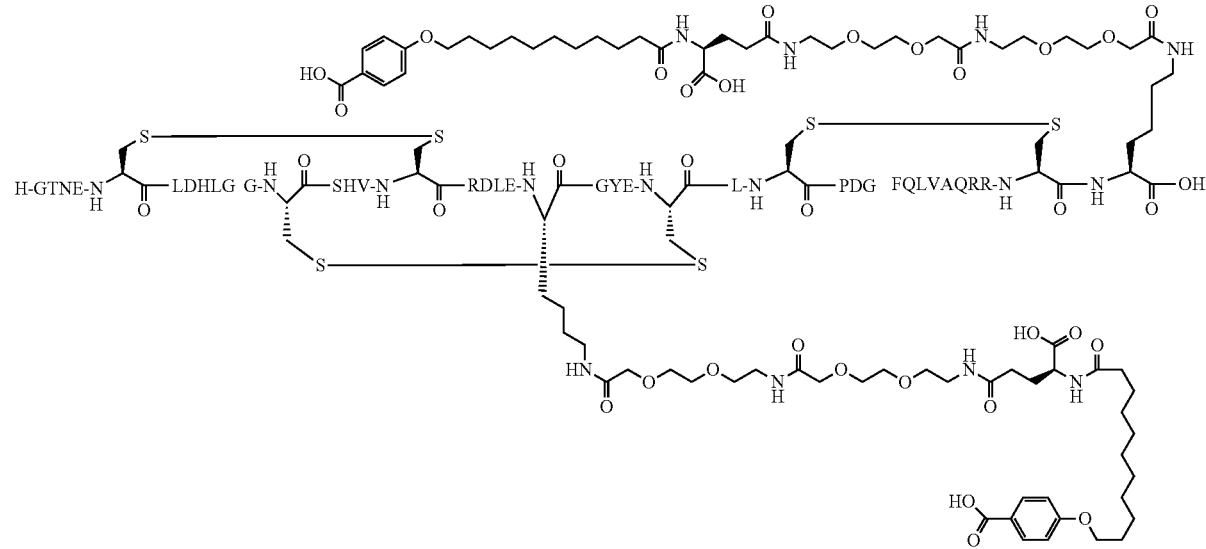

The peptide back-bone is SEQ ID NO: 96
Compound prepared by general method B
LCMS29: Found m/3=1966.7; Found m/4=1475.0; Calc mass=5896.6.

Example 131

N{Alpha}(N{Epsilon-313}-[4-[3-[2-[2-[3-[[(4S)-4-carboxy-4-[11-(4-carboxyphenoxy)undecanoylamino]butanoyl]amino]propoxy]ethoxy]ethoxy]propylamino]-4-oxobutanoyl]-[Leu301,Arg309,Glu312,Lys313]-LDL-R-(293-332)-peptidyl)-N{Epsilon}[4-[3-[2-[2-[3-[[(4S)-4-carboxy-4-[11-(4-carboxyphenoxy)undecanoylamino]butanoyl]amino]propoxy]ethoxy]ethoxy]propylamino]-4-oxobutanoyl]Lys

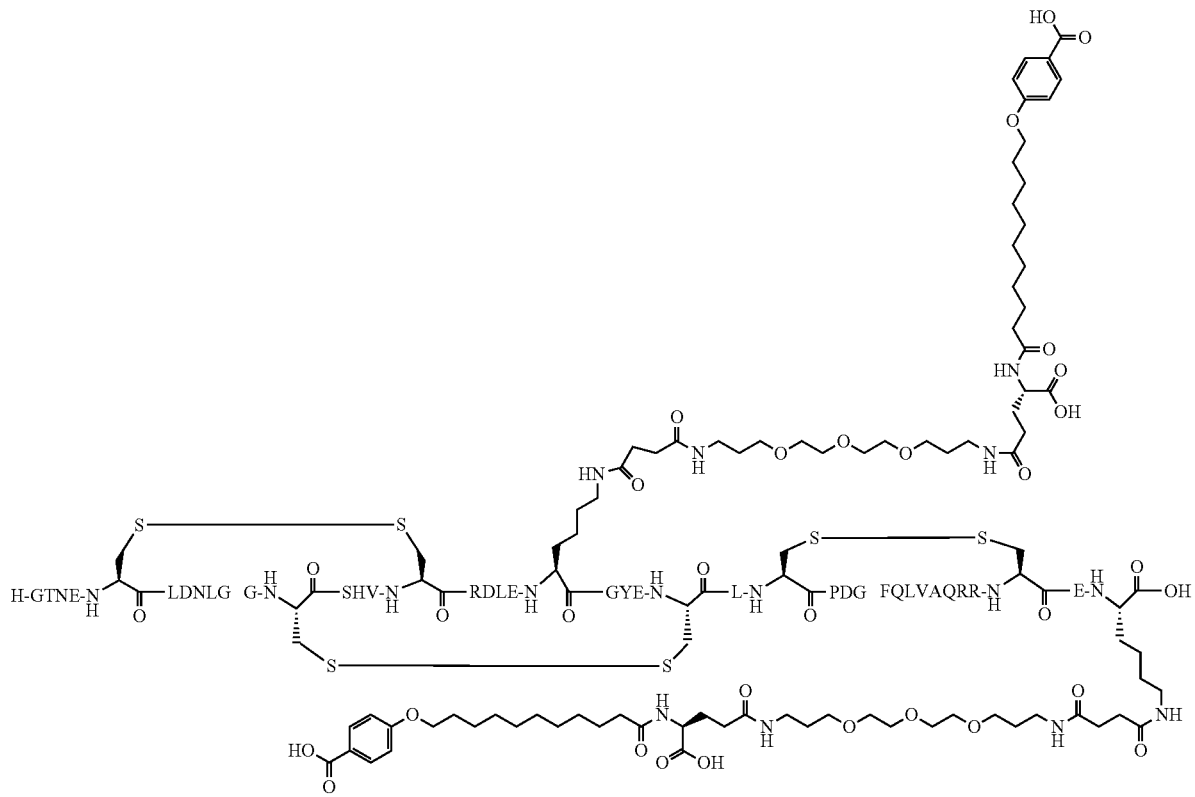

The peptide back-bone is SEQ ID NO: 32
Compound prepared by general method B
LCMS29: Found m/3=2009.9; Found m/4=1507.7; Calc mass=6026.8.

Example 132

N{Epsilon-313}-[4-[3-[2-[2-[3-[[(4S)-4-carboxy-4-[11-(4-carboxyphenoxy)undecanoylamino]butanoyl]amino]propoxy]ethoxy]ethoxy]propylamino]-4-oxobutanoyl],N{Epsilon-332}-[4-[3-[2-[2-[3-[[(4S)-4-carboxy-4-[11-(4-carboxyphenoxy)undecanoylamino]butanoyl]amino]propoxy]ethoxy]ethoxy]propylamino]-4-oxobutanoyl]-[Leu301,Arg309,Glu312,Lys313,Glu321,Lys332]-LDL-R-(293-332)-peptide

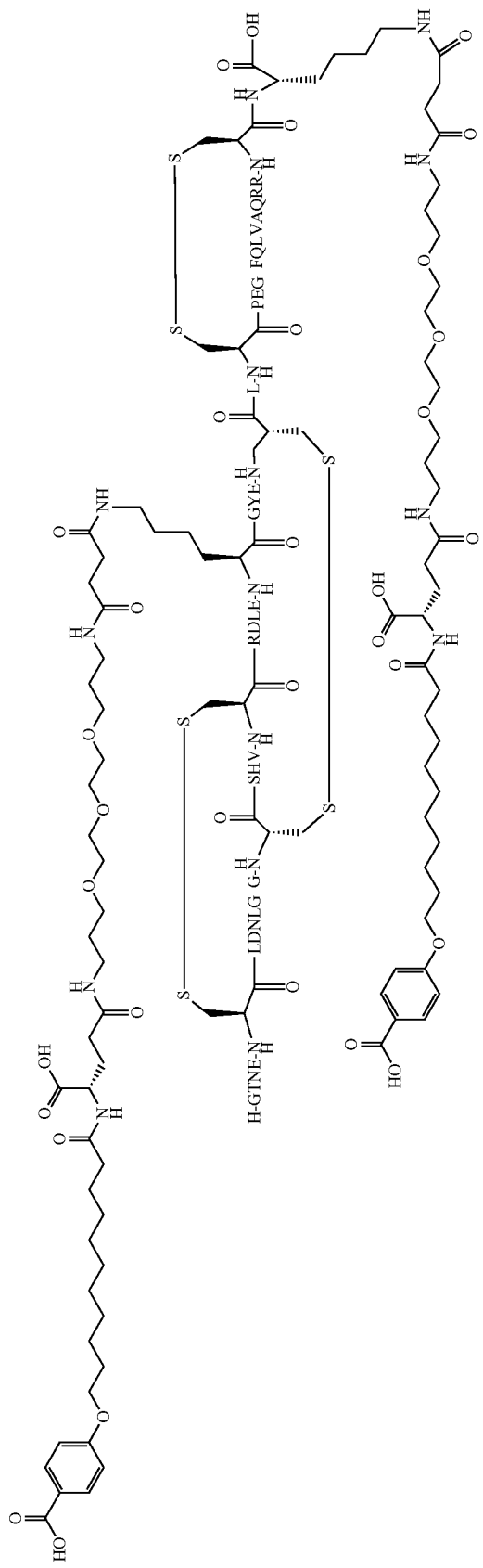

The peptide back-bone is SEQ ID NO: 97
Compound prepared by general method B
LCMS29: Found m/3=1971.3; Found m/4=1478.9; Calc mass=5911.7.

Example 133

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309, Glu312, Lys313,Glu321]-LDL-R-(293-332)-peptidyl)-N{Epsilon}[2-[2-[2-[[2-[2-[2-[[(4S)-4-carboxy-4-[11-(4-carboxyphenoxy) undecanoylamino]butanoyl]amino]ethoxy]ethoxy]acetyl]amino]ethoxy]ethoxy]acetyl]Lys

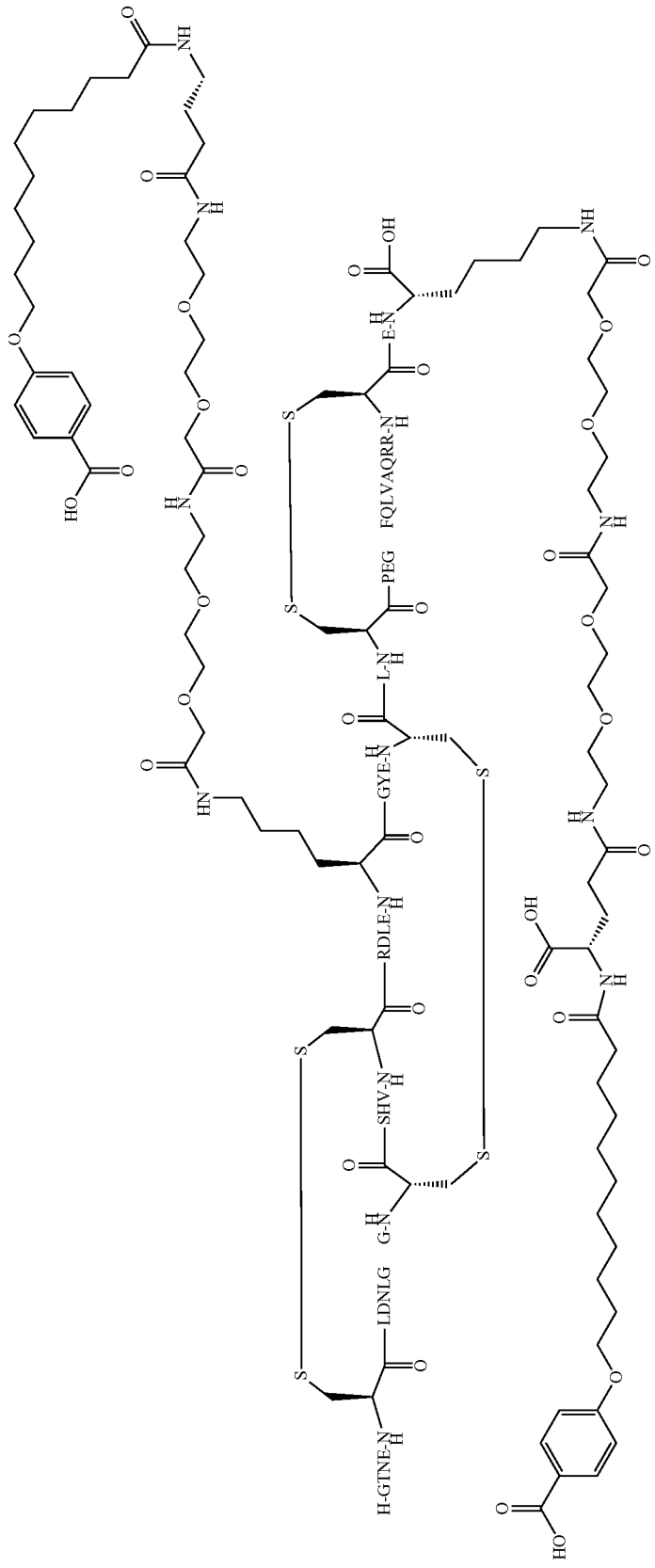

The peptide back-bone is SEQ ID NO: 98
Compound prepared by general method B
LCMS01: Found m/4=1505.0; Found m/5=1204.3; Calc mass=6016.7.

Example 134

N{Alpha}([Leu301,Arg309,Glu312,Glu321]-LDL-
R-(293-332)-peptidyl)-N{Epsilon}[2-[2-[2-[[2-[2-
[2-[[(4S)-4-carboxy-4-(19-carboxynonadecanoy-
lamino)butanoyl]amino]ethoxy]ethoxy]acetyl]
amino]ethoxy]ethoxy]acetyl]Lys

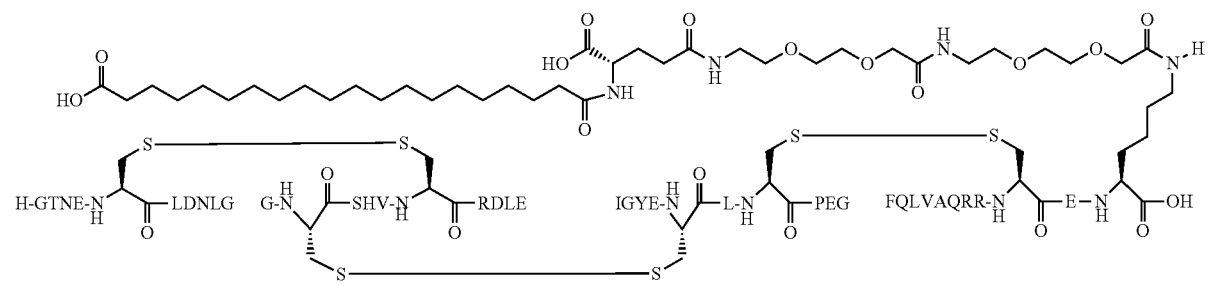

The peptide back-bone is SEQ ID NO: 19
Compound prepared by general method B
LCMS01: Found m/4=1766.7; Found m/5=1325.3; Calc mass=5258.0.

Example 135

N{Epsilon-313}-[2-[2-[2-[[2-[2-[2-[[(4S)-4-carboxy-
4-[11-(4-carboxyphenoxy)undecanoylamino]bu-
tanoyl]amino]ethoxy]ethoxy]acetyl]amino]ethoxy]
ethoxy]acetyl],N{Epsilon-314}-[2-[2-[2-[[2-[2-[2-
[[(4S)-4-carboxy-4-[11-(4-carboxyphenoxy)
undecanoylamino]butanoyl]amino]ethoxy]ethoxy]
acetyl]amino]ethoxy]ethoxy]acetyl]-[Leu301,
Arg309,Glu312,Lys313,Lys314]-LDL-R-(293-332)-
peptide

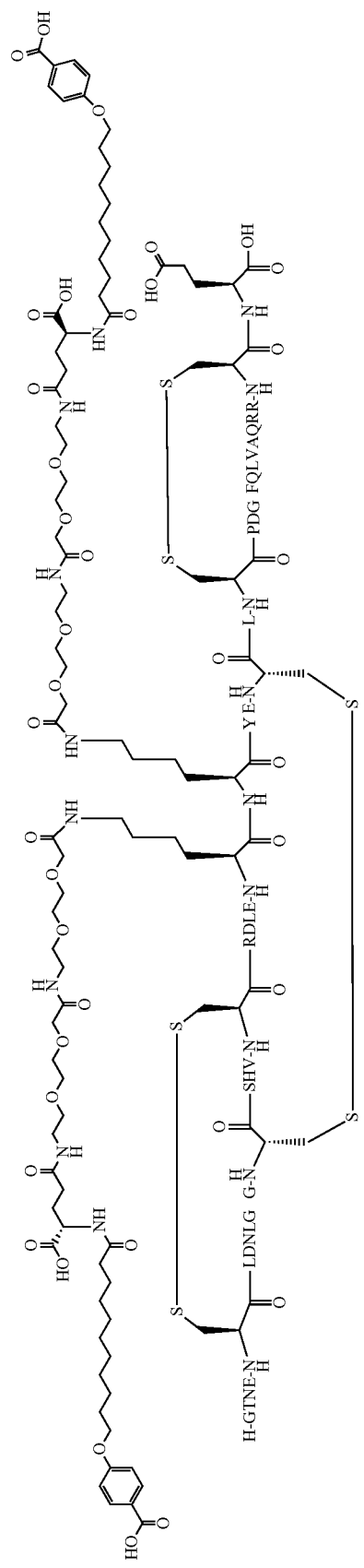

The peptide back-bone is SEQ ID NO: 99
Compound prepared by general method B
LCMS01: Found m/4=1487.3; Found m/5=1190.0; Calc mass=5945.6.

Example 136

N{Epsilon-312}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Lys313]-LDL-R-(293-332)-peptide

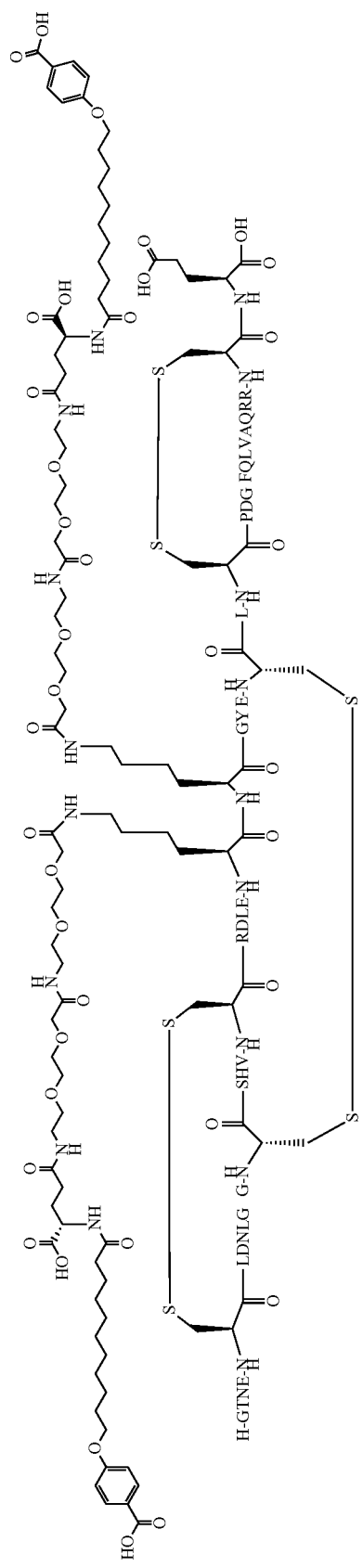

The peptide back-bone is SEQ ID NO: 100
Compound prepared by general method B
LCMS01: Found m/4=1469.3; Found m/5=1175.5; Calc mass=5873.6.

Example 137

N{Epsilon-312}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-314}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Lys314]-LDL-R-(293-332)-peptide

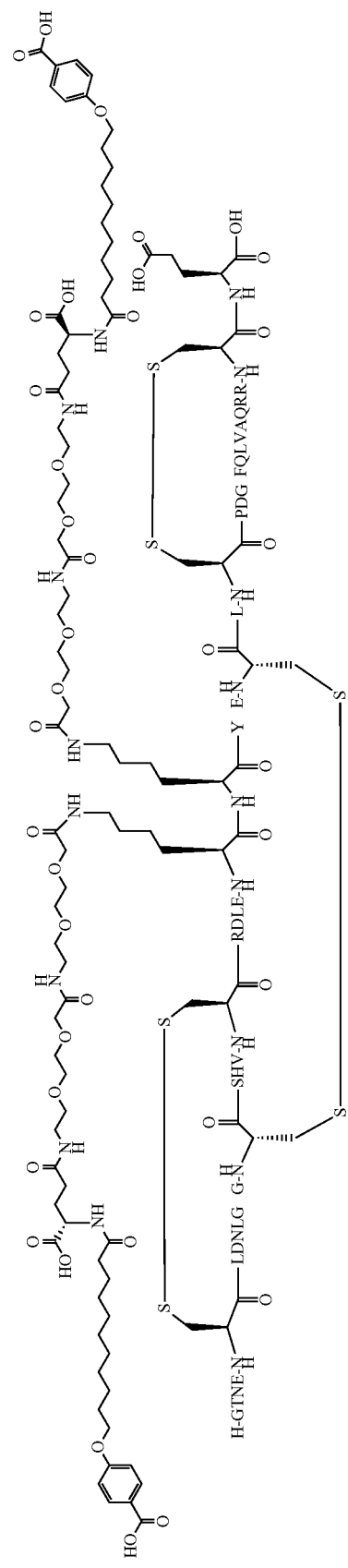

The peptide back-bone is SEQ ID NO: 101
Compound prepared by general method B
LCMS01: Found m/4=1483.3; Found m/5=1186.8; Calc mass=5929.7.

Example 138

N{Epsilon-311}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Leu301,Arg309,Lys311,Glu312,Lys313]-LDL-R-(293-332)-peptide

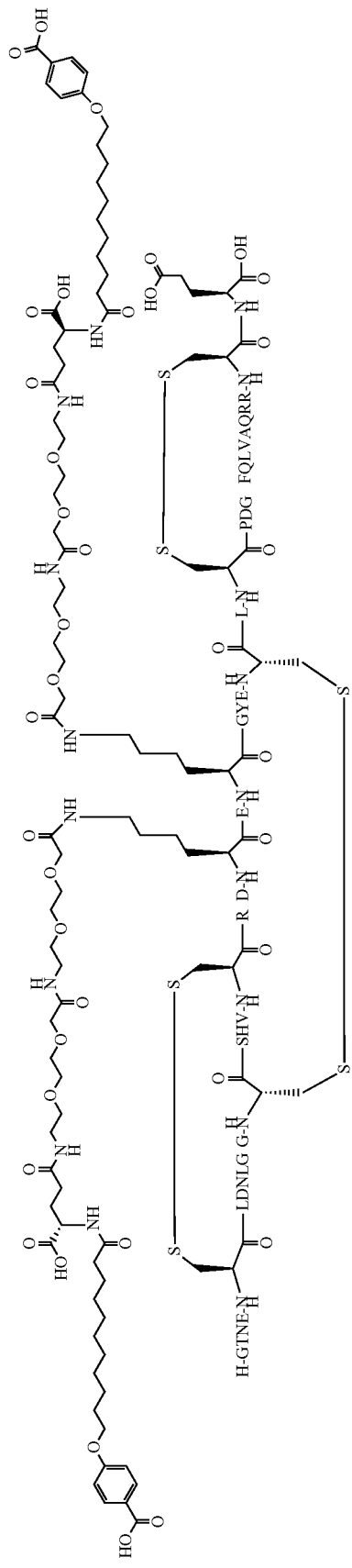

The peptide back-bone is SEQ ID NO: 102
Compound prepared by general method B
LCMS01: Found m/4=1473.0; Found m/5=1178.6; Calc mass=5889.5.
Example 139
N{Alpha}(N{Epsilon-313}-11-(4-carboxyphenoxy)
undecanoyl-[His300,Leu301,Arg309,Glu312,
Lys313]-LDL-R-(293-332)-peptidyl)-N{Epsilon}11-
(4-carboxyphenoxy)undecanoylLys
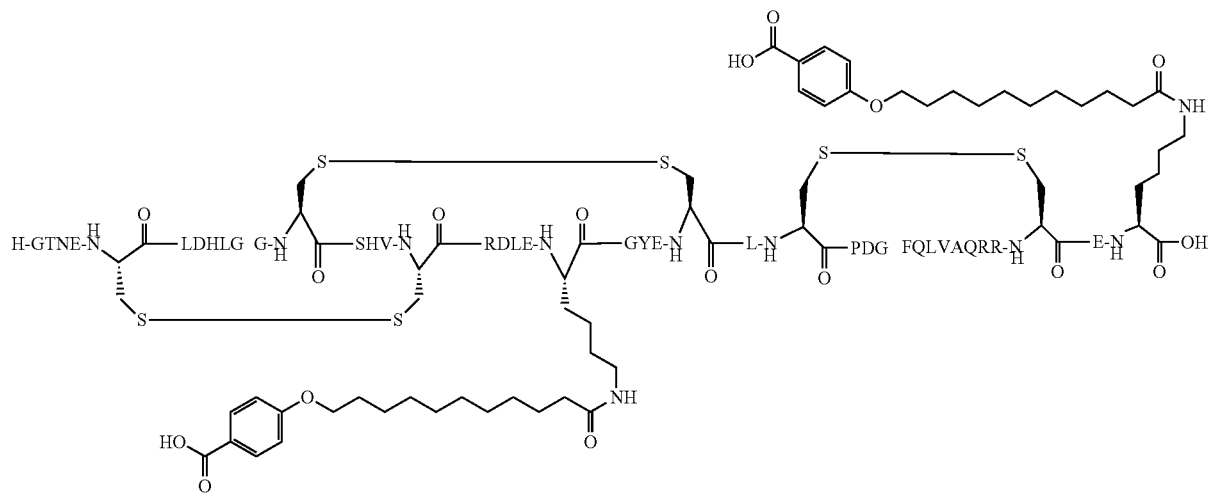

The peptide back-bone is SEQ ID NO: 69
Compound prepared by general method B
LCMS01: Found m/4=1297.4; Found m/5=1038.2; Calc mass=5186.9.

Example 140

N{Alpha}(N{Epsilon-313}-[2-[2-[2-[[2-[2-[2-[[(4S)-4-carboxy-4-[13-(1H-tetrazol-5-yl)tridecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[13-(1H-tetrazol-5-yl)tridecanoylamino]butanoyl]amino]ethoxy]ethoxy]acetyl]amino]ethoxy]ethoxy]acetyl]Lys

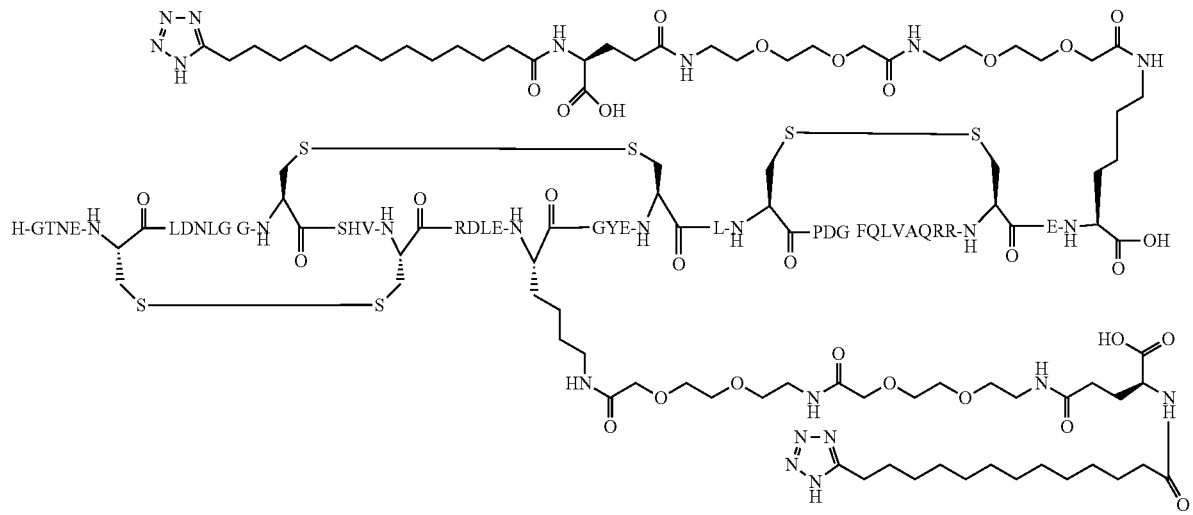

The peptide back-bone is SEQ ID NO: 32
Compound prepared by general method B
LCMS01: Found m/4=1481.6; Found m/5=1185.3; Calc mass=5922.7.

Example 141

N{Alpha}(N{Epsilon-313}-[2-[2-[2-[[2-[2-[2-[[(4S)-4-carboxy-4-(14-sulfotetradecanoylamino)butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-(14-sulfotetradecanoylamino)butanoyl]amino]ethoxy]ethoxy]acetyl]amino]ethoxy]ethoxy]acetyl]Lys

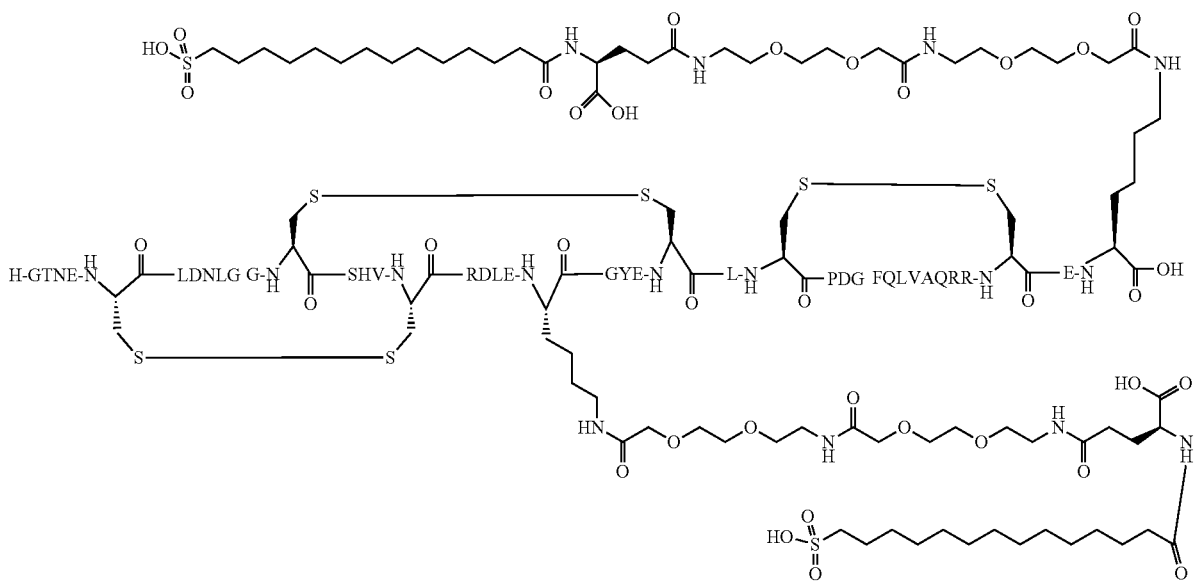

The peptide back-bone is SEQ ID NO: 32
Compound prepared by general method B
LCMS027: Found m/3=1992.6; Found m/4=1494.7; Found m/5=1196.0; Calc mass=5974.8.

Example 142

N{Alpha}(N{Epsilon-313}-[2-[2-[2-[[2-[2-[2-[[(4S)-4-carboxy-4-[13-(methylsulfonylcarbamoylamino)tridecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[13-(methylsulfonylcarbamoylamino)tridecanoylamino]butanoyl]amino]ethoxy]ethoxy]acetyl]amino]ethoxy]ethoxy]acetyl]Lys

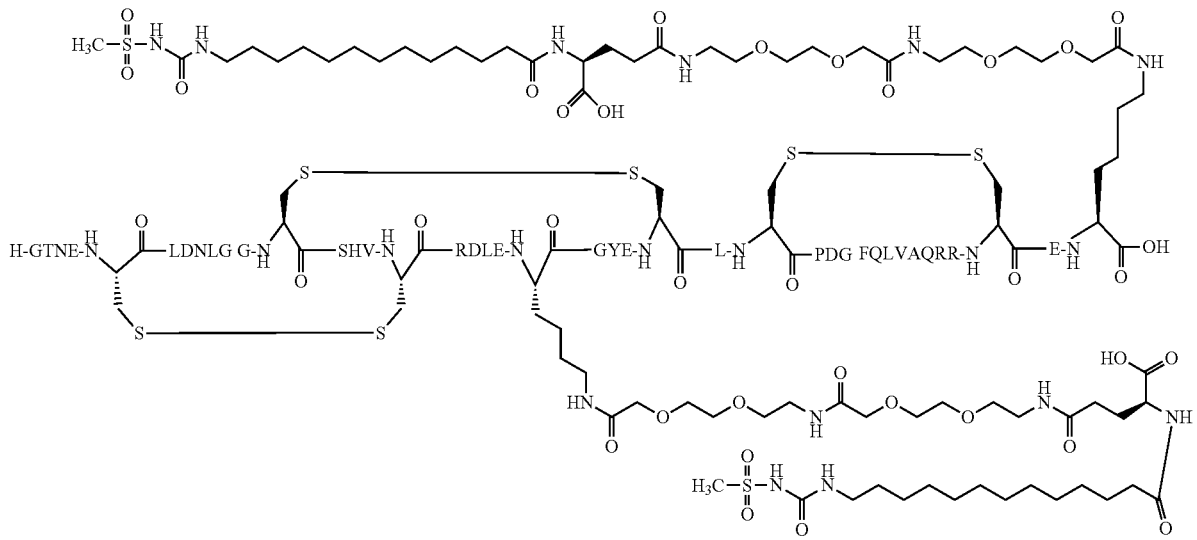

The peptide back-bone is SEQ ID NO: 32
Compound prepared by general method B
LCMS027: Found m/3=2020.7; Found m/4=1515.8; Found m/5=1212.8; Calc mass=6058.8.
Example 143
N{Alpha}(N{Epsilon-313}-[(4S)-4-carboxy-4-[11-(4-carboxyphenoxy)undecanoylamino]butanoyl]-[Leu301,Arg309,Glu312,Lys313,Glu321]-LDL-R-(293-332)-peptidyl)-N{Epsilon}[(4S)-4-carboxy-4-[11-(4-carboxyphenoxy)undecanoylamino]butanoyl] Lys
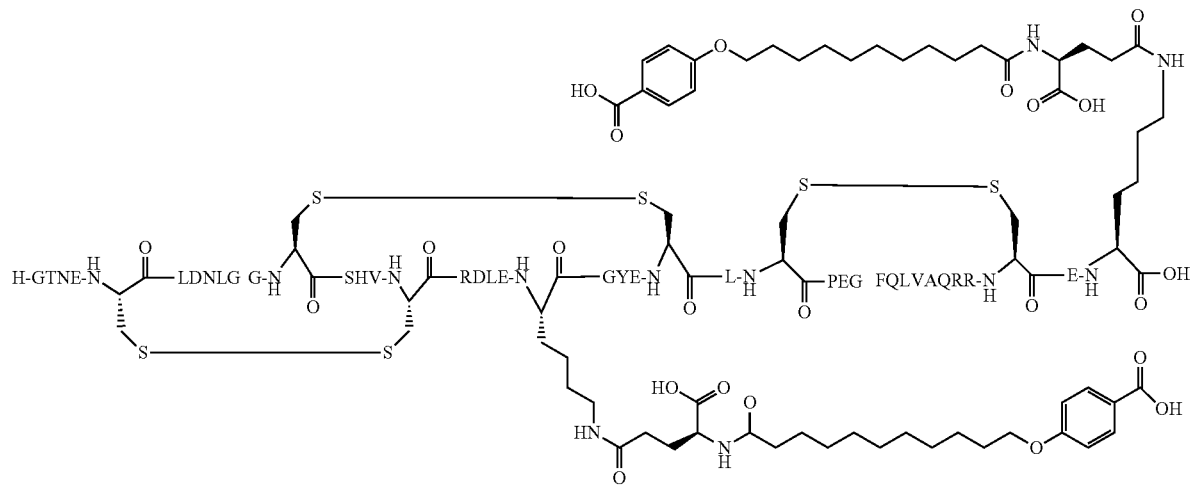

The peptide back-bone is SEQ ID NO: 98
Compound prepared by general method B
LCMS29: Found m/2=2719.0; Found m/3=1812.8; Found m/4=1359.8; Calc mass=5436.1.

Example 144

N{Alpha}(N{Epsilon-313}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys313,Glu321]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys

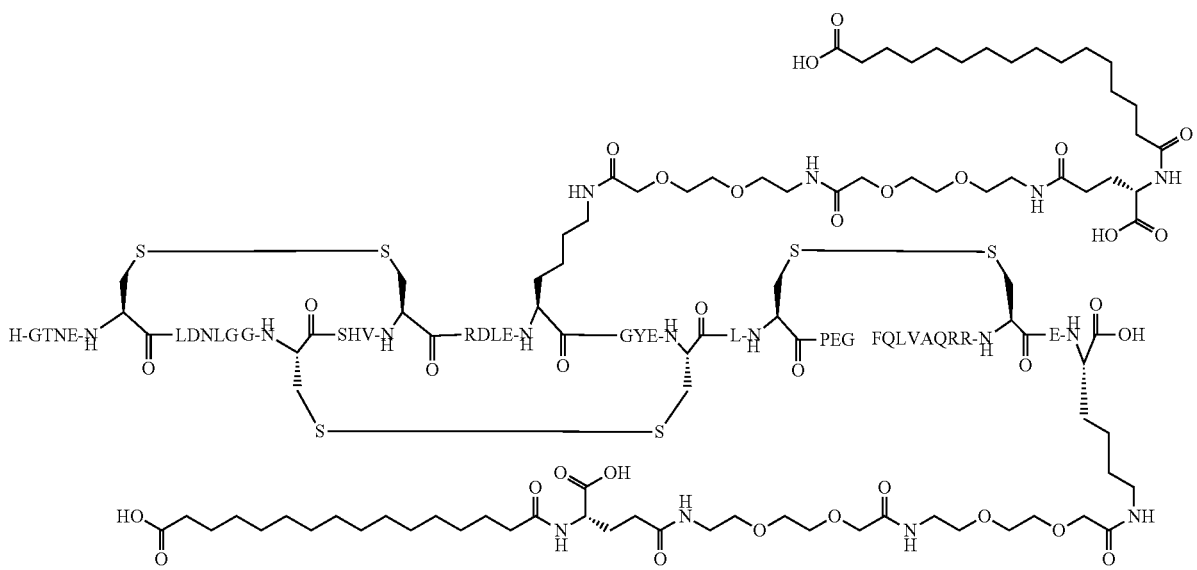

The peptide back-bone is SEQ ID NO: 98
Compound prepared by general method B
LCMS29: Found m/3=1982.2; Found m/4=1486.9; Found m/5=1189.7; Calc mass=5944.7.

Example 145

N{Alpha}(N{Epsilon-313}-[2-[2-[2-[[2-[2-[2-[[(4S)-4-carboxy-4-[16-(1H-tetrazol-5-yl)hexadecanoylamino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[16-(1H-tetrazol-5-yl)hexadecanoylamino]butanoyl]amino]ethoxy]ethoxy]acetyl]amino]ethoxy]ethoxy]acetyl]Lys

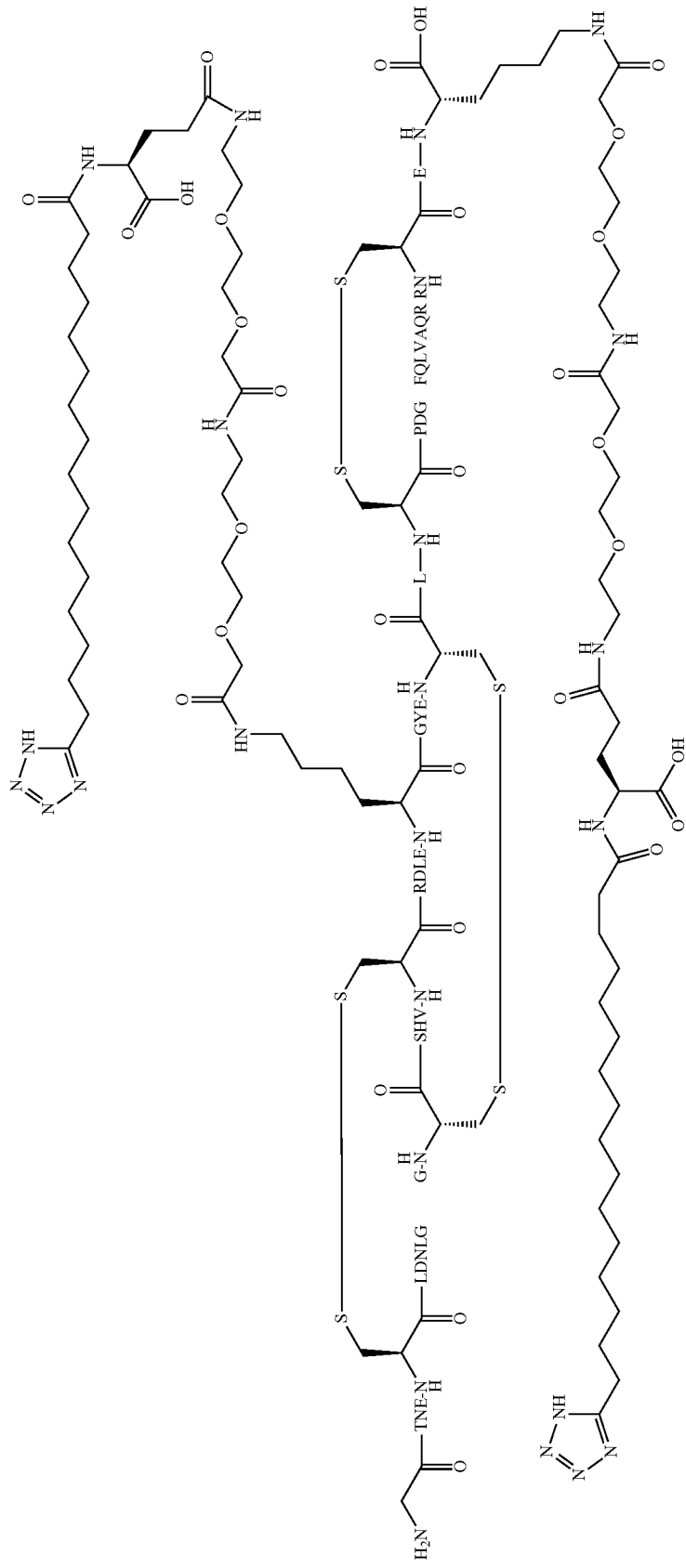

The peptide back-bone is SEQ ID NO: 32
Compound prepared by general method B
LCMS29: Found m/3=2003.3; Found m/4=1502.7; Found m/5=1202.2; Calc mass=6006.8.

Example 146

N{Alpha}(N{Epsilon-313}-[(4S)-4-carboxy-4-(15-carboxypentadecanoylamino)butanoyl]-[Leu301, Arg309,Glu312,Lys313,Glu321]-LDL-R-(293-332)-peptidyl)-N{Epsilon}[(4S)-4-carboxy-4-(15-carboxypentadecanoylamino)butanoyl]Lys

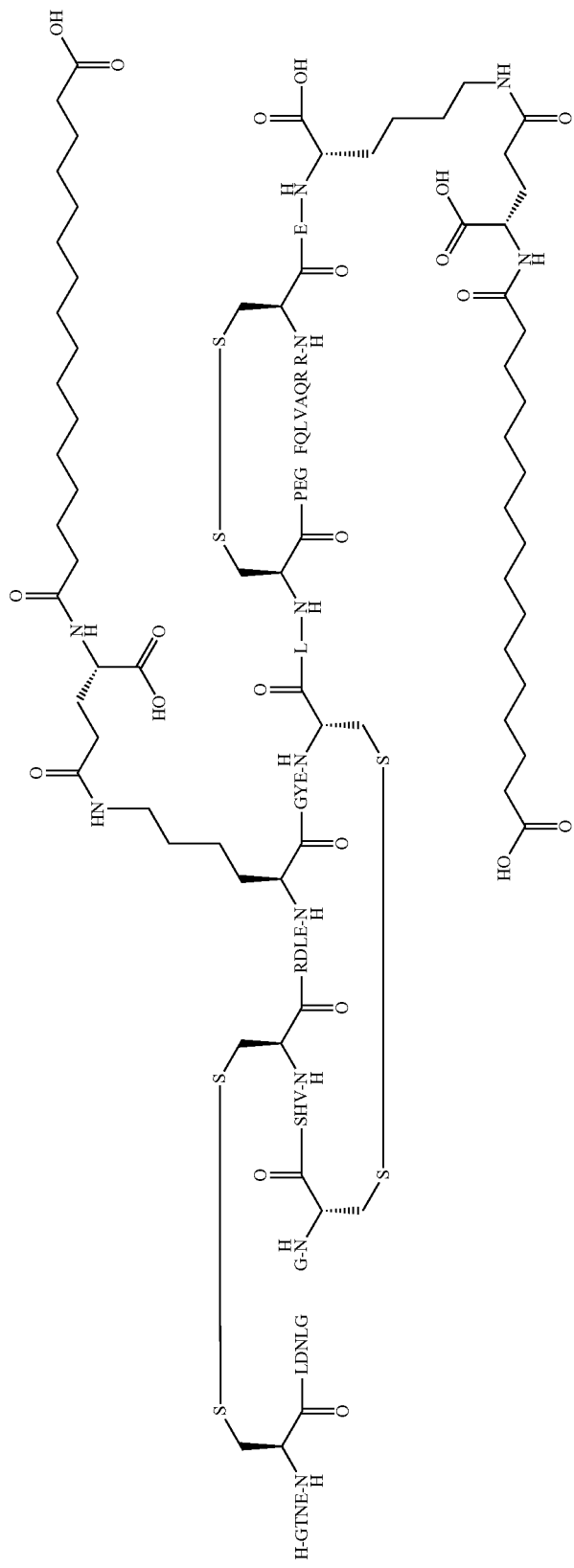

The peptide back-bone is SEQ ID NO: 98
Compound prepared by general method B
LCMS29: Found m/3=1788.8; Found m/4=1341.9; Found m/5=1073.7; Calc mass=5364.1.

Example 147

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[His300,Leu301,Arg309,Glu312,Lys313,Glu321]-LDL-R-(293-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

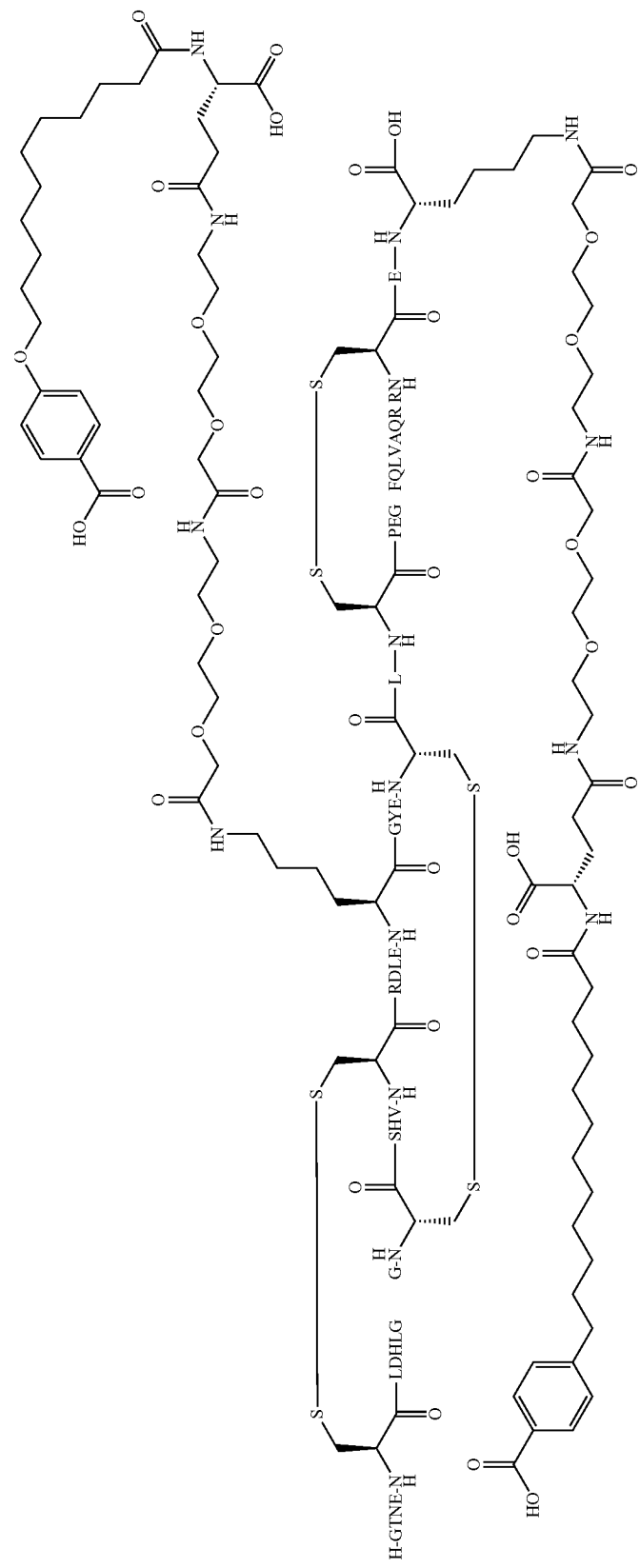

The peptide back-bone is SEQ ID NO: 103
Compound prepared by general method B
LCMS29: Found m/2=3020.8; Found m/3=2014.3; Found m/4=1510.9; Calc mass=6039.8.

Example 148

N{Alpha}(N{Epsilon-313}-[2-[2-[2-[[2-[2-[2-[[2-[2-[2-[[2-[2-[2-[[(4S)-4-carboxy-4- [11-(4-carboxy-phenoxy)undecanoylamino]butanoyl]amino]ethoxy] ethoxy]acetyl]amino]ethoxy]ethoxy]acetyl]amino] ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[2-[2-[2-[[2-[2-[2-[[(4S)-4-carboxy-4-[11-(4-carboxyphenoxy)undecanoylamino]butanoyl]amino] ethoxy]ethoxy]acetyl]amino]ethoxy]ethoxy]acetyl] amino]ethoxy]ethoxy]acetyl]amino]ethoxy]ethoxy] acetyl]Lys

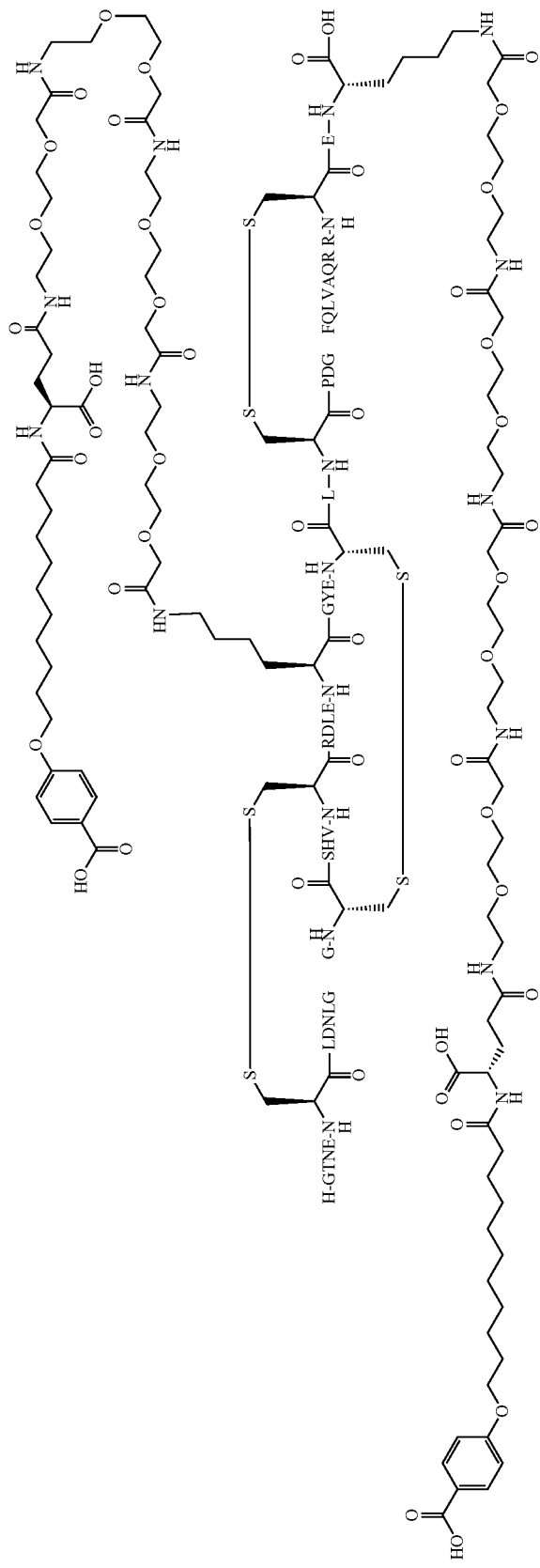

The peptide back-bone is SEQ ID NO: 32
Compound prepared by general method B
LCMS027: Found m/3=2195.5; Found m/4=1646.9; Found m/5=1317.7; Calc mass=6583.3.

Example 149

N{Alpha}(N{Epsilon-313}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[His300,Leu301,Arg309,Glu312,Lys313],des-Gly293-LDL-R-(294-332)-peptidyl)-N{Epsilon}[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]Lys

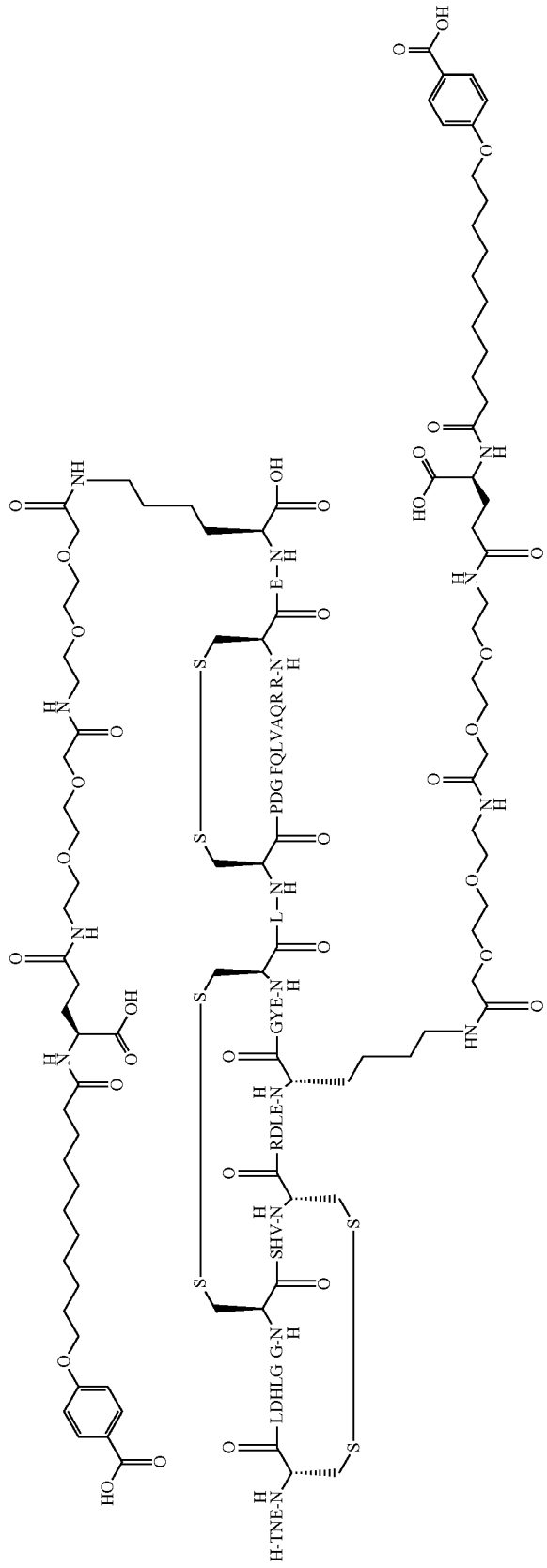

The peptide back-bone is SEQ ID NO: 74
Compound prepared by general method B
LCMS027: Found m/3=1990.6; Found m/4=1493.2; Found m/5=1191.1; Calc mass=5968.7.

Example 150

N{Alpha}(N{Epsilon-328}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys328]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl] Lys

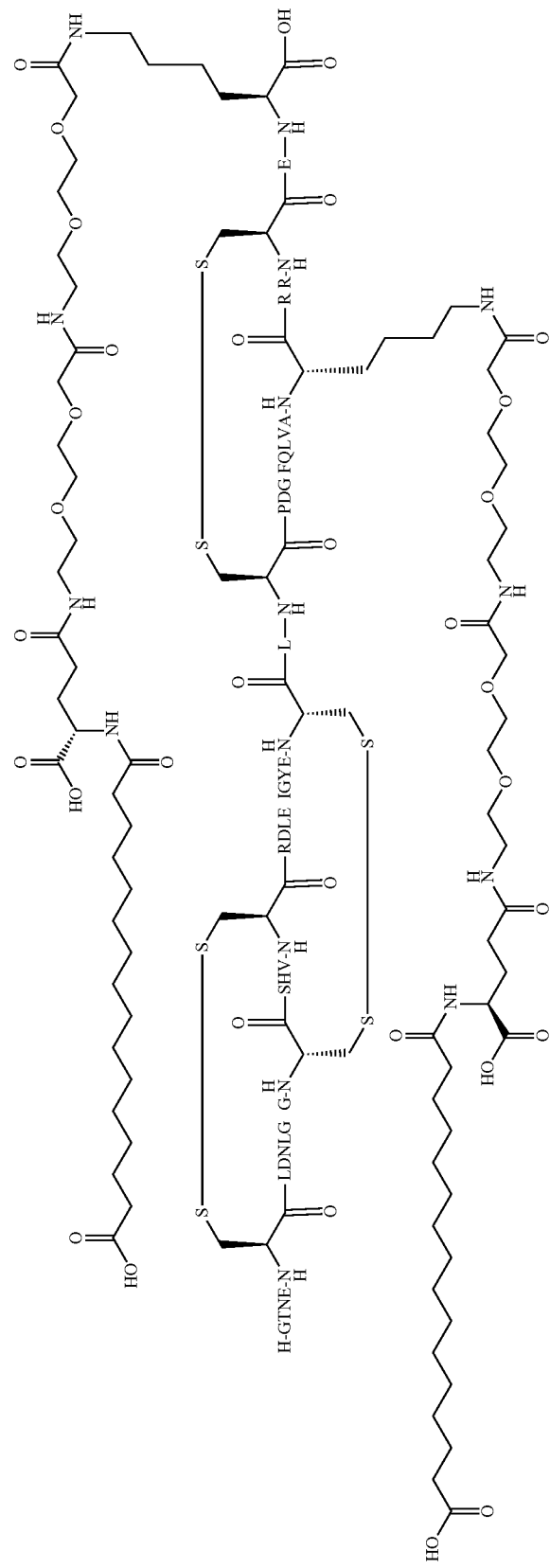

The peptide back-bone is SEQ ID NO: 78
Compound prepared by general method B
LCMS27: Found m/2=2958.7; Found m/3=1973.0; Found m/4=1480.0; Calc mass=5915.7.

Example 151

N{Alpha}(N{Epsilon-328}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Glu321,Lys328]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys

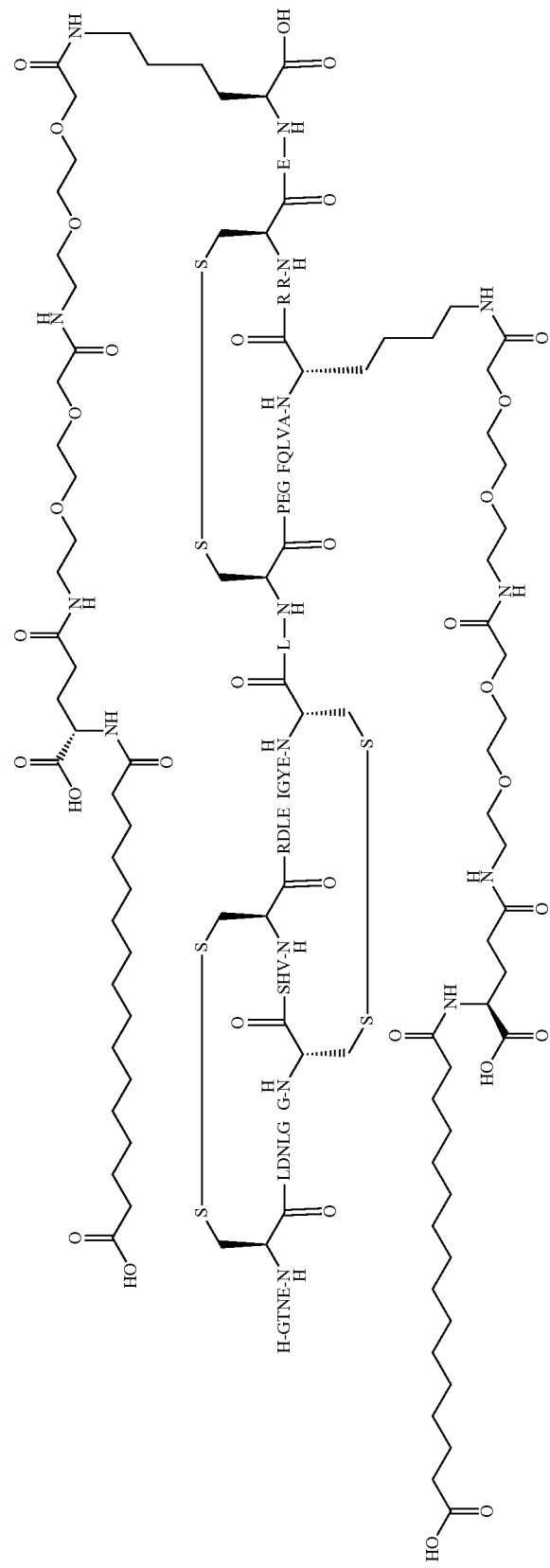

The peptide back-bone is SEQ ID NO: 104
Compound prepared by general method B
LCMS01: Found m/4=1483.2; Found m/5=1186.8; Calc mass=5930.0.

Example 152

N{Alpha}(N{Epsilon-324}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys324]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl] Lys

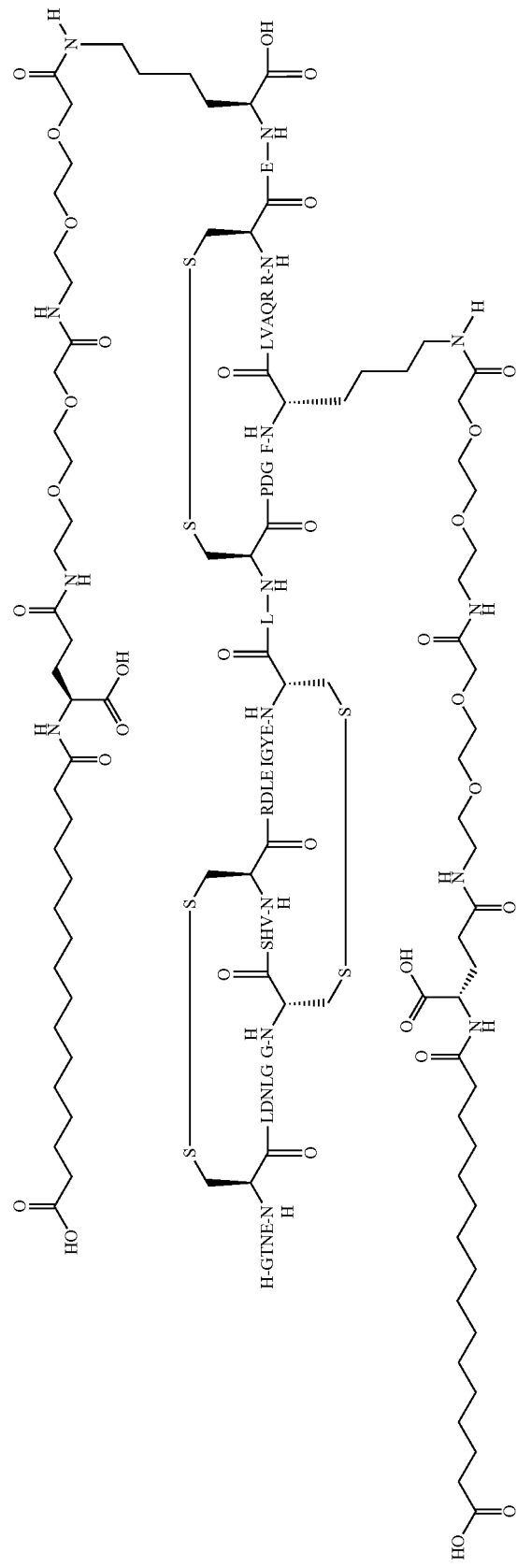

The peptide back-bone is SEQ ID NO: 72
Compound prepared by general method B
LCMS34: Found m/4=1974.6; Found m/5=1183.9; Calc mass=5915.7.

Example 153

N{Alpha}(N{Epsilon-324}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Glu321,Lys324]-LDL-R-(293-332)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys

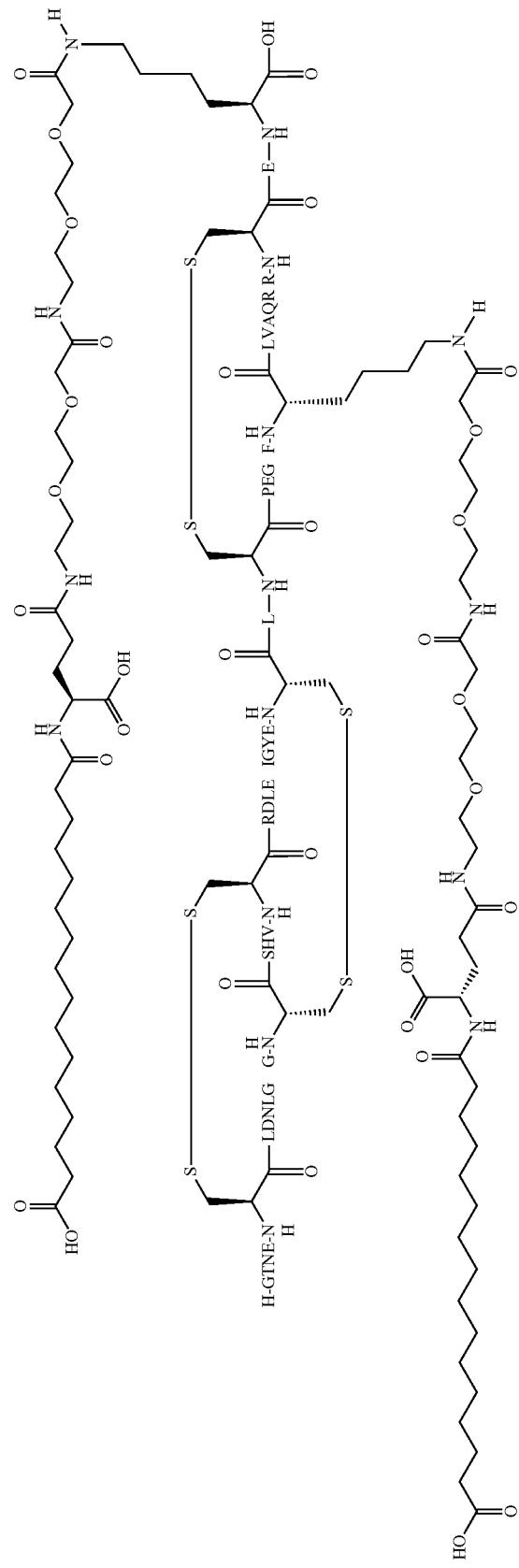

The peptide back-bone is SEQ ID NO: 105
Compound prepared by general method B
LCMS01: Found m/4=1483.3 Found m/5=1186.8 Calc mass=5929.8.

Example 154

N{Alpha}(N{Epsilon-328}-[2-[2-[2-[[2-[2-[2-[[(4S)-4-carboxy-4-(17-carboxyheptadecanoy-lamino)butanoyl]amino]ethoxy]ethoxy]acetyl]amino]ethoxy]ethoxy]acetyl]-[Leu301,Arg309,Glu312,Glu321,Lys328]-LDL-R-(293-332)-peptidyl)-N{Epsilon}[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]Lys

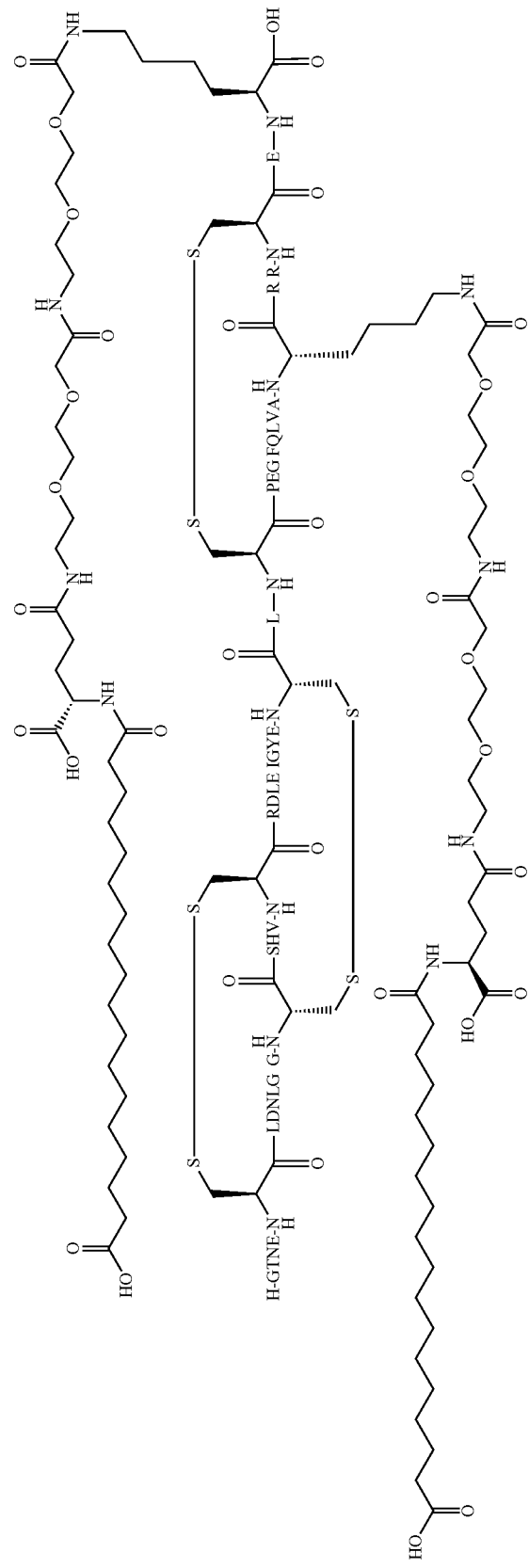

The peptide back-bone is SEQ ID NO: 104
Compound prepared by general method B
LCMS01: Found m/4=1497.3; Found m/5=1198.2; Calc mass=5985.9.

Example 155

N{Epsilon-313}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl],N{Epsilon-321}-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Leu301,Arg309,Glu312,Lys313,Lys321]-LDL-R-(293-332)-peptide

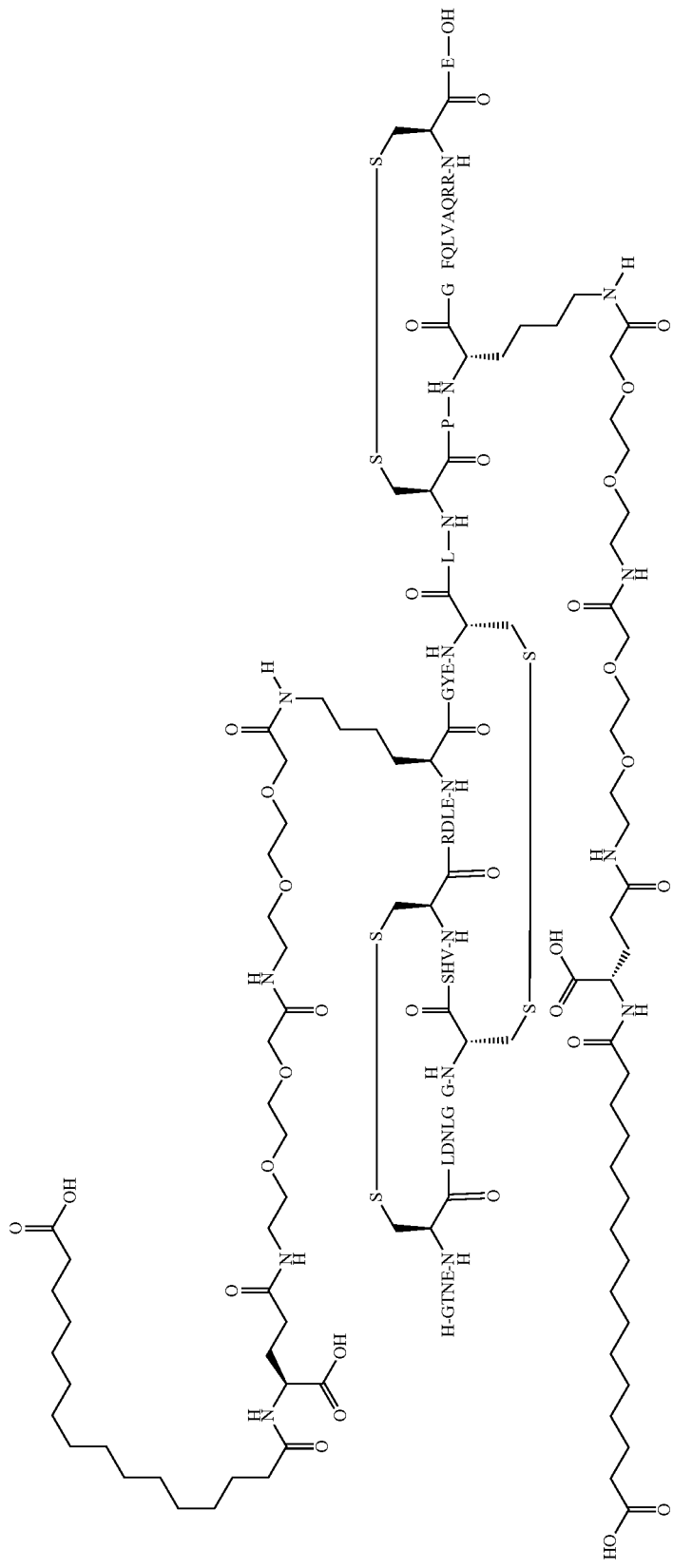

The peptide back-bone is SEQ ID NO: 73.
Compound prepared by general method B
LCMS01: Found m/4=1454.7; Found m/5=1164.0 Calc mass=5815.6.

Example 156

N{Alpha}(N{Epsilon-313}[2-[2-[2-[[2-[2-[2-[[(4S)-4-carboxy-4-[[4-[[11-(4-carboxyphenoxy)unde-canoylamino]methyl]cyclohexanecarbonyl]amino]butanoyl]amino]ethoxy]ethoxy]acetyl]amino]ethoxy]ethoxy]acetyl]-[Leu301,Arg309,Glu312,Lys313]-LDL-R-(293-332)-peptidyl)-N{Epsilon}[2-[2-[2-[[2-[2-[2-[[(4S)-4-carboxy-4-[[4-[[11-(4-carboxyphenoxy)undecanoylamino]methyl]cyclohexanecarbonyl]amino]butanoyl]amino]ethoxy]ethoxy]acetyl]amino]ethoxy]ethoxy]acetyl]Lys

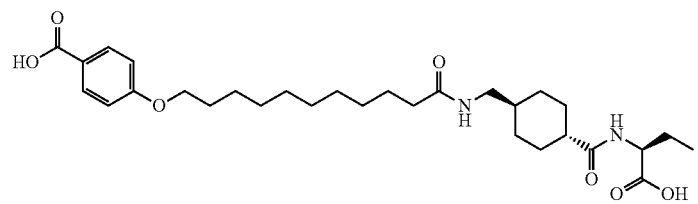

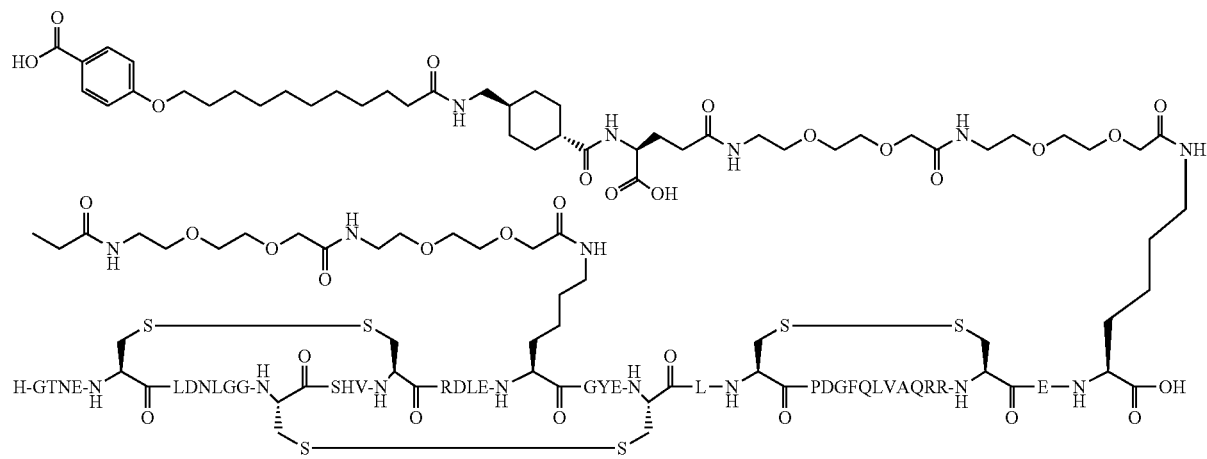

The peptide back-bone is SEQ ID NO: 32
Compound prepared by general method B
LCMS27: Found m/3=2094.6; Found m/4=1571.2; Calc mass=6281.1.

Example 157

N{Alpha}(N{Epsilon-313}-[2-[2-[2-[[2-[2-[2-[[(4S)-4-carboxy-4-[[4-[[11-(4-carboxyphenoxy)undecanoylamino]methyl]cyclohexanecarbonyl]amino]butanoyl]amino]ethoxy]ethoxy]acetyl]amino]ethoxy]ethoxy]acetyl]-[Leu301,Arg309,Glu312,Lys313,Glu321]-LDL-R-(293-332)-peptidyl)-N{Epsilon}[2-[2-[2-[[2-[2-[2-[[(4S)-4-carboxy-4-[[4-[[11-(4-carboxyphenoxy)undecanoylamino]methyl]cyclohexanecarbonyl]amino]butanoyl]amino]ethoxy]ethoxy]acetyl]amino]ethoxy]ethoxy]acetyl]Lys

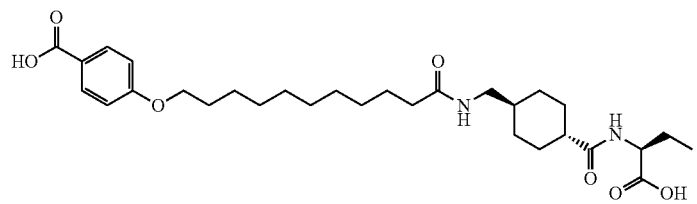

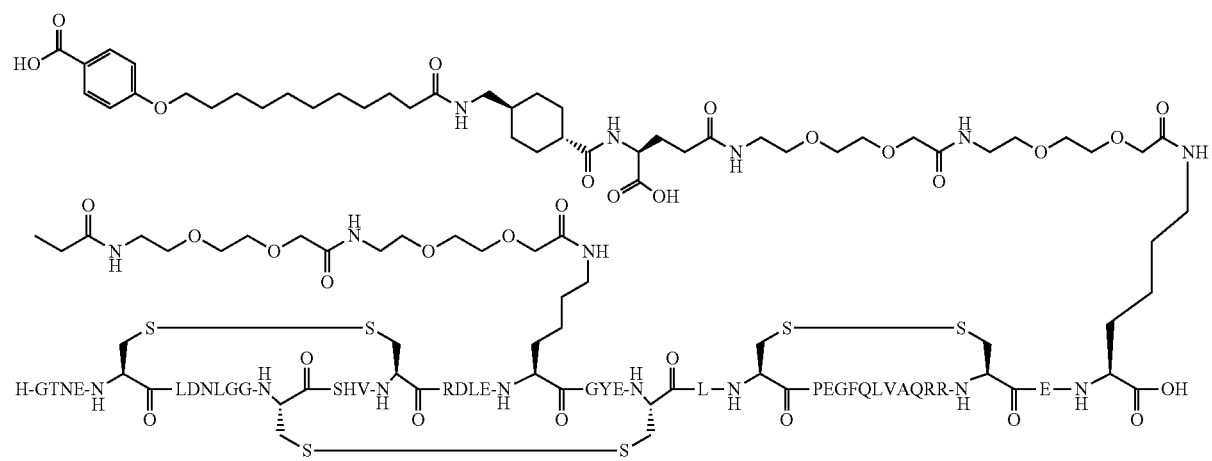

The peptide back-bone is SEQ ID NO: 98
Compound prepared by general method B
LCMS27: Found m/3=2099.3; Found m/4=1574.7; Calc mass=6295.1.

Example 158

N{Alpha}([Leu301,Arg309,Glu312,Glu321]-LDL-R-(293-332)-peptidyl)-N{Epsilon}[2-[2-[2-[[2-[2-[2-[[(4S)-4-carboxy-4-[[4-[(19-carboxynonade-canoylamino)methyl]cyclohexanecarbonyl]amino]butanoyl]amino]ethoxy]ethoxy]acetyl]amino]ethoxy]ethoxy]acetyl]Lys

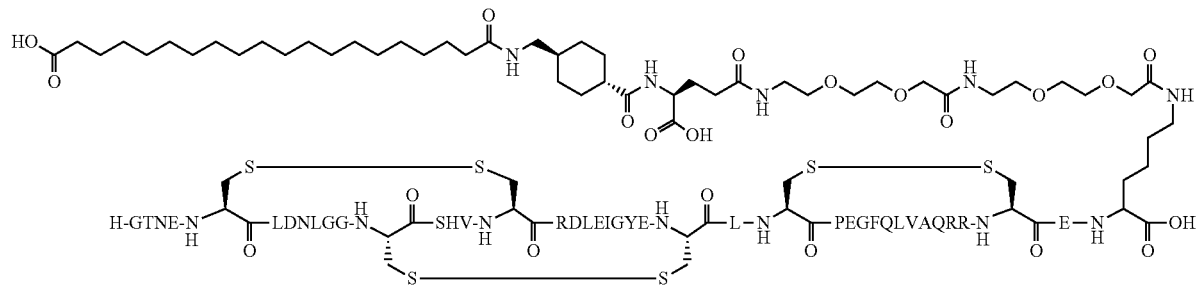

The peptide back-bone is SEQ ID NO: 19
Compound prepared by general method B
LCMS27: Found m/3=1813.2; Found m/4=1360.2; Found m/5=1088.3; Calc mass=5437.2.

Example 159

N{Alpha}([Leu301,Arg309,Glu312,Glu321]-LDL-R-(293-332)-peptidyl)-N{Epsilon}[2-[2-[2-[[2-[2-[2-[[(4S)-4-carboxy-4-[[4-[(17-carboxyheptade-canoylamino)methyl]cyclohexanecarbonyl]amino]butanoyl]amino]ethoxy]ethoxy]acetyl]amino]ethoxy]ethoxy]acetyl]Lys

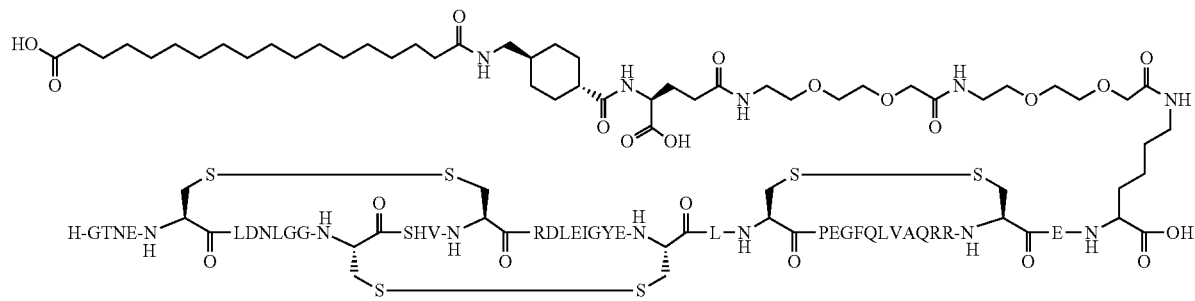

The peptide back-bone is SEQ ID NO: 19
Compound prepared by general method B
LCMS27: Found m/3=1803.9; Found m/4=1353.1; Found m/5=1082.7; Calc mass=5409.2.

TABLE 4

Summary table of Example compounds 1-159

| Example no. | Sequence modifications | Substituent | Attachment sites |
|---|---|---|---|
| 1 | 299A, 301L, 307I, 309R, 310K | HOOC—$(CH_2)_{16}$—CO-gGlu-2xADO-NH—$CH_2$—$(C_6H_4)$—$CH_2$— | N-terminal |
| 2 | 301L, 309R | HOOC—$(CH_2)_{16}$—CO-gGlu-2xADO-NH—$CH_2$—$(C_6H_4)$—$CH_2$— | N-terminal |
| 3 | 301L, 309R, 312E, 333K | HOOC—$(CH_2)_{16}$—CO-gGlu-2xADO | 333K |
| 4 | 301L, 309R | HOOC—$(CH_2)_{16}$—CO-gGlu-2xADO | 312K |
| 5 | 301L, 309R, 312E | HOOC—$(CH_2)_{16}$—CO-gGlu-2xADO-NH—$CH_2$—$(C_6H_4)$—$CH_2$— | N-terminal |
| 6 | 299K, 301L, 309R, 312E | HOOC—$(CH_2)_{16}$—CO-gGlu-2xADO | 299K |
| 7 | 301L, 309R, 312E, 330K | HOOC—$(CH_2)_{16}$—CO-gGlu-2xADO | 330K |
| 8 | 301L, 309R, 312E | HOS(O)2—(CH2)15—CO-gGlu-2xADO-NH—$CH_2$—$(C_6H_4)$—$CH_2$— | N-terminal |
| 9 | 301L, 309R, 312E, 330K | HOOC—$(CH_2)_{16}$—CO-gGlu-2xADO | N-terminal, 330K |
| 10 | 301L, 309R, 312E, 332K | HOOC—$(CH_2)_{16}$—CO-gGlu-2xADO | 332K |
| 11 | 293K, 301L, 309R, 312E | HOOC—$(CH_2)_{16}$—CO-gGlu-2xADO | 293K |
| 12 | 293K, 301L, 309R, 312E, 333K | HOOC—$(CH_2)_{16}$—CO-gGlu-2xADO | 293K, 333K |
| 13 | 293K, 301L, 309R, 312E, 333K | 4-HOOC—$(C_6H_4)$—O—$(CH_2)_{10}$—CO-gGlu-2xADO | 293K, 333K |
| 14 | 301L, 309R, 312E, 332K, 333K | 4-HOOC—$(C_6H_4)$—O—$(CH_2)_{10}$—CO-gGlu-2xADO | 332K, 333K |
| 15 | 301L, 309R, 312E, 330K, 333K | 4-HOOC—$(C_6H_4)$—O—$(CH_2)_{10}$—CO-gGlu-2xADO | 330K, 333K |
| 16 | 301L, 309R, 312E, 321K, 333K | 4-HOOC—$(C_6H_4)$—O—$(CH_2)_{10}$—CO-gGlu-2xADO | 321K, 333K |
| 17 | 301L, 309R, 333K | 4-HOOC—$(C_6H_4)$—O—$(CH_2)_{10}$—CO-gGlu-2xADO | 312K, 333K |
| 18 | 301L, 309R, 312E, 321E, 333K | HOOC—$(CH_2)_{16}$—CO-gGlu-2xADO | 333K |
| 19 | 301L, 309R, 312E | HOOC—$(CH_2)_{16}$—CO-gGlu-2xADO | N-terminal |
| 20 | 301L, 309R, 312E, 321K | HOOC—$(CH_2)_{16}$—CO-gGlu-2xADO | 321K |
| 21 | 301L, 309R, 312E, 324K | HOOC—$(CH_2)_{16}$—CO-gGlu-2xADO | 324K |
| 22 | 301L, 309R, 312O | HOOC—$(CH_2)_{16}$—CO-gGlu-2xADO | N-terminal |
| 23 | 301L, 309R, 312E, 321E, 332K | HOOC—$(CH_2)_{16}$—CO-gGlu-2xADO | 332K |
| 24 | 293K, 301L, 309R, 312E, 321E | HOOC—$(CH_2)_{16}$—CO-gGlu-2xADO | 293K |
| 25 | 293K, 301L, 309R, 312E | HOOC—$(CH_2)_{16}$—CO-gGlu-2xADO | N-terminal, 293K |
| 26 | 300K, 301L, 309R, 312E | HOOC—$(CH_2)_{16}$—CO-gGlu-2xADO | 300K |
| 27 | 293K, 294K, 301L, 309R, 312E | 4-HOOC—$(C_6H_4)$—O—$(CH_2)_{10}$—CO-gGlu-2xADO | 293K, 294K |
| 28 | 293K, 301L, 309R | 4-HOOC—$(C_6H_4)$—O—$(CH_2)_{10}$—CO-gGlu-2xADO | 293K, 312K |
| 29 | 301L, 309K, 312E | HOOC—$(CH_2)_{16}$—CO-gGlu-2xADO | 309K |
| 30 | 301L, 309R, 312E, 318K | HOOC—$(CH_2)_{16}$—CO-gGlu-2xADO | 318K |
| 31 | 301L, 309R, 312E, 313K, 333K | 4-HOOC—$(C_6H_4)$—O—$(CH_2)_{10}$—CO-gGlu-2xADO | 313K, 333K |
| 32 | 301L, 309R, 312E, 326K | HOOC—$(CH_2)_{16}$—CO-gGlu-2xADO | 326K |
| 33 | 301L, 309R, 312E, 325K | HOOC—$(CH_2)_{16}$—CO-gGlu-2xADO | 325K |
| 34 | 301L, 309R, 312E, 323K | HOOC—$(CH_2)_{16}$—CO-gGlu-2xADO | 323K |
| 35 | 301L, 309R, 312E, 322K | HOOC—$(CH_2)_{16}$—CO-gGlu-2xADO | 322K |
| 36 | 301L, 309R, 312E, 320K | HOOC—$(CH_2)_{16}$—CO-gGlu-2xADO | 320K |

TABLE 4-continued

Summary table of Example compounds 1-159

| Example no. | Sequence modifications | Substituent | Attachment sites |
|---|---|---|---|
| 37 | 301L, 309R, 312E, 329K | HOOC—(CH$_2$)$_{16}$—CO-gGlu-2xADO | 329K |
| 38 | 301L, 309R, 312E, 313K | HOOC—(CH$_2$)$_{16}$—CO-gGlu-2xADO | 313K |
| 39 | 301L, 309R, 312E, 328K | HOOC—(CH$_2$)$_{16}$—CO-gGlu-2xADO | 328K |
| 40 | 301L, 309R, 312E, 316K | HOOC—(CH$_2$)$_{16}$—CO-gGlu-2xADO | 316K |
| 41 | 301L, 309R, 312E, 315K | HOOC—(CH$_2$)$_{16}$—CO-gGlu-2xADO | 315K |
| 42 | 300H, 301L, 309R, 312R, 333K | HOOC—(CH$_2$)$_{16}$—CO-gGlu-2xADO | 333K |
| 43 | 301L, 309R, 312E, 314K | HOOC—(CH$_2$)$_{16}$—CO-gGlu-2xADO | 314K |
| 44 | 301L, 309R, 311K, 312E | HOOC—(CH$_2$)$_{16}$—CO-gGlu-2xADO | 311K |
| 45 | 301L, 307K, 309R, 312E | HOOC—(CH$_2$)$_{16}$—CO-gGlu-2xADO | 307K |
| 46 | 301L, 309S, 312R, 333K | HOOC—(CH$_2$)$_{16}$—CO-gGlu-2xADO | 333K |
| 47 | 301L, 309S, 312E, 333K | HOOC—(CH$_2$)$_{16}$—CO-gGlu-2xADO | 333K |
| 48 | 299A, 301L, 307I, 309R, 310K | | |
| 49 | 301L, 309R | | |
| 50 | 301L, 309R, 312E | | |
| 51 | 301L, 306Y, 309S, 312E | HOOC—(CH$_2$)$_{16}$—CO-gGlu-2xADO | N-terminal |
| 52 | 293N, 301L, 309S, 312E | HOOC—(CH$_2$)$_{16}$—CO-gGlu-2xADO | N-terminal |
| 53 | 301L, 306K, 309R, 312E | HOOC—(CH$_2$)$_{16}$—CO-gGlu-2xADO | 306K |
| 54 | 301L, 305K, 309R, 312E | HOOC—(CH$_2$)$_{16}$—CO-gGlu-2xADO | 305K |
| 55 | 301L, 303K, 309R, 312E | HOOC—(CH$_2$)$_{16}$—CO-gGlu-2xADO | 303K |
| 56 | 301L, 302K, 309R, 312E | HOOC—(CH$_2$)$_{16}$—CO-gGlu-2xADO | 302K |
| 57 | 293N, 300H, 301L, 309R, 312R, 333K | HOOC—(CH$_2$)$_{16}$—CO-gGlu-2xADO | 333K |
| 58 | 301K, 309R, 312E | HOOC—(CH$_2$)$_{16}$—CO-gGlu-2xADO | 301K |
| 59 | 298K, 301L, 309R, 312E | HOOC—(CH$_2$)$_{16}$—CO-gGlu-2xADO | 298K |
| 60 | 293N, 301L, 309R, 312R, 333K | HOOC—(CH$_2$)$_{16}$—CO-gGlu-2xADO | 333K |
| 61 | 301L, 307I, 332K | HOOC—(CH$_2$)$_{16}$—CO-gGlu-2xADO | 332K |
| 62 | 301L, 306Y, 312E, 332K | HOOC—(CH$_2$)$_{16}$—CO-gGlu-2xADO | 332K |
| 63 | 301L, 307I, 312E, 332K | HOOC—(CH$_2$)$_{16}$—CO-gGlu-2xADO | 332K |
| 64 | 300H, 301L, 309R | HOOC—(CH$_2$)$_{16}$—CO-gGlu-2xADO-NH—CH$_2$—(C$_6$H$_4$)—CH$_2$— | N-terminal |
| 65 | 300P, 301L, 307I, 309R, 312E | HOOC—(CH$_2$)$_{16}$—CO-gGlu-2xADO | N-terminal |
| 66 | 293N, 301L, 307I, 309R, 312D, 333K | HOOC—(CH$_2$)$_{16}$—CO-gGlu-2xADO | 333K |
| 67 | 293N, 301L, 309R, 312D, 333K | HOOC—(CH$_2$)$_{16}$—CO-gGlu-2xADO | 333K |
| 68 | 301L, 309R, 312E | Tetrazolyl-(CH$_2$)$_{15}$—CO—NH—SO$_2$—(CH$_2$)$_3$—CO-ADO-ADO-NH—CH$_2$—(C$_6$N)—CH$_2$— | N-terminal |
| 69 | 301L, 309R, 312E, 328K, 329H | HOOC—(CH$_2$)$_{16}$—CO-gGlu-2xADO | 328K |
| 70 | 295D, 301L, 309R, 312E, 332K | HOOC—(CH$_2$)$_{16}$—CO-gGlu-2xADO | 332K |
| 71 | 300H, 301L, 309R | HOOC—(CH$_2$)$_{16}$—CO-gGlu-2xADO | 312K |
| 72 | 300H, 301L, 307I, 309R, 312E | HOOC—(CH$_2$)$_{16}$—CO-gGlu-2xADO | N-terminal |
| 73 | 296K, 301L, 309R, 312E | HOOC—(CH$_2$)$_{16}$—CO-gGlu-2xADO | 296K |
| 74 | 294K, 301L, 309R, 312E | HOOC—(CH$_2$)$_{16}$—CO-gGlu-2xADO | 294K |
| 75 | 292K, 301L, 309R, 312E | HOOC—(CH$_2$)$_{16}$—CO-gGlu-2xADO | 292K |
| 76 | des293, 294G, 301L, 309R, 312E, 328K | HOOC—(CH$_2$)$_{16}$—CO-gGlu-2xADO | 328K |

TABLE 4-continued

Summary table of Example compounds 1-159

| Example no. | Sequence modifications | Substituent | Attachment sites |
|---|---|---|---|
| 77 | 301L, 306D, 309R, 312E, 324G, 333K | HOOC—(CH$_2$)$_{16}$—CO-gGlu-2xADO | 333K |
| 78 | 301L, 306D, 309R, 312E, 333K | 4-HOOC—(C$_6$H$_4$)—O—(CH$_2$)$_{10}$—CO-gGlu-3xADO and 4-HOOC—(C$_6$H$_4$)—O—(CH$_2$)$_{10}$—CO-gGlu-2xADO | N-terminal, 333K |
| 79 | 301L, 309R, 312E, 321K, 333K | 4-HOOC—(C$_6$H$_4$)—O—(CH$_2$)$_9$—CO-gGlu-2xADO | 321K, 333K |
| 80 | 301L, 309R, 312E, 333K | HOOC—(CH$_2$)$_{14}$—CO-gGlu-2xADO | 333K |
| 81 | 301L, 309R, 312E, 333K | HOOC—(CH$_2$)$_{18}$—CO-gGlu-2xADO | 333K |
| 82 | 301L, 309R, 312E, 333K | HOOC—(CH$_2$)$_{16}$—CO-gGlu | 333K |
| 83 | 301L, 309R, 312E, 321K, 333K | HOOC—(CH$_2$)$_{12}$—CO-gGlu-2xADO | 321K, 333K |
| 84 | 301L, 309R, 312E, 321K, 333K | HOOC—(CH$_2$)$_{14}$—CO-gGlu-2xADO | 321K, 333K |
| 85 | 300H, 301L, 309R, 312E, 313K, 333K | 4-HOOC—(C$_6$H$_4$)—O—(CH$_2$)$_9$—CO-gGlu-2xADO | 313K, 333K |
| 86 | 301L, 309R, 312E, 313K, 328K | 4-HOOC—(C$_6$H$_4$)—O—(CH$_2$)$_{10}$—CO-gGlu-2xADO | 313K, 328K |
| 87 | 301L, 309R, 312E, 313K, 324K | 4-HOOC—(C$_6$H$_4$)—O—(CH$_2$)$_{10}$—CO-gGlu-2xADO | 313K, 324K |
| 88 | 301L, 309R, 312E, 313K | 4-HOOC—(C$_6$H$_4$)—O—(CH$_2$)$_{10}$—CO-gGlu-2xADO | N-terminal, 313K |
| 89 | 301L, 309R, 312E, 324K, 333K | 4-HOOC—(C$_6$H$_4$)—O—(CH$_2$)$_{10}$—CO-gGlu-2xADO | 324K, 333K |
| 90 | 301L, 309R, 312E, 313K, 321K | 4-HOOC—(C$_6$H$_4$)—O—(CH$_2$)$_{10}$—CO-gGlu-2xADO | 313K, 321K |
| 91 | des293, 300H, 301L, 309R, 312E, 313K, 333K | 4-HOOC—(C$_6$H$_4$)—O—(CH$_2$)$_9$—CO-gGlu-2xADO | 313K, 333K |
| 92 | 300H, 301L, 309R, 312E, 313K, 333K | 4-HOOC—(C$_6$H$_4$)—O—(CH$_2$)$_{10}$—CO-gGlu-2xADO | 313K, 333K |
| 93 | 292A, 301L, 309R, 312E, 313K | 4-HOOC—(C$_6$H$_4$)—O—(CH$_2$)$_{10}$—CO-gGlu-2xADO | N-terminal, 313K |
| 94 | des293, 301L, 309R, 312E, 313K | 4-HOOC—(C$_6$H$_4$)—O—(CH$_2$)$_{10}$—CO-gGlu-2xADO | N-terminal, 313K |
| 95 | des293, 301L, 309R, 312E, 313K | HOOC—(CH$_2$)$_{16}$—CO-gGlu-2xADO | 313K |
| 96 | 301L, 309R, 312E, 313K, 332K | 4-HOOC—(C$_6$H$_4$)—O—(CH$_2$)$_{10}$—CO-gGlu-2xADO | 313K, 332K |
| 97 | 301L, 309R, 312E, 328K, 333K | 4-HOOC—(C$_6$H$_4$)—O—(CH$_2$)$_{10}$—CO-gGlu-2xADO | 328K, 333K |
| 98 | 301L, 309R, 312E, 313K, 333K | 4-HOOC—(C$_6$H$_4$)—O—(CH$_2$)$_{10}$—CO-gGlu | 313K, 333K |
| 99 | 301L, 309R, 312E, 313K, 333K | 4-HOOC—(C$_6$H$_4$)—O—(CH$_2$)$_{10}$—CO-2xgGlu | 313K, 333K |
| 100 | 301L, 309R, 312E, 313K, 333K | 4-HOOC—(C$_6$H$_4$)—O—(CH$_2$)$_{10}$—CO-gGlu-3xGly | 313K, 333K |
| 101 | 301L, 309R, 312E, 313K, 333K | 4-HOOC—(C$_6$H$_4$)—O—(CH$_2$)$_{10}$—CO-2xgGlu-2xADO | 313K, 333K |
| 102 | 301L, 309R, 312E, 313K, 333K | 3-HOOC—(C$_6$H$_4$)—O—(CH$_2$)$_9$—CO-gGlu-2xADO | 313K, 333K |
| 103 | 299A, 301L, 307I, 309R | | |
| 104 | 301L, 309R, 310K | | |
| 105 | 301L | | |
| 106 | 300H, 301L, 309R, 312E, 333K | HOOC—(CH$_2$)$_{16}$—CO-gGlu-2xADO | 333K |
| 107 | 301L, 309R, 312E, 333K | 4-HOOC—(C$_6$H$_4$)—O—(CH$_2$)$_{10}$—CO-gGlu-2xADO | N-terminal, 333K |
| 108 | des293-294, 300H, 301L, 309R, 312E, 313K, 333K | 4-HOOC—(C$_6$H$_4$)—O—(CH$_2$)$_9$—CO-gGlu-2xADO | 313K, 333K |
| 109 | 300H, 301L, 309R, 312E, 313K, 333K | 3-HO-Isoxazole-(CH$_2$)$_{12}$—CO-gGlu-2xADO | 313K, 333K |
| 110 | 301L, 309R, 312E, 313K, 333K | 3-HO-Isoxazole-(CH$_2$)$_{12}$—CO-gGlu-2xADO | 313K, 333K |
| 111 | 301L, 309K, 312E, 333K | 4-HOOC—(C$_6$H$_4$)—O—(CH$_2$)$_{10}$—CO-gGlu-2xADO | 309K, 333K |
| 112 | 301L, 306Y, 312E, 324K, 333K | 4-HOOC—(C$_6$H$_4$)—O—(CH$_2$)$_{10}$—CO-gGlu-2xADO | 324K, 333K |

TABLE 4-continued

Summary table of Example compounds 1-159

| Example no. | Sequence modifications | Substituent | Attachment sites |
|---|---|---|---|
| 113 | 300H, 301L, 309R, 312E, 314K, 333K | 4-HOOC—($C_6H_4$)—O—($CH_2$)$_{10}$—CO-gGlu-2xADO | 314K, 333K |
| 114 | 294W, 301L, 309R, 312E, 333K | 4-HOOC—($C_6H_4$)—O—($CH_2$)$_{10}$—CO-gGlu-2xADO | N-terminal, 333K |
| 115 | 301L, 309K, 312E, 328K | 4-HOOC—($C_6H_4$)—O—($CH_2$)$_{10}$—CO-gGlu-2xADO | 309K, 328K |
| 116 | 301L, 309K, 312E, 313K | 4-HOOC—($C_6H_4$)—O—($CH_2$)$_{10}$—CO-gGlu-2xADO | 309K, 313K |
| 117 | des293, 301L, 309R, 312E, 333K | 4-HOOC—($C_6H_4$)—O—($CH_2$)$_{10}$—CO-gGlu-2xADO | N-terminal, 333K |
| 118 | 301L, 309R, 312E, 324K, 328K | 4-HOOC—($C_6H_4$)—O—($CH_2$)$_{10}$—CO-gGlu-2xADO | 324K, 328K |
| 119 | 292A, 301L, 309R, 312E, 333K | 4-HOOC—($C_6H_4$)—O—($CH_2$)$_{10}$—CO-gGlu-2xADO | N-terminal, 333K |
| 120 | 301L, 306Y, 309R, 312E, 313K, 333K | 4-HOOC—($C_6H_4$)—O—($CH_2$)$_{10}$—CO-gGlu-2xADO | 313K, 333K |
| 121 | 301L, 309R, 312E, 332K | 4-HOOC—($C_6H_4$)—O—($CH_2$)$_{10}$—CO-gGlu-2xADO | N-terminal, 332K |
| 122 | 301L, 309R, 312E, 328K | 4-HOOC—($C_6H_4$)—O—($CH_2$)$_{10}$—CO-gGlu-2xADO | N-terminal, 328K |
| 123 | 301L, 309R, 312E, 324K | 4-HOOC—($C_6H_4$)—O—($CH_2$)$_{10}$—CO-gGlu-2xADO | N-terminal, 324K |
| 124 | 301L, 309K, 312E, 332K | 4-HOOC—($C_6H_4$)—O—($CH_2$)$_{10}$—CO-gGlu-2xADO | 309K, 332K |
| 125 | 301L, 309K, 312E, 324K | 4-HOOC—($C_6H_4$)—O—($CH_2$)$_{10}$—CO-gGlu-2xADO | 309K, 324K |
| 126 | 301L, 309K, 312E | 4-HOOC—($C_6H_4$)—O—($CH_2$)$_{10}$—CO-gGlu-2xADO | N-terminal, 309K |
| 127 | 301L, 309R, 312E, 321K, 332K | 4-HOOC—($C_6H_4$)—O—($CH_2$)$_{10}$—CO-gGlu-2xADO | 321K, 332K |
| 128 | 301L, 309R, 312E, 313K, 333K | HOOC—($CH_2$)$_{14}$—CO-gGlu-2xADO | 313K, 333K |
| 129 | 301L, 309R, 312E, 313K, 333K | HOOC—($CH_2$)$_{14}$—CO-gGlu | 313K, 333K |
| 130 | 300H, 301L, 309R, 312E, 313K, 332K | 4-HOOC—($C_6H_4$)—O—($CH_2$)$_{10}$—CO-gGlu-2xADO | 313K, 332K |
| 131 | 301L, 309R, 312E, 313K, 333K | 4-HOOC—($C_6H_4$)—O—($CH_2$)$_{10}$—CO-gGlu-TtdSuc | 313K, 333K |
| 132 | 301L, 309R, 312E, 313K, 321E, 332K | 4-HOOC—($C_6H_4$)—O—($CH_2$)$_{10}$—CO-gGlu-TtdSuc | 313K, 332K |
| 133 | 301L, 309R, 312E, 313K, 321E, 333K | 4-HOOC—($C_6H_4$)—O—($CH_2$)$_{10}$—CO-gGlu-2xADO | 313K, 333K |
| 134 | 301L, 309R, 312E, 321E, 333K | HOOC—($CH_2$)$_{18}$—CO-gGlu-2xADO | 333K |
| 135 | 301L, 309R, 312E, 313K, 314K | 4-HOOC—($C_6H_4$)—O—($CH_2$)$_{10}$—CO-gGlu-2xADO | 313K, 314K |
| 136 | 301L, 309R, 313K | 4-HOOC—($C_6H_4$)—O—($CH_2$)$_{10}$—CO-gGlu-2xADO | 312K, 313K |
| 137 | 301L, 309R, 314K | 4-HOOC—($C_6H_4$)—O—($CH_2$)$_{10}$—CO-gGlu-2xADO | 312K, 314K |
| 138 | 301L, 309R, 311K, 312E, 313K | 4-HOOC—($C_6H_4$)—O—($CH_2$)$_{10}$—CO-gGlu-2xADO | 311K, 313K |
| 139 | 300H, 301L, 309R, 312E, 313K, 333K | 4-HOOC—($C_6H_4$)—O—($CH_2$)$_9$—CO | 313K, 333K |
| 140 | 301L, 309R, 312E, 313K, 333K | Tetrazolyl-($CH_2$)$_{12}$—CO-gGlu-2xADO | 313K, 333K |
| 141 | 301L, 309R, 312E, 313K, 333K | HOS(O)$_2$—($CH_2$)$_{13}$—CO-gGlu-2xADO | 313K, 333K |
| 142 | 301L, 309R, 312E, 313K, 333K | MeS(O)$_2$NH(CO)NH—($CH_2$)$_{12}$—CO-gGlu-2xADO | 313K, 333K |
| 143 | 301L, 309R, 312E, 313K, 321E, 333K | 4-HOOC—($C_6H_4$)—O—($CH_2$)$_{10}$—CO-gGlu | 313K, 333K |
| 144 | 301L, 309R, 312E, 313K, 321E, 333K | HOOC—($CH_2$)$_{14}$—CO-gGlu-2xADO | 313K, 333K |
| 145 | 301L, 309R, 312E, 313K, 333K | Tetrazolyl-($CH_2$)$_{15}$—CO-gGlu-2xADO | 313K, 333K |
| 146 | 301L, 309R, 312E, 313K, 321E, 333K | HOOC—($CH_2$)$_{14}$—CO-gGlu | 313K, 333K |
| 147 | 300H, 301L, 309R, 312E, 313K, 321E, 333K | 4-HOOC—($C_6H_4$)—O—($CH_2$)$_{10}$—CO-gGlu-2xADO | 313K, 333K |
| 148 | 301L, 309R, 312E, 313K, 333K | 4-HOOC—($C_6H_4$)—O—($CH_2$)$_{10}$—CO-gGlu-4xADO | 313K, 333K |

TABLE 4-continued

Summary table of Example compounds 1-159

| Example no. | Sequence modifications | Substituent | Attachment sites |
|---|---|---|---|
| 149 | des293, 300H, 301L, 309R, 312E, 313K, 333K | 4-HOOC—($C_6H_4$)—O—($CH_2$)$_{10}$—CO-gGlu-2xADO | 313K, 333K |
| 150 | 301L, 309R, 312E, 328K, 333K | HOOC—($CH_2$)$_{14}$—CO-gGlu-2xADO | 328K, 333K |
| 151 | 301L, 309R, 312E, 321E, 328K, 333K | HOOC—($CH_2$)$_{14}$—CO-gGlu-2xADO | 328K, 333K |
| 152 | 301L, 309R, 312E, 324K, 333K | HOOC—($CH_2$)$_{14}$—CO-gGlu-2xADO | 324K, 333K |
| 153 | 301L, 309R, 312E, 321E, 324K, 333K | HOOC—($CH_2$)$_{14}$—CO-gGlu-2xADO | 324K, 333K |
| 154 | 301L, 309R, 312E, 321E, 328K, 333K | HOOC—($CH_2$)$_{16}$—CO-gGlu-2xADO | 328K, 333K |
| 155 | 301L, 309R, 312E, 313K, 321K | HOOC—($CH_2$)$_{14}$—CO-gGlu-2xADO | 313K, 321K |
| 156 | 301L, 309R, 312E, 313K, 333K | 4-HOOC—($C_6H_4$)—O—($CH_2$)$_{10}$—CO-Trx-gGlu-2xADO | 313K, 333K |
| 157 | 301L, 309R, 312E, 313K, 321E, 333K | 4-HOOC—($C_6H_4$)—O—($CH_2$)$_{10}$—CO-Trx-gGlu-2xADO | 313K, 333K |
| 158 | 301L, 309R, 312E, 321E, 333K | HOOC—($CH_2$)$_{18}$—CO-Trx-gGlu-2xADO | 333K |
| 159 | 301L, 309R, 312E, 321E, 333K | HOOC—($CH_2$)$_{16}$—CO-Trx-gGlu-2xADO | 333K |

D. General Methods for Characterisation

D.1.1 PCSK9-LDL-R Binding Competitive (ELISA)

The aim of this assay is to measure the apparent binding affinity of EGF(A) compounds to PCSK9.

Due to their ability to inhibit the interaction of PCSK9 with LDL-R, compounds of the invention may also be referred to as PCSK9 inhibitors.

The day before the experiment, recombinant human Low Density Lipoprotein Receptor (rhLDL-R; NSO-derived; R & D systems #2148-LD) was dissolved at 1 µg/ml in 50 mM sodium carbonate, pH 9.6, and then 100 µl of the solution was added to each well of the assay plates (Maxisorp 96, NUNC #439454) and coated overnight at 4° C. On the day of the experiments, 8 point concentration curves of the EGF(A) compounds containing Biotinylated PCSK9 (0.5 ug/ml, BioSite/BPSBioscience cat #71304) were made in duplicate. EGF(A) compound and biotinylated PCSK9 mixtures were prepared an incubated for 1 hour at room temperature in assay buffer containing 25 mM Hepes, pH 7.2 (15630-056, 100 ml, 1M), 150 mM NaCl (Emsure 1.06404.1000) 1% HSA (Sigma A1887-25G) 0.05% Tween 20(Calbiochem 655205) 2 mM $CaCl_2$ (Sigma 223506-500G). The coated assay plates were then washed 4× in 200 µl assay buffer, and then 100 µl of the mixture of EGF(A) compounds and biotinylated PCSK9 was added to the plates and incubated 2 h at room temperature. The plates were washed 4× in 200 µl assay buffer and then incubated with Streptevadin-HRP (25 ng/ml; VWR #14-30-00) for 1 h at room temperature. The reaction is detected by adding 50 µl TMB-on (KEM-EN-TEC) and incubated 10 min in the dark. Then the reaction was stopped by adding 50 µl 4 M $H_3PO_4$ to the mixture, added by electronic multi pipetting. The plates were then read in a Spectramax at 450 and 620 nm within 1 h. The 620 nm read was used for background subtraction. IC50 values were calculated using Graphpad Prism, by nonlinear regression log(inhibitor) vs. response-variable slope (four parameters), and converted into Ki values using the following formula: Ki=IC50/(1+(Biotin-PCSK9)/(kd(Biotin-PCSK9))), where Kd of the biotin-PCSK9 is 1.096727714 µg/ml and [Biotin-PCSK9]=0.5 (µg/ml).

The results are shown in Table 5.1-5.5 below. Higher Ki values reflects lower apparent binding affinities to PCSK9 and vice versa. It is noticed that few of the compounds display a Ki which is substantially higher than the value measured for EGF66, such as a value above 500 nM, which indicate that the observed binding is not specific. Both the amino acid substitutions of the peptide and/or the one or more side-chain derivation may contribute to the loss of binding to LDL-R. In general a large number of the tested EGF(A) compounds displayed the ability to inhibit PCSK9 in binding to the hLDL-R.

PCSK9 Inhibitor Peptides

Initially a group of peptides include various amino acids substitutions were tested as described in section D1.1 and the results are shown in table 5.1.

TABLE 5.1

Apparent binding affinity (Ki) for PCSK9 peptides

| Ex. No. | Peptide variant | Ki (nM) |
|---|---|---|
| WT | — | — |
| 48 | 299A, 301L, 307I, 309R, 310K | 9.4 |
| 103 | 299A, 301L, 307I, 309R | 0.9 |
| 104 | 301L, 309R, 310K | 7.3 |
| 49 | 301L, 309R | 1.2 |
| 105 | 301L | 2.8 |
| 50 | 301L, 309R, 312E | 1.1 |

EGF66, identified as the most potent peptide variant in WO 2012177741, has 5 mutations. As seen above the inventors of the present case found that several of these mutations were not of great importance for the EC50 value determined in the assay described in D1.1. In particular the inventors found that compounds including the wild type residue Asp (D) in position 310 had higher potencies than compounds with 310K. It also appeared that the key amino substitution is 301 L preferably in combination with 309R. Finally 307I and 299A contributed only modestly to the affinity of the peptides.

N-Terminal Attachment of Substituent

In a subsequent experiment it was tested if attachment of a half-life protractor e.g. a substituent to the peptides influences the EC50 as determined by the assay described in D.1.1. As described herein a substituent may be attached by different technologies and the inventors initially decide to apply attachment via a nitrogen atom using the N-terminal amino acid of the peptides. This was as described in section B accomplished by acylation (in solution or on resin) and alkylation.

As seen in Table 5.2 all the tested compounds have an Ki value below 3.0 suggesting that the various protractor and linker elements are well tolerated. This was unusual as potency is usually negatively influence by attachment of a side chain as previously observer for peptides like GLP-1.

TABLE 5.2

Apparent Ki for N-terminal substituted PCSK9 peptides

| Ex. No. | Peptide variant | Attachment | Ki (nM) |
|---|---|---|---|
| 1 | 299A, 301L, 307I, 309R, 310K | Alkylation | nd |
| 2 | 301L, 309R | Alkylation | 1.7 |
| 64 | 300H, 301L, 309R | Alkylation | 0.7 |
| 5 | 301L, 309R, 312E | Alkylation | 1.3 |
| 8 | 301L, 309R, 312E | Alkylation | 1.2 |
| 19 | 301L, 309R, 312E | Acylation | 1.7 |
| 68 | 301L, 309R, 312E | Alkylation | 0.8 |
| 22 | 301L, 309R, 312Q | Acylation | 2.6 |
| 51 | 301L, 306Y, 309S, 312E | Acylation | 1.6 |
| 52 | 293N, 301L, 309S, 312E | Acylation | 2.1 |
| 65 | 300P, 301L, 307I, 309R, 312E | Acylation | >1000 |
| 72 | 300H, 301L, 307I, 309R, 312E | Acylation | 2.8 |

Lys Attachment of Substituent

In order to evaluate alternative positions for linkage of a substituent to a PCSK9 inhibitor peptide a series of compounds were prepared. A back-bone peptide including three amino acid substitutions; N301L, N309R and K312E were used except in Ex. 58, 29 and 4 in combination with a Lys substitution at various positions. All compounds tested included the 6 cysteine amino acids in positions 297, 304, 308, 317, 319, 331 which are usually engaged in cysteine disulfide bridges. The 312E was included to ensure site specific substitution except in example 4 where attachment to wt 312K is obtained. Extension of the peptide with one Lys is also tested (Ex. 75 and 3). The same substituent as described above including a C18 diacid protractor and a gGlu-2×Ado linker was used in all compounds and attached via acylation. The results are included in Table 5.3.

TABLE 5.3.

Apparent Ki for PCSK derivatives with a substituent attached via a Lys residue

| Ex. No. | Peptide variant | Attachment site | Ki (nM) |
|---|---|---|---|
| 75 | 292K, 301L, 309R, 312E | 292K | 1.5 |
| 11 | 293K, 301L, 309R, 312E | 293K | 2.4 |
| 74 | 294K, 301L, 309R, 312E | 294K | 1.4 |
| 73 | 296K, 301L, 309R, 312E | 296K | 8.9 |
| 59 | 298K, 301L, 309R, 312E | 298K | 610.7 |
| 6 | 299K, 301L, 309R, 312E | 299K | 3.3 |
| 26 | 300K, 301L, 309R, 312E | 300K | 1.3 |

TABLE 5.3.-continued

Apparent Ki for PCSK derivatives with a substituent attached via a Lys residue

| Ex. No. | Peptide variant | Attachment site | Ki (nM) |
|---|---|---|---|
| 58 | 301K, 309R, 312E | 301K | 1000.0 |
| 56 | 301L, 302K, 309R, 312E | 302K | 1032.0 |
| 55 | 301L, 303K, 309R, 312E | 303K | 1.7 |
| 54 | 301L, 305K, 309R, 312E | 305K | 2.1 |
| 53 | 301L, 306K, 309R, 312E | 306K | 1.7 |
| 45 | 301L, 307K, 309R, 312E | 307K | 1000.0 |
| 29 | 301L, 309K, 312E | 309K | 0.8 |
| 44 | 301L, 309R, 311K, 312E | 311K | 1.0 |
| 4 | 301L, 309R | 312K | 1.2 |
| 38 | 301L, 309R, 312E, 313K | 313K | 0.8 |
| 43 | 301L, 309R, 312E, 314K | 314K | 0.9 |
| 41 | 301L, 309R, 312E, 315K | 315K | 3.0 |
| 40 | 301L, 309R, 312E, 316K | 316K | 1.6 |
| 30 | 301L, 309R, 312E, 318K | 318K | 2.0 |
| 36 | 301L, 309R, 312E, 320K | 320K | 5.5 |
| 20 | 301L, 309R, 312E, 321K | 321K | 2.0 |
| 35 | 301L, 309R, 312E, 322K | 322K | 1.5 |
| 34 | 301L, 309R, 312E, 323K | 323K | 1.7 |
| 21 | 301L, 309R, 312E, 324K | 324K | 0.9 |
| 33 | 301L, 309R, 312E, 325K | 325K | 1.4 |
| 32 | 301L, 309R, 312E, 326K | 326K | 1.4 |
| 39 | 301L, 309R, 312E, 328K | 328K | 0.9 |
| 37 | 301L, 309R, 312E, 329K | 329K | 1.0 |
| 7 | 301L, 309R, 312E, 330K | 330K | 1.4 |
| 10 | 301L, 309R, 312E, 332K | 332K | 1.1 |
| 3 | 301L, 309R, 312E, 333K | 333K | 0.8 |

The analysis showed that the majority of the PCSK9 inhibitor peptide maintain functionality. The exceptions were Lys substitution and derivation in either of position 298, 301, 302 and 307 which gave rise to non-functional peptides. It was also observed that Lys introduction and substitution in position 296, 299, 315 and 320K reduced the apparent affinity.

The data thus also confirm the result from table 5.1 indicating that the amino acid substitution of Asn(N) 301 to Leu (L) is essential for the binding.

No data was observed for Lys introduction and substitution in position 295 and 310. As described above it was previously found that maintenance of Asp in 310 was preferred above the 310K substitution. As seen below it was also found that binding is abolished by introduction of Asp (D) in position 295 (Ex. 70).

In summary it was concluded that compounds which do not comprise a substituent attached in any of the positions 295, 298, 302, 307 and 310 or in any of the positions 295, 296, 298, 299, 302, 307, 310, 315 and 320 of the PCSK9 peptide are generally functional. It was further concluded that an amino acid substitution in any of the positions 295, 298, 302, and 310 is generally not attractive. As seen from table 5.1 and 5.2 the V307I mutation none the less seem to be acceptable or even attractive in combination with 301Leu.

It is further considered that peptides with amino acid substitution in one of the positions 295, 296, 298, 302, 310 are likely to have a lower functionality, while substitutions in 299, 315 and 320 only seems to lower functionality slightly. This on the other hand also suggests that a high degree of flexibility may exist for the remaining amino acid residues as Lys substitution and attachment of a sidechain will influence the peptides as much as most other amino acid substitutions.

PCSK9 Inhibitors with Two Substituents

A series of compound with two substituents were prepared. Double substitution may be obtained by acylation, alkylation or a combination at the N-terminal or at Lys (K) residues. Again the N-terminal may be amino acid 293G or a variant amino acid residue such as 292A, 293G, 293K and 294T (in cases where 293G is deleted). The compounds were prepared with different substituents, although the two substituents on the individual compounds are identical. The back-bone used in this study again included the N301L amino acid substitution in combination with N309R and various N-terminal and/or Lys substitutions as required to obtain the specific acylation/alkylation.

TABLE 5.4

Apparent Ki for double substituted PCSK9 inhibitors

| Example No. | Variant 301L, 309R, + | Attachment sites | Ki (nM) |
|---|---|---|---|
| 9 | 312E, 330K | N-terminal, 330K | 2.7 |
| 12 | 293K, 312E, 333K | 293K, 333K | 2.7 |
| 13 | 293K, 312E, 333K | 293K, 333K | 2.1 |
| 14 | 312E, 332K, 333K | 332K, 333K | 1.2 |
| 15 | 312E, 330K, 333K | 330K, 333K | 1.5 |
| 16 | 312E, 321K, 333K | 321K, 333K | 1.1 |
| 17 | 333K | 312K, 333K | 1.8 |
| 25 | 293K, 312E | N-terminal, 293K | 2.0 |
| 27 | 293K, 294K, 312E | 293K, 294K | 0.9 |
| 28 | 293K | 293K, 312K | 0.8 |
| 31 | 312E, 313K, 333K | 313K, 333K | 0.5 |
| 78 | 306D, 312E, 333K | N-terminal, 333K | 2.3 |
| 79 | 312E, 321K, 333K | 321K, 333K | 1.5 |
| 83 | 312E, 321K, 333K | 321K, 333K | 1.5 |
| 84 | 312E, 321K, 333K | 321K, 333K | 1.8 |
| 85 | 300H, 312E, 313K, 333K | 313K, 333K | 0.9 |
| 86 | 312E, 313K, 328K | 313K, 328K | 1.1 |
| 87 | 312E, 313K, 324K | 313K, 324K | 1.0 |
| 88 | 312E, 313K | N-terminal, 313K | 1.2 |
| 89 | 312E, 324K, 333K | 324K, 333K | 1.0 |
| 90 | 312E, 313K, 321K | 313K, 321K | 1.6 |
| 91 | des293, 300H, 312E, 313K, 333K | 313K, 333K | 0.9 |
| 92 | 300H, 312E, 313K, 333K | 313K, 333K | 1.0 |
| 93 | 292A, 312E, 313K | N-terminal (292A), 313K | 1.2 |
| 94 | des293, 312E, 313K | N-terminal (294T), 313K | 0.9 |
| 96 | 312E, 313K, 332K | 313K, 332K | 1.2 |
| 97 | 312E, 328K, 333K | 328K, 333K | 1.2 |
| 98 | 312E, 313K, 333K | 313K, 333K | 0.9 |
| 99 | 312E, 313K, 333K | 313K, 333K | 1.3 |
| 100 | 312E, 313K, 333K | 313K, 333K | 1.4 |
| 101 | 312E, 313K, 333K | 313K, 333K | 0.6 |
| 102 | 312E, 313K, 333K | 313K, 333K | 0.8 |
| 107 | 312E, 333K | N-terminal, 333K | 2.6 |
| 108 | des293-294, 300H, 312E, 313K, 333K | 313K, 333K | 3.8 |
| 109 | 300H, 312E, 313K, 333K | 313K, 333K | 1.0 |
| 110 | 312E, 313K, 333K | 313K, 333K | 1.7 |
| 113 | 300H, 312E, 314K, 333K | 314K, 333K | 1.6 |
| 114 | 294W, 312E, 333K | N-terminal, 333K | 3.1 |
| 117 | des293, 312E, 333K | N-terminal, 333K | 2.5 |
| 118 | 312E, 324K, 328K | 324K, 328K | 1.2 |
| 119 | 292A, 312E, 333K | N-terminal, 333K | 2.1 |
| 120 | 306Y, 312E, 313K, 333K | 313K, 333K | 1.6 |
| 121 | 312E, 332K | N-terminal, 332K | 2.1 |
| 122 | 312E, 328K | N-terminal, 328K | 2.2 |
| 123 | 312E, 324K | N-terminal, 324K | 2.0 |
| 127 | 312E, 321K, 332K | 321K, 332K | 2.4 |
| 128 | 312E, 313K, 333K | 313K, 333K | 1.0 |
| 129 | 312E, 313K, 333K | 313K, 333K | 2.6 |
| 130. | 300H, 312E, 313K, 332K | 313K, 332K | 1.8 |
| 131. | 312E, 313K, 333K | 313K, 333K | 2.6 |
| 132. | 312E, 313K, 321E, 332K | 313K, 332K | 1.9 |
| 133. | 301L, 309R, 312E, 313K, 321E, 333K | 313K, 333K | 1.6 |
| 134. | 312E, 321E, 333K | 333K | 1.9 |
| 135. | 312E, 313K, 314K | 313K, 314K | 3.6 |
| 136. | 313K | 312K, 313K | 2.8 |
| 137. | 314K | 312K, 314K | 4.7 |
| 138. | 311K, 312E, 313K | 311K, 313K | 2.5 |

TABLE 5.4-continued

Apparent Ki for double substituted PCSK9 inhibitors

| 139. | 300H, 312E, 313K, 333K | 313K, 333K | 3.3 |
|---|---|---|---|
| 140. | 312E, 313K, 333K | 313K, 333K | 1.7 |
| 141. | 312E, 313K, 333K | 313K, 333K | 2.2 |
| 142. | 312E, 313K, 333K | 313K, 333K | 1.7 |
| 143. | 312E, 313K, 321E, 333K | 313K, 333K | 1.9 |
| 144. | 312E, 313K, 321E, 333K | 313K, 333K | 2.09 |
| 145. | 312E, 313K, 333K | 313K, 333K | 2.6 |
| 146. | 312E, 313K, 321E, 333K | 313K, 333K | 3.0 |
| 147. | 300H, 312E, 313K, 321E, 333K | 313K, 333K | 1.5 |
| 148. | 312E, 313K, 333K | 313K, 333K | 2.5 |
| 149. | des293, 300H, 312E, 313K, 333K | 313K, 333K | 1.9 |
| 150. | 312E, 328K, 333K | 328K, 333K | 2.3 |
| 151. | 312E, 321E, 328K, 333K | 328K, 333K | 1.8 |
| 152. | 312E, 324K, 333K | 324K, 333K | 1.9 |
| 153. | 312E, 321E, 324K, 333K | 324K, 333K | 2.0 |
| 154. | 312E, 321E, 328K, 333K | 328K, 333K | 1.8 |
| 155. | 312E, 313K, 321K | 313K, 321K | 1.4 |
| 156. | 312E, 313K, 333K | 313K, 333K | 1.2 |
| 157. | 312E, 313K, 321E, 333K | 313K, 333K | 1.3 |

| Example No. | Variant 301L+ | Attachment sites | Ki (nM) |
|---|---|---|---|
| 111 | 309K, 312E, 333K | 309K, 333K | 1.6 |
| 112 | 306Y, 312E, 324K, 333K | 324K, 333K | 1.5 |
| 115 | 309K, 312E, 328K | 309K, 328K | 1.0 |
| 116 | 309K, 312E, 313K | 309K, 313K | 1.1 |
| 124 | 309K, 312E, 332K | 309K, 332K | 1.2 |
| 125 | 309K, 312E, 324K | 309K, 324K | 1.4 |
| 126 | 309K, 312E | N-terminal, 309K | 2.8 |

Again the inventors concluded that the substituents are very well tolerated in a variety of positions and combinations.

Further PCSK9 Inhibitor Derivatives

To explore further the role of various amino acid substitutions in the PCSK9 peptides further compounds were prepared and tested as shown in table 5.5. All compounds include one substituent which is attached via a Lys residue introduced by amino acid substitution or extension with 333K. The back-bone peptides all include the N301L amino acid substitution and optionally one or more of N309R and I312E. The substituents all includes a fatty diacid comprising 16-20 carbon atoms and a linker which is either gGlu alone or extended with Ado-Ado and/or a tranexamic acid (Trx) moiety.

TABLE 5.5

Apparent Ki for further PCSK9 derivatives.

| Example No. | Variant 301L, 309R, 312E+ | Attachment sites | Ki (nM) |
|---|---|---|---|
| 18 | 321E, 333K | 333K | 1.5 |
| 23 | 321E, 332K | 332K | 0.9 |
| 24 | 293K, 321E | 293K | 1.8 |
| 69 | 328K, 329H | 328K | 1.3 |
| 70 | 295D, 332K | 332K | 1325 |
| 76 | des293, 294G, 328K | 328K | 1.3 |
| 77 | 306D, 324G, 333K | 333K | 2.2 |
| 80 | 333K | 333K | 1.9 |
| 81 | 333K | 333K | 1.4 |
| 82 | 333K | 333K | 1.9 |
| 106 | 300H, 333K | 333K | 1.0 |
| 134 | 321E, 333K | 333K | 1.9 |
| 158 | 321E, 333K | 333K | 2.3 |
| 159 | 321E, 333K | 333K | 1.9 |

| Example No. | Variant 301L, 309R, + | Attachment site | Ki |
|---|---|---|---|
| 22 | 312Q | N-term | 2.6 |
| 42 | 300H, 312R, 333K | 333K | 0.7 |

TABLE 5.5-continued

Apparent Ki for further PCSK9 derivatives.

| | | | | |
|---|---|---|---|---|
| 57 | 293N, 300H, 312R, 333K | | 333K | 0.5 |
| 60 | 293N, 312R, 333K | | 333K | 1.0 |
| 66 | 293N, 307I, 312D, 333K | | 333K | 2.1 |
| 67 | 293N, 312D, 333K | | 333K | 2.0 |
| 71 | 300H | | 312K | 0.9 |

| Example No. | Variant 301L, 312E, + | Attachment site | Ki |
|---|---|---|---|
| 47 | 309S, 333K | 333K | 2.7 |
| 62 | 306Y, 332K | 332K | 0.6 |
| 63 | 307I, 332K | 332K | 1.4 |

| Example No. | Variant 301L, + | Attachment site | Ki |
|---|---|---|---|
| 46 | 309S, 312R, 333K | 333K | 1.3 |
| 61 | 307I, 332K | 332K | 0.7 |

The results in table 5.5 above shows that the internal wt lysine in position 312 can be substituted with Glu (E) as well as Gln (Q), Arg (R) or Asp (D). Based on this variation it is contemplated that a broad range of amino acid residues will be tolerated in position 312 without interfering with the inhibitory function of the peptide.

Several other amino acid substitutions were also proven to be well tolerated including G293N, T294G, D299A, N300H, H306Y, H306D, N309S, Q324G and R329H, while as mentioned above N295D and N300P are none attractive amino acid substitutions.

D.1.2 LDL Uptake Assay in HepG2 Cells

An alternative assay to determine the inhibitory potency of the PCSK9 peptides and derivatives thereof measuring uptake of LDL in HepG2 cells is described here below.

Assay Principle:

LDL uptake is primarily mediated by the endogenously expressed hLDLRs, and thus LDL uptake capacity is an indirect measure of LDLR expression. The hLDLRs can be down-regulated by incubation with exogenous PCSK9 in a dose dependent fashion. Thus PCSK9 incubation will decrease the ability of cells to take up LDL molecules. This down-regulation of LDL uptake can then be antagonized by the addition of compounds neutralizing or inhibiting the PCSK9/LDLR binding. Consequently PCSK9 inhibitors can be characterized based on their capacity to increase LDL uptake in the presence of PCSK9 and e.g. counter act the PCSK9 mediated hLDLR down-regulation.

The assay is performed using HepG2 cells (Sigma Aldrich ECACC: Acc no. 85011430) grown in 10% Lipoprotein deficient Foetal Calf Serum (Sigma Aldrich # S5394) and the capacity of the cells to take up BODIPY fluorescently labelled LDL particles (Life technologies Europe BV # L3483) is measured.

Assay Protocol:

The 96 well plates (Perkin Elmer, ViewPlate-96 Black #60005182) were coated with Poly-D-Lysin (10 mg/L, Sigma Aldrich # P6407 dissolved in PBS Gibco #14190-094) for 1 hour at 37° C. in incubator. Then the plates were washed 2× in 100 µl PBS (Gibco #14190-094). Test compositions for 8 point concentration curves of the EGF(A) compounds were prepared all containing PCSK9 (10 ug/ml) diluted in Assay medium (DMEM (Gibco #31966-021), 10% Lipoprotein deficient Foetal Calf Serum (Sigma Aldrich # S5394) and 1% Pen Strep (Cambrex # DE17-602E)), and added on to the plates in a volume of 50 ul/well.

After 30-60 minutes 50.000 HepG2 cells (Sigma-Aldrich: ECACC: Atcc no. 85011430 lot: 136023), diluted in Assay medium were added in a volume of 50 µl/well, and the plates were incubated 20 hours (at 37° C., 5% CO2) in CO2 permeable plastic bags (Antalis Team, LDPE bag 120/35× 300×0,025 mm #281604). Hereafter, the plates were emptied and immediately hereafter 50 µl FL-LDL (Life technologies Europe BV # L3483) in a concentration of 10 µg/ml in Assay Medium was added to each well, and the plates were incubated for 2 hours (at 37° C., 5% CO2) in CO2 permeable plastic bag using the black cover on the lid to protect from light. The plates were emptied and washed 2 times with 100 µl of PBS (Gibco #14190-094). Then 100 µl of PBS (Gibco #14190-094) was added and within 15 min hereafter, the plates were read (bottom read) using the following filters Ex (515 nm)/Em (520 nm) on a Specktra-Max M4 (Molecular Probes, Invitrogen Detection Technologies).

Finally, EC50 values were calculated using GraphPad Prism, nonlinear regression curve fit, sigmoidal dose-response (variable slope).

The results are shown in Table 6 below. Lower EC50 values reflects higher capacity to reverse the PCSK9 mediated down-regulation of LDL uptake, and inversely a high EC50 value is indicative for a compound with low capacity to inhibit the PCSK9 mediated down-regulation of LDL uptake.

As can be seen most compounds display an EC50 in the LDL uptake assay of 100-500 nM which is indicative of compounds with a high capacity to reverse the PCSK9 mediated down-regulation of LDL uptake.

TABLE 6

LDL uptake data in HepG2 cells (EC$_{50}$)

| Example No. | LDL uptake EC$_{50}$ (nM) |
|---|---|
| 1. | ND |
| 2. | 255 |
| 3. | 168 |
| 4. | 302 |
| 5. | 220 |
| 6. | 413 |
| 7. | 304 |
| 8. | 130 |
| 9. | ND |
| 10. | 199 |
| 11. | 401 |
| 12. | ND |
| 13. | 280 |
| 14. | 161 |
| 15. | 211 |
| 16. | 144 |
| 17. | 199 |
| 18. | 172 |
| 19. | 206 |
| 20. | 198 |
| 21. | 174 |
| 22. | 357 |
| 23. | 143 |
| 24. | 160 |
| 25. | ND |
| 26. | 358 |
| 27. | ND |
| 28. | ND |
| 29. | 163 |
| 30. | 182 |
| 31. | 170 |
| 32. | 224 |

TABLE 6-continued

LDL uptake data in HepG2 cells (EC$_{50}$)

| Example No. | LDL uptake EC$_{50}$ (nM) |
|---|---|
| 33. | 245 |
| 34. | 232 |
| 35. | 252 |
| 36. | ND |
| 37. | 188 |
| 38. | 149 |
| 39. | 156 |
| 40. | 231 |
| 41. | ND |
| 42. | 324 |
| 43. | 499 |
| 44. | 237 |
| 45. | ND |
| 46. | ND |
| 47. | 1102 |
| 48. | 1278 |
| 49. | 398 |
| 50. | 164 |
| 51. | ND |
| 52. | ND |
| 53. | ND |
| 54. | 526 |
| 55. | ND |
| 56. | ND |
| 57. | 438 |
| 58. | ND |
| 59. | ND |
| 60. | 261 |
| 61. | 347 |
| 62. | 411 |
| 63. | 197 |
| 64. | 590 |
| 65. | 10000 |
| 66. | 248 |
| 67. | 384 |
| 68. | 124 |
| 69. | 311 |
| 70. | ND |
| 71. | 217 |
| 72. | 222 |
| 73. | ND |
| 74. | 123 |
| 75. | 239 |
| 76. | 272 |
| 77. | 2044 |
| 78. | 546 |
| 79. | ND |
| 80. | 248 |
| 81. | 617 |
| 82. | 203 |
| 83. | 165 |
| 84. | 337 |
| 85. | 157 |
| 86. | 248 |
| 87. | 185 |
| 88. | 298 |
| 89. | 139 |
| 90. | 380 |
| 91. | 114 |
| 92. | 147 |
| 93. | 267 |
| 94. | 375 |
| 95. | 257 |
| 96. | 261 |
| 97. | 138 |
| 98. | 203 |
| 99. | 167 |
| 100. | 174 |
| 101. | 129 |
| 102. | 112 |
| 103. | ND |
| 104. | ND |
| 105. | ND |
| 106. | 195 |
| 107. | 486 |
| 108. | 2555 |
| 109. | 572 |
| 110. | 465 |
| 111. | 316 |
| 112. | 539 |
| 113. | 1383 |
| 114. | 739 |
| 115. | 247 |
| 116. | 330 |
| 117. | 316 |
| 118. | 191 |
| 119. | 327 |
| 120. | 300 |
| 121. | 201 |
| 122. | 241 |
| 123. | 351 |
| 124. | 264 |
| 125. | 334 |
| 126. | 489 |
| 127. | 245 |
| 128. | 351 |
| 129. | 892 |
| 130. | 259 |
| 131. | 218 |
| 132. | 195 |
| 133. | 220 |
| 134. | 180 |
| 135. | 1505 |
| 136. | 455 |
| 137. | 2070 |
| 138. | 480 |
| 139. | 546 |
| 140. | 226 |
| 141. | 210 |
| 142. | 126 |
| 143. | 299 |
| 144. | 484 |
| 145. | 329 |
| 146. | 718 |
| 147. | 246 |
| 148. | 204 |
| 149. | 233 |
| 150. | ND |
| 151. | ND |
| 152. | ND |
| 153. | ND |
| 154. | 148 |
| 155. | 391 |
| 156. | 167 |
| 157. | ND |
| 158. | 303 |
| 159. | 178 |

D.2. PK in Mice

The aim of this study was to measure the PK profile of PCSK9 inhibitors as identified above.

Method:

Female C57bl/J mice from Taconic (Ry, Denmark) were used.

Dosing of Compound: Compounds were dosed either subcutaneously (s.c., 500 nmol/kg) or intravenously (i.v., 250 nmol/kg) in a volume of 5 µL per gram body weight.

Blood Sampling: Blood was sparse sampled at 2 min, 15 min, 30 min, 60 min, 2 hours, 4 hours, 6 hours, 8 hours, 18 hours, 24 hours, 30 hours and 48 hours. Blood (200 µL) was taken from the sublingual vein and transferred to EDTA-coated tubes (Microvette® VetMed 200 K3E, Sarstedt nr 09.1293.100). Plasma was isolated and used for quantification of anti-PCSK9 peptides.

Quantification: Plasma samples were used for quantification of PCSK9 inhibitors using LC-MS.

Sampling and Analysis:

Plasma was pipetted into Micronic tubes on dry ice, and kept at −20° C. until analysed for plasma concentration of the respective PCSK9 inhibitors using LC-MS. The plasma samples (including standard curve and QC samples used for quantitation of unknowns and prepared from blank plasma spiked with PCSK9 inhibitors at a concentration range of 0.5-1000 nM) were protein precipitated using three volumes of 100% methanol or acetonitrile with 1% formic acid (depending on anti-PCSK9 peptide) and centrifuged (16000×g, 4° C., 20 min). The supernatants were injected into the chromatographic system (TurboFlow Transcend 1250 & 10 valve VIM, Thermo Fisher Scientific) which consisted of an initial Turboflow Cyclone purification column 0.5×50 mm (Thermo Fischer Scientific) and an eluting Aeris peptide 3.6 μm XB-C18 column 2.1×50 mm (Phenomenex) kept at 60° C. The anti-PCSK9 peptide was eluted using a chromatographic gradient with mobile phases consisting of mixtures of water and acetonitrile with 0.1% or 1% formic acid (depending on EGF(A) analogue or derivative). The anti-PCSK9 peptide was detected and quantified after on-line infusion of the LC flow to the LTQ OrbiTrap or the Q Exactive mass spectrometer (Thermo Fischer Scientific) equipped with an electrospray interface operated in positive mode, ESI+.

Calculation of PK Properties:

Plasma concentration-time profiles were analysed by a non-compartmental pharmacokinetics analysis using the software Phoenix WinNonlin 6.4. Calculations for both the I.V. and S.C. data were performed using Linear Trapezoidal Linear Interpolation, with the weighting 1/Y^Y. The bioavailability was calculated dividing AUC/Dose for the S.C. profile with the AUC/Dose for the I.V. profile.

Results:

The results are shown in Table 7. In Table 7, Tmax indicates the time to reach the maximum plasma concentration of the tested EGF(A) analogue or derivative. T ½ is the half-life of the EGF(A) analogue or derivative. MRT is mean residence time. F (s.c.) is the bio-availability of the EGF(A) analogue or derivative after subcutaneous injection. Higher T ½ values reflect longer half-life of the tested compound.

The results show that PCSK9 inhibitors of the invention, in particular LDL-R(293-332) analogues substituted with a fatty acid substituent show prolonged half-lifes.

TABLE 7

Pharmacokinetic properties of LDL-R(293-332) analogues and derivatives in mice

| | Substituent | $T_{max}$ (hrs) | i.v. T½ (hrs) | s.c. T½ (hrs) | MRT (hrs) | F (s.c.) (%) |
|---|---|---|---|---|---|---|
| Example 1 | Yes (N-term) | 2 | 16 | 12 | 15 | 99 |
| Example 48 | No | 0.3 | 0.2 | 0.4 | 0.2 | 76 |
| Example 2 | Yes (N-term) | 2 | 14 | 14 | 19 | 100 |
| Example 3 | Yes (via 333K) | 4 | 14 | 14 | 19 | 87 |
| Example 5 | Yes (N-term) | 4 | 13 | 17 | 17 | 94 |
| Example 6 | Yes (via 299K) | 6 | 11 | 11 | 16 | 100 |
| Example 13 | Yes (via 293K and 333K) | 2 | 6 | 7.5 | 11 | 96 |
| Example 19 | Yes (N-term) | 2 | 13 | 14 | 18 | 100 |
| Example 4 | Yes (via 312K) | 8 | 14.3 | 12.8 | 20.3 | 54 |

D.3. hPCSK9 Challenge Model

The aim of this study was to show the change in the LDL receptor expression level in mouse liver in response to inhibiting the action of intravenously injected hPCSK9 with an anti-PCSK9 peptide.

Method

Healthy male BalBC or NMRI mice (Charles River, Germany) are injected with an anti-PCSK9 peptide, either s.c. or i.v. 15-120 minutes before injecting hPCSK9 (Sino Biologicals, China) intravenously in the tail vein at a dose of 0.4 mg/kg. Sixty minutes after the injection of hPCSK9, the animals are anaesthetised in isoflurane and euthanised by cervical dislocation. The liver is then quickly excised and snapfrozen in liquid nitrogen. The livers are kept at −80 degrees celsius until analysis.

LDL-R Western Blotting:

Liver tissue samples (100 mg) were homogenized in 500 μl lysis buffer (Life Technology, FNN0011) containing phosphatase inhibitor cocktail; PhosStop (Roche, 04 906 837 001) and protease inhibitor cocktail; compelate (Roche, 04 693 159 001). After adding 1 steel bead tissues were homogenized for 2.5 min at 30 Hz. After centrifugation at 5000×g for 5 min, total protein content was determined using BCA Protein Assay Kit (Pierce, 23225). Equal amounts of proteins (60 μg) in sample buffer (Life Technology, NP0007) were boiled for 10 min and spun for 2 min at 14000 rpm before loaded onto Criterion XT 3-8% Tris-Acetate gels (BioRad #345-0131) and subjected to SDS-PAGE. The proteins were transferred to nitrocellulose membranes (iBlot 2 NC Regular stacks, novex #1623001) according to manufacturer's instructions (Life Technology). Equal protein transfer was confirmed by Ponceau S (Sigma, P7170) staining of the membranes and the membranes were further blocked in blocking buffer (TBS-T, 2% Tween). LDL-r proteins were detected with Primary rabbit anti LDLr antibody (Cayman Chemical Company #10012422), whereas beta-actin proteins were detected using Primary rabbit anti beta-actin antibody (abcam # ab6276). Both proteins were further visualized with peroxidase-conjugated goat anti-rabbit secondary antibodies (Biorad #170-6516) using the WesternBright Quantum Chemiluminscent (Advansta # K-12042-D10) and imaged using a CCD camera (LAS3000, FujiFilm). Quantitative analysis of chemiluminescent signals from Western blots was done with Multi-Gauge software (Fujifilm).

Results

FIG. 1 shows hepatic LDL-R expression levels measured by Western Blot, presented as scatter plot for the individual animals, n=3-6. "Vehicle-vehicle" is the group of healthy controls (baseline level), "vehicle-hPCSK9" is the group injected with hPCSK9 alone.

The results show that hPCSK9 decreases the expression level of LDL-R and this effect is inhibited by the PCSK9 inhibitors tested.

In Table 8, data are presented as percentage change in relation to the window between baseline level in healthy control animals (set to 100%) and the level after down regulation by hPCSK9 alone (set to 0%).

All 6 tested examples are able to inhibit the action of hPCSK9 on the LDL-R expression level and the level of inhibition observed is similar to the level of inhibition observed using the control molecule Alirocumab.

TABLE 8

| Group/Example | Percentage of baseline (%) | Dose of inhibitor (nmol/kg) |
|---|---|---|
| Vehicle-Vehicle | 100 | 0 |
| Vehicle-hPCSK9 | 0 | 0 |
| Example 2-hPCSK9 | 110 | 300 |
| Example 3-hPCSK9 | 113 | 300 |
| Example 5-hPCSK9 | 123 | 300 |
| Example 6-hPCSK9 | 96 | 300 |
| Example 13-hPCSK9 | 175 | 300 |
| Example 19-hPCSK9 | 190 | 300 |
| Alirocumab-hPCSK9 | 157 | 22 |

Conclusion

Several compound examples have shown efficacy in inhibiting the down-regulation of the LDL-R expression levels by hPCSK9.

D.4. LDL-Cholesterol Reduction in Hamsters

The aim of the study was to evaluate the effects of PCSK9 inhibitors on LDL-C in Golden Syrian hamsters fed a standard chow diet.

Method

Male Golden Syrian Hamsters (Janvier Elevage, Saint Isle, France), 6 weeks of age (91-100 g) were used in the study. After 1 week of acclimatisation, 4-hour fasted hamsters (fasting starts at ~08:00 am) were weighed and bled (100 µL/EDTA) by retro-orbital bleeding under isoflurane anesthesia at ~noon to measure total cholesterol, LDL-cholesterol and HDL-cholesterol. Hamsters were randomized into 5 homogenous groups (n=10/group) according to their 1) LDL-cholesterol, 2) HDL-cholesterol and 3) total cholesterol. After randomization, hamsters were treated by subcutaneous injection once daily for 5 days. Body weight was measured daily during the treatment period.

At 3 days of treatment, 4-hour fasted hamsters were weighed and bled (100 µL/EDTA) by retro-orbital bleeding under isoflurane anesthesia at ~1 hour after the morning doses (at ~noon) to measure total cholesterol, LDL-cholesterol and HDL-cholesterol.

At 5 days of treatment, 4-hour fasted hamsters were weighed and bled (maximal blood volume/EDTA) by retro-orbital bleeding under isoflurane anesthesia at ~1 hour after the morning doses (at ~noon).

Plasma was immediately isolated. For each individual, a ~15 µL plasma volume was kept to measure total cholesterol, LDL-cholesterol and HDL-cholesterol. Another plasma volume (~50 µL) of each individual was then used to make a plasma pool for each treatment group (i.e. 1 pool of ~500 µL per group, 5 pools) for FPLC total cholesterol profile. Hamsters were then sacrificed under isoflurane anesthesia by cervical dislocation and exsanguinated. Liver was harvested, weighed and 2 liver samples (~50 mg and ~100 mg, weight not recorded) were flash frozen in liquid nitrogen and then stored at ~80° C.

The ~50 mg samples were used to evaluate hepatic LDL-receptor and pan-cadherin (loading control) protein expression by Western Blot and densitometry analysis (Image J software). Data are presented as mean+/−SEM. A 1-way or 2-way ANOVA w/Dunnett or Bonferroni post-test, respectively, were used for statistical analysis. A $p<0.05$ was considered significant.

Results

Figure 2:
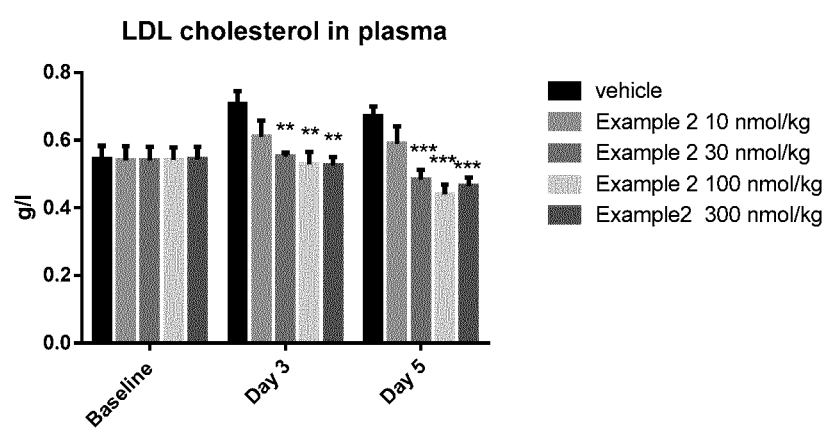
FIG. 2 shows plasma LDL cholesterol in hamsters treated with vehicle or with protracted EGF(A) compounds of example 2.

FIG. 2 shows plasma LDL-cholesterol during the treatment period in hamsters treated by subcutaneous injection once daily for 5 days with vehicle or 10 nmol/kg, 30 nmol/kg, 100 nmol/kg or 300 nmol/kg of Example 2. ($p<0.01$ and *$p<0.001$ vs. test vehicle, two way ANOVA, Dunnetts post hoc analysis).

Figure 3:
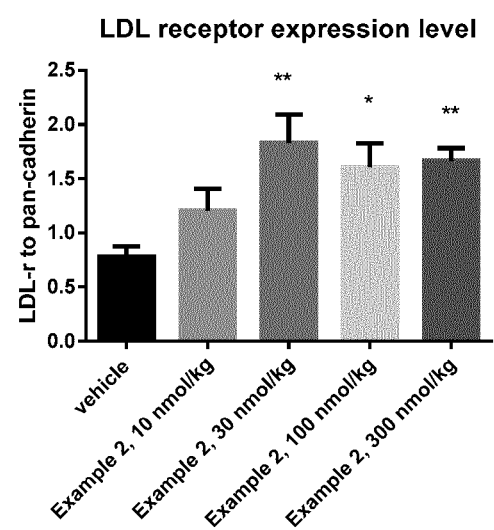
FIG. 3 shows hepatic LDL-R expression in livers of hamsters treated with vehicle or with protracted EGF(A) compounds of example 2 measured by Western Blot.

FIG. 3 shows hepatic LDL-R expression to loading control pan-cadherin from liver samples of hamsters treated by subcutaneous injection once daily for 5 days with vehicle or with Example 2 10 nmol/kg, Example 2 30 nmol/kg, Example 2 100 nmol/kg or Example 2 300 nmol/kg) (*$p<0.05$, $p<0.01$ and *$p<0.001$ vs. vehicle, One way ANOVA, Dunnetts post hoc analysis).

Compared with vehicle body weight and body weight gain were not affected in any treatment (data not shown). All doses reduced LDL-cholesterol (see FIG. 2). This effect was not significant for the lowest dose of Example 2, but the higher doses 100 and 300 nmol/kg reduced LDL-cholesterol levels by up to 35% at day 5. These trends were further confirmed by FPLC analysis, which showed substantial reductions in total cholesterol levels in fractions corresponding to LDL and HDL when hamsters were treated with test items Example 2 (data not shown). A concomitant dose-dependent increase in the LDL-R expression levels in livers was also demonstrated (see FIG. 2 and FIG. 3).

Conclusion

The dose response study demonstrates that it is possible to obtain significant effect on LDL cholesterol at least with a dose of 30 nmol/kg after 3 and 5 days of dosing in Golden Syrian Hamsters on normal chow. The effect on LDL cholesterol is concomitant with significantly higher hepatic LDL-receptor expression levels.

D.5 Dog i.v. PK Study

For dog i.v. PK profile determination, 3-4 beagle dogs (male, 10-16 kg) was dosed i.v. (2 nmol/kg, 0.1 ml/kg) with single or multiple PCSK9 analogues in 70 mM sodium chloride; 50 mM phosphate, 70 ppm polysorbate 20; pH=7.4. Before dosing, dogs were fasted overnight with free access to tap water. Analogues were dosed through saphenous or cephalic vein by single injection through a needle (20 G) or sequential dosing through an inserted venflon. A 0.8 ml of blood sample will be collected into each EDTA-coated tube at 0, 0.25, 0.5, 0.75, 1, 1.5, 2, 4, 6, 8, 10, 24, 48, 72, 120, 144, 168, 192, 216, 240, 288 hours after dosing. For the first 4 hour sampling, blood was collected through an inserted venflon when the dogs were restrained on a platform. The rest of sampling points after 4 hours were collected through the jugular vein by single needle punch (20 G). Immediately after blood collection, each sample was gently inversed for 3-4 times and quickly transferred on an ice box before plasma preparation (10 min, 4° C., 4000 rpm). Plasma samples were kept at −20° C. before bioanalysis. The maximal deviation for blood sampling is 1 min on the day of dosing until 120-min post-dosing, 5 min for 4- to 10-hr time points, and within 1 hour for the rest of the days.

Plasma Analysis:

Plasma from the co-dosing study was pipetted into Micronic tubes on dry ice, and kept at −20° C. until analysed for plasma concentration of the respective PCSK9 derivatives using liquid chromatography mass spectrometry (LC-MS). The plasma samples (including standard curve and QC samples used for quantitation of unknowns and prepared from blank plasma spiked with PCSK9 derivatives at a nominal concentration range of 0.5-500 nM) were protein precipitated using three volumes of methanol (including Example 4 as internal standard) and centrifuged (16000×g, 4° C., 30 min). The supernatants were injected into the chromatographic system (TurboFlow Transcend 1250 & 10 valve VIM, Thermo Fisher Scientific) which consisted of an initial Turboflow Cyclone purification column 0.5×50 mm (Thermo Fischer Scientific) and an eluting Aeris peptide 3.6 µm XB-C18 column 2.1×50 mm (Phenomenex) kept at 60° C. The PCSK9 derivatives were eluted using a chromatographic gradient with mobile phases consisting of mixtures of water and acetonitrile/methanol 50/50 v/v % with 1 v/v % formic acid. The PCSK9 derivatives were detected and quantified after on-line infusion of the LC flow to the Q Exactive mass spectrometer (Thermo Fischer Scientific) equipped with an electrospray interface operated in positive mode, ESI+. During bioanalysis of plasma samples, a varying degree of isomerization was observed for different PCSK9 derivatives. The isomers all have identical monoisotopic masses and are quantitated together.

PK parameters of each tested analogue (eg. $T_{1/2}$) were analyzed by non-compartmental analysis (NCA) using Phoenix WinNonlin software, and half-lifes calculations are based on exposure levels of a total of all isomers with the same molecular mass.

TABLE 9

Half-lives of EGF(A) derivatives in dogs after i.v. dosing

| Example No. | Peptide variant | Dog iv PK co-dosing $T_{1/2}$ (h) |
|---|---|---|
| Example 3 | 301L, 309R, 312E, 333K | 122 |
| Example 31 | 301L, 309R, 312E, 313K, 333K | 117 |
| Example 81 | 301L, 309R, 312E, 333K | 209 |
| Example 91 | des293, 300H, 301L, 309R, 312E, 313K, 333K | 34 |
| Example 95 | des293, 301L, 309R, 312E, 313K | 116 |
| Example 128 | 301L, 309R, 312E, 313K, 333K | 190 |
| Example 133 | 301L, 309R, 312E, 313K, 321E, 333K | 115 |
| Example 143 | 301L, 309R, 312E, 313K, 321E, 333K | 89 |
| Example 144 | 301L, 309R, 312E, 313K, 321E, 333K | 193 |

D.6 Oral Uptake Study in Rats

The current studies investigated gastrointestinal absorption of co-formulated peptides dosed perorally to healthy rats.

Animals:

Male Sprague Dawley rats from Taconic, Denmark, 250 g at arrival. Rats were acclimatised at least one week at Animal Unit, Novo Nordisk NS, prior to study. Bodyweight at study start was approximately 280-300 g. The rats were fasted for 18 h on grid prior to dosing.

Co-Formulation of Peptides

Preparation of liquid formulations for oral co-dosing of PCSK9i analogues in vivo (rats) was carried out as described below.

Target EGF(A) peptide concentration was 200 µM of each analogue, formulated in a target concentration of 55 mg/ml sodium decanoate and water. Five to six different peptide analogues were formulated together in the same formulation.

In short, a stock solution (110 mg/mL) of sodium decanoate was prepared using ultrapure water and pH of the solution was adjusted to 8.0 using HCl.

The APIs were transferred into a 20 mL glass vial and 5 g of ultrapure water was added (assuming 1 mg/mL density) and the APIs were left to dissolve at room temperature on a roller mixer. The pH of the solution was subsequently adjusted to 8.0 with NaOH until the pH stabilized, after which 6.5 g of the sodium decanoate stock (final concentration 55 mg/mL) was added followed by pH adjustment to pH 8.0. The solution was then kept at room temperature on a roller mixer overnight (protected from light). The next day a final pH adjustment to pH 8.0 was performed if required using NaOH.

The final formulation weight was set to 13 g using ultrapure water and subsequently filtered through a 0.22 µm filter. API and sodium decanoate content was determined on the final formulation to ensure an accurate dosing. Formulations were stored at 4° C. until further use.

The concentration of each API in the liquid formulation was determined by UV absorbance at 215 nm. LC methods were developed to ensure that each co-dosing API eluted separately from each other. Standards of known concentrations (determined by CLND) for each API were mixed together, and in total five concentrations of standards were used to generate calibration curves. The final determined concentration was an average taken from three samples, each with two experimental repeats. Caprate concentration in the liquid formulation was determined in a similar fashion, using a calibration curve consisting of three concentrations of standards.

Dosing:

The animals were dosed perorally by gavage with a target dose of 1000 nmol/kg of each peptide and a volume of 5 ml/kg at time=0

Blood Sampling and Plasma Separation

Blood samples were taken at times: 15, 30, 60 and 120 min after dosing. Blood samples (200 µl) were collected into EDTA-coated tubes by puncturing the tongue vein in conscious rats. Samples were centrifuged for 5 minutes at 8000G by 4° C. Plasma (60-75 µl) was separated and pipetted into micronic tubes (75 µl) and immediately frozen at −20° C.

Plasma Analysis:

Plasma from the co-dosing study was pipetted into Micronic tubes on dry ice, and kept at −20° C. until analysed for plasma concentration of the respective PCSK9 derivatives using liquid chromatography mass spectrometry (LC-MS). The plasma samples (including standard curve and QC samples used for quantitation of unknowns and prepared from blank plasma spiked with PCSK9 derivatives at a nominal concentration range of 0.5-500 nM) were protein precipitated using three volumes of methanol or acetonitrile with 1 v/v % formic acid (including Example 4 as internal standard) and centrifuged (16000×g, 4° C., 30 min). The supernatants were injected into the chromatographic system (TurboFlow Transcend 1250 & 10 valve VIM, Thermo Fisher Scientific) which consisted of an initial Turboflow Cyclone purification column 0.5×50 mm (Thermo Fischer Scientific) and an eluting Aeris peptide 3.6 µm XB-C18 column 2.1×50 mm (Phenomenex) kept at 60° C. The PCSK9 derivatives were eluted using a chromatographic gradient with mobile phases consisting of mixtures of water and acetonitrile/methanol 50/50 v/v % with 1 v/v % formic acid. The PCSK9 derivatives were detected and quantified after on-line infusion of the LC flow to the Q Exactive or LTQ OrbiTrap Discovery mass spectrometer (Thermo Fischer Scientific) equipped with an electrospray interface operated in positive mode, ESI+. During bioanalysis of plasma samples, a varying degree of isomerization was observed for different PCSK9 derivatives. The isomers all have identical monoisotopic masses and are quantitated together.

Data Calculations:

From the plasma concentrations determined by LC-MS, maximal plasma concentrations (Cmax) were extracted for each peptide in each rat and Cmax/dose was calculated as mean values±SD for n=6-8 rats. The dose was calculated as the injection volume, adjusted for body weight, multiplied with the actual concentration of the peptide, the unit being pmol/kg.

In each co-formulation group a reference peptide was included (example 3). In below table, Cmax/dose (kg/l) is listed for 8 different peptides together with the Cmax/dose (kg/l) for the reference peptide (Example 3). Cmax calculations are based on exposure levels of a total of all isomers with the same molecular mass. The results show that the EGF(A) derivatives are generally well absorbed.

TABLE 10

Plasma concentrations divided by dose in rats after oral co-dosing of EGF(A) derivatives

| Example no | Cmax/ dose (kg/l) | Cmax/dose for ref. Example 3 (kg/l) |
|---|---|---|
| Example 31 | 0.108 ± 0.086 | 0.053 ± 0.050 |
| Example 81 | 0.024 ± 0.005 | 0.079 ± 0.013 |

TABLE 10-continued

Plasma concentrations divided by dose in rats after oral co-dosing of EGF(A) derivatives

| Example no | Cmax/ dose (kg/l) | Cmax/dose for ref. Example 3 (kg/l) |
|---|---|---|
| Example 91 | 0.116 ± 0.032 | 0.083 ± 0.023 |
| Example 95 | 0.106 ± 0.029 | 0.087 ± 0.023 |
| Example 128 | 0.130 ± 0.013 | 0.087 ± 0.019 |
| Example 133 | 0.071 ± 0.017 | 0.057 ± 0.015 |
| Example 143 | 0.151 ± 0.038 | 0.096 ± 0.029 |
| Example 144 | 0.100 ± 0.025 | 0.057 ± 0.015 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An EGF(A) derivative comprising 1) an EGF(A) peptide analogue of SEQ ID NO: 1 comprising amino acid 301Leu, an amino acid substitution of 312Lys and up to six additional amino acid substitutions, wherein SEQ ID NO: 1 corresponds to amino acids 293-332 of the EGF(A) domain of the LDL-R, and 2) a substituent comprising at least one fatty acid group, wherein the substituent is attached to the EGF(A) peptide analogue.

2. The EGF(A) derivative according to claim 1, wherein said substituent comprises a functional group, wherein said functional group is a carboxylic acid, a sulphonic acid, a tetrazole moiety, a methylsulfonylcarbamoylamino moiety or a 3-hydroxy-isoxazole moiety and further comprises 8-20 consecutive —$CH_2$— groups, wherein said substituent is attached to a lysine residue or the N-terminal residue of said EGF(A) peptide analogue.

3. The EGF(A) derivative according to claim 1, wherein said substituent has Formula I:

$$Z_1—Z_2—Z_3—Z_4—Z_5—Z_6—Z_7—Z_8—Z_9—Z_{10}— \quad [I]$$

wherein
$Z_1$ is selected from:
Chem. 1: HOOC—$(CH_2)_n$—CO—*,
Chem. 2: tetrazolyl-$(CH_2)_n$—CO—*,
Chem. 3: HOOC—$(C_6H_4)$—O—$(CH_2)_m$—CO—*,
Chem. 4: HOS(O)$_2$—$(CH_2)_n$—CO—*,
Chem. 5: MeS(O)$_2$NH(CO)N—$(CH_2)_n$—CO—* and
Chem. 6: 3-HO-Isoxazole-$(CH_2)_n$—CO—*
wherein
n is an integer in the range of 8-20,
m is an integer in the range of 8-11,
the —COOH group in Chem. 3 can be attached to position 2, 3 or 4 on the phenyl ring, the symbol * indicates the attachment point to the nitrogen in $Z_2$ or, if $Z_2$ is a bond, to the nitrogen on the neighbouring Z element; or if $Z_3$-$Z_{10}$ are all bonds, to a lysine residue or the N-terminal residue of said EGF(A) peptide analogue;
$Z_2$ is selected from
Chem. 7: —NH—SO$_2$—$(CH_2)_3$—CO—*,
Chem. 8: —NH—$CH_2$—$(C_6H_{10})$—CO—* and
a bond; and the symbol * indicates the attachment point to $Z_3$ or, if $Z_3$ is a bond, to the neighbouring Z element, or if $Z_4$-$Z_{10}$ are all bonds, to a lysine residue or the N-terminal residue of said EGF(A) peptide analogue;
$Z_3$ is selected from:
γGlu, Glu and a bond;
$Z_4, Z_5, Z_6, Z_7, Z_8, Z_9$ are selected, independently of each other, from:
Glu, γGlu, Gly, Ser, Ala, Thr, Ado, Aeep, Aeeep, TtdSuc and a bond; and
$Z_{10}$ is selected from:
Chem. 14: —NH—$CH_2$—$(C_6H_4)$—$CH_2$—* and a bond, and wherein the symbol * indicates the attachment point to a lysine residue or the N-terminal residue of said EGF(A) peptide analogue.

4. The EGF(A) derivative according to claim 1, wherein the EGF(A) derivative comprises one or two substituent(s) selected from the group consisting of:
HOOC—$(CH_2)_{18}$—CO-gGlu-2×ADO—
HOOC—$(CH_2)_{18}$—CO—NH—$CH_2$—$(C_6H_{10})$—CO-gGlu-2×ADO—
HOOC—$(CH_2)_{16}$—CO-gGlu-2×ADO—
HOOC—$(CH_2)_{16}$—CO-gGlu-2×ADO—NH—$CH_2$—$(C_6H_4)$—$CH_2$—
HOOC—$(CH_2)_{16}$—CO-gGlu-
HOOC—$(CH_2)_{16}$—CO—NH—$CH_2$—$(C_6H_{10})$—CO-gGlu-2×ADO—
HOOC—$(CH_2)_{14}$—CO-gGlu-2×ADO—
HOOC—$(CH_2)_{14}$—CO-gGlu-
HOOC—$(CH_2)_{14}$—CO-gGlu-2×ADO—
HOOC—$(CH_2)_{12}$—CO-gGlu-2×ADO—
4-HOOC—$(C_6H_4)$—O—$(CH_2)_{10}$—CO-gGlu-2×ADO—
4-HOOC—$(C_6H_4)$—O—$(CH_2)_{10}$—CO-gGlu-3×ADO—
4-HOOC—$(C_6H_4)$—O—$(CH_2)_{10}$—CO-gGlu-
4-HOOC—$(C_6H_4)$—O—$(CH_2)_{10}$—CO-2×gGlu-
4-HOOC—$(C_6H_4)$—O—$(CH_2)_{10}$—CO-gGlu-3×Gly-
4-HOOC—$(C_6H_4)$—O—$(CH_2)_{10}$—CO-2×gGlu-2×ADO—
4-HOOC—$(C_6H_4)$—O—$(CH_2)_{10}$—CO-gGlu-TtdSuc-
4-HOOC—$(C_6H_4)$—O—$(CH_2)_9$—CO—
4-HOOC—$(C_6H_4)$—O—$(CH_2)_{10}$—CO-gGlu-4×ADO—
4-HOOC—$(C_6H_4)$—O—$(CH_2)_{10}$—CO—NH—$CH_2$—$(C_6H_{10})$—CO-gGlu-2×ADO—
4-HOOC—$(C_6H_4)$—O—$(CH_2)_9$—CO-gGlu-2×ADO—
3-HOOC—$(C_6H_4)$—O—$(CH_2)_9$—CO-gGlu-2×ADO—
3-HO-Isoxazole-$(CH_2)_{12}$—CO-gGlu-2×ADO—
HOS(O)$_2$—$(CH_2)_{15}$—CO-gGlu-2×ADO—NH—$CH_2$—$(C_6H_4)$—$CH_2$—
HOS(O)$_2$—$(CH_2)_{13}$—CO-gGlu-2×ADO—
Tetrazolyl-$(CH_2)_{15}$—CO—NH—SO$_2$—$(CH_2)_3$—CO-ADO-ADO—NH—$CH_2$—$(C_6H_4)$—$CH_2$—
Tetrazolyl-$(CH_2)_{12}$—CO-gGlu-2×ADO—
Tetrazolyl-$(CH_2)_{15}$—CO-gGlu-2×ADO- and
MeS(O)$_2$NH(CO)NH—$(CH_2)_{12}$—CO-gGlu-2×ADO-.

5. The EGF(A) derivative according to claim 4, wherein amino acid residue(s): 295Asn, 296Glu, 298Leu, 302Gly and/or 310Asp of the EGF(A) peptide analogue are not substituted.

6. The EGF(A) derivative according to claim 4, wherein said EGF(A) peptide analogue further comprises one or two Lys residue(s) selected from the group consisting of: 292Lys, 293Lys, 294Lys, 296Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys, wherein 292Lys represents adding a Lys residue to the N-terminus of SEQ ID NO: 1 and 333Lys represents adding a Lys residue to the C-terminus of SEQ ID NO: 1, and wherein said one or two substituent(s) is attached to said one or two Lys residue(s) in said EGF(A) peptide analogue.

7. The EGF(A) derivative according to claim 4, wherein amino acids 297Cys, 304Cys, 308Cys, 317Cys, 319Cys and 331Cys of the EGF(A) peptide analogue are not substituted.

8. The EGF(A) derivative according to claim 4, wherein said EGF(A) peptide analogue further comprises two Lys residues selected from the pairs consisting of:
i. 293K and 294K
ii. 293K and 333K
iii. 309K and 313K
iv. 309K and 324K
v. 309K and 328K
vi. 309K and 332K
vii. 309K and 333K
viii. 311K and 313K
ix. 311K and 313K
x. 313K and 321K
xi. 313K and 324K
xii. 313K and 328K
xiii. 313K and 332K
xiv. 313K and 333K
xv. 314K and 333K
xvi. 321K and 332K
xvii. 321K and 333K
xviii. 321K and 333K
xix. 324K and 328K
xx. 328K and 333K
xxi. 330K and 333K and
xxii. 332K and 333K,
wherein 333K represents adding a Lys residue to the C-terminus of SEQ ID NO: 1.

9. The EGF(A) derivative according to claim 4, wherein said EGF(A) peptide analogue comprises one or two Lys residue(s) selected from the group consisting of: 313Lys, 324Lys, 328Lys, and 333Lys and one or two substituent(s) is attached to said one or two Lys residue(s) in said EGF(A)

peptide analogue, wherein 333Lys represents adding a Lys residue to the C-terminus of SEQ ID NO: 1.

10. The EGF(A) derivative according to claim 1, wherein amino acids 295Asn, 296Glu, 298Leu, 302Gly and/or 310Asp of the EGF(A) peptide are not substituted.

11. The EGF(A) derivative according to claim 1, wherein amino acid 310Asp of the EGF(A) peptide is not substituted.

12. The EGF(A) derivative according to claim 1, wherein amino acid 295Asn of the EGF(A) peptide is not substituted.

13. The EGF(A) derivative according to claim 1, wherein said EGF(A) peptide analogue further comprises one or two Lys residue(s) selected from the group consisting of: 292Lys, 293Lys, 294Lys, 296Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys, wherein 292Lys represents adding a Lys residue to the N-terminus of SEQ ID NO: 1 and 333Lys represents adding a Lys residue to the C-terminus of SEQ ID NO: 1, and wherein said substituent is attached to said one or two Lys residue(s) in said EGF(A) peptide analogue.

14. The EGF(A) derivative according to claim 1, wherein amino acid 310Asp is not substituted and 312Lys is substituted by Glu, Asp, Gln or Arg.

15. The EGF(A) derivative according to claim 1, wherein amino acid 310Asp is not substituted and 299Asp is not substituted to Glu, Val or His.

16. The EGF(A) derivative according to claim 15, wherein amino acids 295Asn, 296Glu, 298Leu, and/or 302Gly of the EGF(A) peptide analogue are not substituted.

17. The EGF(A) derivative according to claim 15, wherein said EGF(A) peptide analogue further comprises one or two Lys residue(s) selected from the group consisting of: 292Lys, 293Lys, 294Lys, 296Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys, wherein 292Lys represents adding a Lys residue to the N-terminus of SEQ ID NO: 1 and 333Lys represents adding a Lys residue to the C-terminus of SEQ ID NO: 1, and wherein said substituent is attached to said one or two Lys residue(s) in said EGF(A) peptide analogue.

18. The EGF(A) derivative according to claim 1, wherein amino acids 297Cys, 304Cys, 308Cys, 317Cys, 319Cys and 331Cys of the EGF(A) peptide analogue are not substituted.

19. The EGF(A) derivative according to claim 18, wherein amino acids 295Asn, 296Glu, 298Leu, 302Gly and/or 310Asp of the EGF(A) peptide analogue are not substituted.

20. The EGF(A) derivative according to claim 18, wherein said EGF(A) peptide analogue further comprises one or two Lys residue(s) selected from the group consisting of: 292Lys, 293Lys, 294Lys, 296Lys, 299Lys, 300Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys, wherein 292Lys represents adding a Lys residue to the N-terminus of SEQ ID NO: 1 and 333Lys represents adding a Lys residue to the C-terminus of SEQ ID NO: 1, and wherein said substituent is attached to said one or two Lys residue(s) in said EGF(A) peptide analogue.

21. The EGF(A) derivative according to claim 1, wherein said EGF(A) peptide analogue further comprises two Lys residues selected from the pairs consisting of:
 i. 293K and 294K
 ii. 293K and 333K
 iii. 309K and 313K
 iv. 309K and 324K
 v. 309K and 328K
 vi. 309K and 332K
 vii. 309K and 333K
 viii. 311K and 313K
 ix. 313K and 314K
 x. 313K and 321K
 xi. 313K and 324K
 xii. 313K and 328K
 xiii. 313K and 332K
 xiv. 313K and 333K
 xv. 314K and 333K
 xvi. 321K and 332K
 xvii. 321K and 333K
 xviii. 324K and 333K
 xix. 324K and 328K
 xx. 328K and 333K
 xxi. 330K and 333K and
 xxii. 332K and 333K,
wherein 333K represents adding a Lys residue to the C-terminus of SEQ ID NO: 1.

22. The EGF(A) derivative according to claim 1, wherein said EGF(A) peptide analogue comprises one or two Lys residues selected from the group consisting of: 313Lys, 324Lys, 328Lys, and 333Lys and said substituent is attached to said one or two Lys residue in said EGF(A) peptide analogue, wherein 333Lys represents adding a Lys residue to the C-terminus of SEQ ID NO: 1.

23. An EGF(A) derivative comprising an EGF(A) peptide analogue and a substituent, selected from the group consisting of compounds as shown below, wherein in each compound, the amino acid sequence of EGF(A) peptide analogue is shown by SEQ ID NO, the structure of substituent is shown, and attachment site(s) shows the amino acid position(s) where the substituent attaches to the EGF(A) peptide analogue:

| SEQ ID NO | Substituent | Attachment site(s) |
| --- | --- | --- |
| 4 | HOOC—(CH2)$_{16}$—CO-gGlu-2xADO | C-terminal |
| 6 | HOOC—(CH2)$_{16}$—CO-gGlu-2xADO-NH—CH$_2$—(C$_6$H$_4$)—CH$_2$— | N-terminal |
| 7 | HOOC—(CH2)$_{16}$—CO-gGlu-2xADO | 7K |
| 8 | HOOC—(CH2)$_{16}$—CO-gGlu-2xADO | 38K |
| 6 | HOS(O)2—(CH2)15—C0-gGlu-2xADO-NH—CH$_2$—(C$_6$H$_4$)—CH$_2$— | N-terminal |
| 8 | HOOC—(CH2)$_{16}$—CO-gGlu-2xADO | N-terminal, 38K |
| 11 | HOOC—(CH2)$_{16}$—CO-gGlu-2xADO | C-terminal |
| 12 | HOOC—(CH2)$_{16}$—CO-gGlu-2xADO | N-terminal |
| 13 | HOOC—(CH2)$_{16}$—CO-gGlu-2xADO | N-terminal, C-terminal |
| 13 | 4-HOOC—(C$_6$H$_4$)—O—(CH$_2$)$_{10}$—CO-gGlu-2xADO | N-terminal, C-terminal |
| 15 | 4-HOOC—(C$_6$H$_4$)—O—(CH$_2$)$_{10}$—CO-gGlu-2xADO | 40K, C-terminal |
| 16 | 4-HOOC—(C$_6$H$_4$)—O—(CH$_2$)$_{10}$—CO-gGlu-2xADO | 38K, C-terminal |
| 17 | 4-HOOC—(C$_6$H$_4$)—O—(CH$_2$)$_{10}$—CO-gGlu-2xADO | 29K, C-terminal |

-continued

| SEQ ID NO | Substituent | Attachment site(s) |
|---|---|---|
| 19 | HOOC—(CH2)$_{16}$—CO-gGlu-2xADO | C-terminal |
| 6 | HOOC—(CH2)$_{16}$—CO-gGlu-2xADO | N-terminal |
| 21 | HOOC—(CH2)$_{16}$—CO-gGlu-2xADO | 29K |
| 22 | HOOC—(CH2)$_{16}$—CO-gGlu-2xADO | 32K |
| 23 | HOOC—(CH2)$_{16}$—CO-gGlu-2xADO | N-terminal |
| 24 | HOOC—(CH2)$_{16}$—CO-gGlu-2xADO | C-terminal |
| 25 | HOOC—(CH2)$_{16}$—CO-gGlu-2xADO | N-terminal |
| 27 | HOOC—(CH2)$_{16}$—CO-gGlu-2xADO | 8K |
| 28 | 4-HOOC—(C$_6$H$_4$)—O—(CH$_2$)$_{10}$—CO-gGlu-2xADO | N-terminal, 2K |
| 30 | HOOC—(CH2)$_{16}$—CO-gGlu-2xADO | 17K |
| 31 | HOOC—(CH2)$_{16}$—CO-gGlu-2xADO | 26K |
| 32 | 4-HOOC—(C$_6$H$_4$)—O—(CH$_2$)$_{10}$—CO-gGlu-2xADO | 21K, C-terminal |
| 33 | HOOC—(CH2)$_{16}$—CO-gGlu-2xADO | 34K |
| 34 | HOOC—(CH2)$_{16}$—CO-gGlu-2xADO | 33K |
| 35 | HOOC—(CH2)$_{16}$—CO-gGlu-2xADO | 31K |
| 36 | HOOC—(CH2)$_{16}$—CO-gGlu-2xADO | 30K |
| 37 | HOOC—(CH2)$_{16}$—CO-gGlu-2xADO | 28K |
| 38 | HOOC—(CH2)$_{16}$—CO-gGlu-2xADO | 37K |
| 39 | HOOC—(CH2)$_{16}$—CO-gGlu-2xADO | 21K |
| 40 | HOOC—(CH2)$_{16}$—CO-gGlu-2xADO | 36K |
| 41 | HOOC—(CH2)$_{16}$—CO-gGlu-2xADO | 24K |
| 42 | HOOC—(CH2)$_{16}$—CO-gGlu-2xADO | 23K |
| 43 | HOOC—(CH2)$_{16}$—CO-gGlu-2xADO | C-terminal |
| 44 | HOOC—(CH2)$_{16}$—CO-gGlu-2xADO | 22K |
| 45 | HOOC—(CH2)$_{16}$—CO-gGlu-2xADO | 19K |
| 47 | HOOC—(CH2)$_{16}$—CO-gGlu-2xADO | C-terminal |
| 48 | HOOC—(CH2)$_{16}$—CO-gGlu-2xADO | C-terminal |
| 49 | HOOC—(CH2)$_{16}$—CO-gGlu-2xADO | N-terminal |
| 50 | HOOC—(CH2)$_{16}$—CO-gGlu-2xADO | N-terminal |
| 51 | HOOC—(CH2)$_{16}$—CO-gGlu-2xADO | 14K |
| 52 | HOOC—(CH2)$_{16}$—CO-gGlu-2xADO | 13K |
| 53 | HOOC—(CH2)$_{16}$—CO-gGlu-2xADO | 11K |
| 55 | HOOC—(CH2)$_{16}$—CO-gGlu-2xADO | C-terminal |
| 58 | HOOC—(CH2)$_{16}$—CO-gGlu-2xADO | C-terminal |
| 60 | HOOC—(CH2)$_{16}$—CO-gGlu-2xADO | C-terminal |
| 61 | HOOC—(CH2)$_{16}$—CO-gGlu-2xADO | C-terminal |
| 9 | HOOC—(CH2)$_{16}$—CO-gGlu-2xADO | C-terminal |
| 10 | HOOC—(CH2)$_{16}$—CO-gGlu-2xADO | C-terminal |
| 6 | Tetrazolyl-(CH$_2$)$_{15}$—CO—NH—SO$_2$—(CH$_2$)$_3$—CO-ADO-ADO-NH—CH$_2$—(C$_6$H$_4$)—CH$_2$— | N-terminal |
| 14 | HOOC—(CH2)$_{16}$—CO-gGlu-2xADO | 36K |
| 26 | HOOC—(CH2)$_{16}$—CO-gGlu-2xADO | N-terminal |
| 63 | HOOC—(CH2)$_{16}$—CO-gGlu-2xADO | 4K |
| 64 | HOOC—(CH2)$_{16}$—CO-gGlu-2xADO | 2K |
| 65 | HOOC—(CH2)$_{16}$—CO-gGlu-2xADO | N-terminal |
| 67 | HOOC—(CH2)$_{16}$—CO-gGlu-2xADO | C-terminal |
| 68 | 4-HOOC—(C$_6$H$_4$)—O—(CH$_2$)$_{10}$—CO-gGlu-3xADO and 4-HOOC—(C$_6$H$_4$)—O—(CH$_2$)$_{10}$—CO-gGlu-2xADO | N-terminal, C-terminal |
| 17 | 4-HOOC—(C$_6$H$_4$)—O—(CH$_2$)$_9$—CO-gGlu-2xADO | 29K, C-terminal |
| 4 | HOOC—(CH$_2$)$_{14}$—CO-gGlu-2xADO | C-terminal |
| 4 | HOOC—(CH$_2$)$_{18}$—CO-gGlu-2xADO | C-terminal |
| 4 | HOOC—(CH$_2$)$_{16}$—CO-gGlu | C-terminal |
| 17 | HOOC—(CH$_2$)$_{12}$—CO-gGlu-2xADO | 29K, C-terminal |
| 17 | HOOC—(CH$_2$)$_{14}$—CO-gGlu-2xADO | 29K, C-terminal |
| 69 | 4-HOOC—(C$_6$H$_4$)—O—(CH$_2$)$_9$—CO-gGlu-2xADO | 21K, C-terminal |
| 70 | 4-HOOC—(C$_6$H$_4$)—O—(CH$_2$)$_{10}$—CO-gGlu-2xADO | 21K, 36K |
| 71 | 4-HOOC—(C$_6$H$_4$)—O—(CH$_2$)$_{10}$—CO-gGlu-2xADO | 21K, 32K |
| 39 | 4-HOOC—(C$_6$H$_4$)—O—(CH$_2$)$_{10}$—CO-gGlu-2xADO | N-terminal, 21K |
| 72 | 4-HOOC—(C$_6$H$_4$)—O—(CH$_2$)$_{10}$—CO-gGlu-2xADO | 32K, C-terminal |
| 73 | 4-HOOC—(C$_6$H$_4$)—O—(CH$_2$)$_{10}$—CO-gGlu-2xADO | 21K, 29K |
| 69 | 4-HOOC—(C$_6$H$_4$)—O—(CH$_2$)$_{10}$—CO-gGlu-2xADO | 21K, C-terminal |
| 77 | 4-HOOC—(C$_6$H$_4$)—O—(CH$_2$)$_{10}$—CO-gGlu-2xADO | 21K, C-terminal |
| 78 | 4-HOOC—(C$_6$H$_4$)—O—(CH$_2$)$_{10}$—CO-gGlu-2xADO | 36K, C-terminal |
| 32 | 4-HOOC—(C$_6$H$_4$)—O—(CH$_2$)$_{10}$—CO-gGlu | 21K, C-terminal |
| 32 | 4-HOOC—(C$_6$H$_4$)—O—(CH$_2$)$_{10}$—CO-2xgGlu | 21K, C-terminal |
| 32 | 4-HOOC—(C$_6$H$_4$)—O—(CH$_2$)$_{10}$—CO-gGlu-3xGly | 21K, C-terminal |
| 32 | 4-HOOC—(C$_6$H$_4$)—O—(CH$_2$)$_{10}$—CO-2xgG1u-2xADO | 21K, C-terminal |
| 32 | 3-HOOC—(C$_6$H$_4$)—O—(CH2)9—CO-gGlu-2xADO | 21K, C-terminal |
| 82 | HOOC—(CH$_2$)$_{16}$—CO-gGlu-2xADO | C-terminal |
| 4 | 4-HOOC—(C$_6$H$_4$)—O—(CH$_2$)$_{10}$—CO-gGlu-2xADO | N-terminal, C-terminal |
| 69 | 3-HO-Isoxazole-(CH$_2$)$_{12}$—CO-gGlu-2xADO | 21K, C-terminal |
| 32 | 3-HO-Isoxazole-(CH$_2$)$_{12}$—CO-gGlu-2xADO | 21K, C-terminal |
| 84 | 4-HOOC—(C$_6$H$_4$)—O—(CH$_2$)$_{10}$—CO-gGlu-2xADO | 17K, C-terminal |
| 85 | 4-HOOC—(C$_6$H$_4$)—O—(CH$_2$)$_{10}$—CO-gGlu-2xADO | 32K, C-terminal |
| 86 | 4-HOOC—(C$_6$H$_4$)—O—(CH$_2$)$_{10}$—CO-gGlu-2xADO | 22K, C-terminal |
| 87 | 4-HOOC—(C$_6$H$_4$)—O—(CH$_2$)$_{10}$—CO-gGlu-2xADO | N-terminal, C-terminal |

-continued

| SEQ ID NO | Substituent | Attachment site(s) |
|---|---|---|
| 88 | 4-HOOC—$(C_6H_4)$—O—$(CH_2)_{10}$—CO-gGlu-2xADO | 17K, 36K |
| 89 | 4-HOOC—$(C_6H_4)$—O—$(CH_2)_{10}$—CO-gGlu-2xADO | 17K, 21K |
| 90 | 4-HOOC—$(C_6H_4)$—O—$(CH_2)_{10}$—CO-gGlu-2xADO | N-terminal, C-terminal |
| 91 | 4-HOOC—$(C_6H_4)$—O—$(CH_2)_{10}$—CO-gGlu-2xADO | 32K, 36K |
| 92 | 4-HOOC—$(C_6H_4)$—O—$(CH_2)_{10}$—CO-gGlu-2xADO | N-terminal, C-terminal |
| 93 | 4-HOOC—$(C_6H_4)$—O—$(CH_2)_{10}$—CO-gGlu-2xADO | 21K, C-terminal |
| 11 | 4-HOOC—$(C_6H_4)$—O—$(CH_2)_{10}$—CO-gGlu-2xADO | N-terminal, C-terminal |
| 40 | 4-HOOC—$(C_6H_4)$—O—$(CH_2)_{10}$—CO-gGlu-2xADO | N-terminal, 26K |
| 22 | 4-HOOC—$(C_6H_4)$—O—$(CH_2)_{10}$—CO-gGlu-2xADO | N-terminal, 32K |
| 94 | 4-HOOC—$(C_6H_4)$—O—$(CH_2)_{10}$—CO-gGlu-2xADO | 17K, C-terminal |
| 106 | 4-HOOC—$(C_6H_4)$—O—$(CH_2)_{10}$—CO-gGlu-2xADO | 17K, 32K |
| 30 | 4-HOOC—$(C_6H_4)$—O—$(CH_2)_{10}$—CO-gGlu-2xADO | N-terminal, 17K |
| 95 | 4-HOOC—$(C_6H_4)$—O—$(CH_2)_{10}$—CO-gGlu-2xADO | 29K, C-terminal |
| 32 | HOOC—$(CH_2)_{14}$—CO-gGlu-2xADO | 21K, C-terminal |
| 32 | HOOC—$(CH_2)_{14}$—CO-gGlu | 21K, C-terminal |
| 96 | 4-HOOC—$(C_6H_4)$—O—$(CH_2)_{10}$—CO-gGlu-2xADO | 21K, C-terminal |
| 32 | 4-HOOC—$(C_6H_4)$—O—$(CH_2)_{10}$—CO-gGlu-TtdSuc | 21K, C-terminal |
| 97 | 4-HOOC—$(C_6H_4)$—O—$(CH_2)_{10}$—CO-gGlu-TtdSuc | 21K, C-terminal |
| 98 | 4-HOOC—$(C_6H_4)$—O—$(CH_2)_{10}$—CO-gGlu-2xADO | 21K, C-terminal |
| 19 | HOOC—$(CH_2)_{18}$—CO-gGlu-2xADO | C-terminal |
| 99 | 4-HOOC—$(C_6H_4)$—O—$(CH_2)_{10}$—CO-gGlu-2xADO | 21K, 22K |
| 102 | 4-HOOC—$(C_6H_4)$—O—$(CH_2)_{10}$—CO-gGlu-2xADO | 19K, 21K |
| 69 | 4-HOOC—$(C_6H_4)$—O—$(CH2)_9$-CO | 21K, C-terminal |
| 32 | Tetrazolyl-$(CH_2)_{12}$—CO-gGlu-2xADO | 21K, C-terminal |
| 32 | $HOS(O)_2$—$(CH_2)_{15}$—C0-gGlu-2xADO | 21K, C-terminal |
| 32 | $MeS(O)_2NH(CO)NH$—$(CH_2)_{12}$—C0-gGlu-2xADO | 21K, C-terminal |
| 98 | 4-HOOC—$(C_6H_4)$—O—$(CH_2)_{10}$—CO-gGlu | 21K, C-terminal |
| 98 | HOOC—$(CH_2)_{14}$—CO-gGlu-2xADO | 21K, C-terminal |
| 32 | Tetrazolyl-$(CH_2)_{15}$—CO-gGlu-2xADO | 21K, C-terminal |
| 98 | HOOC—$(CH_2)_{14}$—CO-gGlu | 21K, C-terminal |
| 103 | 4-HOOC—$(C_6H_4)$—O—$(CH_2)_{10}$—CO-gGlu-2xADO | 21K, C-terminal |
| 32 | 4-HOOC—$(C_6H_4)$—O—$(CH_2)_{10}$—CO-gGlu-4xADO | 21K, C-terminal |
| 78 | HOOC—$(CH_2)_{14}$—CO-gGlu-2xADO | 36K, C-terminal |
| 104 | HOOC—$(CH_2)_{14}$—CO-gGlu-2xADO | 36K, C-terminal |
| 72 | HOOC—$(CH_2)_{14}$—CO-gGlu-2xADO | 32K, C-terminal |
| 105 | HOOC—$(CH_2)_{14}$—CO-gGlu-2xADO | 32K, C-terminal |
| 104 | HOOC—$(CH_2)_{16}$—CO-gGlu-2xADO | 36K, C-terminal |
| 73 | HOOC—$(CH_2)_{14}$—CO-gGlu-2xADO | 21K, 29K |
| 32 | 4-HOOC—$(C_6H_4)$—O—$(CH_2)_{10}$—CO-Trx-gGlu-2xADO | 21K, C-terminal |
| 98 | 4-HOOC—$(C_6H_4)$—O—$(CH_2)_{10}$—CO-Trx-gGlu-2xADO | 21K, C-terminal |
| 19 | HOOC—$(CH_2)_{18}$—CO-Trx-gGlu-2xADO | C-terminal |
| 19 | HOOC—$(CH_2)_{16}$—CO-Trx-gGlu-2xADO | C-terminal. |

24. An EGF(A) derivative comprising an EGF(A) peptide analogue attached to a substituent comprising at least one fatty acid group, wherein the EGF(A) peptide analogue is selected from the group consisting of SEQ ID NOs: 3-4, 6-19, 21-45, 47-53, 55, and 58-106.

25. The EGF(A) derivative according to claim 24, comprising one or two substituent(s) selected from the group consisting of:

HOOC—$(CH_2)_{18}$—CO-gGlu-2xADO—
HOOC—$(CH_2)_{18}$—CO—NH—$CH_2$—$(C_6H_{10})$—CO-gGlu-2xADO—
HOOC—$(CH_2)_{16}$—CO-gGlu-2xADO—
HOOC—$(CH_2)_{16}$—CO-gGlu-2xADO—NH—$CH_2$—$(C_6H_4)$—$CH_2$—
HOOC—$(CH_2)_{16}$—CO-gGlu-
HOOC—$(CH_2)_{16}$—CO—NH—$CH_2$—$(C_6H_{10})$—CO-gGlu-2xADO—
HOOC—$(CH_2)_{14}$—CO-gGlu-2xADO—
HOOC—$(CH_2)_{14}$—CO-gGlu-
HOOC—$(CH_2)_{14}$—CO-gGlu-2xADO—
HOOC—$(CH_2)_{12}$—CO-gGlu-2xADO—
4-HOOC—$(C_6H_4)$—O—$(CH_2)_{10}$—CO-gGlu-2xADO—
4-HOOC—$(C_6H_4)$—O—$(CH_2)_{10}$—CO-gGlu-3xADO—
4-HOOC—$(C_6H_4)$—O—$(CH_2)_{10}$—CO-gGlu-
4-HOOC—$(C_6H_4)$—O—$(CH_2)_{10}$—CO-2xgGlu-
4-HOOC—$(C_6H_4)$—O—$(CH_2)_{10}$—CO-gGlu-3xGly-
4-HOOC—$(C_6H_4)$—O—$(CH_2)_{10}$—CO-2xgGlu-2xADO—
4-HOOC—$(C_6H_4)$—O—$(CH_2)_{10}$—CO-gGlu-TtdSuc-
4-HOOC—$(C_6H_4)$—O—$(CH_2)_9$—CO—
4-HOOC—$(C_6H_4)$—O—$(CH_2)_{10}$—CO-gGlu-4xADO—
4-HOOC—$(C_6H_4)$—O—$(CH_2)_{10}$—CO—NH—$CH_2$—$(C_6H_{10})$—CO-gGlu-2xADO—
4-HOOC—$(C_6H_4)$—O—$(CH_2)_9$—CO-gGlu-2xADO—
3-HOOC—$(C_6H_4)$—O—$(CH_2)_9$—CO-gGlu-2xADO—
3-HO-Isoxazole-$(CH_2)_{12}$—CO-gGlu-2xADO—
$HOS(O)_2$—$(CH_2)_{15}$—CO-gGlu-2xADO—NH—$CH_2$—$(C_6H_4)$—$CH_2$—
$HOS(O)_2$—$(CH_2)_{13}$—CO-gGlu-2xADO—
Tetrazolyl-$(CH_2)_{15}$—CO—NH—$SO_2$—$(CH_2)_3$—CO-ADO-ADO—NH—$CH_2$—$(C_6H_4)$—$CH_2$—
Tetrazolyl-$(CH_2)_{12}$—CO-gGlu-2xADO—
Tetrazolyl-$(CH_2)_{15}$—CO-gGlu-2xADO- and
$MeS(O)_2NH(CO)NH$—$(CH_2)_{12}$—CO-gGlu-2xADO-.

26. An EGF(A) derivative selected from the group consisting of:
  i.

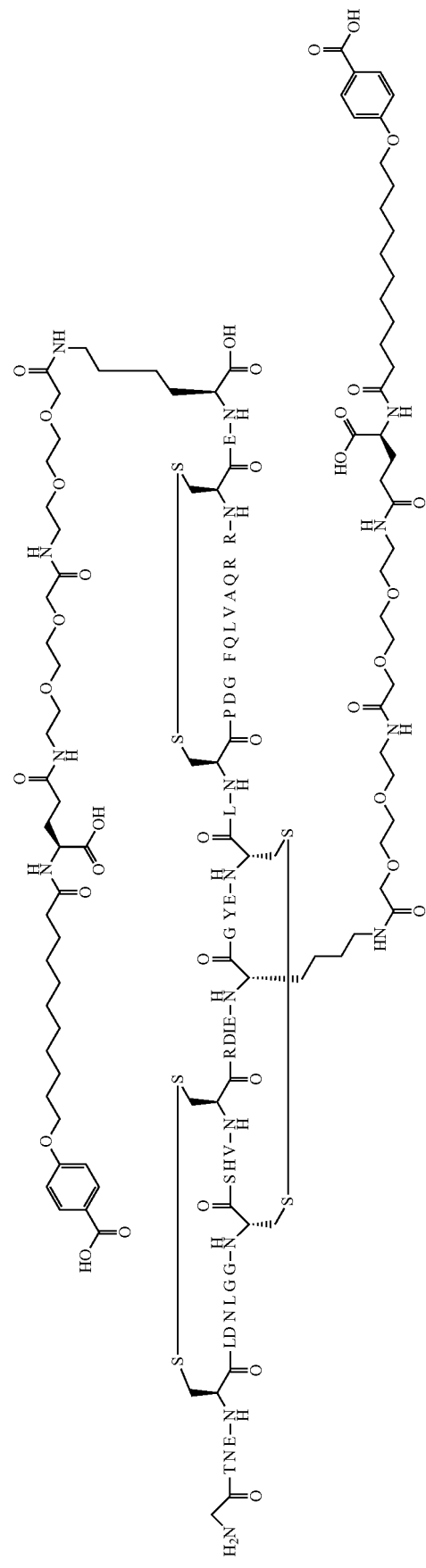

wherein the amino acid sequence of EGF(A) derivative (i) is SEQ ID NO: 32,
  ii.

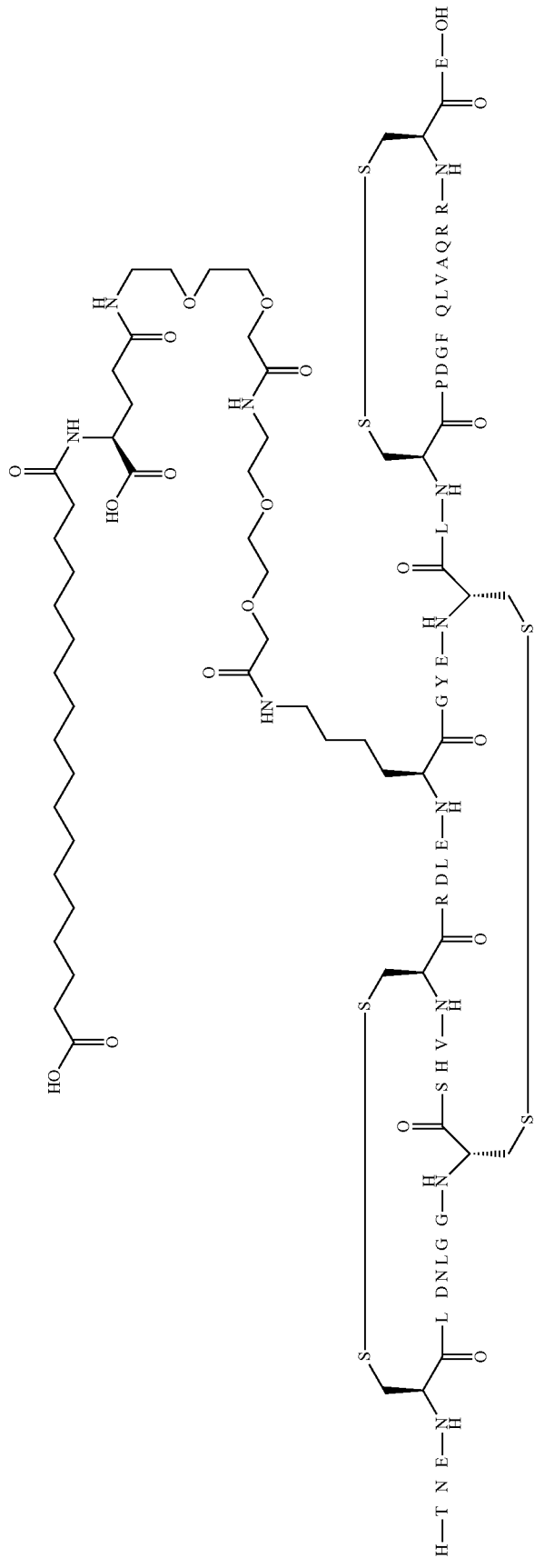

wherein the amino acid sequence of EGF(A) derivative (ii) is SEQ ID NO: 76,
   iii.

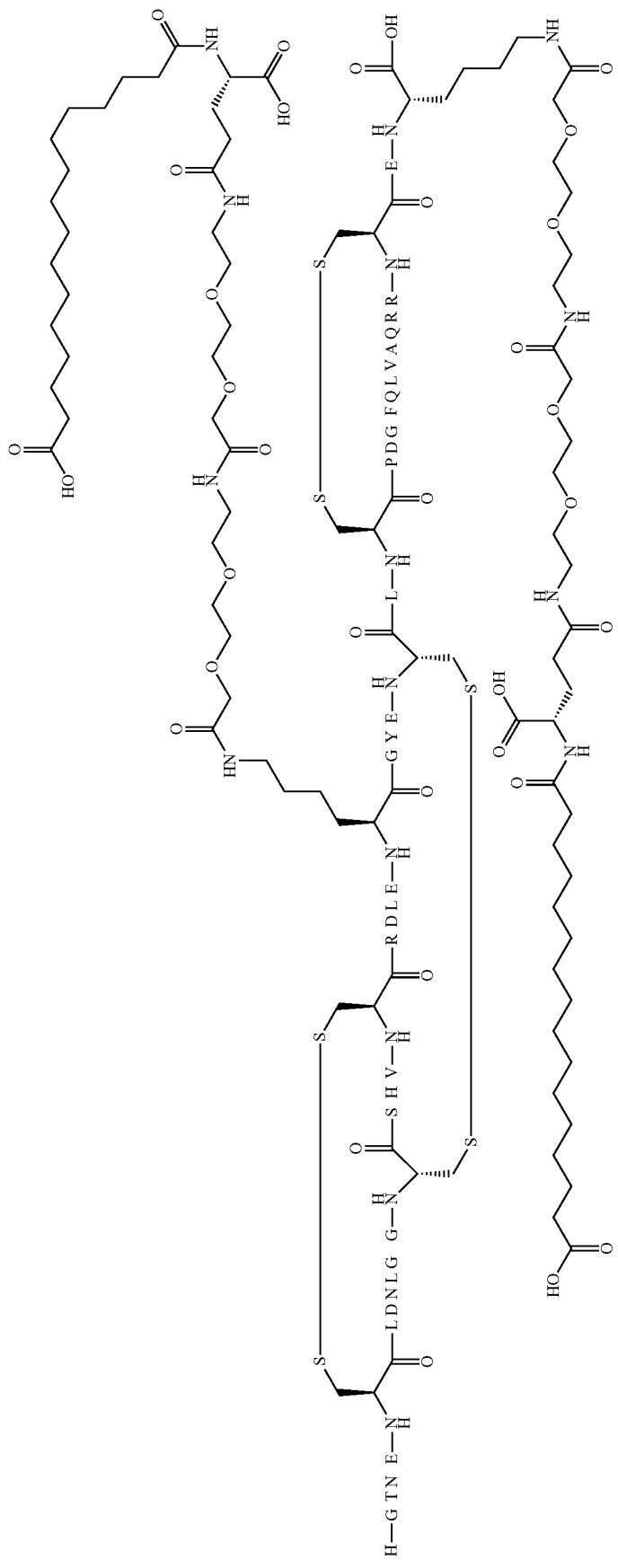

wherein the amino acid sequence of EGF(A) derivative (iii) is SEQ ID NO: 32,
iv.
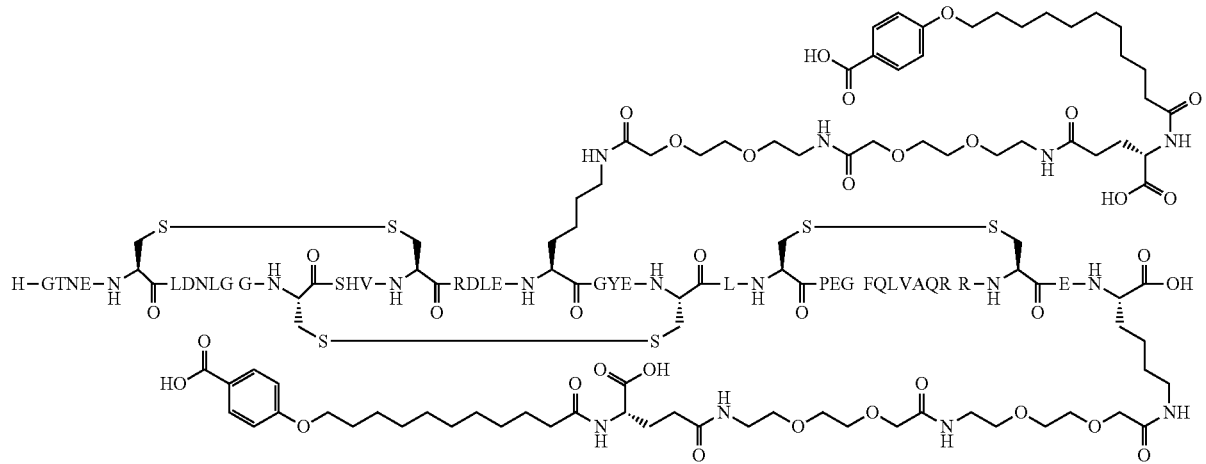
wherein the amino acid sequence of EGF(A) derivative (iv) is SEQ ID NO: 98,
v. N{Alpha}(N{Epsilon-313}-[(4S)-4-carboxy-4-[11-(4-carboxyphenoxy)undecanoylamino]butanoyl]-[Leu301,Arg309,Glu312,Lys313,Glu321]-LDL-R-(293-332)-peptidyl)-N{Epsilon}[(4S)-4-carboxy-4-[11-(4-carboxyphenoxy)undecanoylamino]butanoyl] Lys,
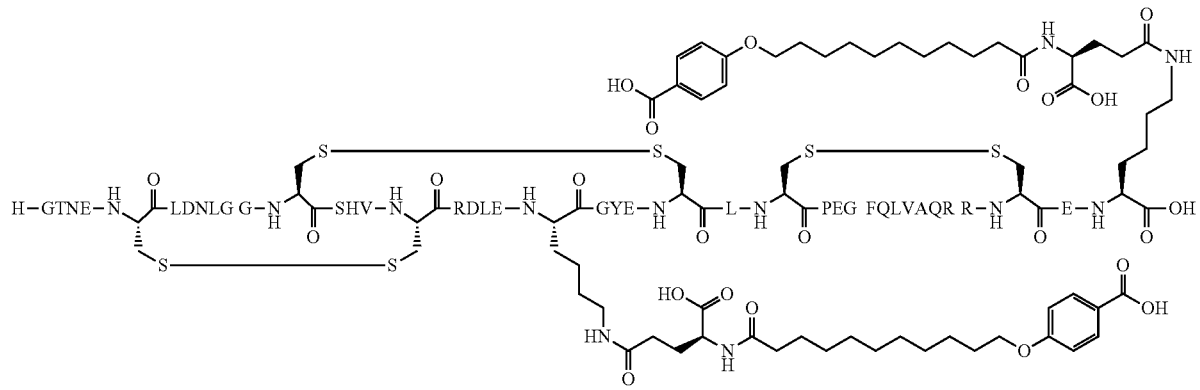

wherein the amino acid sequence of EGF(A) derivative (v) is SEQ ID NO: 98,
vi.
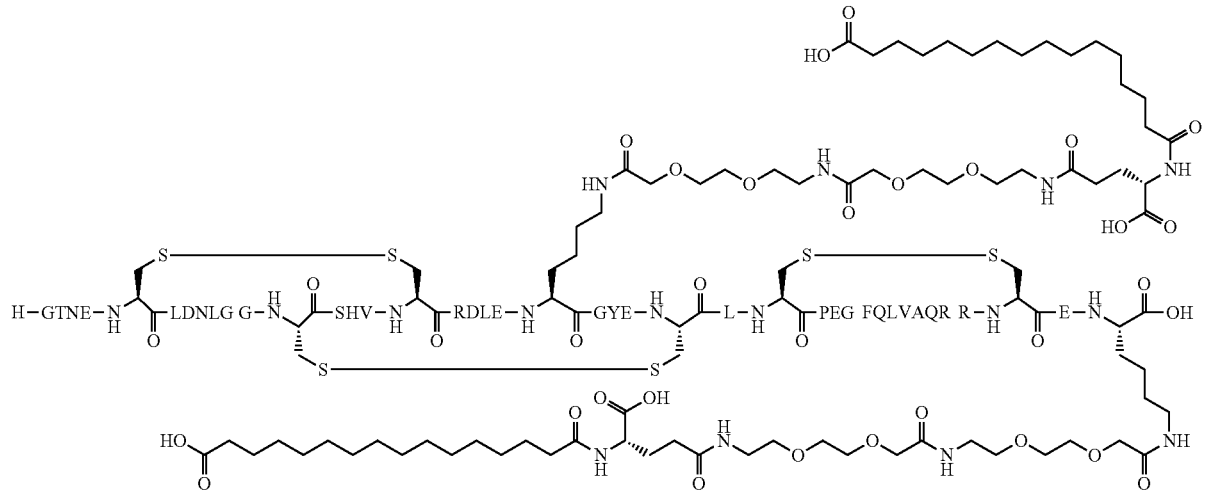
wherein the amino acid sequence of EGF(A) derivative (vi) is SEQ ID NO: 98,
vii.
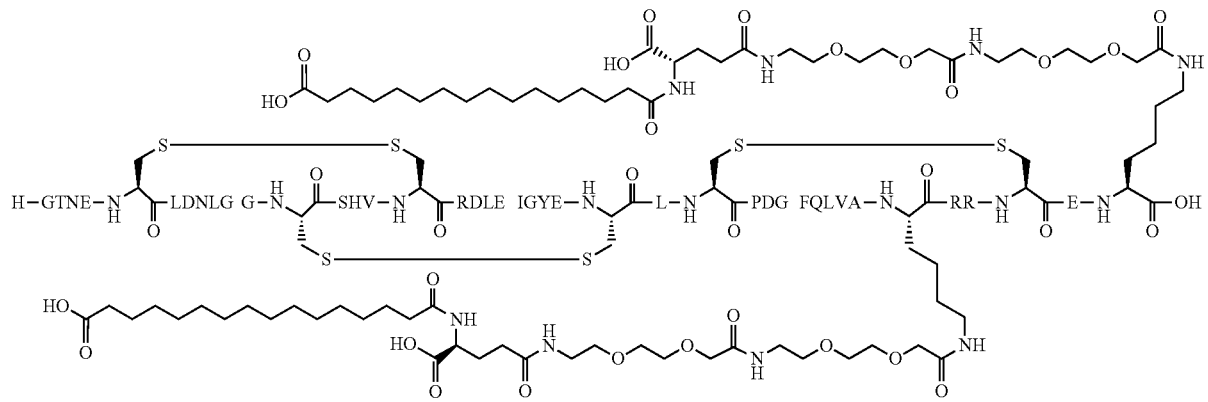
wherein the amino acid sequence of EGF(A) derivative (vii) is SEQ ID NO:78,
viii.
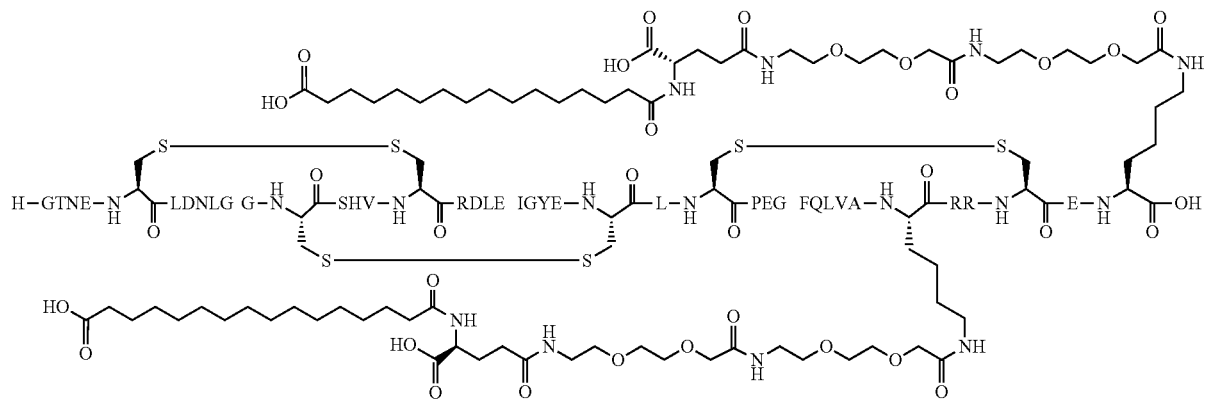

wherein the amino acid sequence of EGF(A) derivative (viii) is SEQ ID NO:104,
ix.
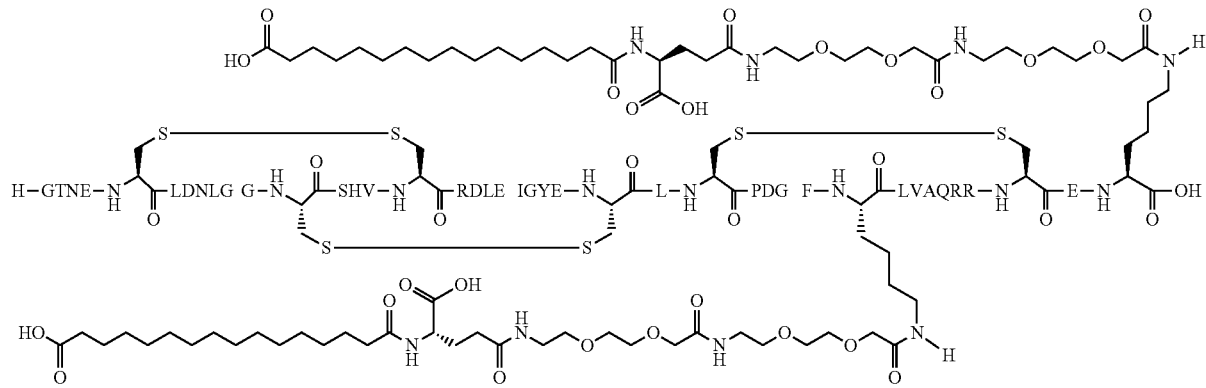
wherein the amino acid sequence of EGF(A) derivative (ix) is SEQ ID NO:72, and
x.
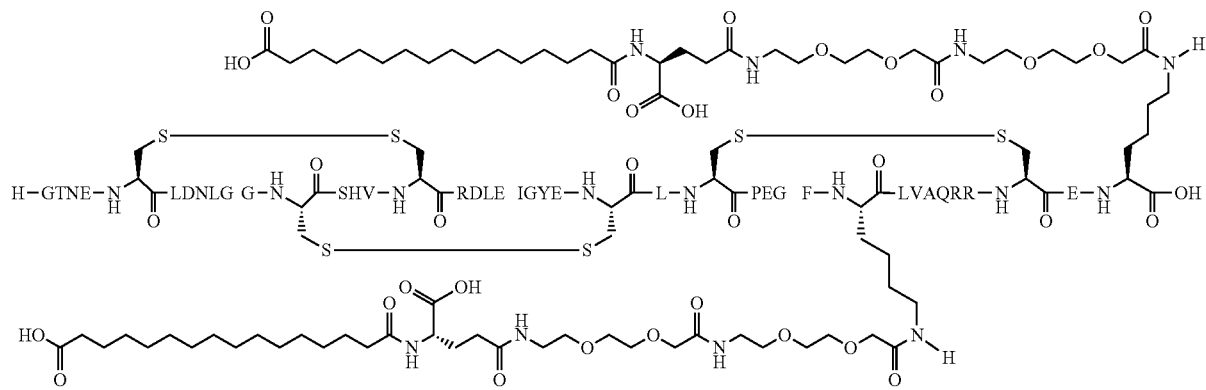
wherein the amino acid sequence of EGF(A) derivative (x) is SEQ ID NO:105.
27. A compound of
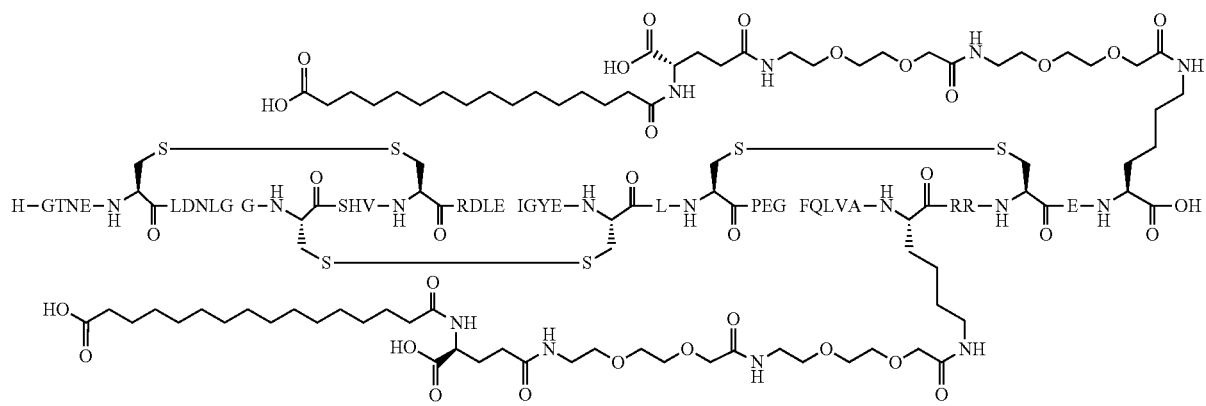

wherein the amino acid sequence of the compound is SEQ ID NO: 104.
28. An EGF(A) derivative selected from the group consisting of:
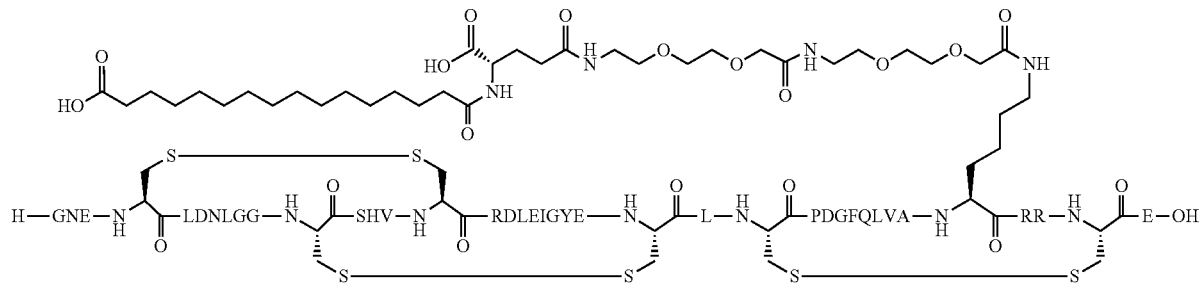
wherein the amino acid sequence of EGF(A) derivative
(a) is SEQ ID NO: 66,
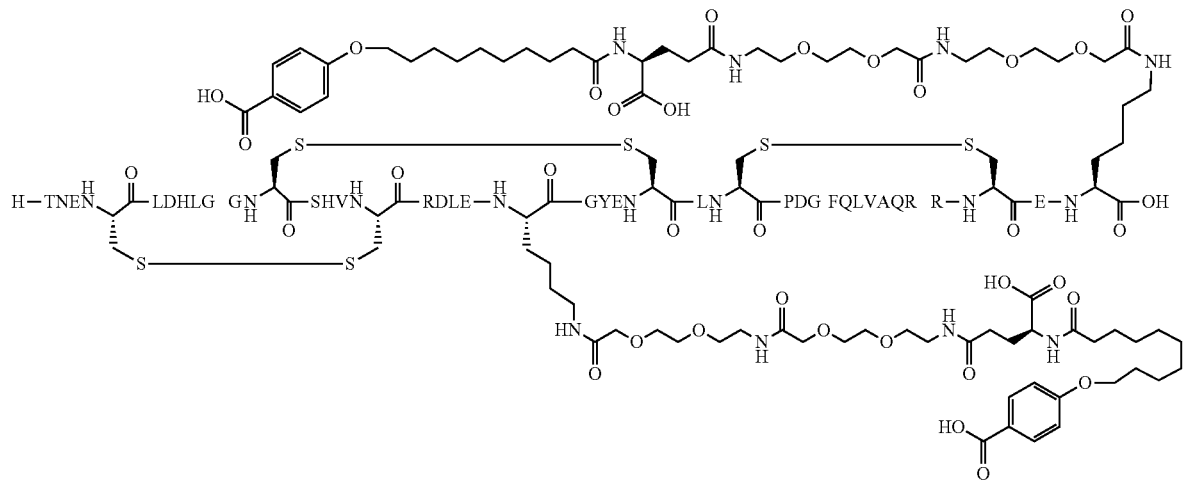
wherein the amino acid sequence of EGF(A) derivative
(b) is SEQ ID NO:74,
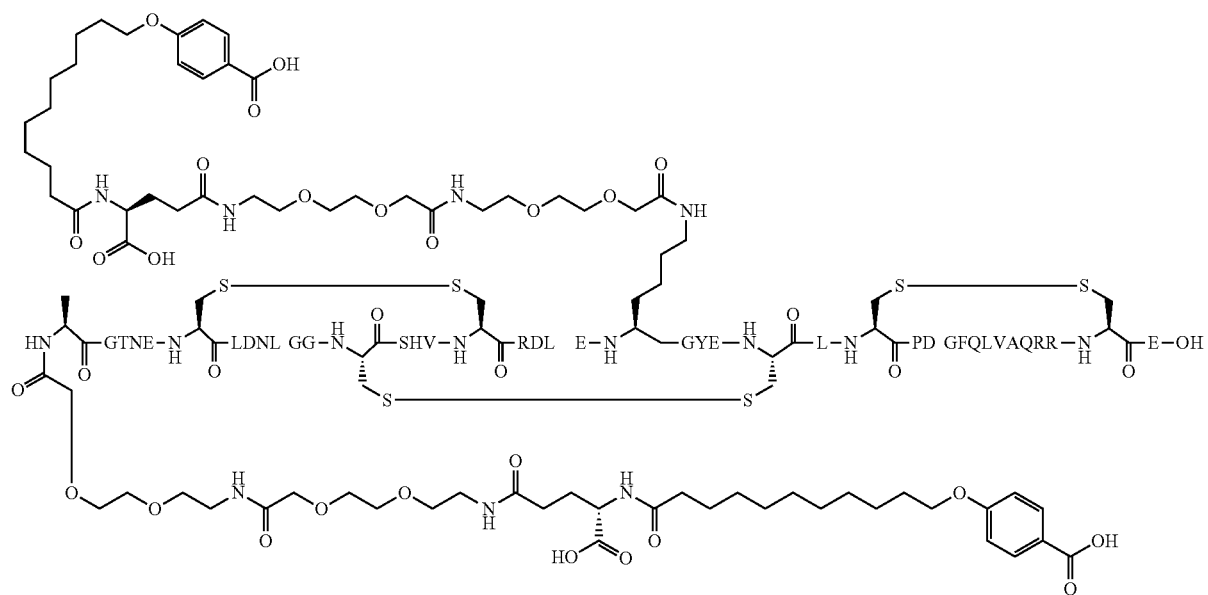

wherein the amino acid sequence of EGF(A) derivative
(c) is SEQ ID NO:75,
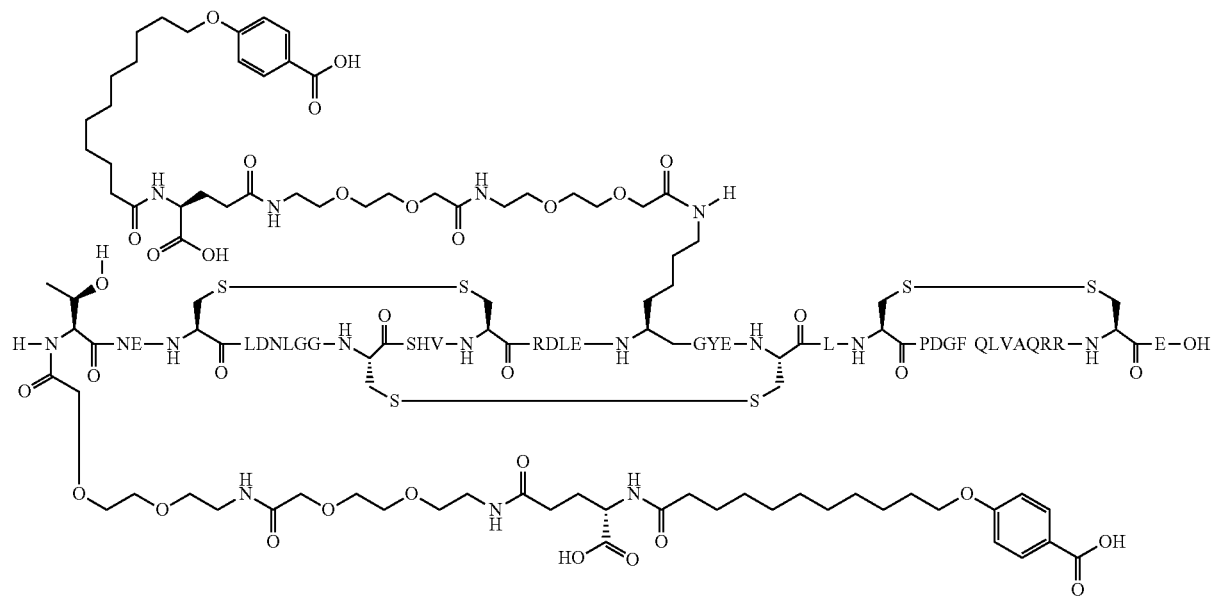
wherein the amino acid sequence of EGF(A) derivative
(d) is SEQ ID NO:76,
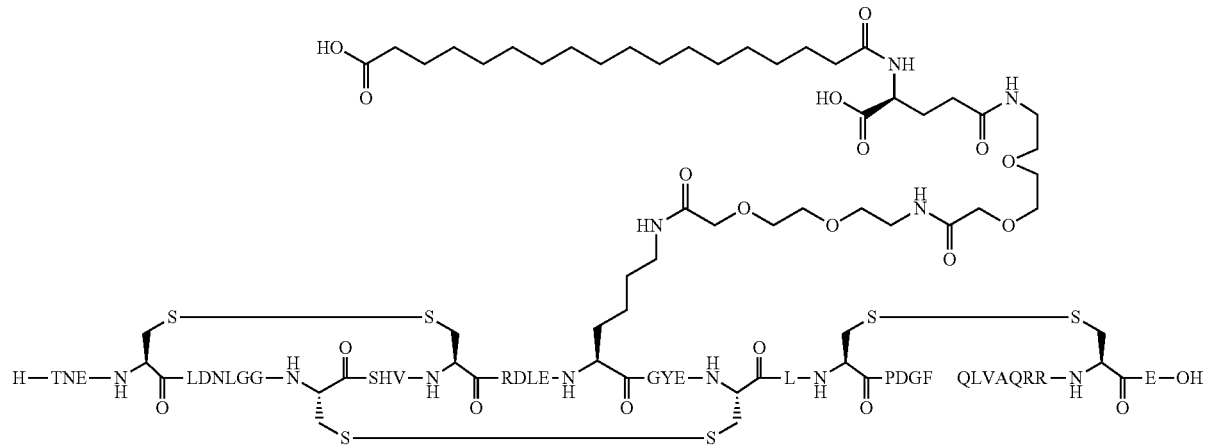
wherein the amino acid sequence of EGF(A) derivative
(e) is SEQ ID NO:76,

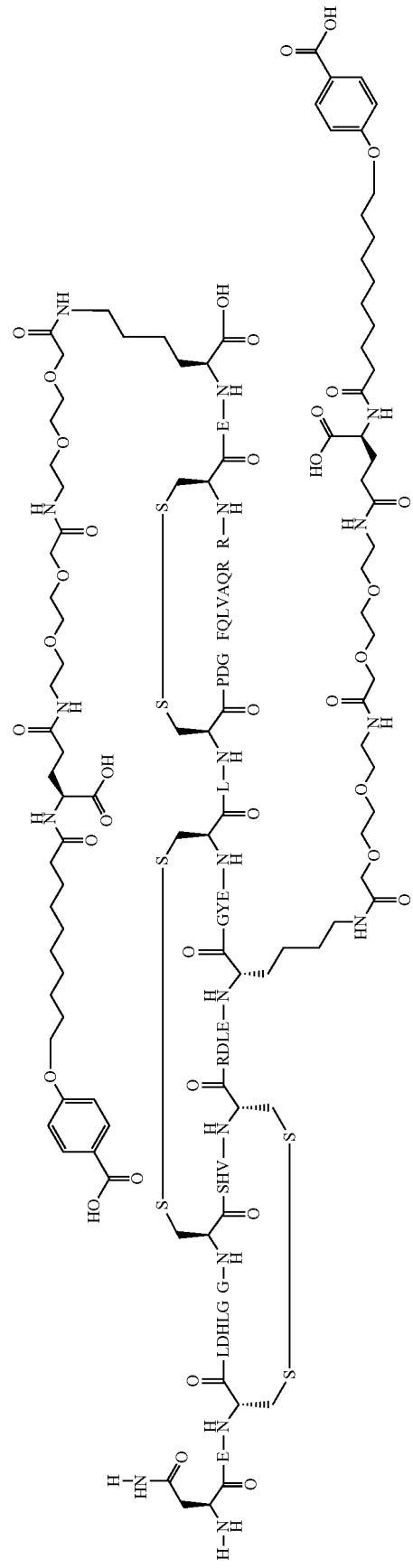

wherein the amino acid sequence of EGF(A) derivative (f) is SEQ ID NO:83,

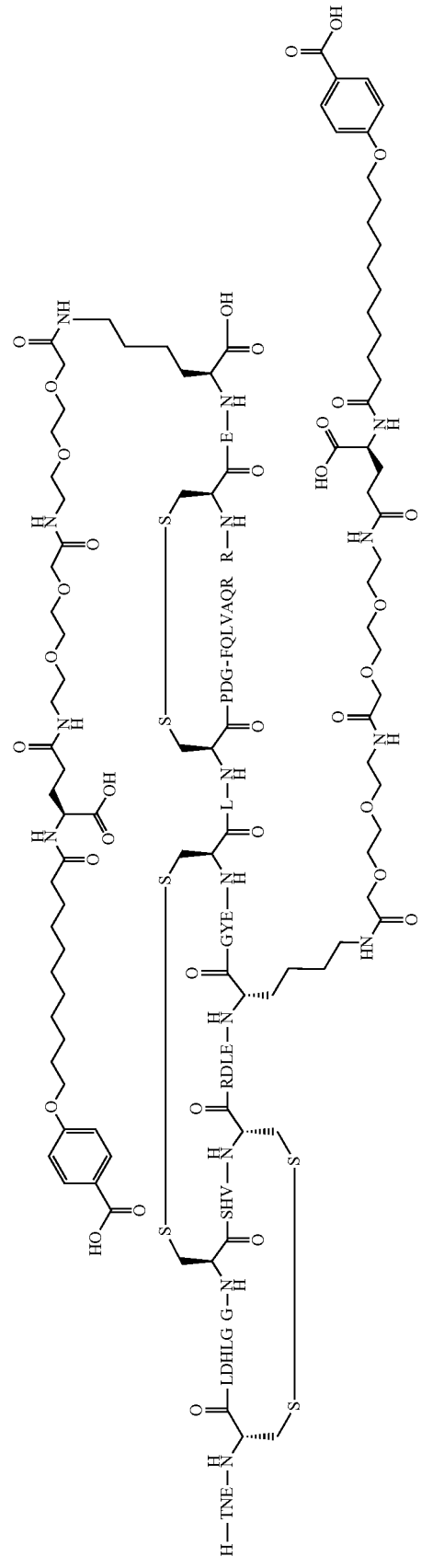

wherein the amino acid sequence of EGF(A) derivative (g) is SEQ ID NO: 74, and

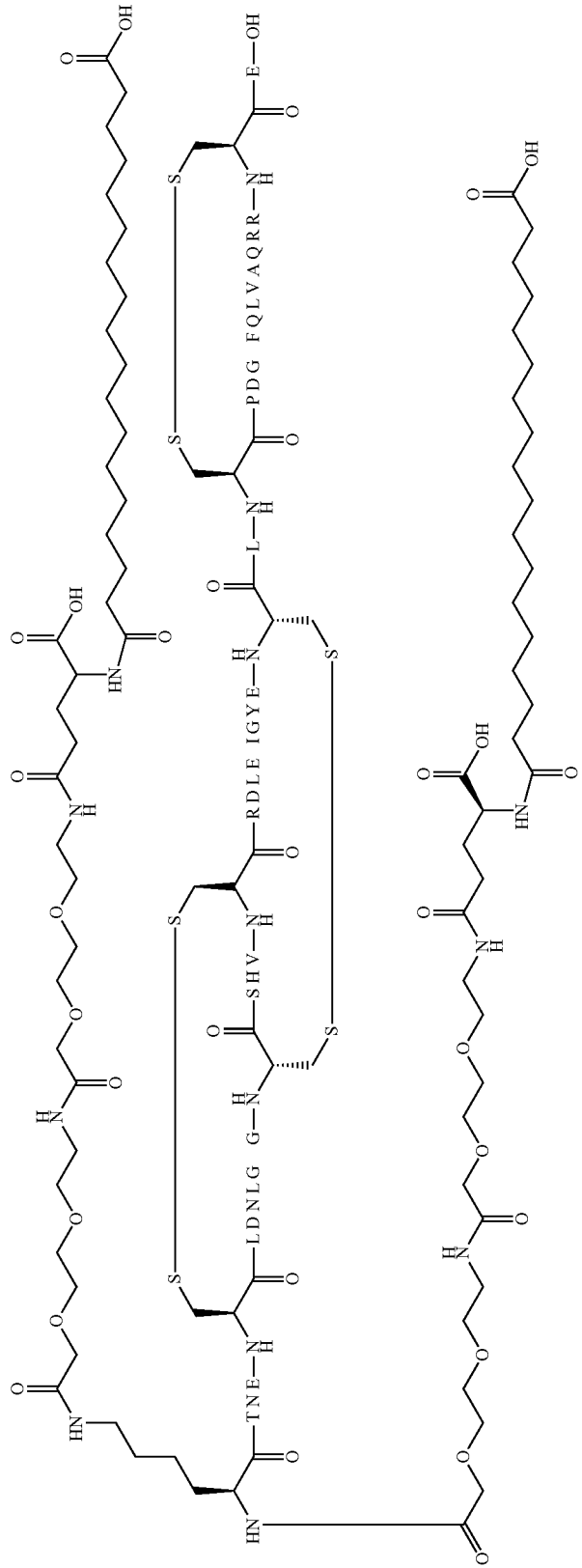

wherein the amino acid sequence of EGF(A) derivative (h) is SEQ ID NO: 12.

* * * * *

UNITED STATES PATENT AND TRADEMARK OFFICE
CERTIFICATE OF CORRECTION

PATENT NO. : 10,822,385 B2  
APPLICATION NO. : 16/069932  
DATED : November 3, 2020  
INVENTOR(S) : Jianhe Chen et al.

It is certified that error appears in the above-identified patent and that said Letters Patent is hereby corrected as shown below:

In the Claims

At Column 416, Claim number 23, beginning at Line number 52, please amend as follows:

| SEQ ID NO: | Substituent | Attachment site(s) |
|---|---|---|
| 4 | HOOC-(CH$_2$)$_{16}$-CO-gGlu-2xADO | C-terminal |
| 6 | HOOC-(CH$_2$)$_{16}$-CO-gGlu-2xADO-NH-CH$_2$-(C$_6$H$_4$)-CH$_2$- | N-terminal |
| 7 | HOOC-(CH$_2$)$_{16}$-CO-gGlu-2xADO | 7K |
| 8 | HOOC-(CH$_2$)$_{16}$-CO-gGlu-2xADO | 38K |
| 6 | HOS(O)$_2$-(CH$_2$)$_{15}$-CO-gGlu-2xADO-NH-CH$_2$-(C$_6$H$_4$)-CH$_2$- | N-terminal |
| 8 | HOOC-(CH$_2$)$_{16}$-CO-gGlu-2xADO | N-terminal, |

Signed and Sealed this  
Twenty-seventh Day of July, 2021

Drew Hirshfeld  
*Performing the Functions and Duties of the*  
*Under Secretary of Commerce for Intellectual Property and*  
*Director of the United States Patent and Trademark Office*

| SEQ ID NO: | Substituent | Attachment site(s) |
|---|---|---|
| | | 38K |
| 11 | HOOC-(CH$_2$)$_{16}$-CO-gGlu-2xADO | C-terminal |
| 12 | HOOC-(CH$_2$)$_{16}$-CO-gGlu-2xADO | N-terminal |
| 13 | HOOC-(CH$_2$)$_{16}$-CO-gGlu-2xADO | N-terminal, C-terminal |
| 13 | 4-HOOC-(C$_6$H$_4$)-O-(CH$_2$)$_{10}$-CO-gGlu-2xADO | N-terminal, C-terminal |
| 15 | 4-HOOC-(C$_6$H$_4$)-O-(CH$_2$)$_{10}$-CO-gGlu-2xADO | 40K, C-terminal |
| 16 | 4-HOOC-(C$_6$H$_4$)-O-(CH$_2$)$_{10}$-CO-gGlu-2xADO | 38K, C-terminal |
| 17 | 4-HOOC-(C$_6$H$_4$)-O-(CH$_2$)$_{10}$-CO-gGlu-2xADO | 29K, C-terminal |
| 19 | HOOC-(CH$_2$)$_{16}$-CO-gGlu-2xADO | C-terminal |
| 6 | HOOC-(CH$_2$)$_{16}$-CO-gGlu-2xADO | N-terminal |
| 21 | HOOC-(CH$_2$)$_{16}$-CO-gGlu-2xADO | 29K |
| 22 | HOOC-(CH$_2$)$_{16}$-CO-gGlu-2xADO | 32K |
| 23 | HOOC-(CH$_2$)$_{16}$-CO-gGlu-2xADO | N-terminal |
| 24 | HOOC-(CH$_2$)$_{16}$-CO-gGlu-2xADO | C-terminal |
| 25 | HOOC-(CH$_2$)$_{16}$-CO-gGlu-2xADO | N-terminal |
| 27 | HOOC-(CH$_2$)$_{16}$-CO-gGlu-2xADO | 8K |
| 28 | 4-HOOC-(C$_6$H$_4$)-O-(CH$_2$)$_{10}$-CO-gGlu-2xADO | N-terminal, 2K |
| 30 | HOOC-(CH$_2$)$_{16}$-CO-gGlu-2xADO | 17K |
| 31 | HOOC-(CH$_2$)$_{16}$-CO-gGlu-2xADO | 26K |
| 32 | 4-HOOC-(C$_6$H$_4$)-O-(CH$_2$)$_{10}$-CO-gGlu-2xADO | 21K, C-terminal |
| 33 | HOOC-(CH$_2$)$_{16}$-CO-gGlu-2xADO | 34K |
| 34 | HOOC-(CH$_2$)$_{16}$-CO-gGlu-2xADO | 33K |

| SEQ ID NO: | Substituent | Attachment site(s) |
|---|---|---|
| 35 | HOOC-(CH$_2$)$_{16}$-CO-gGlu-2xADO | 31K |
| 36 | HOOC-(CH$_2$)$_{16}$-CO-gGlu-2xADO | 30K |
| 37 | HOOC-(CH$_2$)$_{16}$-CO-gGlu-2xADO | 28K |
| 38 | HOOC-(CH$_2$)$_{16}$-CO-gGlu-2xADO | 37K |
| 39 | HOOC-(CH$_2$)$_{16}$-CO-gGlu-2xADO | 21K |
| 40 | HOOC-(CH$_2$)$_{16}$-CO-gGlu-2xADO | 36K |
| 41 | HOOC-(CH$_2$)$_{16}$-CO-gGlu-2xADO | 24K |
| 42 | HOOC-(CH$_2$)$_{16}$-CO-gGlu-2xADO | 23K |
| 43 | HOOC-(CH$_2$)$_{16}$-CO-gGlu-2xADO | C-terminal |
| 44 | HOOC-(CH$_2$)$_{16}$-CO-gGlu-2xADO | 22K |
| 45 | HOOC-(CH$_2$)$_{16}$-CO-gGlu-2xADO | 19K |
| 47 | HOOC-(CH$_2$)$_{16}$-CO-gGlu-2xADO | C-terminal |
| 48 | HOOC-(CH$_2$)$_{16}$-CO-gGlu-2xADO | C-terminal |
| 49 | HOOC-(CH$_2$)$_{16}$-CO-gGlu-2xADO | N-terminal |
| 50 | HOOC-(CH$_2$)$_{16}$-CO-gGlu-2xADO | N-terminal |
| 51 | HOOC-(CH$_2$)$_{16}$-CO-gGlu-2xADO | 14K |
| 52 | HOOC-(CH$_2$)$_{16}$-CO-gGlu-2xADO | 13K |
| 53 | HOOC-(CH$_2$)$_{16}$-CO-gGlu-2xADO | 11K |
| 55 | HOOC-(CH$_2$)$_{16}$-CO-gGlu-2xADO | C-terminal |
| 58 | HOOC-(CH$_2$)$_{16}$-CO-gGlu-2xADO | C-terminal |
| 60 | HOOC-(CH$_2$)$_{16}$-CO-gGlu-2xADO | C-terminal |
| 61 | HOOC-(CH$_2$)$_{16}$-CO-gGlu-2xADO | C-terminal |
| 9 | HOOC-(CH$_2$)$_{16}$-CO-gGlu-2xADO | C-terminal |
| 10 | HOOC-(CH$_2$)$_{16}$-CO-gGlu-2xADO | C-terminal |
| 6 | Tetrazolyl-(CH$_2$)$_{15}$-CO-NH-SO$_2$-(CH$_2$)$_3$-CO- | N-terminal |

| SEQ ID NO: | Substituent | Attachment site(s) |
|---|---|---|
| | ADO-ADO-NH-CH$_2$-(C$_6$H$_4$)-CH$_2$- | |
| 14 | HOOC-(CH[[2]]$_2$)$_{16}$-CO-gGlu-2xADO | 36K |
| 26 | HOOC-(CH[[2]]$_2$)$_{16}$-CO-gGlu-2xADO | N-terminal |
| 63 | HOOC-(CH[[2]]$_2$)$_{16}$-CO-gGlu-2xADO | 4K |
| 64 | HOOC-(CH[[2]]$_2$)$_{16}$-CO-gGlu-2xADO | 2K |
| 65 | HOOC-(CH[[2]]$_2$)$_{16}$-CO-gGlu-2xADO | N-terminal |
| 67 | HOOC-(CH[[2]]$_2$)$_{16}$-CO-gGlu-2xADO | C-terminal |
| 68 | 4-HOOC-(C$_6$H$_4$)-O-(CH$_2$)$_{10}$-CO-gGlu-3xADO and 4-HOOC-(C$_6$H$_4$)-O-(CH$_2$)$_{10}$-CO-gGlu-2xADO | N-terminal, C-terminal |
| 17 | 4-HOOC-(C$_6$H$_4$)-O-(CH$_2$)$_9$-CO-gGlu-2xADO | 29K, C-terminal |
| 4 | HOOC-(CH$_2$)$_{14}$-CO-gGlu-2xADO | C-terminal |
| 4 | HOOC-(CH$_2$)$_{18}$-CO-gGlu-2xADO | C-terminal |
| 4 | HOOC-(CH$_2$)$_{16}$-CO-gGlu | C-terminal |
| 17 | HOOC-(CH$_2$)$_{12}$-CO-gGlu-2xADO | 29K, C-terminal |
| 17 | HOOC-(CH$_2$)$_{14}$-CO-gGlu-2xADO | 29K, C-terminal |
| 69 | 4-HOOC-(C$_6$H$_4$)-O-(CH$_2$)$_9$-CO-gGlu-2xADO | 21K, C-terminal |
| 70 | 4-HOOC-(C$_6$H$_4$)-O-(CH$_2$)$_{10}$-CO-gGlu-2xADO | 21K, 36K |
| 71 | 4-HOOC-(C$_6$H$_4$)-O-(CH$_2$)$_{10}$-CO-gGlu-2xADO | 21K, 32K |
| 39 | 4-HOOC-(C$_6$H$_4$)-O-(CH$_2$)$_{10}$-CO-gGlu-2xADO | N-terminal, 21K |
| 72 | 4-HOOC-(C$_6$H$_4$)-O-(CH$_2$)$_{10}$-CO-gGlu-2xADO | 32K, C-terminal |
| 73 | 4-HOOC-(C$_6$H$_4$)-O-(CH$_2$)$_{10}$-CO-gGlu-2xADO | 21K, 29K |
| 69 | 4-HOOC-(C$_6$H$_4$)-O-(CH$_2$)$_{10}$-CO-gGlu-2xADO | 21K, C-terminal |
| 77 | 4-HOOC-(C$_6$H$_4$)-O-(CH$_2$)$_{10}$-CO-gGlu-2xADO | 21K, C-terminal |
| 78 | 4-HOOC-(C$_6$H$_4$)-O-(CH$_2$)$_{10}$-CO-gGlu-2xADO | 36K, C-terminal |

| SEQ ID NO: | Substituent | Attachment site(s) |
|---|---|---|
| 32 | 4-HOOC-$(C_6H_4)$-O-$(CH_2)_{10}$-CO-gGlu | 21K, C-terminal |
| 32 | 4-HOOC-$(C_6H_4)$-O-$(CH_2)_{10}$-CO-2xgGlu | 21K, C-terminal |
| 32 | 4-HOOC-$(C_6H_4)$-O-$(CH_2)_{10}$-CO-gGlu-3xGly | 21K, C-terminal |
| 32 | 4-HOOC-$(C_6H_4)$-O-$(CH_2)_{10}$-CO-2xgGlu-2xADO | 21K, C-terminal |
| 32 | 3-HOOC-$(C_6H_4)$-O-$(CH_2)_9$-CO-gGlu-2xADO | 21K, C-terminal |
| 82 | HOOC-$(CH_2)_{16}$-CO-gGlu-2xADO | C-terminal |
| 4 | 4-HOOC-$(C_6H_4)$-O-$(CH_2)_{10}$-CO-gGlu-2xADO | N-terminal, C-terminal |
| 69 | 3-HO-Isoxazole-$(CH_2)_{12}$-CO-gGlu-2xADO | 21K, C-terminal |
| 32 | 3-HO-Isoxazole-$(CH_2)_{12}$-CO-gGlu-2xADO | 21K, C-terminal |
| 84 | 4-HOOC-$(C_6H_4)$-O-$(CH_2)_{10}$-CO-gGlu-2xADO | 17K, C-terminal |
| 85 | 4-HOOC-$(C_6H_4)$-O-$(CH_2)_{10}$-CO-gGlu-2xADO | 32K, C-terminal |
| 86 | 4-HOOC-$(C_6H_4)$-O-$(CH_2)_{10}$-CO-gGlu-2xADO | 22K, C-terminal |
| 87 | 4-HOOC-$(C_6H_4)$-O-$(CH_2)_{10}$-CO-gGlu-2xADO | N-terminal, C-terminal |
| 88 | 4-HOOC-$(C_6H_4)$-O-$(CH_2)_{10}$-CO-gGlu-2xADO | 17K, 36K |
| 89 | 4-HOOC-$(C_6H_4)$-O-$(CH_2)_{10}$-CO-gGlu-2xADO | 17K, 21K |
| 90 | 4-HOOC-$(C_6H_4)$-O-$(CH_2)_{10}$-CO-gGlu-2xADO | N-terminal, C-terminal |
| 91 | 4-HOOC-$(C_6H_4)$-O-$(CH_2)_{10}$-CO-gGlu-2xADO | 32K, 36K |
| 92 | 4-HOOC-$(C_6H_4)$-O-$(CH_2)_{10}$-CO-gGlu-2xADO | N-terminal, C-terminal |
| 93 | 4-HOOC-$(C_6H_4)$-O-$(CH_2)_{10}$-CO-gGlu-2xADO | 21K, C-terminal |
| 11 | 4-HOOC-$(C_6H_4)$-O-$(CH_2)_{10}$-CO-gGlu-2xADO | N-terminal, C-terminal |

| SEQ ID NO: | Substituent | Attachment site(s) |
|---|---|---|
| 40 | 4-HOOC-$(C_6H_4)$-O-$(CH_2)_{10}$-CO-gGlu-2xADO | N-terminal, 26K |
| 22 | 4-HOOC-$(C_6H_4)$-O-$(CH_2)_{10}$-CO-gGlu-2xADO | N-terminal, 32K |
| 94 | 4-HOOC-$(C_6H_4)$-O-$(CH_2)_{10}$-CO-gGlu-2xADO | 17K, C-terminal |
| 106 | 4-HOOC-$(C_6H_4)$-O-$(CH_2)_{10}$-CO-gGlu-2xADO | 17K, 32K |
| 30 | 4-HOOC-$(C_6H_4)$-O-$(CH_2)_{10}$-CO-gGlu-2xADO | N-terminal, 17K |
| 95 | 4-HOOC-$(C_6H_4)$-O-$(CH_2)_{10}$-CO-gGlu-2xADO | 29K, C-terminal |
| 32 | HOOC-$(CH_2)_{14}$-CO-gGlu-2xADO | 21K, C-terminal |
| 32 | HOOC-(CH2)14-CO-gGlu | 21K, C-terminal |
| 96 | 4-HOOC-$(C_6H_4)$-O-$(CH_2)_{10}$-CO-gGlu-2xADO | 21K, C-terminal |
| 32 | 4-HOOC-$(C_6H_4)$-O-$(CH_2)_{10}$-CO-gGlu-TtdSuc | 21K, C-terminal |
| 97 | 4-HOOC-$(C_6H_4)$-O-$(CH_2)_{10}$-CO-gGlu-TtdSuc | 21K, C-terminal |
| 98 | 4-HOOC-$(C_6H_4)$-O-$(CH_2)_{10}$-CO-gGlu-2xADO | 21K, C-terminal |
| 19 | HOOC-$(CH_2)_{18}$-CO-gGlu-2xADO | C-terminal |
| 99 | 4-HOOC-$(C_6H_4)$-O-$(CH_2)_{10}$-CO-gGlu-2xADO | 21K, 22K |
| 102 | 4-HOOC-$(C_6H_4)$-O-$(CH_2)_{10}$-CO-gGlu-2xADO | 19K, 21K |
| 69 | 4-HOOC-$(C_6H_4)$-O-$(CH_2)_9$-CO | 21K, C-terminal |
| 32 | Tetrazolyl-$(CH_2)_{12}$-CO-gGlu-2xADO | 21K, C-terminal |
| 32 | HOS(O)$_2$-$(CH_2)_{13}$-CO-gGlu-2xADO | 21K, C-terminal |
| 32 | MeS(O)$_2$NH(CO)NH-$(CH_2)_{12}$-CO-gGlu-2xADO | 21K, C-terminal |
| 98 | 4-HOOC-$(C_6H_4)$-O-$(CH_2)_{10}$-CO-gGlu | 21K, C-terminal |
| 98 | HOOC-$(CH_2)_{14}$-CO-gGlu-2xADO | 21K, C-terminal |
| 32 | Tetrazolyl-$(CH_2)_{15}$-CO-gGlu-2xADO | 21K, C-terminal |
| 98 | HOOC-$(CH_2)_{14}$-CO-gGlu | 21K, C-terminal |
| 103 | 4-HOOC-$(C_6H_4)$-O-$(CH_2)_{10}$-CO-gGlu-2xADO | 21K, C-terminal |

| SEQ ID NO: | Substituent | Attachment site(s) |
|---|---|---|
| 32 | 4-HOOC-($C_6H_4$)-O-$(CH_2)_{10}$-CO-gGlu-4xADO | 21K, C-terminal |
| 78 | HOOC-$(CH_2)_{14}$-CO-gGlu-2xADO | 36K, C-terminal |
| 104 | HOOC-$(CH_2)_{14}$-CO-gGlu-2xADO | 36K, C-terminal |
| 72 | HOOC-$(CH_2)_{14}$-CO-gGlu-2xADO | 32K, C-terminal |
| 105 | HOOC-$(CH_2)_{14}$-CO-gGlu-2xADO | 32K, C-terminal |
| 104 | HOOC-$(CH_2)_{16}$-CO-gGlu-2xADO | 36K, C-terminal |
| 73 | HOOC-$(CH_2)_{14}$-CO-gGlu-2xADO | 21K, 29K |
| 32 | 4-HOOC-($C_6H_4$)-O-$(CH_2)_{10}$-CO-Trx-gGlu-2xADO | 21K, C-terminal |
| 98 | 4-HOOC-($C_6H_4$)-O-$(CH_2)_{10}$-CO-Trx-gGlu-2xADO | 21K, C-terminal |
| 19 | HOOC-$(CH_2)_{18}$-CO-Trx-gGlu-2xADO | C-terminal |
| 19 | HOOC-$(CH_2)_{16}$-CO-Trx-gGlu-2xADO | C-terminal |
| SEQ ID NO: | Substituent | Attachment site(s) |
| 4 | HOOC-$(CH_2)_{16}$-CO-gGlu-2xADO | C-terminal |
| 6 | HOOC-$(CH_2)_{16}$-CO-gGlu-2xADO-NH-$CH_2$-($C_6H_4$)-$CH_2$- | N-terminal |
| 7 | HOOC-$(CH_2)_{16}$-CO-gGlu-2xADO | 7K |
| 8 | HOOC-$(CH_2)_{16}$-CO-gGlu-2xADO | 38K |
| 6 | HOS(O)2-$(CH2)15$-CO-gGlu-2xADO-NH-$CH_2$-($C_6H_4$)-$CH_2$- | N-terminal |
| 8 | HOOC-$(CH_2)_{16}$-CO-gGlu-2xADO | N-terminal, 38K |
| 11 | HOOC-$(CH_2)_{16}$-CO-gGlu-2xADO | C-terminal |
| 12 | HOOC-$(CH_2)_{16}$-CO-gGlu-2xADO | N-terminal |
| 13 | HOOC-$(CH_2)_{16}$-CO-gGlu-2xADO | N-terminal, |

| SEQ ID NO: | Substituent | Attachment site(s) |
|---|---|---|
| | | C-terminal |
| 13 | 4-HOOC-($C_6H_4$)-O-$(CH_2)_{10}$-CO-gGlu-2xADO | N-terminal, C-terminal |
| 15 | 4-HOOC-($C_6H_4$)-O-$(CH_2)_{10}$-CO-gGlu-2xADO | 40K, C-terminal |
| 16 | 4-HOOC-($C_6H_4$)-O-$(CH_2)_{10}$-CO-gGlu-2xADO | 38K, C-terminal |
| 17 | 4-HOOC-($C_6H_4$)-O-$(CH_2)_{10}$-CO-gGlu-2xADO | 29K, C-terminal |
| 19 | HOOC-$(CH_2)_{16}$-CO-gGlu-2xADO | C-terminal |
| 6 | HOOC-$(CH_2)_{16}$-CO-gGlu-2xADO | N-terminal |
| 21 | HOOC-$(CH_2)_{16}$-CO-gGlu-2xADO | 29K |
| 22 | HOOC-$(CH_2)_{16}$-CO-gGlu-2xADO | 32K |
| 23 | HOOC-$(CH_2)_{16}$-CO-gGlu-2xADO | N-terminal |
| 24 | HOOC-$(CH_2)_{16}$-CO-gGlu-2xADO | C-terminal |
| 25 | HOOC-$(CH_2)_{16}$-CO-gGlu-2xADO | N-terminal |
| 27 | HOOC-$(CH_2)_{16}$-CO-gGlu-2xADO | 8K |
| 28 | 4-HOOC-($C_6H_4$)-O-$(CH_2)_{10}$-CO-gGlu-2xADO | N-terminal, 2K |
| 30 | HOOC-$(CH_2)_{16}$-CO-gGlu-2xADO | 17K |
| 31 | HOOC-$(CH_2)_{16}$-CO-gGlu-2xADO | 26K |
| 32 | 4-HOOC-($C_6H_4$)-O-$(CH_2)_{10}$-CO-gGlu-2xADO | 21K, C-terminal |
| 33 | HOOC-$(CH_2)_{16}$-CO-gGlu-2xADO | 34K |
| 34 | HOOC-$(CH_2)_{16}$-CO-gGlu-2xADO | 33K |
| 35 | HOOC-$(CH_2)_{16}$-CO-gGlu-2xADO | 31K |
| 36 | HOOC-$(CH_2)_{16}$-CO-gGlu-2xADO | 30K |
| 37 | HOOC-$(CH_2)_{16}$-CO-gGlu-2xADO | 28K |
| 38 | HOOC-$(CH_2)_{16}$-CO-gGlu-2xADO | 37K |

| SEQ ID NO: | Substituent | Attachment site(s) |
|---|---|---|
| 39 | HOOC-$(CH_2)_{16}$-CO-gGlu-2xADO | 21K |
| 40 | HOOC-$(CH_2)_{16}$-CO-gGlu-2xADO | 36K |
| 41 | HOOC-$(CH_2)_{16}$-CO-gGlu-2xADO | 24K |
| 42 | HOOC-$(CH_2)_{16}$-CO-gGlu-2xADO | 23K |
| 43 | HOOC-$(CH_2)_{16}$-CO-gGlu-2xADO | C-terminal |
| 44 | HOOC-$(CH_2)_{16}$-CO-gGlu-2xADO | 22K |
| 45 | HOOC-$(CH_2)_{16}$-CO-gGlu-2xADO | 19K |
| 47 | HOOC-$(CH_2)_{16}$-CO-gGlu-2xADO | C-terminal |
| 48 | HOOC-$(CH_2)_{16}$-CO-gGlu-2xADO | C-terminal |
| 49 | HOOC-$(CH_2)_{16}$-CO-gGlu-2xADO | N-terminal |
| 50 | HOOC-$(CH_2)_{16}$-CO-gGlu-2xADO | N-terminal |
| 51 | HOOC-$(CH_2)_{16}$-CO-gGlu-2xADO | 14K |
| 52 | HOOC-$(CH_2)_{16}$-CO-gGlu-2xADO | 13K |
| 53 | HOOC-$(CH_2)_{16}$-CO-gGlu-2xADO | 11K |
| 55 | HOOC-$(CH_2)_{16}$-CO-gGlu-2xADO | C-terminal |
| 58 | HOOC-$(CH_2)_{16}$-CO-gGlu-2xADO | C-terminal |
| 60 | HOOC-$(CH_2)_{16}$-CO-gGlu-2xADO | C-terminal |
| 61 | HOOC-$(CH_2)_{16}$-CO-gGlu-2xADO | C-terminal |
| 9 | HOOC-$(CH_2)_{16}$-CO-gGlu-2xADO | C-terminal |
| 10 | HOOC-$(CH_2)_{16}$-CO-gGlu-2xADO | C-terminal |
| 6 | Tetrazolyl-$(CH_2)_{15}$-CO-NH-$SO_2$-$(CH_2)_3$-CO-ADO-ADO-NH-$CH_2$-$(C_6H_4)$-$CH_2$- | N-terminal |
| 14 | HOOC-$(CH_2)_{16}$-CO-gGlu-2xADO | 36K |
| 26 | HOOC-$(CH_2)_{16}$-CO-gGlu-2xADO | N-terminal |
| 63 | HOOC-$(CH_2)_{16}$-CO-gGlu-2xADO | 4K |

| SEQ ID NO: | Substituent | Attachment site(s) |
|---|---|---|
| 64 | HOOC-$(CH_2)_{16}$-CO-gGlu-2xADO | 2K |
| 65 | HOOC-$(CH_2)_{16}$-CO-gGlu-2xADO | N-terminal |
| 67 | HOOC-$(CH_2)_{16}$-CO-gGlu-2xADO | C-terminal |
| 68 | 4-HOOC-$(C_6H_4)$-O-$(CH_2)_{10}$-CO-gGlu-3xADO and 4-HOOC-$(C_6H_4)$-O-$(CH_2)_{10}$-CO-gGlu-2xADO | N-terminal, C-terminal |
| 17 | 4-HOOC-$(C_6H_4)$-O-$(CH_2)_9$-CO-gGlu-2xADO | 29K, C-terminal |
| 4 | HOOC-$(CH_2)_{14}$-CO-gGlu-2xADO | C-terminal |
| 4 | HOOC-$(CH_2)_{18}$-CO-gGlu-2xADO | C-terminal |
| 4 | HOOC-$(CH_2)_{16}$-CO-gGlu | C-terminal |
| 17 | HOOC-$(CH_2)_{12}$-CO-gGlu-2xADO | 29K, C-terminal |
| 17 | HOOC-$(CH_2)_{14}$-CO-gGlu-2xADO | 29K, C-terminal |
| 69 | 4-HOOC-$(C_6H_4)$-O-$(CH_2)_9$-CO-gGlu-2xADO | 21K, C-terminal |
| 70 | 4-HOOC-$(C_6H_4)$-O-$(CH_2)_{10}$-CO-gGlu-2xADO | 21K, 36K |
| 71 | 4-HOOC-$(C_6H_4)$-O-$(CH_2)_{10}$-CO-gGlu-2xADO | 21K, 32K |
| 39 | 4-HOOC-$(C_6H_4)$-O-$(CH_2)_{10}$-CO-gGlu-2xADO | N-terminal, 21K |
| 72 | 4-HOOC-$(C_6H_4)$-O-$(CH_2)_{10}$-CO-gGlu-2xADO | 32K, C-terminal |
| 73 | 4-HOOC-$(C_6H_4)$-O-$(CH_2)_{10}$-CO-gGlu-2xADO | 21K, 29K |
| 69 | 4-HOOC-$(C_6H_4)$-O-$(CH_2)_{10}$-CO-gGlu-2xADO | 21K, C-terminal |
| 77 | 4-HOOC-$(C_6H_4)$-O-$(CH_2)_{10}$-CO-gGlu-2xADO | 21K, C-terminal |
| 78 | 4-HOOC-$(C_6H_4)$-O-$(CH_2)_{10}$-CO-gGlu-2xADO | 36K, C-terminal |
| 32 | 4-HOOC-$(C_6H_4)$-O-$(CH_2)_{10}$-CO-gGlu | 21K, C-terminal |
| 32 | 4-HOOC-$(C_6H_4)$-O-$(CH_2)_{10}$-CO-2xgGlu | 21K, C-terminal |
| 32 | 4-HOOC-$(C_6H_4)$-O-$(CH_2)_{10}$-CO-gGlu-3xGly | 21K, C-terminal |
| 32 | 4-HOOC-$(C_6H_4)$-O-$(CH_2)_{10}$-CO-2xgGlu-2xADO | 21K, C-terminal |
| 32 | 3-HOOC-$(C_6H_4)$-O-$(CH_2)_9$-CO-gGlu-2xADO | 21K, C-terminal |

| SEQ ID NO: | Substituent | Attachment site(s) |
|---|---|---|
| 82 | HOOC-$(CH_2)_{16}$-CO-gGlu-2xADO | C-terminal |
| 4 | 4-HOOC-$(C_6H_4)$-O-$(CH_2)_{10}$-CO-gGlu-2xADO | N-terminal, C-terminal |
| 69 | 3-HO-Isoxazole-$(CH_2)_{12}$-CO-gGlu-2xADO | 21K, C-terminal |
| 32 | 3-HO-Isoxazole-$(CH_2)_{12}$-CO-gGlu-2xADO | 21K, C-terminal |
| 84 | 4-HOOC-$(C_6H_4)$-O-$(CH_2)_{10}$-CO-gGlu-2xADO | 17K, C-terminal |
| 85 | 4-HOOC-$(C_6H_4)$-O-$(CH_2)_{10}$-CO-gGlu-2xADO | 32K, C-terminal |
| 86 | 4-HOOC-$(C_6H_4)$-O-$(CH_2)_{10}$-CO-gGlu-2xADO | 22K, C-terminal |
| 87 | 4-HOOC-$(C_6H_4)$-O-$(CH_2)_{10}$-CO-gGlu-2xADO | N-terminal, C-terminal |
| 88 | 4-HOOC-$(C_6H_4)$-O-$(CH_2)_{10}$-CO-gGlu-2xADO | 17K, 36K |
| 89 | 4-HOOC-$(C_6H_4)$-O-$(CH_2)_{10}$-CO-gGlu-2xADO | 17K, 21K |
| 90 | 4-HOOC-$(C_6H_4)$-O-$(CH_2)_{10}$-CO-gGlu-2xADO | N-terminal, C-terminal |
| 91 | 4-HOOC-$(C_6H_4)$-O-$(CH_2)_{10}$-CO-gGlu-2xADO | 32K, 36K |
| 92 | 4-HOOC-$(C_6H_4)$-O-$(CH_2)_{10}$-CO-gGlu-2xADO | N-terminal, C-terminal |
| 93 | 4-HOOC-$(C_6H_4)$-O-$(CH_2)_{10}$-CO-gGlu-2xADO | 21K, C-terminal |
| 11 | 4-HOOC-$(C_6H_4)$-O-$(CH_2)_{10}$-CO-gGlu-2xADO | N-terminal, C-terminal |
| 40 | 4-HOOC-$(C_6H_4)$-O-$(CH_2)_{10}$-CO-gGlu-2xADO | N-terminal, 26K |
| 22 | 4-HOOC-$(C_6H_4)$-O-$(CH_2)_{10}$-CO-gGlu-2xADO | N-terminal, 32K |
| 94 | 4-HOOC-$(C_6H_4)$-O-$(CH_2)_{10}$-CO-gGlu-2xADO | 17K, C-terminal |
| 106 | 4-HOOC-$(C_6H_4)$-O-$(CH_2)_{10}$-CO-gGlu-2xADO | 17K, 32K |
| 30 | 4-HOOC-$(C_6H_4)$-O-$(CH_2)_{10}$-CO-gGlu-2xADO | <u>N-terminal,</u> 17K |
| 95 | 4-HOOC-$(C_6H_4)$-O-$(CH_2)_{10}$-CO-gGlu-2xADO | 29K, C-terminal |
| 32 | HOOC-$(CH_2)_{14}$-CO-gGlu-2xADO | 21K, C-terminal |

| SEQ ID NO: | Substituent | Attachment site(s) |
|---|---|---|
| 32 | HOOC-(CH2)14-CO-gGlu | 21K, C-terminal |
| 96 | 4-HOOC-(C$_6$H$_4$)-O-(CH$_2$)$_{10}$-CO-gGlu-2xADO | 21K, C-terminal |
| 32 | 4-HOOC-(C$_6$H$_4$)-O-(CH$_2$)$_{10}$-CO-gGlu-TtdSuc | 21K, C-terminal |
| 97 | 4-HOOC-(C$_6$H$_4$)-O-(CH$_2$)$_{10}$-CO-gGlu-TtdSuc | 21K, C-terminal |
| 98 | 4-HOOC-(C$_6$H$_4$)-O-(CH$_2$)$_{10}$-CO-gGlu-2xADO | 21K, C-terminal |
| 19 | HOOC-(CH$_2$)$_{18}$-CO-gGlu-2xADO | C-terminal |
| 99 | 4-HOOC-(C$_6$H$_4$)-O-(CH$_2$)$_{10}$-CO-gGlu-2xADO | 21K, 22K |
| 102 | 4-HOOC-(C$_6$H$_4$)-O-(CH$_2$)$_{10}$-CO-gGlu-2xADO | 19K, 21K |
| 69 | 4-HOOC-(C$_6$H$_4$)-O-(CH$_2$)$_9$-CO | 21K, C-terminal |
| 32 | Tetrazolyl-(CH$_2$)$_{12}$-CO-gGlu-2xADO | 21K, C-terminal |
| 32 | HOS(O)$_2$-(CH$_2$)$_{13}$-CO-gGlu-2xADO | 21K, C-terminal |
| 32 | MeS(O)$_2$NH(CO)NH-(CH$_2$)$_{12}$-CO-gGlu-2xADO | 21K, C-terminal |
| 98 | 4-HOOC-(C$_6$H$_4$)-O-(CH$_2$)$_{10}$-CO-gGlu | 21K, C-terminal |
| 98 | HOOC-(CH$_2$)$_{14}$-CO-gGlu-2xADO | 21K, C-terminal |
| 32 | Tetrazolyl-(CH$_2$)$_{15}$-CO-gGlu-2xADO | 21K, C-terminal |
| 98 | HOOC-(CH$_2$)$_{14}$-CO-gGlu | 21K, C-terminal |
| 103 | 4-HOOC-(C$_6$H$_4$)-O-(CH$_2$)$_{10}$-CO-gGlu-2xADO | 21K, C-terminal |
| 32 | 4-HOOC-(C$_6$H$_4$)-O-(CH$_2$)$_{10}$-CO-gGlu-4xADO | 21K, C-terminal |
| 78 | HOOC-(CH$_2$)$_{14}$-CO-gGlu-2xADO | 36K, C-terminal |
| 104 | HOOC-(CH$_2$)$_{14}$-CO-gGlu-2xADO | 36K, C-terminal |
| 72 | HOOC-(CH$_2$)$_{14}$-CO-gGlu-2xADO | 32K, C-terminal |
| 105 | HOOC-(CH$_2$)$_{14}$-CO-gGlu-2xADO | 32K, C-terminal |
| 104 | HOOC-(CH$_2$)$_{16}$-CO-gGlu-2xADO | 36K, C-terminal |
| 73 | HOOC-(CH$_2$)$_{14}$-CO-gGlu-2xADO | 21K, 29K |
| 32 | 4-HOOC-(C$_6$H$_4$)-O-(CH$_2$)$_{10}$-CO-Trx-gGlu- | 21K, C-terminal |

| SEQ ID NO: | Substituent | Attachment site(s) |
|---|---|---|
|  | 2xADO |  |
| 98 | 4-HOOC-(C$_6$H$_4$)-O-(CH$_2$)$_{10}$-CO-Trx-gGlu-2xADO | 21K, C-terminal |
| 19 | HOOC-(CH$_2$)$_{18}$-CO-Trx-gGlu-2xADO | C-terminal |
| 19 | HOOC-(CH$_2$)$_{16}$-CO-Trx-gGlu-2xADO | C-terminal |

At Column 437, Claim number 28, beginning at Line number 2, please amend as follows:
28. An EGF(A) derivative selected from the group consisting of:

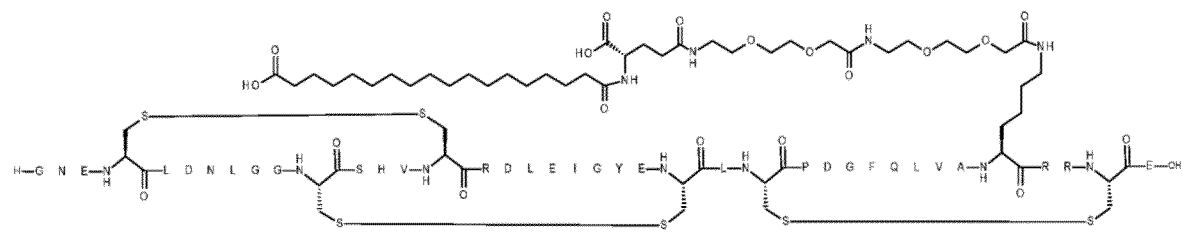

a.
wherein the amino acid sequence of EGF(A) derivative (a) is SEQ ID NO: 66,

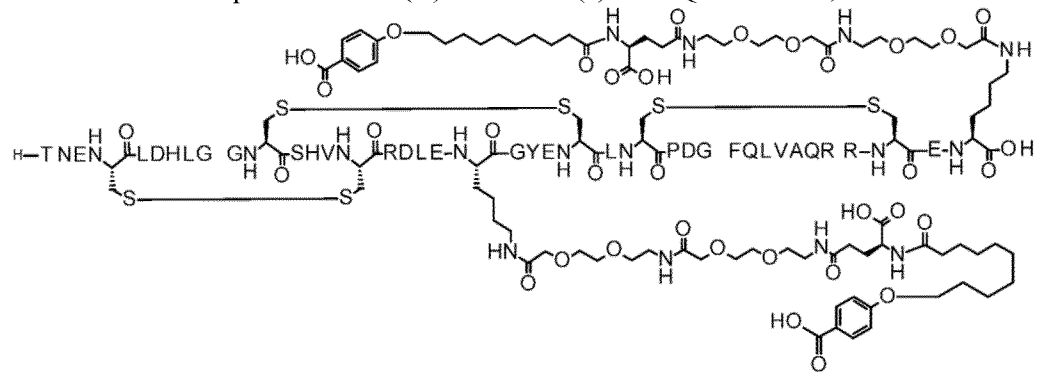

b.
wherein the amino acid sequence of EGF(A) derivative (b) is SEQ ID NO:74,

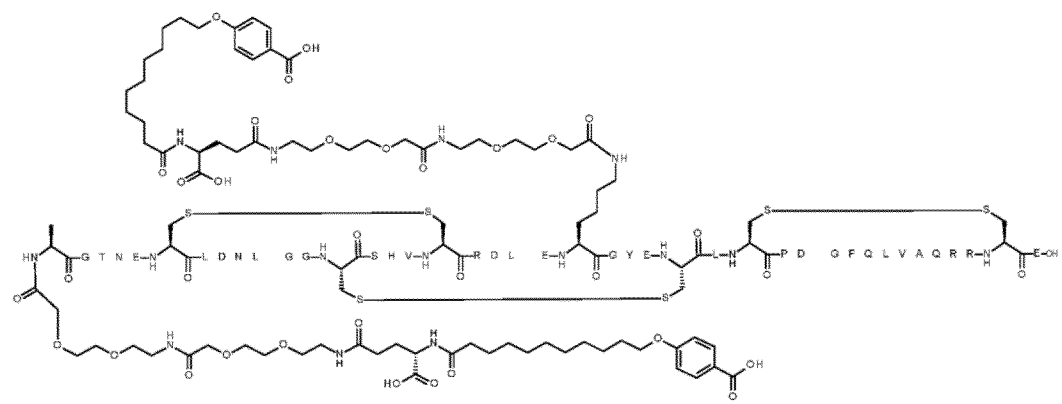

c.

wherein the amino acid sequence of EGF(A) derivative (c) is SEQ ID NO:75,
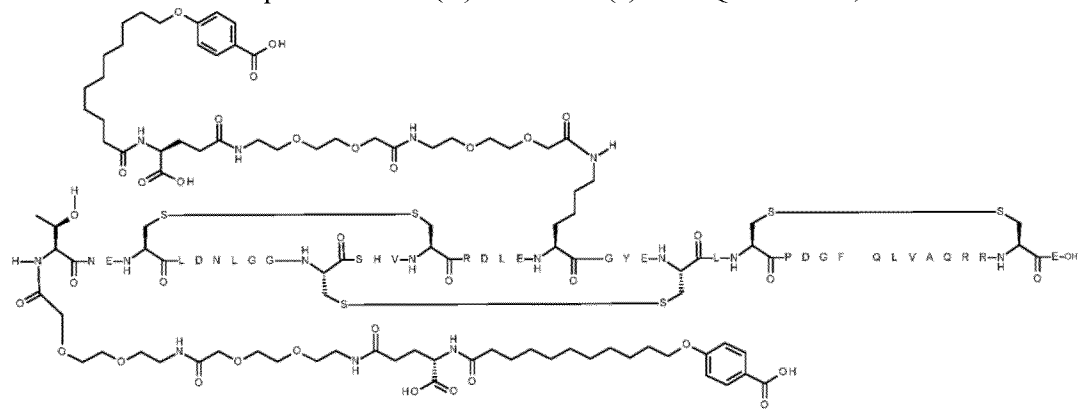
d.
wherein the amino acid sequence of EGF(A) derivative (d) is SEQ ID NO:76,
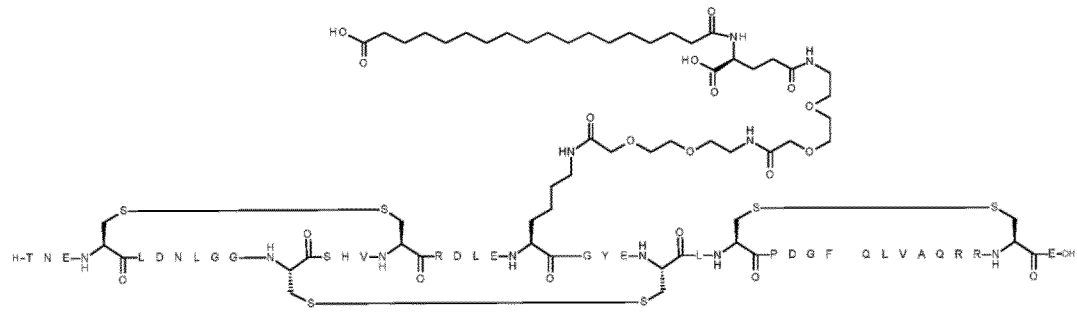
e.
wherein the amino acid sequence of EGF(A) derivative (e) is SEQ ID NO:76,
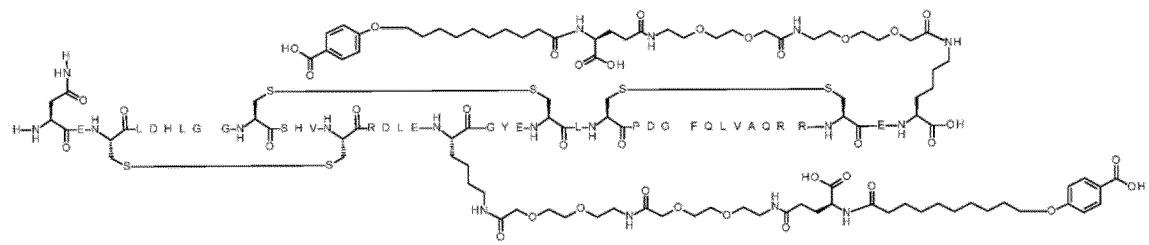
f.
wherein the amino acid sequence of EGF(A) derivative (f) is SEQ ID NO:83,
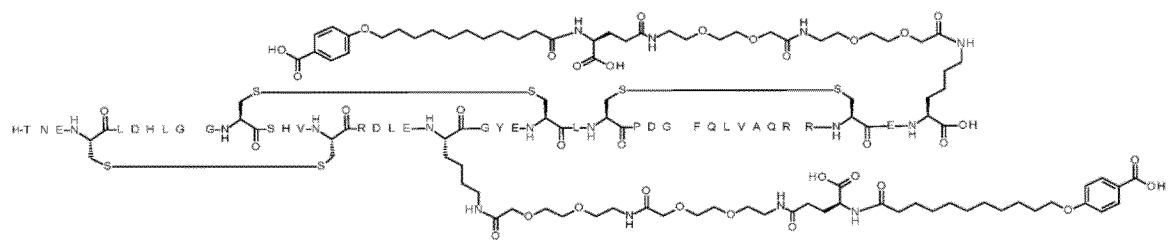
g.
wherein the amino acid sequence of EGF(A) derivative (g) is SEQ ID NO: 74, and
h.

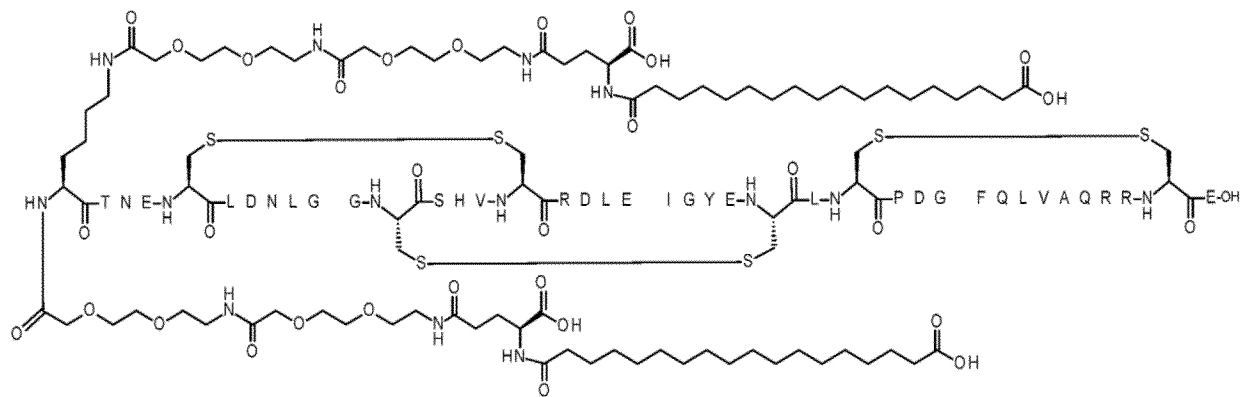
wherein the amino acid sequence of EGF(A) derivative (h) is SEQ ID NO: 12.

SEQUENCE LISTING

```
<160> NUMBER OF SEQ ID NOS: 106

<210> SEQ ID NO 1
<211> LENGTH: 40
<212> TYPE: PRT
<213> ORGANISM: Artificial Sequence
<220> FEATURE:
<223> OTHER INFORMATION: Synthetic sequence

<400> SEQUENCE: 1

Gly Thr Asn Glu Cys Leu Asp Asn Asn Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic sequence

<400> SEQUENCE: 2

Gly Thr Asn Glu Cys Leu Ala Asn Leu Gly Gly Cys Ser His Ile Cys
1               5                   10                  15

Arg Lys Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic sequence
```

```
<400> SEQUENCE: 3

Gly Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 4
<211> LENGTH: 41
<212> TYPE: PRT
<213> ORGANISM: Artificial Sequence
<220> FEATURE:
<223> OTHER INFORMATION: Synthetic sequence

<400> SEQUENCE: 4

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic

<400> SEQUENCE: 5

Gly Thr Asn Glu Cys Leu Asp Pro Leu Gly Gly Cys Ser His Ile Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic sequence

<400> SEQUENCE: 6

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 7
<211> LENGTH: 40
<212> TYPE: PRT
<213> ORGANISM: Artificial Sequence
<220> FEATURE:
<223> OTHER INFORMATION: Synthetic sequence

<400> SEQUENCE: 7

Gly Thr Asn Glu Cys Leu Lys Asn Leu Gly Gly Cys Ser His Val Cys
```

```
                1               5                   10                  15
Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic sequence

<400> SEQUENCE: 8

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Lys Cys Glu
        35                  40

<210> SEQ ID NO 9
<211> LENGTH: 41
<212> TYPE: PRT
<213> ORGANISM: Artificial Sequence
<220> FEATURE:
<223> OTHER INFORMATION: Synthetic

<400> SEQUENCE: 9

Asn Thr Asn Glu Cys Leu Asp Asn Leu Gly Gly Cys Ser His Ile Cys
1               5                   10                  15

Arg Asp Leu Asp Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 10
<211> LENGTH: 41
<212> TYPE: PRT
<213> ORGANISM: Artificial Sequence
<220> FEATURE:
<223> OTHER INFORMATION: Synthetic sequence

<400> SEQUENCE: 10

Asn Thr Asn Glu Cys Leu Asp Asn Leu Gly Gly Cys Ser His Val Cys
1               5                   10                  15

Arg Asp Leu Asp Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 11
<211> LENGTH: 40
<212> TYPE: PRT
<213> ORGANISM: Artificial Sequence
<220> FEATURE:
<223> OTHER INFORMATION: Synthetic sequence

<400> SEQUENCE: 11

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
```

-continued

```
            20                  25                  30

Leu Val Ala Gln Arg Arg Cys Lys
        35                  40

<210> SEQ ID NO 12
<211> LENGTH: 40
<212> TYPE: PRT
<213> ORGANISM: Artificial Sequence
<220> FEATURE:
<223> OTHER INFORMATION: Synthetic sequence

<400> SEQUENCE: 12

Lys Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 13
<211> LENGTH: 41
<212> TYPE: PRT
<213> ORGANISM: Artificial Sequence
<220> FEATURE:
<223> OTHER INFORMATION: Synthetic sequence

<400> SEQUENCE: 13

Lys Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic sequence

<400> SEQUENCE: 14

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Lys His Arg Cys Glu
        35                  40

<210> SEQ ID NO 15
<211> LENGTH: 41
<212> TYPE: PRT
<213> ORGANISM: Artificial Sequence
<220> FEATURE:
<223> OTHER INFORMATION: Synthetic sequence

<400> SEQUENCE: 15

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Lys Lys
```

<210> SEQ ID NO 16
<211> LENGTH: 41
<212> TYPE: PRT
<213> ORGANISM: Artificial Sequence
<220> FEATURE:
<223> OTHER INFORMATION: Synthetic sequence

<400> SEQUENCE: 16

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Lys Cys Glu Lys
        35                  40

<210> SEQ ID NO 17
<211> LENGTH: 41
<212> TYPE: PRT
<213> ORGANISM: Artificial Sequence
<220> FEATURE:
<223> OTHER INFORMATION: Synthetic sequence

<400> SEQUENCE: 17

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Glu Lys
        35                  40

<210> SEQ ID NO 18
<211> LENGTH: 41
<212> TYPE: PRT
<213> ORGANISM: Artificial Sequence
<220> FEATURE:
<223> OTHER INFORMATION: Synthetic sequence

<400> SEQUENCE: 18

Gly Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 19
<211> LENGTH: 41
<212> TYPE: PRT
<213> ORGANISM: Artificial Sequence
<220> FEATURE:
<223> OTHER INFORMATION: Synthetic sequence

<400> SEQUENCE: 19

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Lys
        35                  40

-continued

```
<210> SEQ ID NO 20
<211> LENGTH: 40
<212> TYPE: PRT
<213> ORGANISM: Artificial Sequence
<220> FEATURE:
<223> OTHER INFORMATION: Synthetic

<400> SEQUENCE: 20

Gly Thr Asp Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 21
<211> LENGTH: 40
<212> TYPE: PRT
<213> ORGANISM: Artificial Sequence
<220> FEATURE:
<223> OTHER INFORMATION: Synthetic sequence

<400> SEQUENCE: 21

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Glu
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic sequence

<400> SEQUENCE: 22

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
            20                  25                  30

Leu Val Ala Gln Arg Arg Cys Glu
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic sequence

<400> SEQUENCE: 23

Gly Thr Asn Glu Cys Leu Asp Asn Leu Gly Gly Cys Ser His Val Cys
1               5                   10                  15

Arg Asp Leu Gln Ile Gly Tyr Glu Cys Leu Cys Pro Asp Gly Phe Gln
            20                  25                  30

Leu Val Ala Gln Arg Arg Cys Glu
        35                  40

<210> SEQ ID NO 24
<211> LENGTH: 40
<212> TYPE: PRT
```

```
<213> ORGANISM: Artificial Sequence
<220> FEATURE:
<223> OTHER INFORMATION: Synthetic sequence

<400> SEQUENCE: 24

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Lys
        35                  40

<210> SEQ ID NO 25
<211> LENGTH: 40
<212> TYPE: PRT
<213> ORGANISM: Artificial Sequence
<220> FEATURE:
<223> OTHER INFORMATION: Synthetic sequence

<400> SEQUENCE: 25

Lys Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 26
<211> LENGTH: 40
<212> TYPE: PRT
<213> ORGANISM: Artificial Sequence
<220> FEATURE:
<223> OTHER INFORMATION: Synthetic sequence

<400> SEQUENCE: 26

Gly Thr Asn Glu Cys Leu Asp His Leu Gly Gly Cys Ser His Ile Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic sequence

<400> SEQUENCE: 27

Gly Thr Asn Glu Cys Leu Asp Lys Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 28
<211> LENGTH: 40
<212> TYPE: PRT
<213> ORGANISM: Artificial Sequence
<220> FEATURE:
<223> OTHER INFORMATION: Synthetic sequence
```

```
<400> SEQUENCE: 28

Lys Lys Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 29
<211> LENGTH: 40
<212> TYPE: PRT
<213> ORGANISM: Artificial Sequence
<220> FEATURE:
<223> OTHER INFORMATION: Synthetic sequence

<400> SEQUENCE: 29

Lys Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 30
<211> LENGTH: 40
<212> TYPE: PRT
<213> ORGANISM: Artificial Sequence
<220> FEATURE:
<223> OTHER INFORMATION: Synthetic sequence

<400> SEQUENCE: 30

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic sequence

<400> SEQUENCE: 31

Gly Thr Asn Glu Cys Leu Asp Asn Leu Gly Gly Cys Ser His Val Cys
1               5                   10                  15

Arg Asp Leu Glu Ile Gly Tyr Glu Cys Lys Cys Pro Asp Gly Phe Gln
            20                  25                  30

Leu Val Ala Gln Arg Arg Cys Glu
        35                  40

<210> SEQ ID NO 32
<211> LENGTH: 41
<212> TYPE: PRT
<213> ORGANISM: Artificial Sequence
<220> FEATURE:
<223> OTHER INFORMATION: Synthetic sequence

<400> SEQUENCE: 32
```

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic sequence

<400> SEQUENCE: 33

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Lys Ala Gln Arg Arg Cys Glu
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic sequence

<400> SEQUENCE: 34

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Lys Val Ala Gln Arg Arg Cys Glu
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic sequence

<400> SEQUENCE: 35

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Lys Gln
            20                  25                  30

Leu Val Ala Gln Arg Arg Cys Glu
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic sequence

<400> SEQUENCE: 36

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Lys Phe Gln
            20                  25                  30

Leu Val Ala Gln Arg Arg Cys Glu
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthetic sequence

<400> SEQUENCE: 37

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Lys Asp Gly Phe Gln
            20                  25                  30

Leu Val Ala Gln Arg Arg Cys Glu
        35                  40

<210> SEQ ID NO 38
<211> LENGTH: 40
<212> TYPE: PRT
<213> ORGANISM: Artificial Sequence
<220> FEATURE:
<223> OTHER INFORMATION: Synthetic sequence

<400> SEQUENCE: 38

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Lys Arg Cys Glu
        35                  40

<210> SEQ ID NO 39
<211> LENGTH: 40
<212> TYPE: PRT
<213> ORGANISM: Artificial Sequence
<220> FEATURE:
<223> OTHER INFORMATION: Synthetic sequence

<400> SEQUENCE: 39

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic sequence

<400> SEQUENCE: 40

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Lys Arg Arg Cys Glu
        35                  40

<210> SEQ ID NO 41
<211> LENGTH: 40
<212> TYPE: PRT
<213> ORGANISM: Artificial Sequence
<220> FEATURE:
<223> OTHER INFORMATION: Synthetic sequence

<400> SEQUENCE: 41

Gly Thr Asn Glu Cys Leu Asp Asn Leu Gly Gly Cys Ser His Val Cys
1               5                   10                  15

Arg Asp Leu Glu Ile Gly Tyr Lys Cys Leu Cys Pro Asp Gly Phe Gln
            20                  25                  30

Leu Val Ala Gln Arg Arg Cys Glu
        35                  40

<210> SEQ ID NO 42
<211> LENGTH: 40
<212> TYPE: PRT
<213> ORGANISM: Artificial Sequence
<220> FEATURE:
<223> OTHER INFORMATION: Synthetic sequence

<400> SEQUENCE: 42

Gly Thr Asn Glu Cys Leu Asp Asn Leu Gly Gly Cys Ser His Val Cys
1               5                   10                  15

Arg Asp Leu Glu Ile Gly Lys Glu Cys Leu Cys Pro Asp Gly Phe Gln
            20                  25                  30

Leu Val Ala Gln Arg Arg Cys Glu
        35                  40

<210> SEQ ID NO 43
<211> LENGTH: 41
<212> TYPE: PRT
<213> ORGANISM: Artificial Sequence
<220> FEATURE:
<223> OTHER INFORMATION: Synthetic sequence

<400> SEQUENCE: 43

Gly Thr Asn Glu Cys Leu Asp His Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 44
<211> LENGTH: 40
<212> TYPE: PRT
<213> ORGANISM: Artificial Sequence
<220> FEATURE:
<223> OTHER INFORMATION: Synthetic sequence

<400> SEQUENCE: 44

Gly Thr Asn Glu Cys Leu Asp Asn Leu Gly Gly Cys Ser His Val Cys
1               5                   10                  15

Arg Asp Leu Glu Ile Lys Tyr Glu Cys Leu Cys Pro Asp Gly Phe Gln
            20                  25                  30

Leu Val Ala Gln Arg Arg Cys Glu
        35                  40

<210> SEQ ID NO 45
<211> LENGTH: 40
<212> TYPE: PRT
<213> ORGANISM: Artificial Sequence
<220> FEATURE:
<223> OTHER INFORMATION: Synthetic sequence

<400> SEQUENCE: 45

```
Gly Thr Asn Glu Cys Leu Asp Asn Leu Gly Gly Cys Ser His Val Cys
1               5                   10                  15

Arg Asp Lys Glu Ile Gly Tyr Glu Cys Leu Cys Pro Asp Gly Phe Gln
            20                  25                  30

Leu Val Ala Gln Arg Arg Cys Glu
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Synthetic sequence

<400> SEQUENCE: 46

```
Gly Thr Asn Glu Cys Leu Asp Asn Leu Gly Gly Cys Ser His Lys Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40
```

<210> SEQ ID NO 47
<211> LENGTH: 41
<212> TYPE: PRT
<213> ORGANISM: Artificial Sequence
<220> FEATURE:
<223> OTHER INFORMATION: Synthetic sequence

<400> SEQUENCE: 47

```
Gly Thr Asn Glu Cys Leu Asp Asn Leu Gly Gly Cys Ser His Val Cys
1               5                   10                  15

Ser Asp Leu Arg Ile Gly Tyr Glu Cys Leu Cys Pro Asp Gly Phe Gln
            20                  25                  30

Leu Val Ala Gln Arg Arg Cys Glu Lys
        35                  40
```

<210> SEQ ID NO 48
<211> LENGTH: 41
<212> TYPE: PRT
<213> ORGANISM: Artificial Sequence
<220> FEATURE:
<223> OTHER INFORMATION: Synthetic sequence

<400> SEQUENCE: 48

```
Gly Thr Asn Glu Cys Leu Asp Asn Leu Gly Gly Cys Ser His Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu Lys
        35                  40
```

<210> SEQ ID NO 49
<211> LENGTH: 40

```
<212> TYPE: PRT
<213> ORGANISM: Artificial Sequence
<220> FEATURE:
<223> OTHER INFORMATION: Synthetic sequence

<400> SEQUENCE: 49

Gly Thr Asn Glu Cys Leu Asp Asn Leu Gly Gly Cys Ser Tyr Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 50
<211> LENGTH: 40
<212> TYPE: PRT
<213> ORGANISM: Artificial Sequence
<220> FEATURE:
<223> OTHER INFORMATION: Synthetic sequence

<400> SEQUENCE: 50

Asn Thr Asn Glu Cys Leu Asp Asn Leu Gly Gly Cys Ser His Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 51
<211> LENGTH: 40
<212> TYPE: PRT
<213> ORGANISM: Artificial Sequence
<220> FEATURE:
<223> OTHER INFORMATION: Synthetic sequence

<400> SEQUENCE: 51

Gly Thr Asn Glu Cys Leu Asp Asn Leu Gly Gly Cys Ser Lys Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic sequence

<400> SEQUENCE: 52

Gly Thr Asn Glu Cys Leu Asp Asn Leu Gly Gly Cys Lys His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 53
<211> LENGTH: 40
<212> TYPE: PRT
<213> ORGANISM: Artificial Sequence
<220> FEATURE:
```

<223> OTHER INFORMATION: Synthetic sequence

<400> SEQUENCE: 53

Gly Thr Asn Glu Cys Leu Asp Asn Leu Gly Lys Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 54
<211> LENGTH: 40
<212> TYPE: PRT
<213> ORGANISM: Artificial Sequence
<220> FEATURE:
<223> OTHER INFORMATION: Synthetic sequence

<400> SEQUENCE: 54

Gly Thr Asn Glu Cys Leu Asp Asn Leu Lys Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 55
<211> LENGTH: 41
<212> TYPE: PRT
<213> ORGANISM: Artificial Sequence
<220> FEATURE:
<223> OTHER INFORMATION: Synthetic sequence

<400> SEQUENCE: 55

Asn Thr Asn Glu Cys Leu Asp His Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Synthetic sequence

<400> SEQUENCE: 56

Gly Thr Asn Glu Cys Leu Asp Asn Lys Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 57
<211> LENGTH: 40
<212> TYPE: PRT
<213> ORGANISM: Artificial Sequence
<220> FEATURE:
<223> OTHER INFORMATION: Synthetic sequence

<400> SEQUENCE: 57

```
Gly Thr Asn Glu Cys Lys Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 58
<211> LENGTH: 41
<212> TYPE: PRT
<213> ORGANISM: Artificial Sequence
<220> FEATURE:
<223> OTHER INFORMATION: Synthetic sequence

<400> SEQUENCE: 58

Asn Thr Asn Glu Cys Leu Asp Asn Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic sequence

<400> SEQUENCE: 59

Gly Thr Asn Glu Cys Leu Asp Asn Leu Gly Gly Cys Ser His Ile Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Lys
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic sequence

<400> SEQUENCE: 60

Gly Thr Asn Glu Cys Leu Asp Asn Leu Gly Gly Cys Ser Tyr Val Cys
1               5                   10                  15

Asn Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic sequence

<400> SEQUENCE: 61

Gly Thr Asn Glu Cys Leu Asp Asn Leu Gly Gly Cys Ser His Ile Cys
1               5                   10                  15
```

-continued

```
Asn Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic sequence

<400> SEQUENCE: 62

Gly Thr Asn Glu Cys Leu Asp His Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 63
<211> LENGTH: 40
<212> TYPE: PRT
<213> ORGANISM: Artificial Sequence
<220> FEATURE:
<223> OTHER INFORMATION: Synthetic sequence

<400> SEQUENCE: 63

Gly Thr Asn Lys Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 64
<211> LENGTH: 40
<212> TYPE: PRT
<213> ORGANISM: Artificial Sequence
<220> FEATURE:
<223> OTHER INFORMATION: Synthetic sequence

<400> SEQUENCE: 64

Gly Lys Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 65
<211> LENGTH: 41
<212> TYPE: PRT
<213> ORGANISM: Artificial Sequence
<220> FEATURE:
<223> OTHER INFORMATION: Synthetic sequence

<400> SEQUENCE: 65

Lys Gly Thr Asn Glu Cys Leu Asp Asn Leu Gly Gly Cys Ser His Val
1               5                   10                  15

Cys Arg Asp Leu Glu Ile Gly Tyr Glu Cys Leu Cys Pro Asp Gly Phe
            20                  25                  30
```

```
Gln Leu Val Ala Gln Arg Arg Cys Glu
        35                  40

<210> SEQ ID NO 66
<211> LENGTH: 39
<212> TYPE: PRT
<213> ORGANISM: Artificial Sequence
<220> FEATURE:
<223> OTHER INFORMATION: Synthetic sequence

<400> SEQUENCE: 66

Gly Asn Glu Cys Leu Asp Asn Leu Gly Gly Cys Ser His Val Cys Arg
1               5                   10                  15

Asp Leu Glu Ile Gly Tyr Glu Cys Leu Cys Pro Asp Gly Phe Gln Leu
            20                  25                  30

Val Ala Lys Arg Arg Cys Glu
        35

<210> SEQ ID NO 67
<211> LENGTH: 41
<212> TYPE: PRT
<213> ORGANISM: Artificial Sequence
<220> FEATURE:
<223> OTHER INFORMATION: Synthetic sequence

<400> SEQUENCE: 67

Gly Thr Asn Glu Cys Leu Asp Asn Leu Gly Gly Cys Ser Asp Val Cys
1               5                   10                  15

Arg Asp Leu Glu Ile Gly Tyr Glu Cys Leu Cys Pro Asp Gly Phe Gly
            20                  25                  30

Leu Val Ala Gln Arg Arg Cys Glu Lys
        35                  40

<210> SEQ ID NO 68
<211> LENGTH: 41
<212> TYPE: PRT
<213> ORGANISM: Artificial Sequence
<220> FEATURE:
<223> OTHER INFORMATION: Synthetic sequence

<400> SEQUENCE: 68

Gly Thr Asn Glu Cys Leu Asp Asn Leu Gly Gly Cys Ser Asp Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 69
<211> LENGTH: 41
<212> TYPE: PRT
<213> ORGANISM: Artificial Sequence
<220> FEATURE:
<223> OTHER INFORMATION: Synthetic sequence

<400> SEQUENCE: 69

Gly Thr Asn Glu Cys Leu Asp His Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40
```

<210> SEQ ID NO 70
<211> LENGTH: 40
<212> TYPE: PRT
<213> ORGANISM: Artificial Sequence
<220> FEATURE:
<223> OTHER INFORMATION: Synthetic sequence

<400> SEQUENCE: 70

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Lys Arg Arg Cys Glu
        35                  40

<210> SEQ ID NO 71
<211> LENGTH: 40
<212> TYPE: PRT
<213> ORGANISM: Artificial Sequence
<220> FEATURE:
<223> OTHER INFORMATION: Synthetic sequence

<400> SEQUENCE: 71

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Lys
            20                  25                  30

Leu Val Ala Gln Arg Arg Cys Glu
        35                  40

<210> SEQ ID NO 72
<211> LENGTH: 41
<212> TYPE: PRT
<213> ORGANISM: Artificial Sequence
<220> FEATURE:
<223> OTHER INFORMATION: Synthetic sequence

<400> SEQUENCE: 72

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
            20                  25                  30

Leu Val Ala Gln Arg Arg Cys Glu Lys
        35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic sequence

<400> SEQUENCE: 73

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Lys Gly Phe Gln
            20                  25                  30

Leu Val Ala Gln Arg Arg Cys Glu
        35                  40

<210> SEQ ID NO 74

```
<211> LENGTH: 40
<212> TYPE: PRT
<213> ORGANISM: Artificial Sequence
<220> FEATURE:
<223> OTHER INFORMATION: Synthetic sequence

<400> SEQUENCE: 74

Thr Asn Glu Cys Leu Asp His Leu Gly Gly Cys Ser His Val Cys Arg
1               5                   10                  15

Asp Leu Glu Lys Gly Tyr Glu Cys Leu Cys Pro Asp Gly Phe Gln Leu
            20                  25                  30

Val Ala Gln Arg Arg Cys Glu Lys
        35                  40

<210> SEQ ID NO 75
<211> LENGTH: 41
<212> TYPE: PRT
<213> ORGANISM: Artificial Sequence
<220> FEATURE:
<223> OTHER INFORMATION: Synthetic sequence

<400> SEQUENCE: 75

Ala Gly Thr Asn Glu Cys Leu Asp Asn Leu Gly Gly Cys Ser His Val
1               5                   10                  15

Cys Arg Asp Leu Glu Lys Gly Tyr Glu Cys Leu Cys Pro Asp Gly Phe
            20                  25                  30

Gln Leu Val Ala Gln Arg Arg Cys Glu
        35                  40

<210> SEQ ID NO 76
<211> LENGTH: 39
<212> TYPE: PRT
<213> ORGANISM: Artificial Sequence
<220> FEATURE:
<223> OTHER INFORMATION: Synthetic sequence

<400> SEQUENCE: 76

Thr Asn Glu Cys Leu Asp Asn Leu Gly Gly Cys Ser His Val Cys Arg
1               5                   10                  15

Asp Leu Glu Lys Gly Tyr Glu Cys Leu Cys Pro Asp Gly Phe Gln Leu
            20                  25                  30

Val Ala Gln Arg Arg Cys Glu
        35

<210> SEQ ID NO 77
<211> LENGTH: 40
<212> TYPE: PRT
<213> ORGANISM: Artificial Sequence
<220> FEATURE:
<223> OTHER INFORMATION: Synthetic sequence

<400> SEQUENCE: 77

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Lys
        35                  40

<210> SEQ ID NO 78
<211> LENGTH: 41
<212> TYPE: PRT
<213> ORGANISM: Artificial Sequence
```

<220> FEATURE:
<223> OTHER INFORMATION: Synthetic sequence

<400> SEQUENCE: 78

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Lys Arg Arg Cys Glu Lys
        35                  40

<210> SEQ ID NO 79
<211> LENGTH: 40
<212> TYPE: PRT
<213> ORGANISM: Artificial Sequence
<220> FEATURE:
<223> OTHER INFORMATION: Synthetic sequence

<400> SEQUENCE: 79

Gly Thr Asn Glu Cys Leu Ala Asn Leu Gly Gly Cys Ser His Ile Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 80
<211> LENGTH: 40
<212> TYPE: PRT
<213> ORGANISM: Artificial Sequence
<220> FEATURE:
<223> OTHER INFORMATION: GTNECLDNLG GCSHVCRKLK IGYECLCPDG FQLVAQRRCE

<400> SEQUENCE: 80

Gly Thr Asn Glu Cys Leu Asp Asn Leu Gly Gly Cys Ser His Val Cys
1               5                   10                  15

Arg Lys Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 81
<211> LENGTH: 40
<212> TYPE: PRT
<213> ORGANISM: Artificial Sequence
<220> FEATURE:
<223> OTHER INFORMATION: Synthetic sequence

<400> SEQUENCE: 81

Gly Thr Asn Glu Cys Leu Asp Asn Leu Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 82
<211> LENGTH: 41
<212> TYPE: PRT
<213> ORGANISM: Artificial Sequence
<220> FEATURE:
<223> OTHER INFORMATION: synthetic

```
<400> SEQUENCE: 82

Gly Thr Asn Glu Cys Leu Asp His Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 83
<211> LENGTH: 39
<212> TYPE: PRT
<213> ORGANISM: Artificial Sequence
<220> FEATURE:
<223> OTHER INFORMATION: synthetic

<400> SEQUENCE: 83

Asn Glu Cys Leu Asp His Leu Gly Gly Cys Ser His Val Cys Arg Asp
1               5                   10                  15

Leu Glu Lys Gly Tyr Glu Cys Leu Cys Pro Asp Gly Phe Gln Leu Val
            20                  25                  30

Ala Gln Arg Arg Cys Glu Lys
        35

<210> SEQ ID NO 84
<211> LENGTH: 41
<212> TYPE: PRT
<213> ORGANISM: Artificial Sequence
<220> FEATURE:
<223> OTHER INFORMATION: synthetic

<400> SEQUENCE: 84

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 85
<211> LENGTH: 41
<212> TYPE: PRT
<213> ORGANISM: Artificial Sequence
<220> FEATURE:
<223> OTHER INFORMATION: synthetic

<400> SEQUENCE: 85

Gly Thr Asn Glu Cys Leu Asp Asn Leu Gly Gly Cys Ser Tyr Val Cys
1               5                   10                  15

Asn Asp Leu Glu Ile Gly Tyr Glu Cys Leu Cys Pro Asp Gly Phe Lys
            20                  25                  30

Leu Val Ala Gln Arg Arg Cys Glu Lys
        35                  40

<210> SEQ ID NO 86
<211> LENGTH: 41
<212> TYPE: PRT
<213> ORGANISM: Artificial Sequence
<220> FEATURE:
<223> OTHER INFORMATION: synthetic

<400> SEQUENCE: 86

Gly Thr Asn Glu Cys Leu Asp His Leu Gly Gly Cys Ser His Val Cys
```

```
1               5                   10                  15
Arg Asp Leu Glu Ile Lys Tyr Glu Cys Leu Cys Pro Asp Gly Phe Gln
            20                  25                  30

Leu Val Ala Gln Arg Arg Cys Glu Lys
        35                  40
```

<210> SEQ ID NO 87
<211> LENGTH: 41
<212> TYPE: PRT
<213> ORGANISM: Artificial Sequence
<220> FEATURE:
<223> OTHER INFORMATION: synthetic

<400> SEQUENCE: 87

```
Gly Trp Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40
```

<210> SEQ ID NO 88
<211> LENGTH: 40
<212> TYPE: PRT
<213> ORGANISM: Artificial Sequence
<220> FEATURE:
<223> OTHER INFORMATION: synthetic

<400> SEQUENCE: 88

```
Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Lys Arg Arg Cys Glu
        35                  40
```

<210> SEQ ID NO 89
<211> LENGTH: 40
<212> TYPE: PRT
<213> ORGANISM: Artificial Sequence
<220> FEATURE:
<223> OTHER INFORMATION: synthetic

<400> SEQUENCE: 89

```
Gly Thr Asn Glu Cys Leu Asp Asn Leu Gly Gly Cys Ser His Val Cys
1               5                   10                  15

Lys Asp Leu Glu Lys Gly Tyr Glu Cys Leu Cys Pro Asp Gly Phe Gln
            20                  25                  30

Leu Val Ala Gln Arg Arg Cys Glu
        35                  40
```

<210> SEQ ID NO 90
<211> LENGTH: 40
<212> TYPE: PRT
<213> ORGANISM: Artificial Sequence
<220> FEATURE:
<223> OTHER INFORMATION: synthetic

<400> SEQUENCE: 90

```
Thr Asn Glu Cys Leu Asp Asn Leu Gly Gly Cys Ser His Val Cys Arg
1               5                   10                  15

Asp Leu Glu Ile Gly Tyr Glu Cys Leu Cys Pro Asp Gly Phe Gln Leu
```

```
                20                  25                  30

Val Ala Gln Arg Arg Cys Glu Lys
        35                  40

<210> SEQ ID NO 91
<211> LENGTH: 40
<212> TYPE: PRT
<213> ORGANISM: Artificial Sequence
<220> FEATURE:
<223> OTHER INFORMATION: synthetic

<400> SEQUENCE: 91

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
            20                  25                  30

Leu Val Ala Lys Arg Arg Cys Glu
        35                  40

<210> SEQ ID NO 92
<211> LENGTH: 42
<212> TYPE: PRT
<213> ORGANISM: Artificial Sequence
<220> FEATURE:
<223> OTHER INFORMATION: synthetic

<400> SEQUENCE: 92

Ala Gly Thr Asn Glu Cys Leu Asp Asn Leu Gly Gly Cys Ser His Val
1               5                   10                  15

Cys Arg Asp Leu Glu Ile Gly Tyr Glu Cys Leu Cys Pro Asp Gly Phe
            20                  25                  30

Gln Leu Val Ala Gln Arg Arg Cys Glu Lys
        35                  40

<210> SEQ ID NO 93
<211> LENGTH: 41
<212> TYPE: PRT
<213> ORGANISM: Artificial Sequence
<220> FEATURE:
<223> OTHER INFORMATION: synthetic

<400> SEQUENCE: 93

Gly Thr Asn Glu Cys Leu Asp Asn Leu Gly Gly Cys Ser Tyr Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40

<210> SEQ ID NO 94
<211> LENGTH: 40
<212> TYPE: PRT
<213> ORGANISM: Artificial Sequence
<220> FEATURE:
<223> OTHER INFORMATION: synthetic

<400> SEQUENCE: 94

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Lys
```

<210> SEQ ID NO 95
<211> LENGTH: 40
<212> TYPE: PRT
<213> ORGANISM: Artificial Sequence
<220> FEATURE:
<223> OTHER INFORMATION: synthetic

<400> SEQUENCE: 95

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Lys
        35                  40

<210> SEQ ID NO 96
<211> LENGTH: 40
<212> TYPE: PRT
<213> ORGANISM: Artificial Sequence
<220> FEATURE:
<223> OTHER INFORMATION: synthetic

<400> SEQUENCE: 96

Gly Thr Asn Glu Cys Leu Asp His Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Lys
        35                  40

<210> SEQ ID NO 97
<211> LENGTH: 40
<212> TYPE: PRT
<213> ORGANISM: Artificial Sequence
<220> FEATURE:
<223> OTHER INFORMATION: synthetic

<400> SEQUENCE: 97

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Lys
        35                  40

<210> SEQ ID NO 98
<211> LENGTH: 41
<212> TYPE: PRT
<213> ORGANISM: Artificial Sequence
<220> FEATURE:
<223> OTHER INFORMATION: synthetic

<400> SEQUENCE: 98

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Glu Lys
        35                  40

<210> SEQ ID NO 99
<211> LENGTH: 40
<212> TYPE: PRT
<213> ORGANISM: Artificial Sequence
<220> FEATURE:
<223> OTHER INFORMATION: synthetic

<400> SEQUENCE: 99

```
Gly Thr Asn Glu Cys Leu Asp Asn Leu Gly Gly Cys Ser His Val Cys
1               5                   10                  15

Arg Asp Leu Glu Lys Lys Tyr Glu Cys Leu Cys Pro Asp Gly Phe Gln
            20                  25                  30

Leu Val Ala Gln Arg Arg Cys Glu
        35                  40
```

<210> SEQ ID NO 100
<211> LENGTH: 40
<212> TYPE: PRT
<213> ORGANISM: Artificial Sequence
<220> FEATURE:
<223> OTHER INFORMATION: synthetic

<400> SEQUENCE: 100

```
Gly Thr Asn Glu Cys Leu Asp Asn Leu Gly Gly Cys Ser His Val Cys
1               5                   10                  15

Arg Asp Leu Lys Lys Gly Tyr Glu Cys Leu Cys Pro Asp Gly Phe Gln
            20                  25                  30

Leu Val Ala Gln Arg Arg Cys Glu
        35                  40
```

<210> SEQ ID NO 101
<211> LENGTH: 40
<212> TYPE: PRT
<213> ORGANISM: Artificial Sequence
<220> FEATURE:
<223> OTHER INFORMATION: synthetic

<400> SEQUENCE: 101

```
Gly Thr Asn Glu Cys Leu Asp Asn Leu Gly Gly Cys Ser His Val Cys
1               5                   10                  15

Arg Asp Leu Lys Ile Lys Tyr Glu Cys Leu Cys Pro Asp Gly Phe Gln
            20                  25                  30

Leu Val Ala Gln Arg Arg Cys Glu
        35                  40
```

<210> SEQ ID NO 102
<211> LENGTH: 40
<212> TYPE: PRT
<213> ORGANISM: Artificial Sequence
<220> FEATURE:
<223> OTHER INFORMATION: synthetic

<400> SEQUENCE: 102

```
Gly Thr Asn Glu Cys Leu Asp Asn Leu Gly Gly Cys Ser His Val Cys
1               5                   10                  15

Arg Asp Lys Glu Lys Gly Tyr Glu Cys Leu Cys Pro Asp Gly Phe Gln
            20                  25                  30

Leu Val Ala Gln Arg Arg Cys Glu
        35                  40
```

<210> SEQ ID NO 103
<211> LENGTH: 41
<212> TYPE: PRT

```
<213> ORGANISM: Artificial Sequence
<220> FEATURE:
<223> OTHER INFORMATION: synthetic

<400> SEQUENCE: 103

Gly Thr Asn Glu Cys Leu Asp His Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Glu Lys
        35                  40

<210> SEQ ID NO 104
<211> LENGTH: 41
<212> TYPE: PRT
<213> ORGANISM: Artificial Sequence
<220> FEATURE:
<223> OTHER INFORMATION: synthetic

<400> SEQUENCE: 104

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Lys Arg Arg Cys Glu Lys
        35                  40

<210> SEQ ID NO 105
<211> LENGTH: 41
<212> TYPE: PRT
<213> ORGANISM: Artificial Sequence
<220> FEATURE:
<223> OTHER INFORMATION: synthetic

<400> SEQUENCE: 105

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Lys
            20                  25                  30

Leu Val Ala Gln Arg Arg Cys Glu Lys
        35                  40

<210> SEQ ID NO 106
<211> LENGTH: 40
<212> TYPE: PRT
<213> ORGANISM: Artificial sequence
<220> FEATURE:
<223> OTHER INFORMATION: Synthetic

<400> SEQUENCE: 106

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Lys
            20                  25                  30

Leu Val Ala Gln Arg Arg Cys Glu
        35                  40
```